United States Patent
Priest et al.

(10) Patent No.: US 10,016,418 B2
(45) Date of Patent: *Jul. 10, 2018

(54) COMPOUNDS USEFUL AS MODULATORS OF TRPM8

(71) Applicant: Senomyx, Inc., San Diego, CA (US)

(72) Inventors: Chad Priest, Leucadia, CA (US); Alain Noncovich, San Diego, CA (US); Andrew Patron, San Marcos, CA (US); Jane Ung, San Diego, CA (US)

(73) Assignee: Seaomyx, Inc., San Diego, CA (US)

( * ) Notice: Subject to any disclaimer, the term of this patent is extended or adjusted under 35 U.S.C. 154(b) by 14 days.

This patent is subject to a terminal disclaimer.

(21) Appl. No.: 15/205,608

(22) Filed: Jul. 8, 2016

(65) Prior Publication Data

US 2016/0317532 A1  Nov. 3, 2016

Related U.S. Application Data

(63) Continuation of application No. 13/883,349, filed as application No. PCT/US2011/059312 on Nov. 4, 2011, now Pat. No. 9,394,287.

(Continued)

(51) Int. Cl.
| | |
|---|---|
| A61K 31/497 | (2006.01) |
| A61K 31/165 | (2006.01) |
| A61K 31/381 | (2006.01) |
| A61K 31/4155 | (2006.01) |
| A61K 31/415 | (2006.01) |
| A61K 31/422 | (2006.01) |
| A61K 31/426 | (2006.01) |

(Continued)

(52) U.S. Cl.
CPC ............ *A61K 31/497* (2013.01); *A01N 37/18* (2013.01); *A01N 43/10* (2013.01); *A01N 43/40* (2013.01); *A01N 43/56* (2013.01); *A01N 43/60* (2013.01); *A01N 43/76* (2013.01); *A01N 43/78* (2013.01); *A01N 43/80* (2013.01); *A01N 43/90* (2013.01); *A23L 27/88* (2016.08); *A23L 33/10* (2016.08); *A61K 8/42* (2013.01); *A61K 8/49* (2013.01); *A61K 8/494* (2013.01); *A61K 8/4926* (2013.01); *A61K 8/4973* (2013.01); *A61K 8/4986* (2013.01); *A61K 8/69* (2013.01); *A61K 31/165* (2013.01); *A61K 31/381* (2013.01); *A61K 31/415* (2013.01); *A61K 31/4155* (2013.01); *A61K 31/422* (2013.01); *A61K 31/426* (2013.01); *A61K 31/437* (2013.01); *A61K 31/4409* (2013.01); *A61K 31/4436* (2013.01); *A61Q 19/00* (2013.01); *C07C 233/11* (2013.01); *C07C 235/20* (2013.01); *C07C 235/24* (2013.01); *C07C 235/34* (2013.01); *C07D 213/40* (2013.01); *C07D 213/75* (2013.01); *C07D 231/40* (2013.01); *C07D 277/28* (2013.01); *C07D 307/52* (2013.01); *C07D 333/20* (2013.01); *C07D 333/24* (2013.01); *C07D 333/32* (2013.01); *C07D 405/12* (2013.01); *C07D 407/12* (2013.01); *C07D 409/12* (2013.01); *C07D 409/14* (2013.01); *C07D 413/12* (2013.01); *C07D 417/12* (2013.01); *C07D 471/04* (2013.01); *A23V 2002/00* (2013.01); *A61K 2800/10* (2013.01); *A61K 2800/40* (2013.01); *A61Q 1/02* (2013.01); *A61Q 5/02* (2013.01); *A61Q 5/12* (2013.01); *A61Q 9/02* (2013.01); *A61Q 11/00* (2013.01); *A61Q 15/00* (2013.01); *A61Q 17/02* (2013.01); *A61Q 17/04* (2013.01); *A61Q 19/001* (2013.01); *A61Q 19/10* (2013.01); *C07C 2601/14* (2017.05)

(58) Field of Classification Search
None
See application file for complete search history.

(56) References Cited

U.S. PATENT DOCUMENTS

| | | |
|---|---|---|
| 4,404,018 A | 9/1983 | Stach et al. |
| 4,753,674 A * | 6/1988 | Takematsu ............. A01N 39/02 504/244 |

(Continued)

FOREIGN PATENT DOCUMENTS

| | | | |
|---|---|---|---|
| CN | 1193901 | 9/1998 | |
| CS | 276621 | * 5/1992 | ........... C07C 235/00 |

(Continued)

OTHER PUBLICATIONS

Database Registry Chemical Abstracts Service, Columbus, Ohio, Accession No. RN 1234789-30-0 and RN1234794-81-0, Entered STN: Aug. 4, 2010.*

(Continued)

*Primary Examiner* — Samantha L Shterengarts
(74) *Attorney, Agent, or Firm* — Armstrong Teasdale LLP

(57) ABSTRACT

The present invention includes compounds useful as modulators of TRPM8, such as compounds of Formula (I) and the subgenus and species thereof; personal products containing those compounds; and the use of those compounds and the personal products, particularly the use of increasing or inducing chemesthetic sensations, such as cooling or cold sensations.

(I)

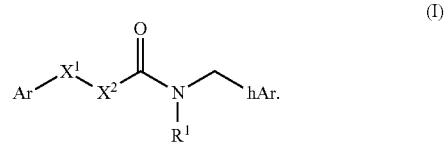

17 Claims, No Drawings

Related U.S. Application Data

(60) Provisional application No. 61/410,634, filed on Nov. 5, 2010, provisional application No. 61/443,490, filed on Feb. 16, 2011.

(51) Int. Cl.

| | | |
|---|---|---|
| A61K 31/437 | (2006.01) | |
| A61K 31/4409 | (2006.01) | |
| A61K 31/4436 | (2006.01) | |
| C07C 233/11 | (2006.01) | |
| C07C 235/20 | (2006.01) | |
| C07C 235/24 | (2006.01) | |
| C07C 235/34 | (2006.01) | |
| C07D 213/40 | (2006.01) | |
| C07D 213/75 | (2006.01) | |
| C07D 231/40 | (2006.01) | |
| C07D 277/28 | (2006.01) | |
| C07D 307/52 | (2006.01) | |
| C07D 333/20 | (2006.01) | |
| C07D 333/24 | (2006.01) | |
| C07D 333/32 | (2006.01) | |
| C07D 405/12 | (2006.01) | |
| C07D 407/12 | (2006.01) | |
| C07D 409/12 | (2006.01) | |
| C07D 409/14 | (2006.01) | |
| C07D 413/12 | (2006.01) | |
| C07D 417/12 | (2006.01) | |
| C07D 471/04 | (2006.01) | |
| A61K 8/42 | (2006.01) | |
| A61K 8/49 | (2006.01) | |
| A61K 8/69 | (2006.01) | |
| A61Q 19/00 | (2006.01) | |
| A01N 43/10 | (2006.01) | |
| A01N 43/40 | (2006.01) | |
| A01N 43/56 | (2006.01) | |
| A01N 43/60 | (2006.01) | |
| A01N 43/76 | (2006.01) | |
| A01N 43/80 | (2006.01) | |
| A01N 43/90 | (2006.01) | |
| A23L 27/00 | (2016.01) | |
| A23L 33/10 | (2016.01) | |
| A01N 37/18 | (2006.01) | |
| A01N 43/78 | (2006.01) | |
| A61Q 1/02 | (2006.01) | |
| A61Q 5/02 | (2006.01) | |
| A61Q 5/12 | (2006.01) | |
| A61Q 9/02 | (2006.01) | |
| A61Q 11/00 | (2006.01) | |
| A61Q 15/00 | (2006.01) | |
| A61Q 17/02 | (2006.01) | |
| A61Q 17/04 | (2006.01) | |
| A61Q 19/10 | (2006.01) | |

(56) References Cited

U.S. PATENT DOCUMENTS

| | | | |
|---|---|---|---|
| 5,294,643 A * | 3/1994 | Fuse | C07C 235/34 514/471 |
| 5,780,473 A | 7/1998 | Murugesan et al. | |
| 6,310,078 B1 | 10/2001 | Connolly et al. | |
| 7,482,469 B2 | 1/2009 | Palin et al. | |
| 9,394,287 B2 | 7/2016 | Priest et al. | |
| 2004/0092524 A1 | 5/2004 | Perez et al. | |
| 2005/0282822 A1 | 12/2005 | Alstermark et al. | |
| 2006/0045953 A1 | 3/2006 | Tachdjian et al. | |
| 2006/0122181 A1 | 6/2006 | Ikemoto et al. | |
| 2006/0142265 A1 | 6/2006 | Berman et al. | |
| 2009/0023798 A1 | 1/2009 | Magda et al. | |
| 2010/0022530 A1 | 1/2010 | Schiemann et al. | |
| 2010/0160337 A1 | 6/2010 | Matthews | |
| 2010/0196357 A1 * | 8/2010 | Huang | C07D 221/18 424/130.1 |
| 2010/0256108 A1 * | 10/2010 | Yamaguchi | C07D 231/56 514/210.18 |
| 2011/0145970 A1 | 6/2011 | Subkowski et al. | |
| 2012/0263659 A1 | 10/2012 | Subkowski et al. | |
| 2013/0324557 A1 | 12/2013 | Priest et al. | |
| 2014/0194433 A1 | 7/2014 | Subkowski et al. | |
| 2017/0096418 A1 | 4/2017 | Patron et al. | |

FOREIGN PATENT DOCUMENTS

| | | |
|---|---|---|
| DE | 19838138 | 3/1999 |
| DE | 20110355 | 8/2001 |
| DE | 20111037 | 8/2001 |
| EP | 0 105 590 | 4/1984 |
| EP | 0 189 774 | 8/1986 |
| EP | 0 381 033 | 8/1990 |
| EP | 0 407 200 | 1/1991 |
| EP | 0 471 612 | 2/1992 |
| EP | 0 530 537 | 3/1993 |
| EP | 0 650 974 | 5/1995 |
| EP | 0 751 132 | 1/1997 |
| EP | 2 192 116 | 6/2010 |
| JP | 6-25276 | 2/1994 |
| JP | 7-133226 | 5/1995 |
| JP | 2006-232706 | 9/2006 |
| WO | WO 93/02037 | 2/1993 |
| WO | WO 95/32001 | 11/1995 |
| WO | WO 96/05168 | 2/1996 |
| WO | WO 97/29073 | 8/1997 |
| WO | WO 97/29075 | 8/1997 |
| WO | WO 98/04260 | 2/1998 |
| WO | WO 98/47876 | 10/1998 |
| WO | WO 99/32477 | 7/1999 |
| WO | WO 99/54279 | 10/1999 |
| WO | WO 00/69810 | 11/2000 |
| WO | WO 01/25181 | 4/2001 |
| WO | WO 01/27103 | 4/2001 |
| WO | WO 01/56560 | 8/2001 |
| WO | WO 02/26703 | 4/2002 |
| WO | WO 02/066469 | 8/2002 |
| WO | WO 02/079144 | 10/2002 |
| WO | WO 02/080899 | 10/2002 |
| WO | WO 03/068224 | 8/2003 |
| WO | WO 2004/022551 | 3/2004 |
| WO | WO 2004/026823 | 4/2004 |
| WO | WO 2004/063147 | 7/2004 |
| WO | WO 2004/082586 | 9/2004 |
| WO | WO 2004/085420 | 10/2004 |
| WO | WO 2004/110983 | 12/2004 |
| WO | WO 2004/113270 | 12/2004 |
| WO | WO 2005/011685 | 2/2005 |
| WO | WO 2005/046679 | 5/2005 |
| WO | WO 2006/066879 | 6/2006 |
| WO | WO 2006/067587 | 6/2006 |
| WO | WO 2006/100502 | 9/2006 |
| WO | WO 2007/017093 | 2/2007 |
| WO | WO 2007/046075 | 4/2007 |
| WO | WO 2007/053131 | 5/2007 |
| WO | WO 2007/076055 | 7/2007 |
| WO | WO 2007/104560 | 9/2007 |
| WO | WO 2008/009122 | 1/2008 |
| WO | WO 2008/046582 | 4/2008 |
| WO | WO 2008/054598 | 5/2008 |
| WO | WO 2009/011336 | 1/2009 |
| WO | WO 2010/001365 | 1/2010 |
| WO | WO 2010/026094 | 3/2010 |
| WO | WO 2011/061330 | 5/2011 |
| WO | WO 2011/072275 | 6/2011 |
| WO | WO 2012/101244 | 8/2012 |

(56) References Cited

FOREIGN PATENT DOCUMENTS

| WO | WO 2014/130582 | 8/2014 |
|---|---|---|
| WO | WO 2015/136947 | 9/2015 |

OTHER PUBLICATIONS

Ito, Nobuyuki. Cancer Science 94(1), (2003) 3-8.*

Karanewsky et al., Sep. 11, 2015, Toxicological evaluation of a novel cooling compound: 2-(4-methylphenoxy)-N-)1H-pyrazol-3-1)-N-(2-thienylmethyl) acetamide, *Toxicology Reports*, 2:1291-1309.

Database Registry Accession No. RN 901655-36-5; Entered STN: Aug. 16, 2006.

Database Registry Accession No. RN 901665-59-6; Entered STN: Aug. 16, 2006.

Database Registry Accession No. RN 905755-83-1; Entered STN: Sep. 3, 2006.

Database Registry Accession No. RN 905756-90-3; Entered STN: Sep. 3, 2006.

Database Registry Accession No. RN 922391-60-4; Entered STN: Feb. 22, 2007.

Database Registry Accession No. RN 922393-80-4; Entered STN: Feb. 22, 2007.

Database Registry Accession No. RN 923497-17-0; Entered STN: Feb. 27, 2007.

Database Registry Accession No. RN 955668-53-8; Entered STN: Nov. 23, 2007.

Database Registry Accession No. RN 1007009-55-3; Entered STN: Mar. 7, 2008.

Database Registry Accession No. RN 1007049-46-8; Entered STN: Mar. 7, 2008.

Database Registry Accession No. RN 1007051-53-7; Entered STN: Mar. 7, 2008.

Database Registry Accession No. RN 1007051-92-4; Entered STN: Mar. 7, 2008.

Database Registry Accession No. RN 1007052-38-1; Entered STN: Mar. 7, 2008.

Database Registry Accession No. RN 1007086-30-7; Entered STN: Mar. 7, 2008.

Database Registry Accession No. RN 1007086-59-0; Entered STN: Mar. 7, 2008.

Database Registry Accession No. RN 1007226-03-0; Entered STN: Mar. 10, 2008.

Database Registry Accession No. RN 1007226-08-5; Entered STN: Mar. 10, 2008.

Database Registry Accession No. RN 1007226-10-9; Entered STN: Mar. 10, 2008.

Database Registry Accession No. RN 1235292-79-1; Entered STN: Aug. 5, 2010.

Wei et al., 2009, "New small molecule inhibitors of hepatits C virus," Bioorganic & Medicinal Chemistry Letters, 19:6926-6930.

Dababase Registry Chemical Abstracts Service, Columbus, Ohio, Accession No. RN 1235642-55-3, RN 1235642-12-2, RN 1235640-51-3, RN 1235637-76-9, RN 1235637-37-2, Entered STN: Aug. 10, 2010; RN 1235393-49-3, RN 1235383-21-7 and RN 1235382-77-0, Entered STN: Aug. 5, 2010.

Database Registry Chemical Abstracts Service, Columbus Ohio, Accession No. RN 1234859-11-0, RN 1234938-70-5, RN 1234974-55-0, RN 1235004-46-2, RN 1235017-13-6, RN 1235037-66-7, RN 1235038-33-1, RN 1235356-38-3, and RN 1235393-28-8, entered STN: Aug. 4/5, 2010.

Milkiewicz, et al., 2003, "Synthesis of a Novel Series of 10-Oxa-3-aza-tricyclo[5.2.1.01,5] dec-8-en-4-ones Through an Intramolecular Diels-Alder Reaction," Tetrahedron Lett. 44(39):7341-7343.

Le Diguarher, et al., 2003, "Parallel Liquid Synthesis of N,N'-Disubsituted 3-Amino Azepin-2-ones as Potent and Specific Farnesyl Transferase Inhibitors," Bioorganic & Medicinal Chemistry, 11(14):3193-3204.

DeFalco, et al. 2010, "5-Benzyloxytryptamine as an antagonist of TRPM8," Bioorganic & Medical Chemistry Letters, 20(23):7076-7079.

Database Registry Chemical Abstracts Service, Columbs, Ohio, Accession No. RN 898480-00-7, RN 898482-20-7, RN 898493-76-0, entered STN: Aug. 3, 2006.

Database Registry Chemical Abstracts Service, Accession No. RN:337325-30-1, Entered STN: May 22, 2001.

Database Registry Chemical Abstracts Service, Accession No. RN:620572-55-6, Entered STN: Nov. 25, 2003.

Database Registry Chemical Abstracts Service, Accession No. RN:852214-40-5, Entered STN: Jun. 14, 2005.

Database Registry Chemical Abstracts Service, Accession No. RN:877951-49-0, Entered STN: Mar. 24, 2006.

Database Registry Chemical Abstracts Service, Accession No. RN:860082-46-8, Entered STN: Aug. 12, 2005.

Database Registry Chemical Abstracts Service, Accession No. RN:898493-76-0, Entered STN: Aug. 3, 2006.

Database Registry Chemical Abstracts Service, Accession No. RN:898511-90-5, Entered STN: Aug. 3, 2006.

Database Registry Chemical Abstracts Service, Accession No. RN:898493-72-6, Entered STN: Aug. 3, 2006.

Database Registry Chemical Abstracts Service, Accession No. RN:898500-56-6, Entered STN: Aug. 3, 2006.

Database Registry Chemical Abstracts Service, Accession No. RN:901656-97-1, Entered STN: Aug. 16, 2006.

Database Registry Chemical Abstracts Service, Accession No. RN:901665-56-3, Entered STN: Aug. 16, 2006.

Database Registry Chemical Abstracts Service, Accession No. RN:901663-34-1, Entered STN: Aug. 16, 2006.

Database Registry Chemical Abstracts Service, Accession No. RN:901665-55-2, Entered STN: Aug. 16, 2006.

Database Registry Chemical Abstracts Service, Accession No. RN:901655-30-9, Entered STN: Aug. 16, 2006.

Database Registry Chemical Abstracts Service, Accession No. RN:901669-23-6, Entered STN: Aug. 16, 2006.

Database Registry Chemical Abstracts Service, Accession No. RN:901665-74-5, Entered STN: Aug. 16, 2006.

Database Registry Chemical Abstracts Service, Accession No. RN:905793-41-1, Entered STN: Sep. 3, 2006.

Database Registry Chemical Abstracts Service, Accession No. RN:919043-80-4, Entered STN: Feb. 2, 2007.

Database Registry Chemical Abstracts Service, Accession No. RN:923847-39-6, Entered STN: Feb. 28, 2007.

Database Registry Chemical Abstracts Service, Accession No. RN:930440-82-7, Entered STN: Apr. 17, 2007.

Database Registry Chemical Abstracts Service, Accession No. RN:942842-92-4, Entered STN: Jul. 19, 2007.

Database Registry Chemical Abstracts Service, Accession No. RN:942770-87-8, Entered STN: Jul. 19, 2007.

Database Registry Chemical Abstracts Service, Accession No. RN:942788-10-5, Entered STN: Jul. 19, 2007.

Database Registry Chemical Abstracts Service, Accession No. RN:1089571-33-4, Entered STN: Dec. 24, 2008.

Database Registry Chemical Abstracts Service, Accession No. RN:1110862-41-3, Entered STN: Feb. 24, 2009.

Database Registry Chemical Abstracts Service, Accession No. RN:1197570-84-5, Entered STN: Dec. 16, 2009.

Database Registry Chemical Abstracts Service, Accession No. RN:1199511-36-8, Entered STN: Dec. 30, 2009.

Database Registry Chemical Abstracts Service, Accession No. RN:1199510-42-3, Entered STN: Dec. 30, 2009.

Database Registry Chemical Abstracts Service, Accession No. RN:1199512-94-1, Entered STN: Dec. 30, 2009.

Database Registry Chemical Abstracts Service, Accession No. RN:1244936-54-6, Entered STN: Oct. 3, 2010.

International Search Report, PCT appl. No. PCT/US2011/059312, 5 pages (dated Jun. 28, 2012).

Written Opinion of the International Searching Authority, PCT appl. No. PCT/US2011/059312, 7 pages, dated Jun. 28, 2012.

Supplementary EP Search Report for application EP 11838869.3 dated Feb. 20, 2014.

(56) References Cited

OTHER PUBLICATIONS

Database Registry Accession Nos. RN 1235655-65-8, RN 1235643-36-3, RN 1235642-55-3, RN 1235642-12-2, RN 1235640-51-3, RN 1235638-73-9, RN 1235637-76-9, RN 1235637-37-2, RN 1235631-76-1, RN 1235628-81-5, RN 1235617-11-4, Entered STN: Aug. 10, 2010; RN 1235393-49-3, RN 1235393-28-8, RN 1235383-21-7, RN 1235382-77-0, RN 1235372-21-0, RN 1235368-05-4, RN 1235356-38-3, RN 1235345-47-7, RN 1235333-26-2, RN 1235320-73-6, RN 1235317-04-0, RN 1235312-02-3, RN 1235305-87-9, RN 1235305-47-1, RN 1235292-79-1, RN 1235268-08-2, RN 1235243-29-4, RN 1235197-88-2, RN 1235196-31-2, RN 1235187-27-5, RN 1235180-91-2, RN 1235172-08-3, RN 1235171-23-9, RN 1235156-37-2, RN 1235138-00-7, RN 1235135-92-8, RN 1235119-78-4, RN 1235094-71-9, RN 1235092-22-4, RN 1235086-54-0, RN 1235082-79-7, RN 1235081-09-0, RN 1235074-27-7, RN 1235072-28-2, RN 1235069-45-0, RN 1235067-53-4, RN 1235065-33-4, RN 1235055-73-8, RN 1235051-16-7, RN 1235049-25-8, RN 1235041-25-4, RN 1235038-56-8, RN 1235038-33-1, RN 1235028-93-9, RN 1235026-61-5, RN 1235018-37-7, RN 1235015-26-5, Entered STN: Aug. 5, 2010; RN 1234993-87-3, RN 1234987-78-0, RN 1234977-46-8, RN 1234977-31-1, RN 1234975-63-3, RN 1234974-55-0, RN 1234954-95-0, RN 1234951-18-8, RN 1234944-23-0, RN 1234938-94-3, RN 1234938-70-5, RN 1234937-56-4, RN 1234926-82-9, RN 1234917-60-2, RN 1234915-96-8, RN 1234914-76-1, RN 1234911-71-7, RN 1234902-69-2, RN 1234893-19-6, RN 1234887-56-9, RN 1234885-60-9, RN 1234878-41-1, RN 1234878-09-1, RN 1234868-08-6, RN 1234863-61-6, RN 1234859-11-0, RN 1234856-91-7, RN 1234855-49-2, RN 1234849-04-7, RN 1234808-05-9, RN 1234807-84-1, RN 1234794-94-5, RN 1234794-81-0, RN 1234789-30-0, Entered STN: Aug. 4, 2010; RN 905762-83-6, RN—905756-90-3, RN 905755-83-1, Entered STN: Sep. 3, 2006; RN 901665-59-6, Entered STN: Aug. 16, 2006; RN 898652-69-2, Entered STN: Aug. 4, 2006; RN 898506-42-8, RN 898500-84-0, RN 898500-63-5, RN 898497-90-0, RN 898492-26-7, RN 898491-95-7, RN 898482-20-7, RN 898482-06-9, RN 898480-00-7, Entered STN: Aug. 3. 2006.

\* cited by examiner

COMPOUNDS USEFUL AS MODULATORS OF TRPM8

INCORPORATION BY REFERENCE TO ANY PRIORITY APPLICATIONS

Any and all priority claims identified in the Application Data Sheet, or any correction thereto, are hereby incorporated by reference under 37 CFR 1.57. For example, this application is a continuation of U.S. patent application Ser. No. 13/883,349 filed May 3, 2013, assigned U.S. Pat. No. 9,394,287, which is a U.S. National Phase of International Application No. PCT/US2011/059312, filed on Nov. 4, 2011 designating the U.S. and published on May 10, 2012 as WO 2012/061698, which claims the benefit of priority to U.S. Provisional Application No. 61/410,634, filed on Nov. 5, 2010 and entitled "Compounds Useful as Agonists of hTRPM8", and U.S. Provisional Application No. 61/443,490, filed on Feb. 16, 2011 and entitled "Compounds Useful as Agonists of hTRPM8", the contents of each of which are herein incorporated by reference in their entireties for all purposes.

FIELD OF THE INVENTION

The present invention relates to compounds useful as modulators of TRPM8.

BACKGROUND OF THE INVENTION

The present invention provides compounds useful as modulators of the Melastatin Transient Receptor Potential Channel 8 (TRPM8). TRPM8 is a channel involved in the chemesthetic sensation, such as cool to cold temperatures as well as the sensation of known cooling agents, such as Menthol and Icilin. However, many of the currently known TRPM8 modulators have deficiencies with regard to strength and/or duration of effect, skin and/or mucosa irritation, odor, taste, solubility, and/or toxicity.

SUMMARY OF THE INVENTION

In one embodiment, the present invention provides a compound having structural Formula (I):

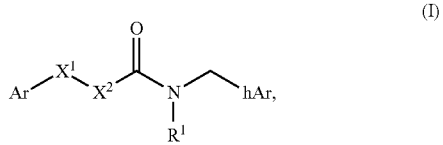

(I)

or a salt or solvate thereof;
wherein
Ar is optionally substituted aryl, optionally substituted carbocyclyl, or optionally substituted heteroaryl;
$X^1$-$X^2$ is O—$CR^{2a}R^{2b}$, $CHR^3$—$CHR^4$, $CR^5$=$CR^6$, or cycloalkyl; or alternatively Ar—$X^1$-$X^2$— is a bicyclic heteroaryl;
$R^{2a}$, $R^{2b}$, $R^3$, $R^4$, $R^5$, and $R^6$ are independently hydrogen or lower alkyl;
hAr is an optionally substituted five- or six-membered heteroaryl containing one or more heteroatoms selected from nitrogen, oxygen, and sulfur; and
$R^1$ is optionally substituted alkyl, optionally substituted heteroalkyl, optionally substituted alkenyl, optionally substituted aryl, optionally substituted heteroaryl, optionally substituted carbocyclyl, or optionally substituted heterocyclyl.

In another embodiment, the present invention provides a personal product comprising a compound of the present invention, or a salt or solvate thereof.

In another embodiment, the present invention provides a method of modulating transient receptor potential channel melastatin member 8 (TRPM8) comprising contacting the receptor with a compound of the present invention, or a salt or solvate thereof.

In another embodiment, the present invention provides a method of modulating the cooling sensation of a composition comprising combining the composition with a compound of the present invention, or a salt or solvate thereof, to form a modified composition.

In another embodiment, the present invention provides a method of inducing a cooling sensation in a human or animal comprising contacting the human or animal with a compound of the present invention, or a salt or solvate thereof.

DETAILED DESCRIPTIONS OF THE INVENTION

Various embodiments and advantages of the present invention will be set forth in part in the description that follows, and in part will be obvious from the description, or may be learned by practice of the invention. It is to be understood that both the foregoing general description and the following detailed description are exemplary and explanatory only and are not restrictive of the invention as described.

Definitions

The terms "a" and "an" do not denote a limitation of quantity, but rather denote the presence of at least one of the referenced item. The term "or" or "and/or" is used as a function word to indicate that two words or expressions are to be taken together or individually. The terms "comprising", "having", "including", and "containing" are to be construed as open-ended terms (i.e., meaning "including, but not limited to"). The endpoints of all ranges directed to the same component or property are inclusive and independently combinable.

The term "present compound(s)" or "compound(s) of the present invention" refers to compounds encompassed by structural formulae disclosed herein and includes any subgenus and specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds of the invention include, but are not limited to, $^2$H, $^3$H, $^{13}$C, $^{14}$C, $^{15}$N, $^{18}$O, $^{17}$O, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule. The term "tautomer" as used herein refers to isomers that change into one another with great ease so that they can exist together in equilibrium.

"Alkyl," by itself or as part of another substituent, refers to a saturated branched, straight-chain or cyclic monovalent hydrocarbon radical derived by the removal of one hydrogen atom from a single carbon atom of a parent alkane. The term "alkyl" includes "cycloakyl" as defined herein below. Typical alkyl groups include, but are not limited to, methyl; ethyl; propyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl). $C_1$-$C_6$ alkyl is also known as "lower alkyl".

It is noted that when an alkyl group is further connected to another atom, it becomes an "alkylene" group. In other words, the term "alkylene" refers to a divalent alkyl. For example, —CH$_2$CH$_3$ is an ethyl, while —CH$_2$CH$_2$— is an ethylene. That is, "Alkylene," by itself or as part of another substituent, refers to a saturated or unsaturated, branched, straight-chain or cyclic divalent hydrocarbon radical derived by the removal of two hydrogen atoms from a single carbon atom or two different carbon atoms of a parent alkane, alkene or alkyne. The term "alkylene" includes "cycloalkylene" as defined herein below. The term "alkylene" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. In some embodiments, an alkylene group comprises from 1 to 20 carbon atoms ($C_1$-$C_{20}$ alkylene). In other embodiments, an alkylene group comprises from 1 to 10 carbon atoms ($C_1$-$C_{10}$ alkylene). In still other embodiments, an alkylene group comprises from 1 to 6 carbon atoms ($C_1$-$C_6$ alkylene).

"Alkenyl," by itself or as part of another substituent, refers to an unsaturated branched, straight-chain or cyclic monovalent hydrocarbon radical having at least one carbon-carbon double bond derived by the removal of one hydrogen atom from a single carbon atom of a parent alkene. The term "alkenyl" includes "cycloalkenyl" as defined herein below. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkoxy," by itself or as part of another substituent, refers to a radical of the formula —O—R$^{199}$, where R$^{199}$ is alkyl or substituted alkyl as defined herein.

"Acyl" by itself or as part of another substituent refers to a radical —C(O)R$^{200}$, where R$^{200}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 15 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or sp$^3$ carbon atom, is replaced with an aryl group as, as defined herein. That is, arylakyl can also be considered as an alkyl substituted by aryl. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Carbocyclic," or "Carbocyclyl," by itself or as part of another substituent, refers to a saturated or partially saturated, buy noy aromatic, cyclic monovalent hydrocarbon radical, including cycloalkyl, cycloalkenyl, and cycloalkynyl as defined herein. Typical carbocyclyl groups include, but are not limited to, groups derived from cyclopropane, cyclobutane, cyclopentane, cyclohexane, and the like. In some embodiments, the cycloalkyl group comprises from 3 to 10 ring atoms ($C_3$-$C_{10}$ cycloalkyl). In other embodiments, the cycloalkyl group comprises from 3 to 7 ring atoms ($C_3$-$C_7$ cycloalkyl). The carbocyclyl may be further substituted by one or more heteroatoms including, but not limited to, N, P, O, S, and Si, which attach to the carbon atoms of the cycloalkyl via monovalent or multivalent bond.

"Heteroalkyl," by themselves or as part of other substituents, refer to alkyl groups, in which one or more of the carbon atoms, are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl group. Typical heteroatomic groups which can be included in these groups include, but are not limited to, —O—, —S—, —O—O—, —S—S—, —O—S—, —NR$^{201}$R$^{202}$—, =N—N=, —N=N—, —N=N— NR$^{203}$R$^{204}$, —PR$^{205}$—, —P(O)$_2$—, —POR$^{206}$—, —O—P (O)$_2$—, —SO—, —SO$_2$—, —SnR$^{207}$R$^{208}$— and the like, where R$^{201}$, R$^{202}$, R$^{203}$, R$^{204}$, R$^{205}$, R$^{206}$, R$^{207}$ and R$^{208}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heterocyclic," or "Heterocyclyl," by itself or as part of another substituent, refers to a carbocyclic radical in which one or more carbon atoms are independently replaced with the same or different heteroatom. The heterocyclyl may be further substituted by one or more heteroatoms including, but not limited to, N, P, O, S, and Si, which attach to the carbon atoms of the heterocyclyl via monovalent or multivalent bond. Typical heteroatoms to replace the carbon atom(s) include, but are not limited to, N, P, O, S, Si, etc. Typical heterocyclyl groups include, but are not limited to, groups derived from epoxides, azirines, thiiranes, imidazolidine, morpholine, piperazine, piperidine, pyrazolidine, pyrrolidone, quinuclidine, and the like. In some embodiments, the heterocyclyl group comprises from 3 to 10 ring atoms (3-10 membered heterocyclyl) In other embodiments, the heterocyclyl group comprise from 5 to 7 ring atoms (5-7 membered heterocyclyl). A cycloheteroalkyl group may be substituted at a heteroatom, for example, a nitrogen atom, with a ($C_1$-$C_6$) alkyl group. As specific examples, N-methylimidazolidinyl, N-methyl-morpholinyl, N-methyl-piperazinyl, N-methyl-piperidinyl, N-methyl-pyrazolidinyl and N-methyl-pyrrolidinyl are included within the definition of "heterocyclyl." A heterocyclyl group may be attached to the remainder of the molecule via a ring carbon atom or a ring heteroatom.

"Halo," by itself or as part of another substituent refers to a radical —F, —Cl, —Br or —I.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is ($C_1$-$C_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is ($C_1$-$C_3$) alkyl and the heteroaryl moiety is a 5-10 membered heteroaryl.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Solvate" means a compound formed by solvation (the combination of solvent molecules with molecules or ions of the solute), or an aggregate that consists of a solute ion or molecule, i.e., a compound of the present invention, with one or more solvent molecules. When water is the solvent, the corresponding solvate is "hydrate".

"N-oxide", also known as amine oxide or amine-N-oxide, means a compound that derives from a compound of the present invention via oxidation of an amine group of the compound of the present invention. An N-oxide typically contains the functional group $R_3N^+$—$O^-$ (sometimes written as $R_3N$=O or $R_3N{\rightarrow}O$).

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —OS$(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —OC(S)O $R^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl. As another specific example, a substituted alkyl is meant to include -alkylene-O-alkyl, -alkylene-heteroaryl, -alkylene-cycloheteroalkyl, -alkylene-C(O)$OR^b$, -alkylene-C(O)$NR^bR^b$, and —$CH_2$—$CH_2$—C(O)—$CH_3$. The one or more substituent groups, taken together with the atoms to which they are bonded, may form a cyclic ring including cycloalkyl and cycloheteroalkyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —OS$(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —OS$(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art.

The term "substituted" specifically envisions and allows for one or more substitutions that are common in the art. However, it is generally understood by those skilled in the art that the substituents should be selected so as to not adversely affect the useful characteristics of the compound or adversely interfere with its function. Suitable substituents may include, for example, halogen groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, arylalkyl or heteroarylalkyl groups, arylalkoxy or heteroarylalkoxy groups, amino groups, alkyl- and dialkylamino groups, carbamoyl groups, alkylcarbonyl groups, carboxyl groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups, cycloalkyl groups, cyano groups, $C_1$-$C_6$ alkylthio groups, arylthio groups, nitro groups, keto groups, acyl groups, boronate or boronyl groups, phosphate or phosphonyl groups, sulfamyl groups, sulfonyl groups, sulfinyl groups, and combinations thereof. In the case of substituted combinations, such as "substituted arylalkyl," either the aryl or the alkyl group may be substituted, or both the aryl and the alkyl groups may be substituted with one or more substituents. Additionally, in some cases, suitable substituents may combine to form one or more rings as known to those of skill in the art.

The term "optionally substituted" denotes the presence or absence of the substituent group. For example, optionally substituted alkyl includes both unsubstituted alkyl and substituted alkyl. The substituents used to substitute a specified group can be further substituted, typically with one or more of the same or different groups selected from the various groups specified above.

"Carrier" refers to a diluent, adjuvant, excipient or vehicle with which a compound is administered.

A "personal product", as used herein, refers to any product that is used by or useful for a person or animal, optionally in contact with the person or animal during its intended use, e.g., in surface contact such as skin or mucosa contact with the person or animal during its intended use.

As used herein, an "ingestible composition" includes any substance that, either alone or together with another substance, can be taken by mouth whether intended for consumption or not. The ingestible composition includes both "food or beverage products" and "non-edible products". By "Food or beverage products", it is meant any edible product intended for consumption by humans or animals, including solids, semi-solids, or liquids (e.g., beverages). The term "non-edible products" or "noncomestible composition" includes any product or composition that can be taken by humans or animals for purposes other than consumption or as food or beverage. For example, the non-edible product or noncomestible composition includes supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products such as sweetened lip balms and other personal care products that may or may not contain any sweetener.

A "ingestibly acceptable carrier or excipient" is a medium and/or composition that is used to prepare a desired dispersed dosage form of the inventive compound, in order to administer the inventive compound in a dispersed/diluted form, so that the biological effectiveness of the inventive compound is maximized. The medium and/or composition may be in any form depending on the intended use of a product, e.g., solid, semi-solid, liquid, paste, gel, lotion, cream, foamy material, suspension, solution, or any combinations thereof (such as a liquid containing solid contents). Ingestibly acceptable carriers includes many common food ingredients, such as water at neutral, acidic, or basic pH, fruit or vegetable juices, vinegar, marinades, beer, wine, natural water/fat emulsions such as milk or condensed milk, edible oils and shortenings, fatty acids and their alkyl esters, low molecular weight oligomers of propylene glycol, glyceryl esters of fatty acids, and dispersions or emulsions of such hydrophobic substances in aqueous media, salts such as sodium chloride, wheat flours, solvents such as ethanol, solid edible diluents such as vegetable powders or flours, or other liquid vehicles; dispersion or suspension aids; surface active agents; isotonic agents; thickening or emulsifying agents, preservatives; solid binders; lubricants and the like.

A "flavor" herein refers to the perception of taste in a subject, which include sweet, sour, salty, bitter and umami (also known as savory). The subject may be a human or an animal.

A "flavoring agent" herein refers to a compound or the ingestibly acceptable salt or solvate thereof that induces a flavor or taste in an animal or a human. The flavoring agent can be natural, semi-synthetic, or synthetic.

A "modulator" herein refers to a compound that can regulate the activity of TRPM8. Such regulation includes activating TRPM8, blocking TRPM8, or potentiating/reducing the activation of TRPM8. That is, the modulators include agonists, antagonists, enhancers, and etc.

The term "chemesthesis" or "chemesthetic sensation" herein refers to the sensibility of bodily surface, e.g., the skin and/or mucosal surfaces which arise either when the bodily surface is exposed to heat or coldness or when chemical compounds activate receptors associated with senses that mediate pain, touch, and thermal/cold perception. Particularly, these chemical-induced reactions do not fit into the traditional sense categories of taste and smell. Examples of chemesthetic sensations include the burn-like irritation from chili pepper, the coolness of menthol in mouthwashes and topical analgesic creams, the stinging or tingling of carbonation in the nose and mouth, and the tear-induction of onions. That is, chemesthetic sensations can arise by direct chemical activation of ion channels on sensory nerve fibers, e.g. TRPM8. Because chemoresponsive nerve fibers are present in all types of skin, chemesthetic sensations can be aroused from anywhere on the body's surface as well as from mucosal surfaces in the nose, mouth, eyes, etc.

A "chemesthetic sensation modifier" or "chemesthetic sensation modifying agent" herein refers to a compound, or a salt or solvate thereof, that modulates, including enhancing or potentiating, inducing, or blocking, the chemesthetic sensation in an animal or a human.

A "chemesthetic sensation modulating amount" herein refers to an amount of a compound of the present invention that is sufficient to alter (either induce, increase, or decrease) the chemesthetic sensation in a personal product, sufficiently to be perceived by an animal or human subject. In many embodiments of the invention, at least about 0.001 ppm of the present compound would need to be present in order for most animal or human subjects to perceive a modulation of the chemesthetic sensation in a personal product comprising the present compound. A broad range of concentration that would typically be employed in order to economically provide a desirable degree of chemesthetic sensation modulation can be from about 0.001 ppm to 1000 ppm, or from about 0.01 ppm to about 500 ppm, or from about 0.05 ppm to about 300 ppm, or from about 0.1 ppm to about 200 ppm, or from about 0.5 ppm to about 150 ppm, or from about 1 ppm to about 100 ppm.

A "chemesthetic sensation inducing amount" or "chemesthetic sensation increasing amount" herein refers to an amount of a compound that is sufficient to induce or increase a chemesthetic sensation as perceived by an animal or a human. A broad range of a chemesthetic sensation inducing/increasing amount can be from about 0.001 ppm to 100 ppm, or a narrow range from about 0.1 ppm to about 10 ppm. Alternative ranges of chemesthetic sensation inducing/increasing amounts can be from about 0.01 ppm to about 30 ppm, from about 0.05 ppm to about 15 ppm, from about 0.1 ppm to about 5 ppm, or from about 0.1 ppm to about 3 ppm.

Embodiments of the Compounds

In one embodiment, the present invention provides a compound having structural Formula (I):

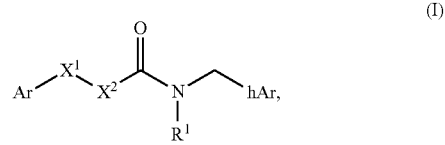

or a salt or solvate thereof;
wherein
Ar is optionally substituted aryl, optionally substituted carbocyclyl, or optionally substituted heteroaryl;
$X^1$-$X^2$ is O—$CR^{2a}R^{2b}$, $CHR^3$—$CHR^4$, $CR^5$=$CR^6$, or cycloalkyl; or alternatively Ar—$X^1$-$X^2$— is a bicyclic heteroaryl;
$R^{2a}$, $R^{2b}$, $R^3$, $R^4$, $R^5$, and $R^6$ are independently hydrogen or lower alkyl;
hAr is an optionally substituted five-membered heteroaryl containing one or more heteroatoms selected from nitrogen, oxygen, and sulfur; and
$R^1$ is optionally substituted alkyl, optionally substituted heteroalkyl, optionally substituted alkenyl, optionally substituted aryl, optionally substituted heteroaryl, optionally substituted carbocyclyl, or optionally substituted heterocyclyl.

In one embodiment of Formula (I), Ar is optionally substituted aryl, and the optionally substituted aryl is optionally substituted phenyl.

In one embodiment of Formula (I), Ar is optionally substituted heteroaryl, wherein the heteroaryl is a five- or six-membered heteroaryl containing one or more heteroatoms selected from nitrogen, oxygen, and sulfur. In certain embodiments, the optionally substituted heteroaryl is an optionally substituted group selected from the group consisting of pyrrolyl, furanyl, thienyl, pyrazolyl, triazolyl, oxazolyl, thiazolyl, isoxazolyl, isothiazolyl, pyridyl, pyrimidyl, and triazinyl.

In one embodiment of Formula (I), the optional substituent as mentioned above is one or more of group selected from the group consisting of alkyl, heteroalkyl, alkenyl, alkoxy, hydroxyl, amino, N-alkyl amino, N-dialkyl amino, halo, nitro, cyano, acyl, carboxyl, carboxyl ester, or amide; or two substituents, together with the atoms to which they are attached, form an optionally substituted carbocyclyl or heterocyclyl containing one or more heteroatom(s) selected from nitrogen, oxygen, and sulfur.

In one embodiment of Formula (I), $R^{2b}$, $R^3$, $R^4$, $R^5$, and $R^6$ are all hydrogen.

In one embodiment of Formula (I), hAr is selected from the group consisting of pyrrolyl, furanyl, thienyl, pyrazolyl, triazolyl, oxazolyl, thiazolyl, isoxazolyl, and isothiazolyl, each of which is optionally substituted.

In one embodiment of Formula (I), $R^1$ is optionally substituted alkyl, wherein the alkyl is straight, branched, cyclic, or a combination thereof.

In one embodiment of Formula (I), $R^1$ is optionally substituted aryl or optionally substituted heteroaryl. Examples of the aryl and heteroaryl include, but are not limited to, phenyl, pyrrolyl, furanyl, thienyl, pyrazolyl, triazolyl, oxazolyl, thiazolyl, pyridyl, pyrimidyl, and triazinyl, each of which is optionally substituted.

In one embodiment of Formula (I), $X^1$-$X^2$ is O—$CH_2$, O—$CH(CH_3)$, or O—$CH(CH_2CH_3)$.

In one embodiment of Formula (I), $X^1$-$X^2$ is $CH_2$—$CH_2$ or CH=CH.

In one embodiment of Formula (I), $X^1$-$X^2$ is cyclopropyl, cyclobutyl, or cyclopentyl.

In one embodiment of Formula (I), the compound can be represented by a structural Formula (II):

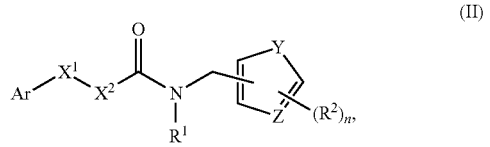

wherein

Ar is optionally substituted aryl, optionally substituted carbocyclyl, or optionally substituted heteroaryl;

Y is oxygen or sulfur;

Z is nitrogen or CR;

R is hydrogen or lower alkyl;

$X^1$-$X^2$ is O—$CR^{2a}R^{2b}$, $CHR^3$—$CHR^4$, $CR^5$=$CR^6$, or cycloalkyl;

$R^{2a}$, $R^{2b}$, $R^3$, $R^4$, $R^5$, and $R^6$ are independently hydrogen or lower alkyl;

$R^1$ is optionally substituted alkyl, optionally substituted heteroalkyl, optionally substituted alkenyl, optionally substituted aryl, optionally substituted heteroaryl, optionally substituted carbocyclyl, or optionally substituted heterocyclyl;

n is 0, 1, 2, or 3; and each $R^2$ is independently optionally substituted alkyl, optionally substituted heteroalkyl, optionally substituted alkenyl, alkoxy, hydroxyl, amino, N-alkyl amino, N-dialkyl amino, halo, nitro, cyano, acyl, carboxyl, carboxyl ester, or amide.

In one embodiment of Formula (II), the compound can be represented by a structural Formula (III):

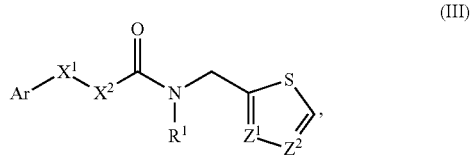

wherein

Ar is optionally substituted aryl, optionally substituted carbocyclyl, or optionally substituted heteroaryl;

$X^1$-$X^2$ is O—$CR^{2a}R^{2b}$, $CHR^3$—$CHR^4$, $CR^5$=$CR^6$, or cycloalkyl;

$R^{2a}$, $R^{2b}$, $R^3$, $R^4$, $R^5$, and $R^6$ are independently hydrogen or lower alkyl;

$Z^1$ and $Z^2$ are independently nitrogen or CH, provided that $Z^1$ and $Z^2$ are not both nitrogen; and $R^1$ is optionally substituted alkyl, optionally substituted heteroalkyl, optionally substituted alkenyl, optionally substituted aryl, optionally substituted heteroaryl, optionally substituted carbocyclyl, or optionally substituted heterocyclyl.

In one embodiment of Formula (III), Ar is optionally substituted aryl; and $X^1$-$X^2$ is O—$CR^{2a}R^{2b}$, $CH_2$—$CH_2$, or CH=CH; $R^{2a}$ and $R^{2b}$ are independently hydrogen or lower alkyl; $R^1$ is optionally substituted alkyl, optionally substituted heteroalkyl, optionally substituted alkenyl, optionally substituted aryl, optionally substituted heteroaryl, optionally substituted carbocyclyl, or optionally substituted heterocyclyl.

In one embodiment of Formula (III), Ar is optionally substituted phenyl.

In one embodiment of Formula (III), Ar is optionally substituted heteroaryl; and $X^1$-$X^2$ is O—$CR^{2a}R^{2b}$, $CH_2$—$CH_2$, or CH=CH; $R^{2a}$ and $R^{2b}$ are independently hydrogen or lower alkyl; $R^1$ is optionally substituted alkyl, optionally substituted heteroalkyl, optionally substituted alkenyl, optionally substituted aryl, optionally substituted heteroaryl, optionally substituted carbocyclyl, or optionally substituted heterocyclyl.

In one embodiment of Formula (III), $R^1$ is optionally substituted alkyl, optionally substituted aryl, or optionally substituted heteroaryl.

In one embodiment of Formula (III), $R^{2a}$ and $R^{2b}$ are hydrogen. In one embodiment of Formula (III), $R^{2a}$ is hydrogen, and $R^{2b}$ is lower alkyl.

In one embodiment of Formula (I), the compound can be represented by a structural Formula (IV):

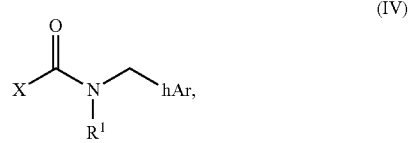

wherein

X is a bicyclic heteroaryl;

hAr is an optionally substituted five-membered heteroaryl containing one or more heteroatoms selected from nitrogen, oxygen, and sulfur; and R[1] is optionally substituted alkyl, optionally substituted heteroalkyl, optionally substituted alkenyl, optionally substituted aryl, optionally substituted heteroaryl, optionally substituted carbocyclyl, or optionally substituted heterocyclyl.

In one embodiment of Formula (I), hAr is thienyl or furanyl.

In one embodiment of Formula (I), X is optionally substituted benzofuranyl.

In one embodiment of Formula (I), R[1] is optionally substituted alkyl, optionally substituted aryl, or optionally substituted heteroaryl.

In some specific embodiments of the present invention, the present compounds are selected from the group consisting of the compound of Table A and Table B below:

Table A.

TABLE A

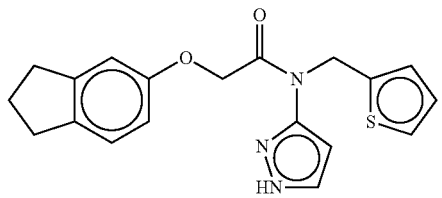 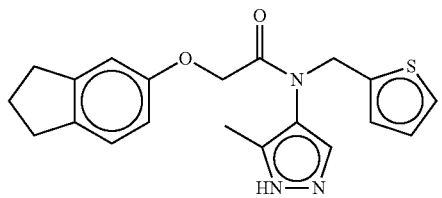

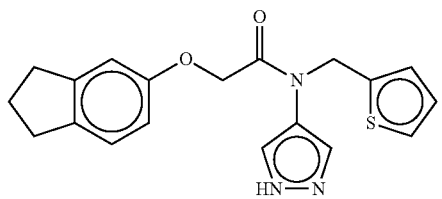 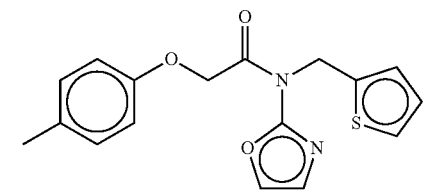

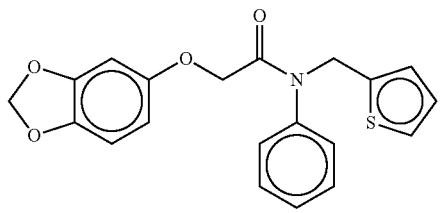 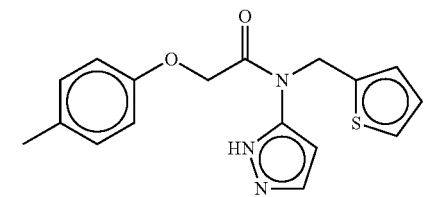

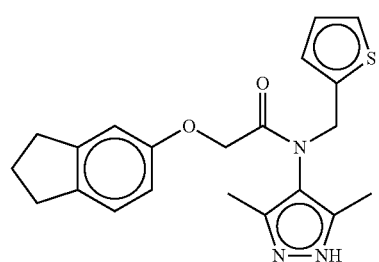 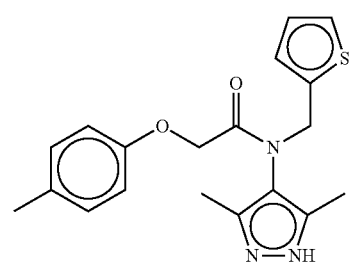

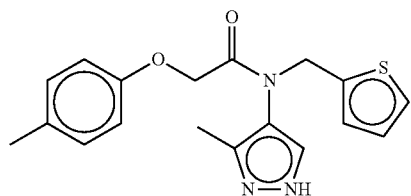 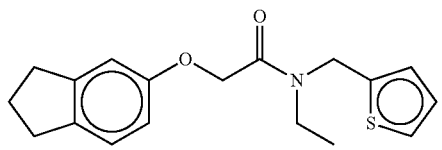

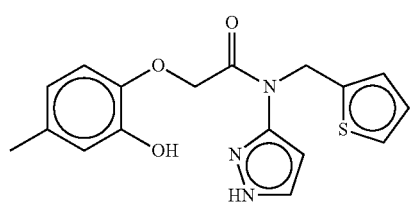 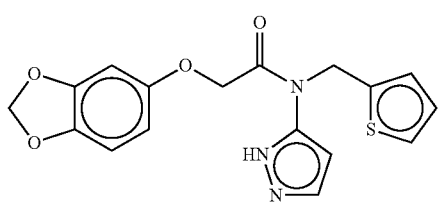

TABLE A-continued
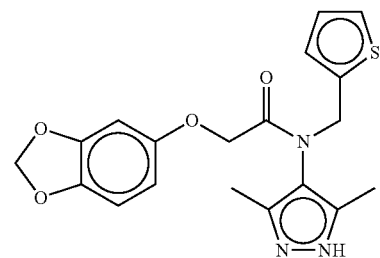 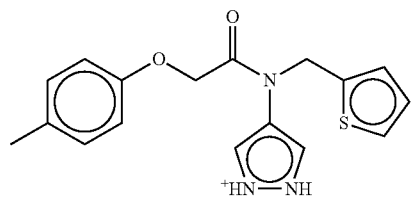
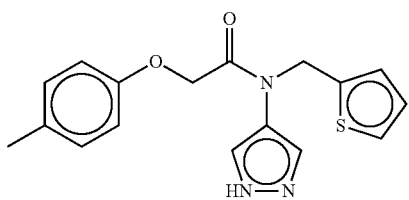 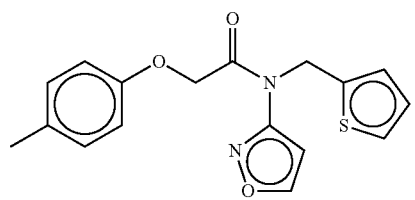
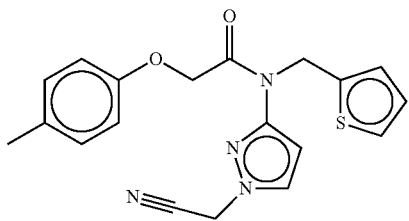 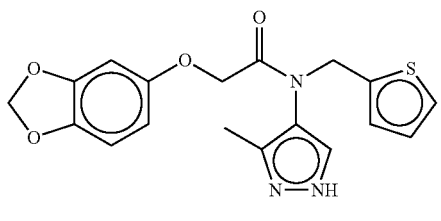
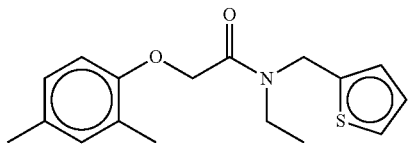 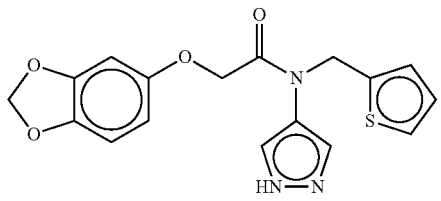
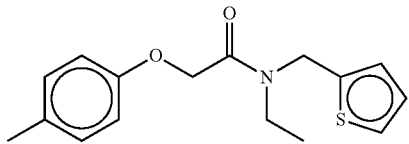 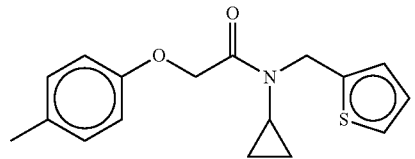
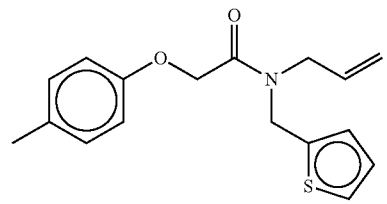 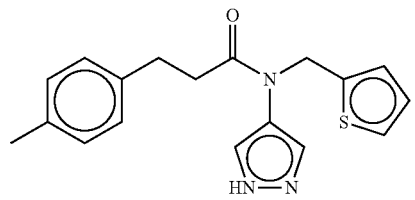
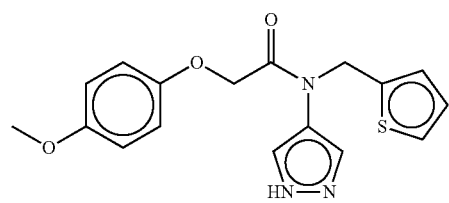 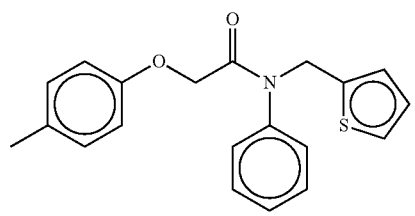

TABLE A-continued
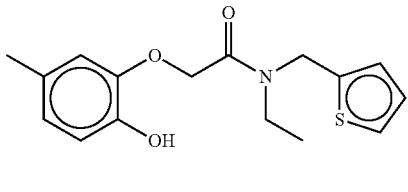 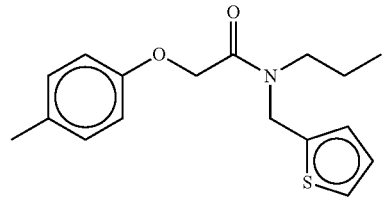
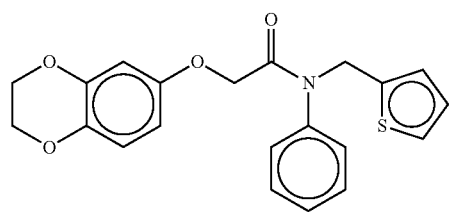 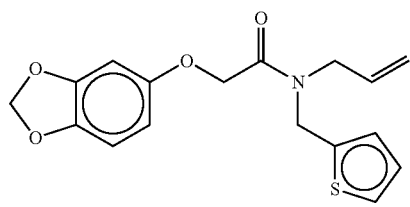
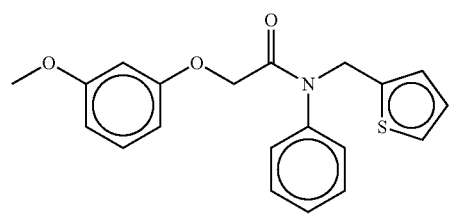 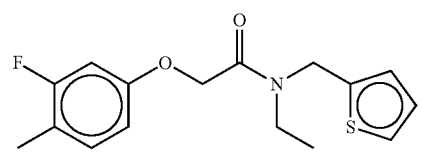
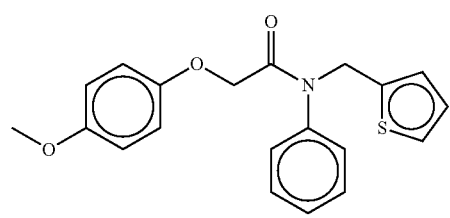 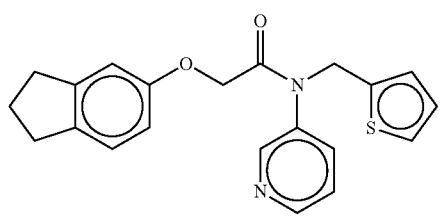
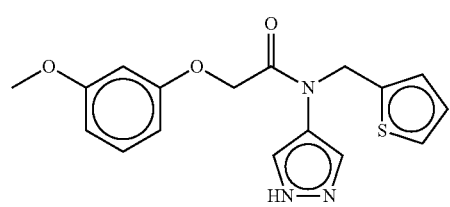 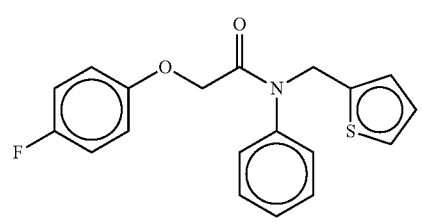
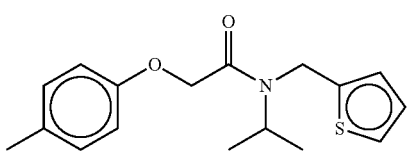 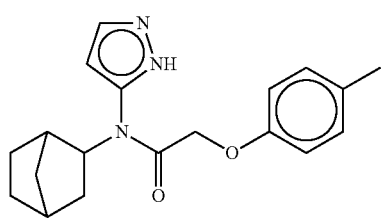
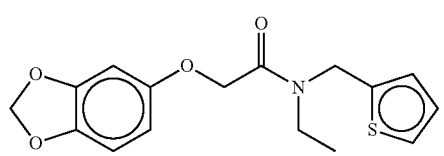 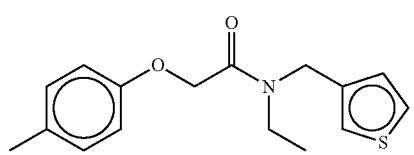

TABLE A-continued
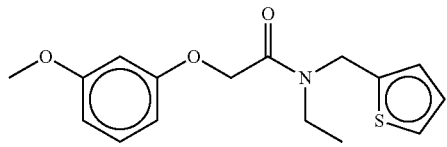 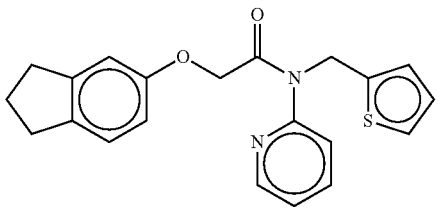
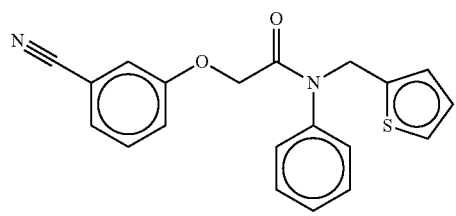 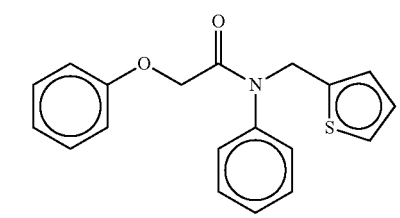
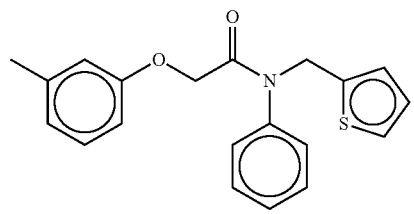 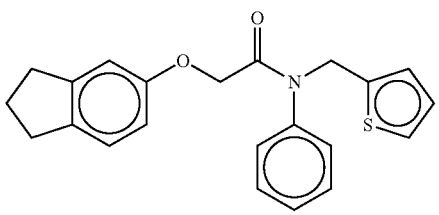
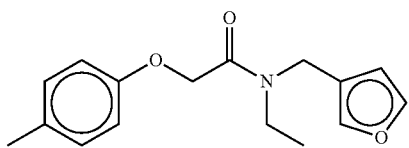 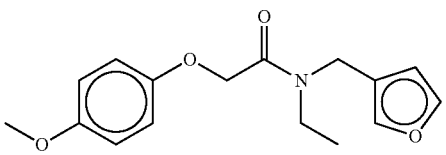
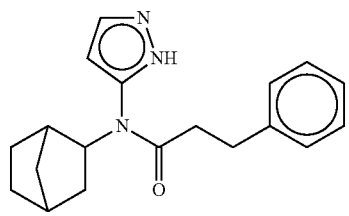 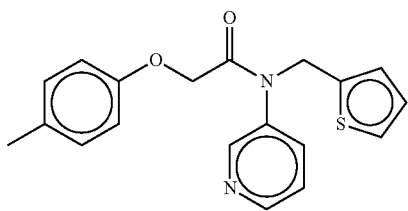
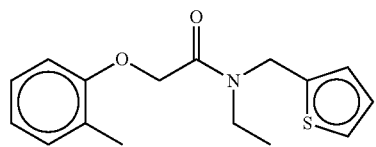 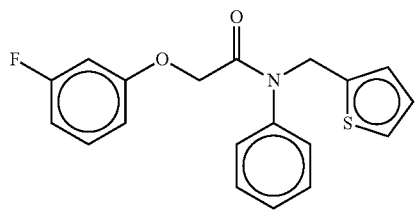
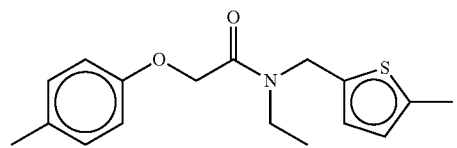 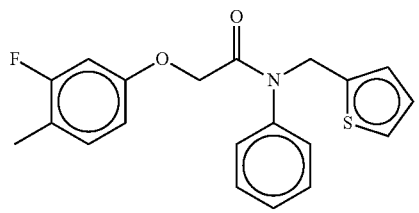
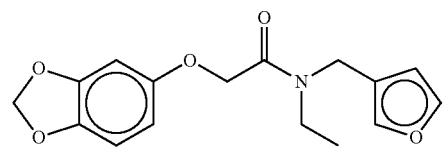 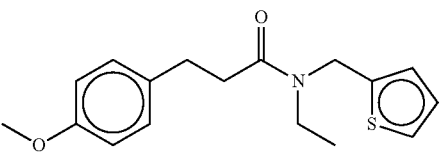

TABLE A-continued
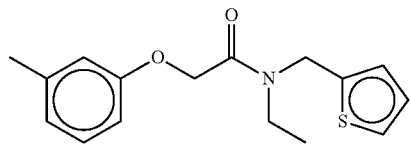 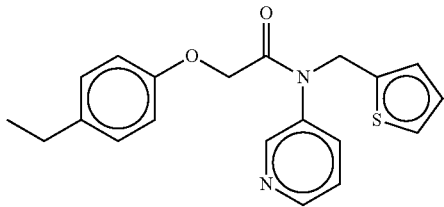
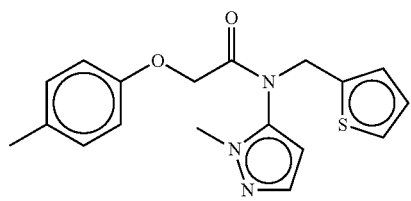 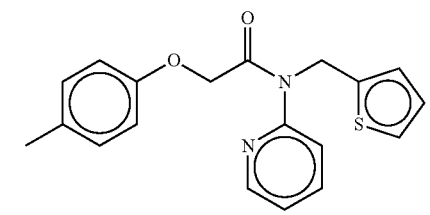
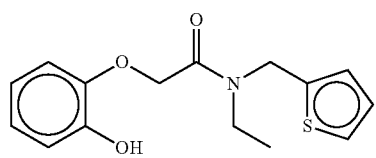 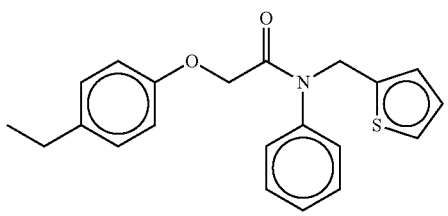
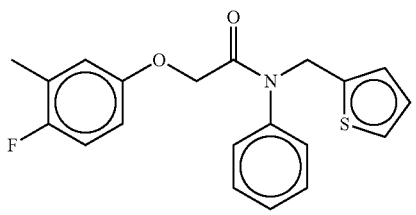 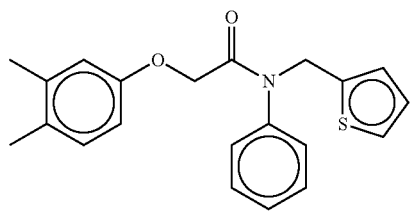
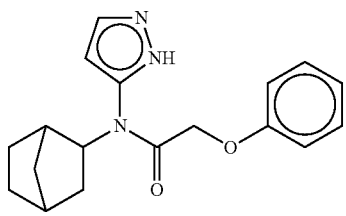 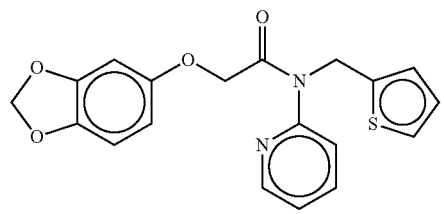
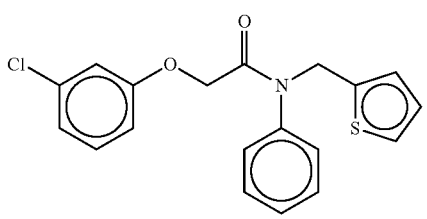 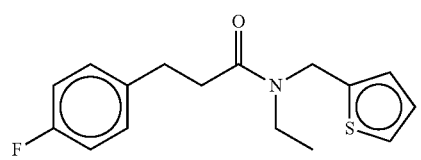
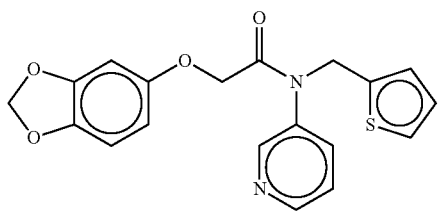 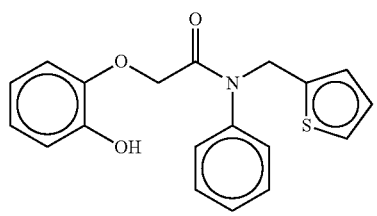

TABLE A-continued
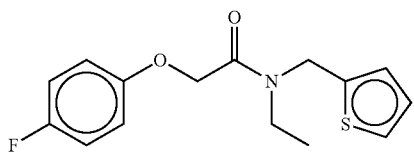
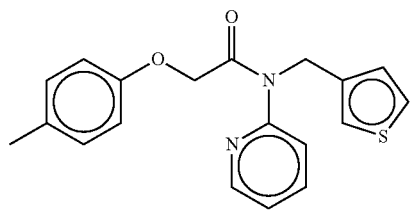
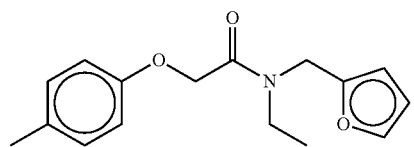
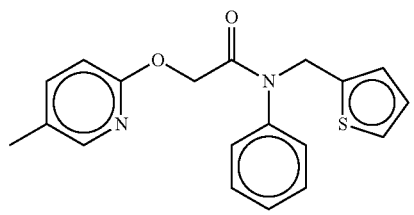
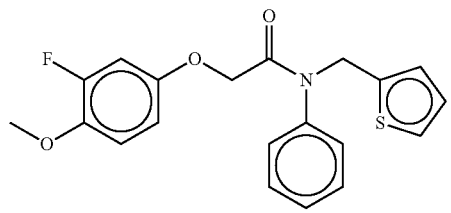
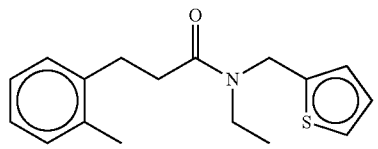
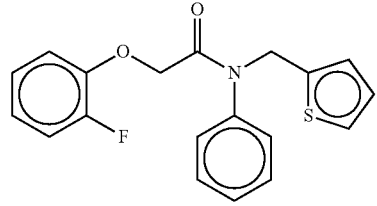
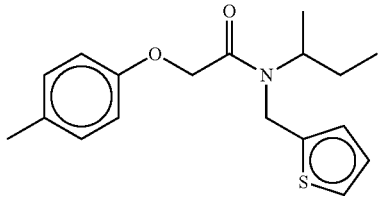
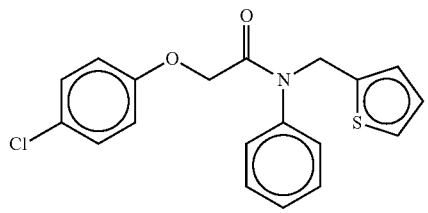
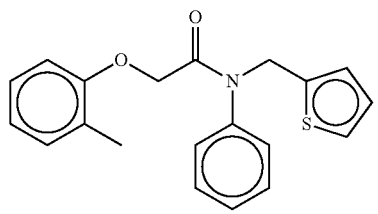
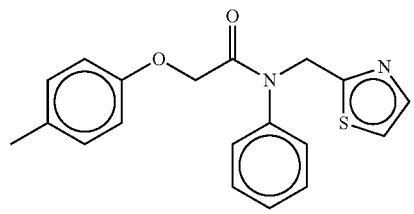
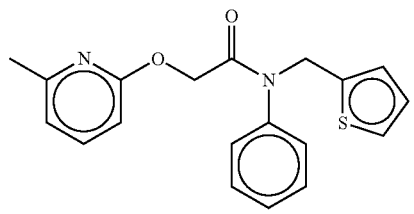
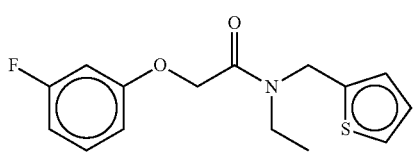
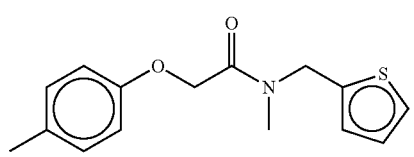

TABLE A-continued
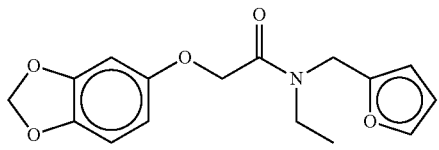 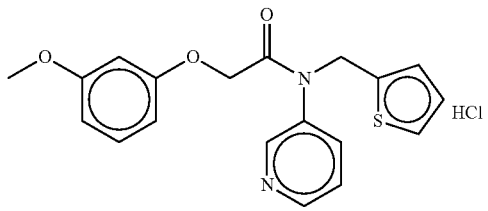
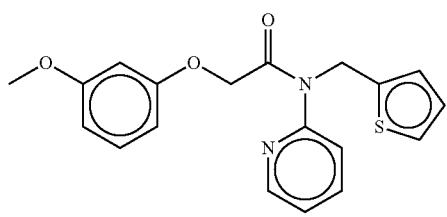 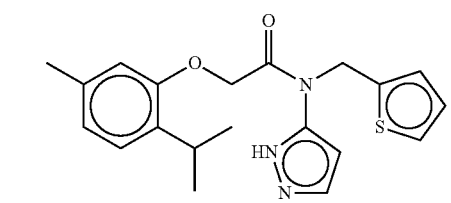
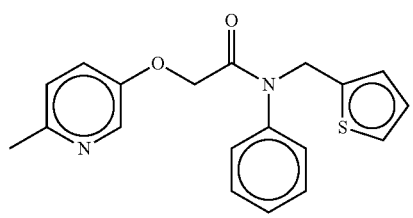 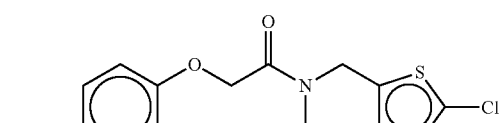
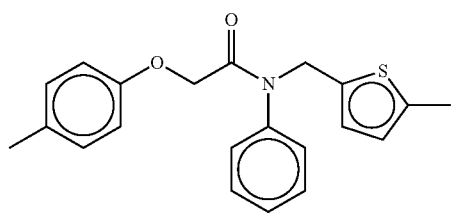 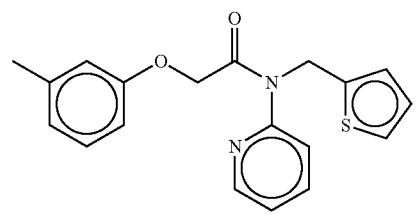
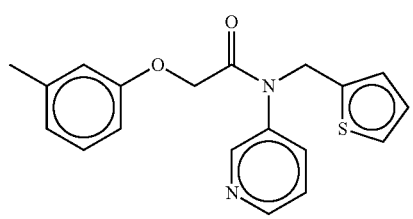 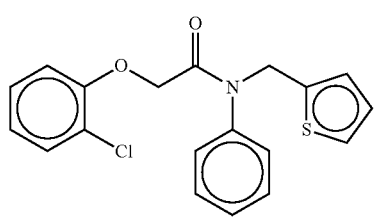
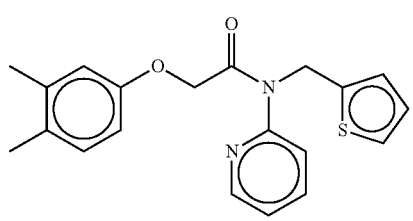 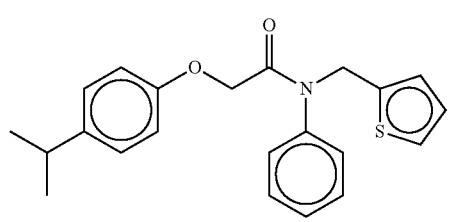
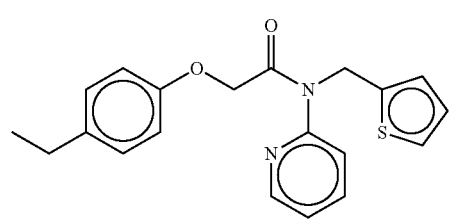 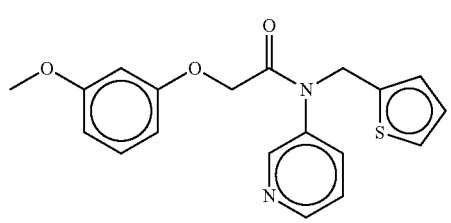

TABLE A-continued
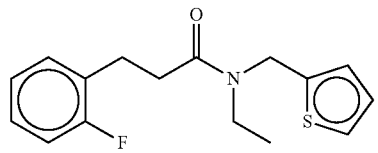
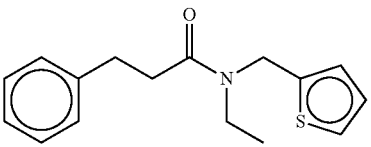
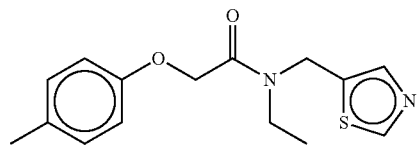
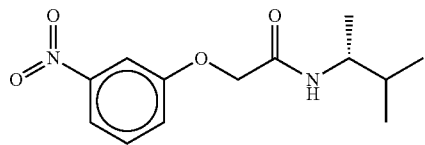
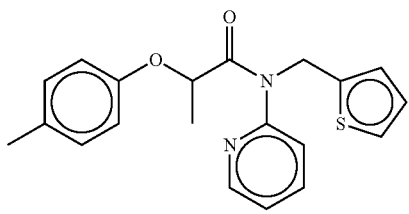
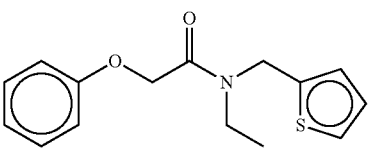
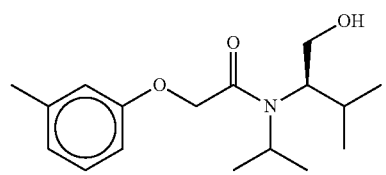
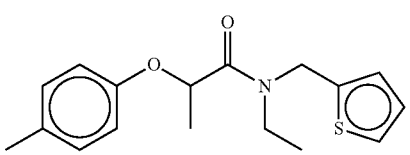
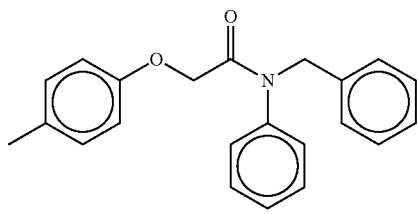
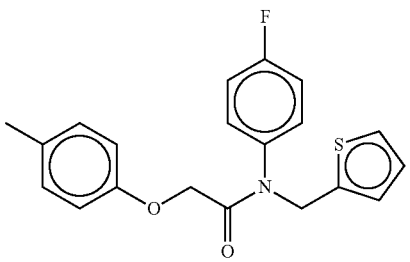
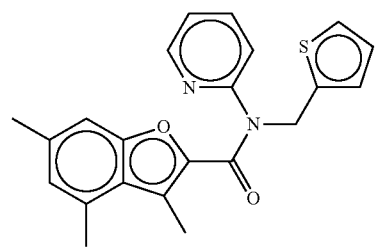
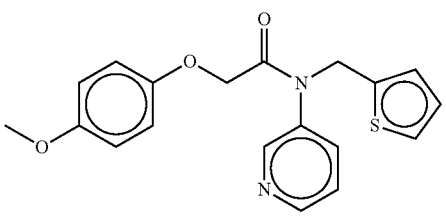
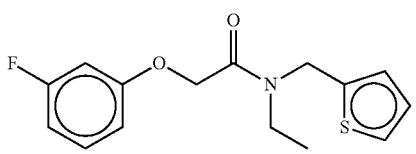
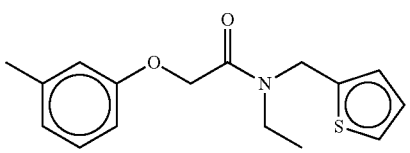
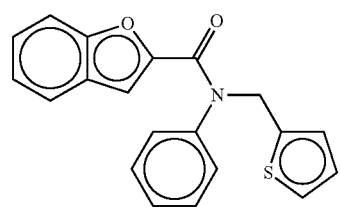
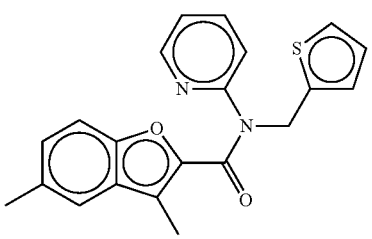

TABLE A-continued
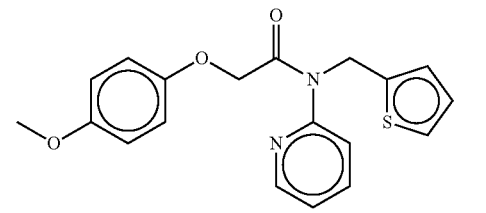 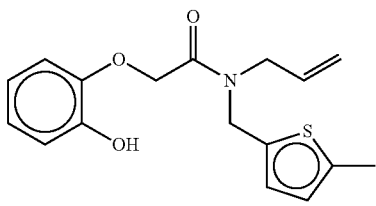
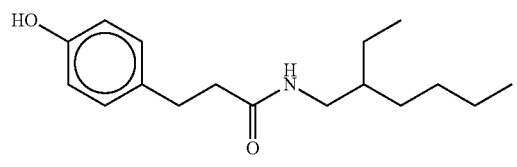 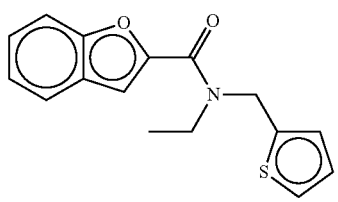
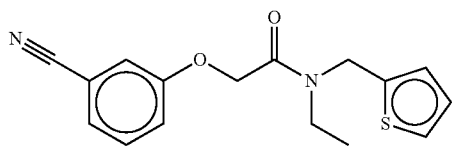 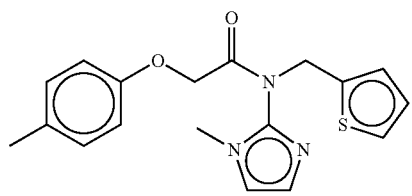
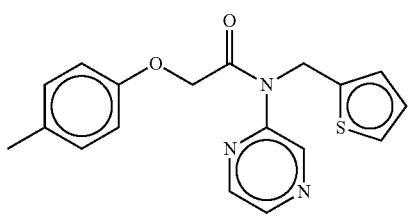 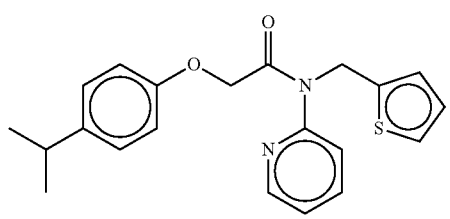
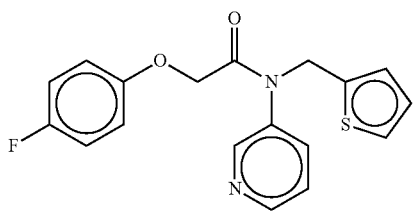 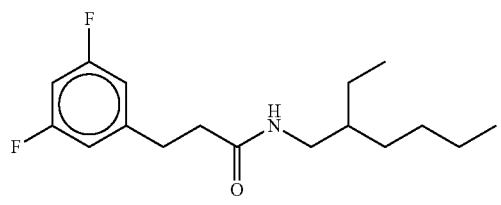
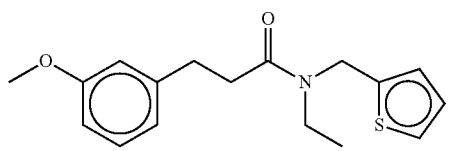 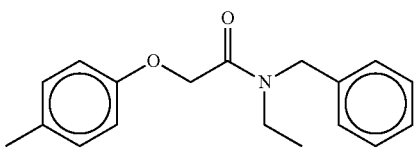
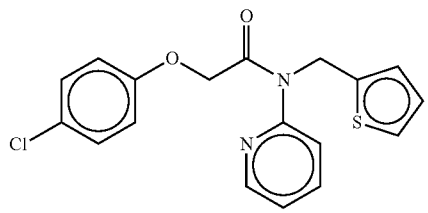 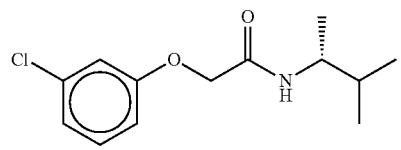
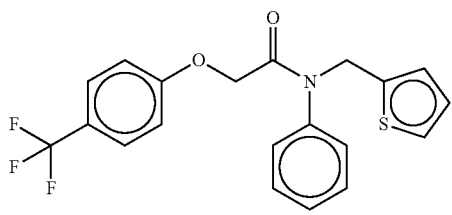 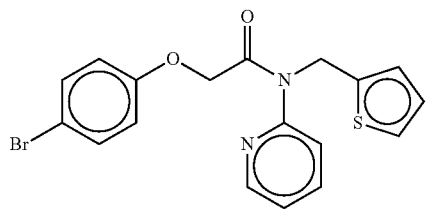

TABLE A-continued
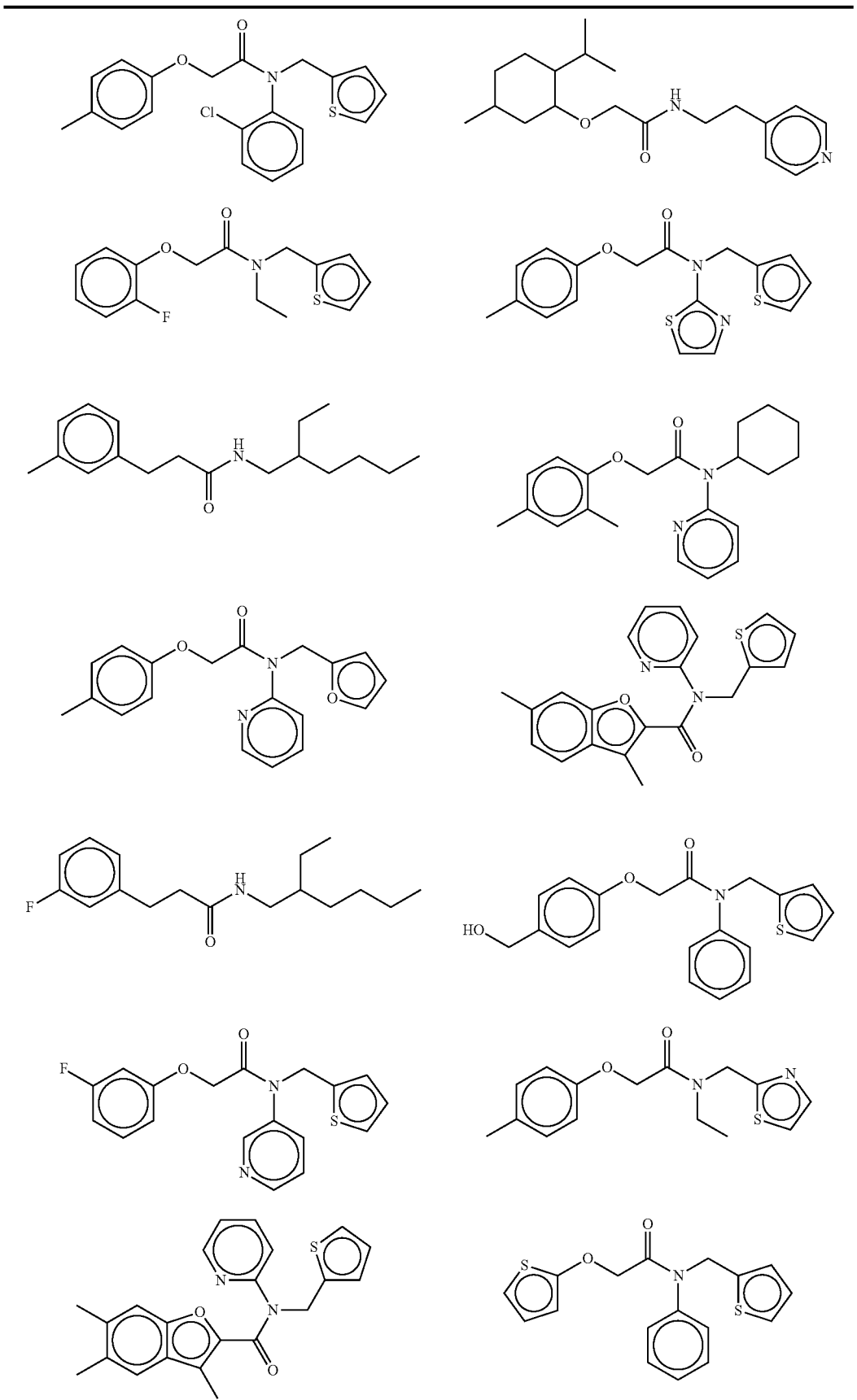

TABLE A-continued
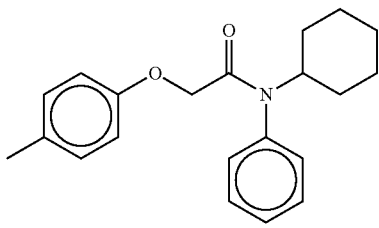 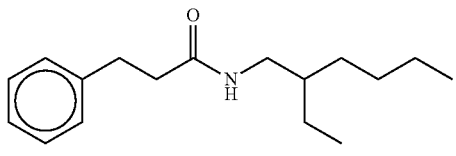
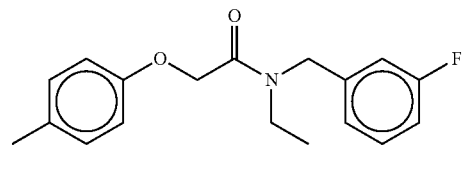 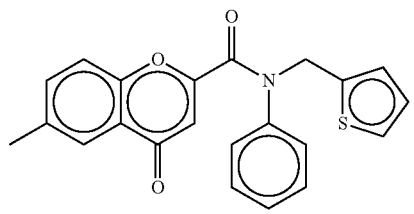
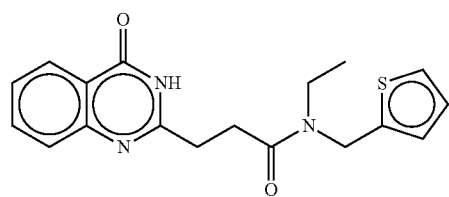 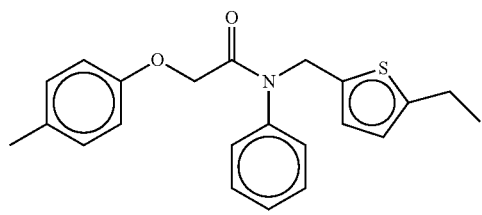
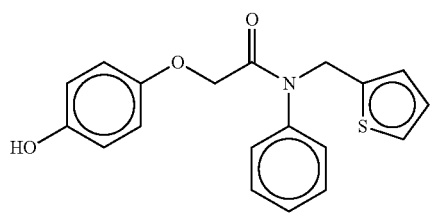 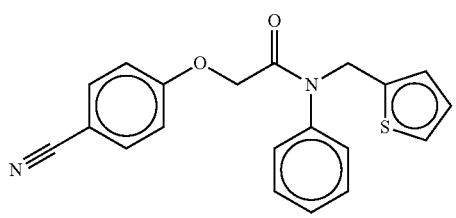
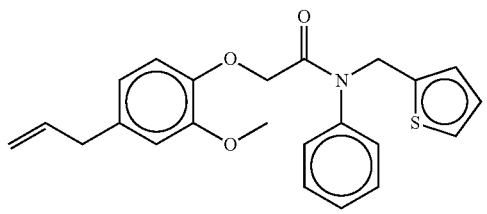 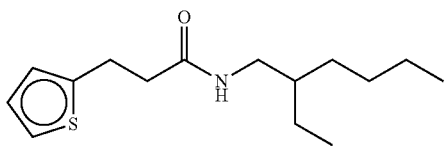
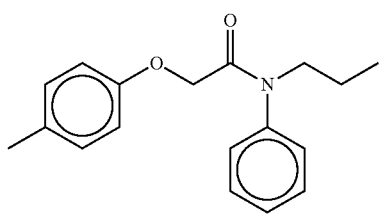 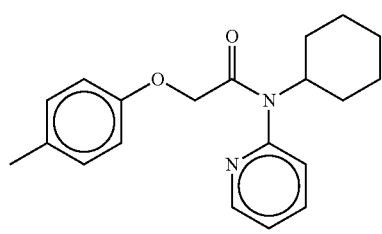
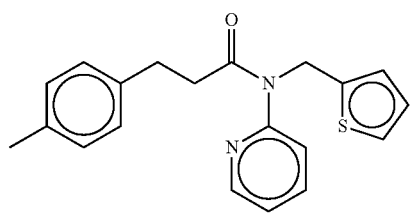 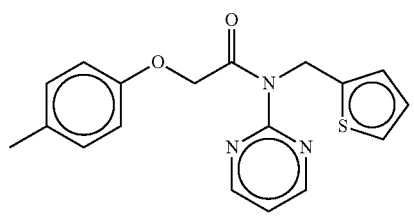

TABLE A-continued
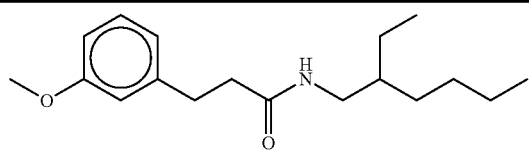
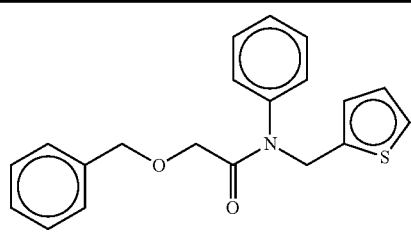
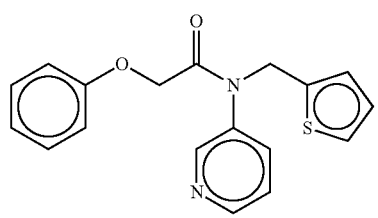
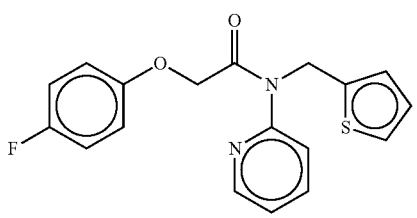
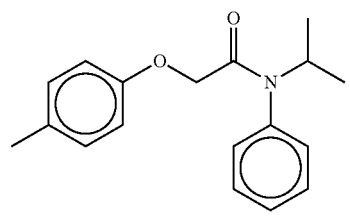
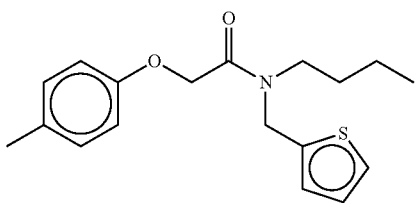
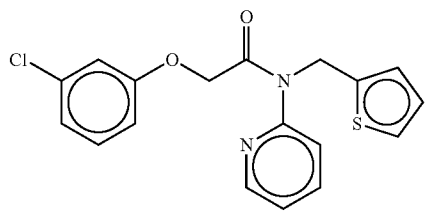
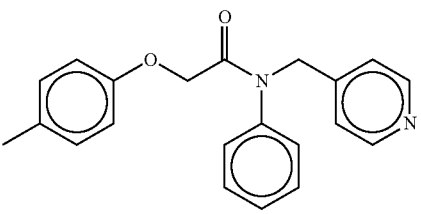
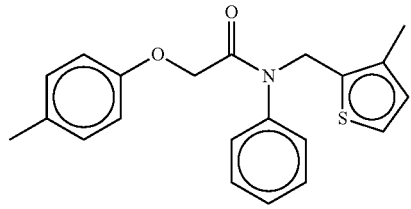
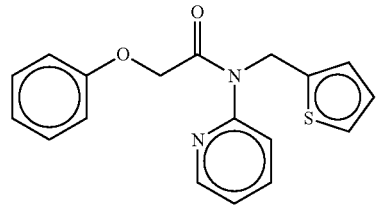
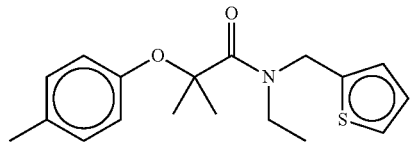
| TABLE B | TABLE B-continued |
|---|---|
| 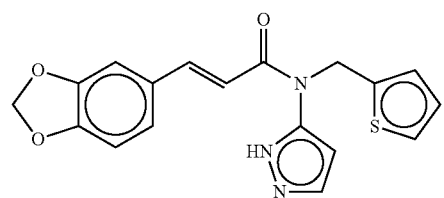 | 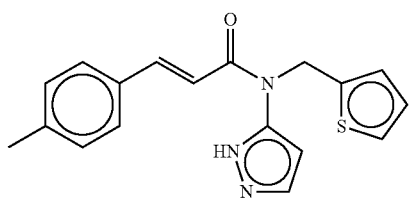 |

TABLE B-continued
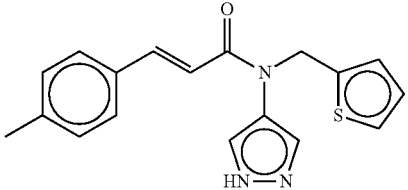
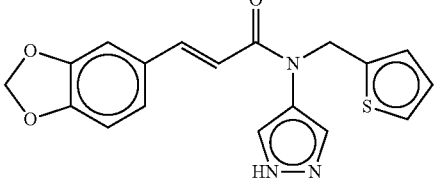
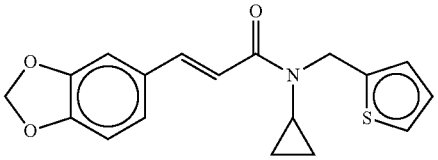
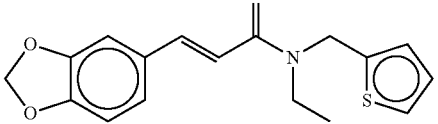
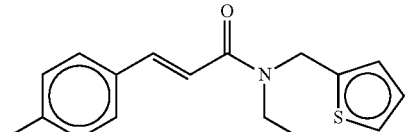
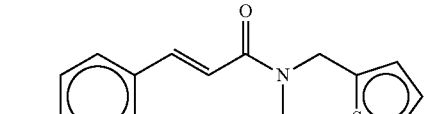
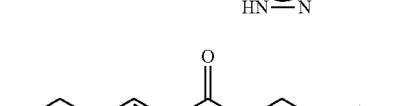
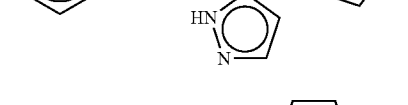
TABLE B-continued
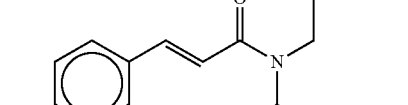
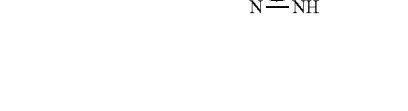
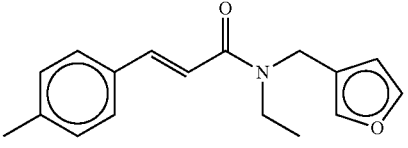
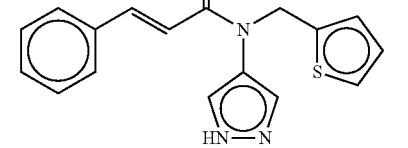
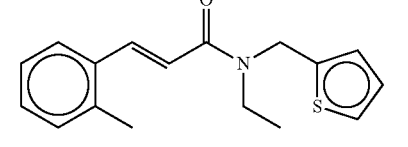
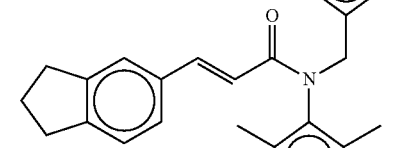
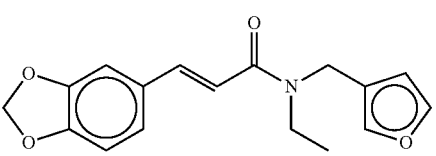
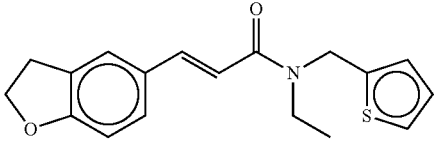

TABLE B-continued
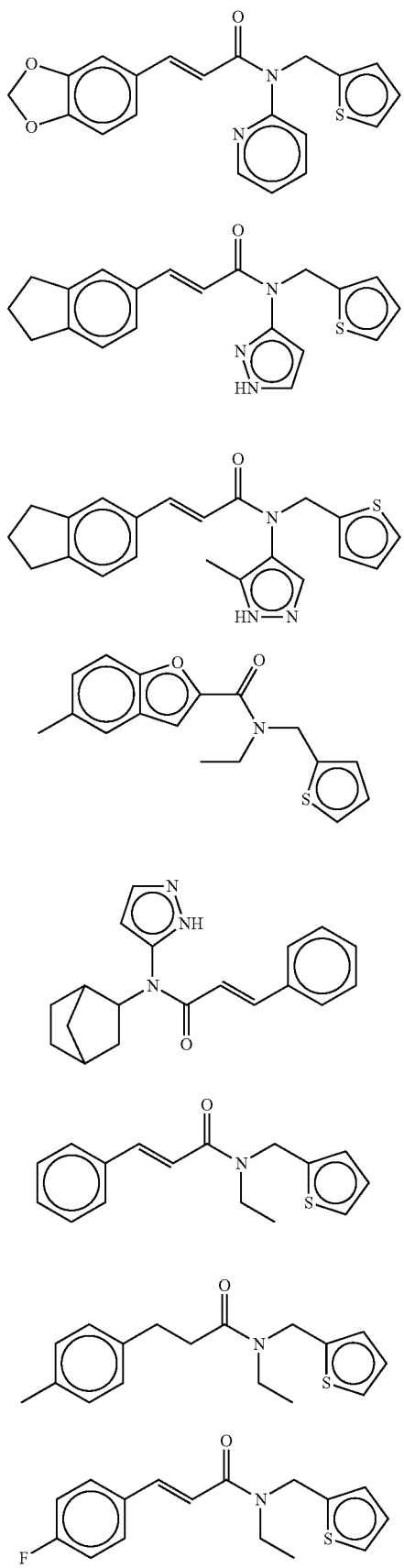
TABLE B-continued
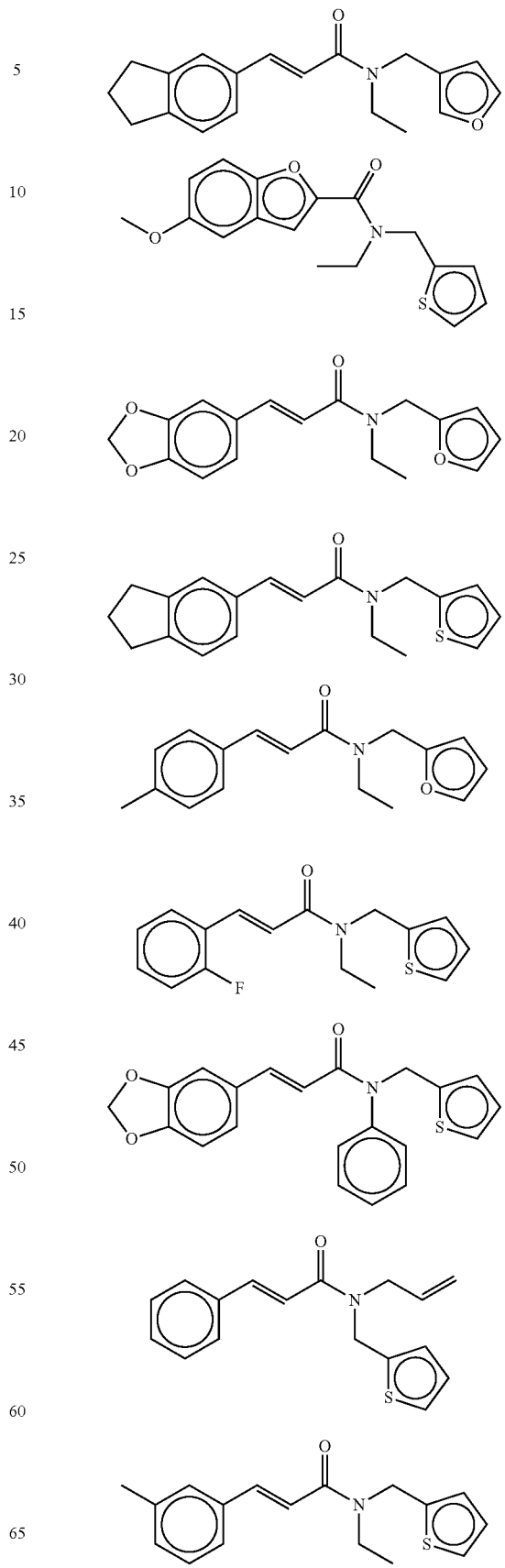

TABLE B-continued
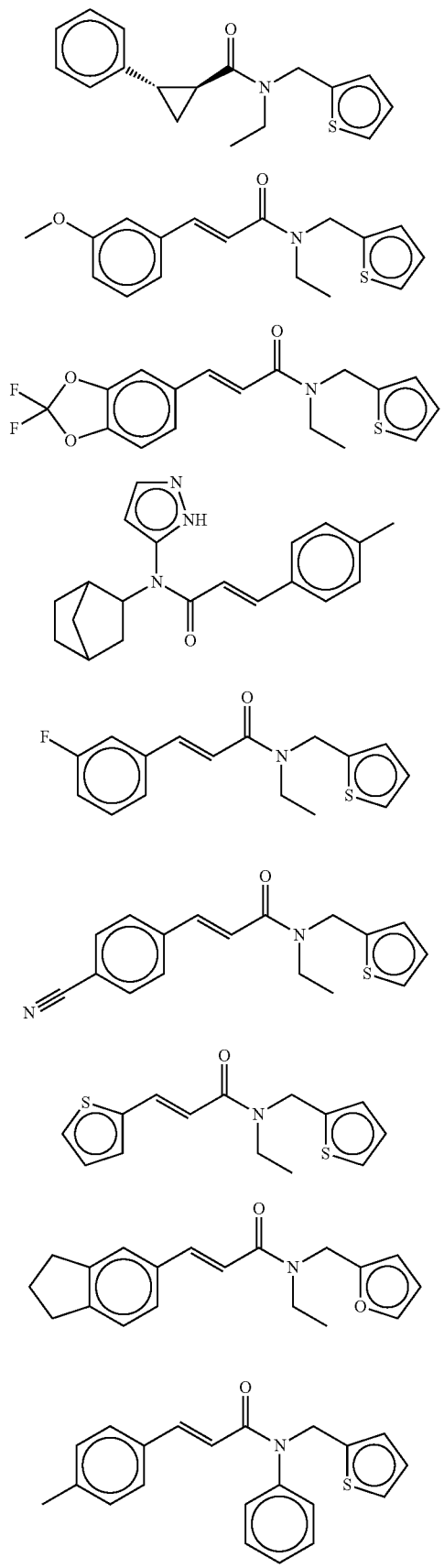
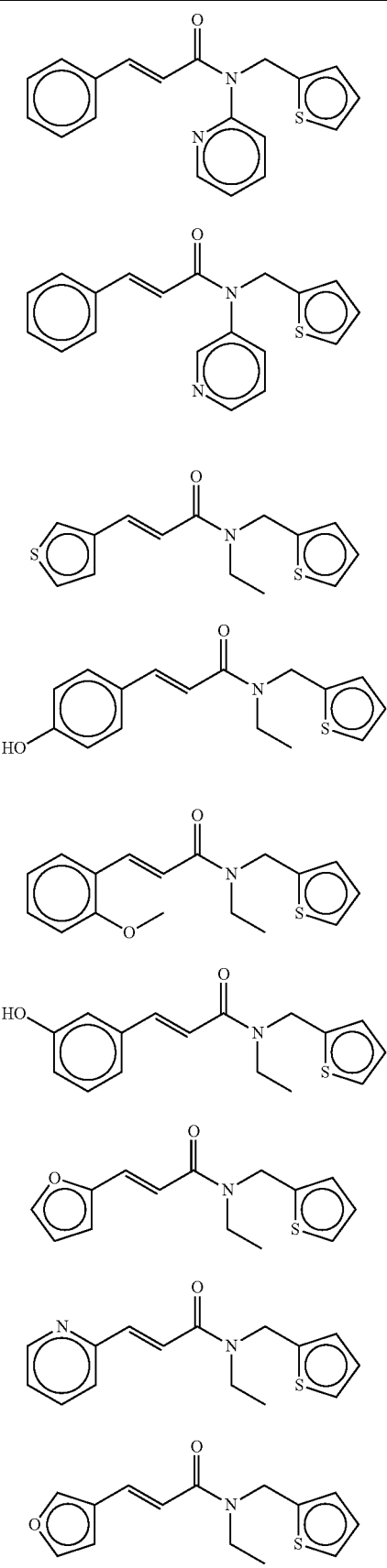

TABLE B-continued

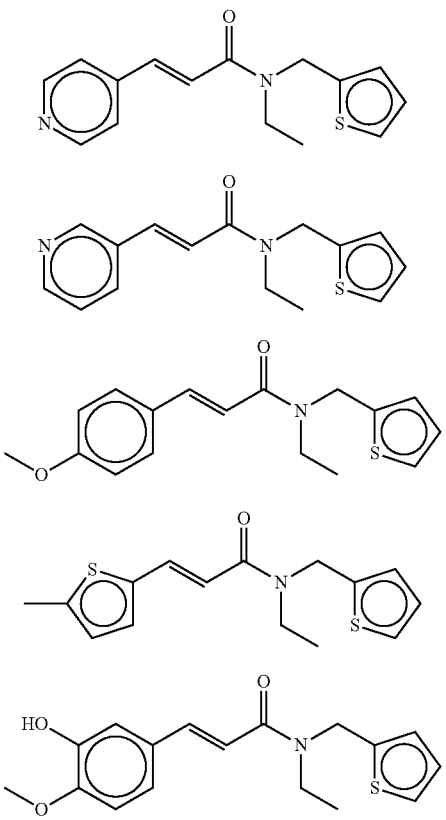

Embodiments of the Utilities of the Present Compounds

The compounds of the present invention, or a salt or solvate thereof, can be used as modulators, e.g., agonists, of the TRPM8 receptor in personal products for modulating, e.g., inducing, chemesthetic sensations, particularly the cold or cool sensations.

The present compounds are important to the flavorings and fragrance industry because they can increase or induce/generate a cooling or cold sensation which is often associated with freshness and cleanliness.

As modulators of the TRPM8 receptor, the present compounds also have repellent effect on insects, therapeutic effect in antitumor treatments (e.g. an influencing of prostate tumors), activity in the treatment of inflammatory pain/hyperalgesia, and efficacy (as TRPM8 antagonists) in the treatment of bladder syndrome or overactive bladder.

The personal product can be provided as a composition, which comprises one or more of the present compound and optionally at least one carrier. The composition can be in any physical form, such as a solid, semi-solid, plaster, solution, suspension, lotion, cream, foam, gel, paste, emulsion, or a combination thereof. Examples of the composition include, but are not limited to, a pharmaceutical composition, an ingestible composition, a chemesthetic concentrate, a personal care composition, and a combination thereof. In one embodiment of the present invention, the composition comprises a chemesthetic sensation modulating amount of the present compound. In another embodiment of the present invention, the composition comprises a chemesthetic sensation inducing amount of the present compound. In certain embodiments, the chemesthetic sensation is a cold or cooling sensation. In one embodiment of the composition, the present compound is in a concentration ranging from about 0.0001 ppm to 100,000 ppm. In another embodiment of the composition, the present compound is in a concentration ranging from about 0.001 ppm to 10,000 ppm. In another embodiment of the composition, the present compound is in a concentration ranging from about 0.01 ppm to 1,000 ppm. In another embodiment of the composition, the present compound is in a concentration ranging from about 0.1 ppm to 500 ppm. In another embodiment of the composition, the present compound is in a concentration ranging from about 1 ppm to 500 ppm. In another embodiment of the composition, the present compound is in a concentration ranging from about 10 ppm to 500 ppm. In another embodiment of the composition, the present compound is in a concentration ranging from about 1 ppm to 400 ppm.

The present ingestible composition typically comprises one or more compounds of the present invention and at least one ingestibly acceptable carrier. The ingestible composition includes both "food or beverage products" and "non-edible products". By "food or beverage products", it is meant any edible product intended for consumption by humans or animals, including solids, semi-solids, or liquids (e.g., beverages). The term "non-edible products" or "noncomestible composition" includes nutraceutical compositions, dietary supplements, nutritional compositions, and functional food products (e.g., any fresh or processed food claimed to have a health-promoting and/or disease-preventing properties beyond the basic nutritional function of supplying nutrients).

In one embodiment, the present compounds are added to food or beverage products or formulations. Examples of food and beverage products or formulations include, but are not limited to coatings, frostings, or glazes for comestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionary category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese-based soups).

"Dehydrated and Culinary Food Category" usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The drinks, either hot or cold, include, but are not limited to coffee or ice coffee, such as fresh, instant, and combined coffee; tea or ice tea, such as black, green, white, oolong, and flavored tea; and other drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionary category generally refers to edible product that is sweet to the taste. Examples of confectionary include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles.

The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is note limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for comestible composition, particularly food and beverage products or formulations, are provided as follows. Exemplary comestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorices, other sugar confectionery, gum, chewing gum, sugarized gum, sugar-free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary comestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof.

In one embodiment, the pharmaceutical composition comprises one or more compounds of the present invention and at least one pharmaceutically acceptable carrier. The pharmaceutical composition includes both the prescription medications and the over-the-counter medications. The present compound may or may not be the therapeutically active ingredient in the pharmaceutical composition. The pharmaceutical composition can be used by any mode of administration known to one skilled in the art, particularly by topical administration, such as application of analgesic cream to the skin surface. In general, over the counter (OTC) product and oral hygiene product generally refer to product for household and/or personal use which may be sold without a prescription and/or without a visit to a medical professional. Examples of the OTC products include, but are not limited to vitamins and dietary supplements; topical analgesics and/or anesthetic; cough, cold and allergy remedies; antihistamines and/or allergy remedies; and combinations thereof. Vitamins and dietary supplements include, but are not limited to vitamins, dietary supplements, tonics/bottled nutritive drinks, child-specific vitamins, dietary supplements, any other products of or relating to or providing nutrition, and combinations thereof. Topical analgesics and/or anesthetic include any topical creams/ointments/gels used to alleviate superficial or deep-seated aches and pains, e.g. muscle pain; teething gel; patches with analgesic ingredient; and combinations thereof. Cough, cold and allergy remedies include, but are not limited to decongestants, cough remedies, pharyngeal preparations, medicated confectionery, antihistamines and child-specific cough, cold and allergy remedies; and combination products. Antihistamines and/or allergy remedies include, but are not limited to any systemic treatments for hay fever, nasal allergies, insect bites and stings. Examples of oral hygiene product include, but are not limited to mouth cleaning strips, toothpaste, toothbrushes, mouthwashes/dental rinses, denture care, mouth fresheners, mouth moisturizers, at-home teeth whiteners and dental floss.

As used herein, a "personal care composition" refers to a composition to be directly applied to the skin, mucosal, or other surface area of the body. Examples of personal care composition include, but are not limited to, an oral care composition, such as toothpaste, chewing gum, breath refresher, dentifrices, and mouthwashes; a skincare or haircare composition, such as sunscreen cream, sunburn lotions, shaving cream, plasters, shampoos, conditioners, face cleaners, soaps, bath oils or bath foam, antiperspirants, and deodorant; a cosmetic composition, such as moisturizer, lip balms, foundation, etc.; an insect repellent composition; or an insecticide composition.

In one embodiment of the invention, the present compounds are provided in a chemesthetic concentrate formulation, e.g., suitable for subsequent processing to produce a ready-to-use (i.e., ready-to-serve) product. By "a chemesthetic concentrate formulation", it is meant a formulation which should be reconstituted with one or more diluting medium to become a ready-to-use composition. The term "ready-to-use composition" is used herein interchangeably with "ingestible composition", which denotes any substance that, either alone or together with another substance, can be taken by mouth whether intended for consumption or not. In one embodiment, the ready-to-use composition includes a composition that can be directly consumed by a human or animal. The chemesthetic concentrate formulation is typically used by mixing with or diluted by one or more diluting medium, e.g., any consumable or ingestible ingredient or product, to impart or modify a chemesthetic sensation to the diluting medium. Such a use process is often referred to as reconstitution. The reconstitution can be conducted in a household setting or an industrial setting. For example, a frozen fruit juice concentrate can be reconstituted with water or other aqueous medium by a consumer in a kitchen to obtain the ready-to-use fruit juice beverage. In another example, a mouthwash concentrate can be reconstituted with water or other aqueous medium by a manufacture in large industrial scales to produce the ready-to-use mouthwash. Since the chemesthetic concentrate formulation has the present compound and optionally a flavoring agent and/or flavor modifying agent in a concentration higher than the ready-to-use composition, the chemesthetic concentrate formulation is typically not suitable for being consumed directly without reconstitution. There are many benefits of using and producing a chemesthetic concentrate formulation. For example, one benefit is the reduction in weight and volume for transportation as the chemesthetic concentrate formulation can be reconstituted at the time of usage by the addition of suitable solvent, solid or liquid.

In one embodiment, the chemesthetic concentrate formulation comprises i) as chemesthetic sensation modifying ingredient, a compound of the present invention; ii) a carrier; and iii) optionally at least one adjuvant. The term "as chemesthetic sensation modifying ingredient" denotes that the compound of the present invention acts as a modulator of a chemesthetic sensation (such as, a cold or cooling sensation modulator) in the formulation. The term "carrier" denotes a usually inactive accessory substance, such as solvents, binders, or other inert medium, which is used in combination with the present compound and one or more optional adjuvants to form the formulation. For example, water or starch can be a carrier for a flavoring concentrate formulation. In some embodiments, the carrier is the same as the diluting medium for reconstituting the chemesthetic concentrate formulation; and in other embodiments, the carrier is different from the diluting medium. The term "carrier" as used herein includes, but is not limited to, ingestibly acceptable carrier.

The term "adjuvant" denotes an additive which supplements, stabilizes, maintains, or enhances the intended function or effectiveness of the active ingredient, such as the compound of the present invention. In one embodiment, the at least one adjuvant comprises one or more flavoring agents. The flavoring agent may be of any flavor known to one skilled in the art or consumers, such as the flavor of chocolate, coffee, tea, mocha, French vanilla, peanut butter, chai, or combinations thereof. In another embodiment, the at least one adjuvant comprises one or more sweeteners. In another embodiment, the at least one adjuvant comprises one or more ingredients selected from the group consisting of a emulsifier, a stabilizer, an antimicrobial preservative, an antioxidant, vitamins, minerals, fats, starches, protein concentrates and isolates, salts, and combinations thereof. Examples of emulsifiers, stabilizers, antimicrobial preservatives, antioxidants, vitamins, minerals, fats, starches, protein concentrates and isolates, and salts are described in U.S. Pat. No. 6,468,576, the contents of which are hereby incorporated by reference in its entirety for all purposes.

In one embodiment, the present chemesthetic concentrate formulation can be in a form selected from the group consisting of liquid including solution and suspension, solid, foamy material, paste, gel, cream, and a combination thereof, such as a liquid containing certain amount of solid contents. In one embodiment, the chemesthetic concentrate formulation is in form of a liquid including aqueous-based and nonaqueous-based. The present chemesthetic concentrate formulation can be carbonated or non-carbonated.

The chemesthetic concentrate formulation may further comprise a freezing point depressant, nucleating agent, or both as the at least one adjuvant. The freezing point depressant is a ingestibly acceptable compound or agent which can depress the freezing point of a liquid or solvent to which the compound or agent is added. That is, a liquid or solution containing the freezing point depressant has a lower freezing point than the liquid or solvent without the freezing point depressant. In addition to depress the onset freezing point, the freezing point depressant may also lower the water activity of the flavoring concentrate formulation. The examples of the freezing point depressant include, but are not limited to, carbohydrates, oils, ethyl alcohol, polyol, e.g., glycerol, and combinations thereof. The nucleating agent denotes a ingestibly acceptable compound or agent which is able to facilitate nucleation. The presence of nucleating agent in the flavoring concentrate formulation can improve the mouthfeel of the frozen slushes of a frozen slush and to help maintain the physical properties and performance of the slush at freezing temperatures by increasing the number of desirable ice crystallization centers. Examples of nucleating agents include, but are not limited to, calcium silicate, calcium carbonate, titanium dioxide, and combinations thereof.

In one embodiment, the chemesthetic concentrate formulation is formulated to have a low water activity for extended shelf life. Water activity is the ratio of the vapor pressure of water in a formulation to the vapor pressure of pure water at the same temperature. In one embodiment, the chemesthetic concentrate formulation has a water activity of less than about 0.85. In another embodiment, the chemesthetic concentrate formulation has a water activity of less than about 0.80. In another embodiment, the chemesthetic concentrate formulation has a water activity of less than about 0.75.

In one embodiment, the chemesthetic concentrate formulation has the present compound in a concentration that is at least 2 times of the concentration of the compound in a ready-to-use composition. In one embodiment, the chemesthetic concentrate formulation has the present compound in a concentration that is at least 5 times of the concentration of the compound in a ready-to-use composition. In one embodiment, the chemesthetic concentrate formulation has the present compound in a concentration that is at least 10 times of the concentration of the compound in a ready-to-use composition. In one embodiment, the chemesthetic concentrate formulation has the present compound in a concentration that is at least 15 times of the concentration of the compound in a ready-to-use composition. In one embodiment, the chemesthetic concentrate formulation has the present compound in a concentration that is at least 20 times of the concentration of the compound in a ready-to-use composition. In one embodiment, the chemesthetic concentrate formulation has the present compound in a concentration that is at least 30 times of the concentration of the compound in a ready-to-use composition. In one embodiment, the chemesthetic concentrate formulation has the present compound in a concentration that is at least 40 times of the concentration of the compound in a ready-to-use composition. In one embodiment, the chemesthetic concentrate formulation has the present compound in a concentration that is at least 50 times of the concentration of the compound in a ready-to-use composition. In one embodiment, the chemesthetic concentrate formulation has the present compound in a concentration that is at least 60 times of the concentration of the compound in a ready-to-use composition. In one embodiment, the chemesthetic concentrate formulation has the present compound in a concentration that is up to 100 times of the concentration of the compound in a ready-to-use composition.

The personal product can be provided as a textile product. Examples of the textile product includes, but are not limited to, shirts, pants, socks, towels, and etc. The present compound can be applied to the textile product in any suitable methods known to one skilled in the art. For example, the present compound can be associated with the textile by spin-coating, imprinting, in the form of microencapsulation, direct incorporation into the textile material (e.g. extruding), covalent coupling of suitable derivatives of the modulators (via suitable spacer/linker groups, with the help of which the molecule is reversibly or irreversibly bonded to the packaging material).

The personal product can be provided as packaging materials. Examples of the packaging materials include paper and plastic wrapping, which may be in various processing forms including fibers, fabrics, and moldings. The present compound can be applied to the packaging material in any suitable methods known to one skilled in the art. For example, the present compound can be associated with the packaging material by spin-coating, imprinting, in the form of microencapsulation, direct incorporation into the packaging material (e.g. extruding), covalent coupling of suitable derivatives of the modulators (via suitable spacer/linker groups, with the help of which the molecule is reversibly or irreversibly bonded to the packaging material.

The compounds of the present invention can be used for modulating transient receptor potential channel melastatin member 8 (TRPM8) by contacting the receptor with a compound of the present invention. This modulation process can be carried out either in vitro or in vivo. In one embodiment, the compound is a TRPM8 receptor agonist.

The compounds of the present invention can also be formulated into a precursor of the above-described compositions. By "precursor", it is meant a substance or composition from which another composition, such as those described above, is formed. For example, the present compounds may be provided as a concentrated formulation or composition which may be further mixed or diluted to form another composition suitable for consumption or personal use.

The present compounds can be used to modify the chemesthetic sensation of a composition by contacting the present compounds with the composition to form a taste-modified composition. In one embodiment, the present compounds can convey or impart a cooling taste to a composition.

In one embodiment, the present invention provides a method of modulating the cold or cooling sensation of a composition comprising combining the composition with a compound of the present invention, or a salt or solvate thereof, to form a modified composition.

In one embodiment, the present invention provides a method of inducing a cold or cooling sensation in a human or animal by contacting the human or animal with a compound of the present invention.

Biological Assay

A mammalian cell line derivative which stably expresses hTRPM8 was used in biological assays in association with testing the present compounds with cool-tasting or -feeling properties (Servant et al. US 2007/0259354 A1 and references cited therein). Typical compound concentrations tested were 100 μM, 50 μM, 10 μM, 1 μM, and 0.5 μM. The present compounds have shown strong activity as agonists of hTRPM8. Assay results for compounds are illustrated in Table 1 below. Specifically, the Examples listed in Table 1, i.e., Compounds A1 to Compounds U10 are the specific compounds, i.e., Examples, as described above.

TABLE 1

| Compound | EC50 (uM) | EC50 WS-3 Ratio |
|---|---|---|
| A1 | 0.000009 | 782471 |
| B1 | 0.000001 | 1000000 |
| C1 | 0.000017 | 502141 |
| D1 | 0.000254 | 119614 |
| E1 | 0.000391 | 22099 |
| F1 | 0.000205 | 21178 |
| G1 | 0.00019 | 18711 |
| H1 | 0.000279 | 15169 |
| I1 | 0.000425 | 9981 |
| J1 | 0.000575 | 9607 |
| K1 | 0.000643 | 6336 |
| L1 | 0.00047 | 7808 |
| M1 | 0.0012 | 4571 |
| N1 | 0.0010 | 4432 |
| O1 | 0.0014 | 3821 |
| P1 | 0.0018 | 3444 |
| Q1 | 0.0023 | 1968 |
| R1 | 0.0023 | 1764 |
| S1 | 0.0033 | 886 |
| T1 | 0.0057 | 823 |
| U1 | 0.0077 | 577 |
| V1 | 0.0069 | 630 |
| W1 | 0.0150 | 365 |
| X1 | 0.0232 | 222 |
| Y1 | 0.0197 | 207 |
| Z1 | 0.0211 | 204 |
| A2 | 0.0171 | 165 |
| B2 | 0.0486 | 149 |
| C2 | 0.0319 | 134 |
| D2 | 0.0383 | 134 |
| E2 | 0.0304 | 111 |
| F2 | 0.0525 | 101 |
| G2 | 0.0431 | 96 |
| H2 | 0.0450 | 91 |
| I2 | 0.0522 | 77 |
| G2 | 0.0791 | 76 |
| K2 | 0.0717 | 66 |
| L2 | 0.0619 | 60 |
| M2 | 0.0613 | 58 |
| N2 | 0.625 | 7 |
| O2 | 0.536 | 7 |
| P2 | 0.061 | 47 |
| Q2 | 0.088 | 49 |
| R2 | 0.111 | 37 |
| S2 | 0.112 | 36 |
| T2 | 0.116 | 36 |
| U2 | 0.170 | 32 |
| V2 | 0.128 | 32 |
| W2 | 0.136 | 32 |
| X2 | 0.116 | 30 |
| Y2 | 0.109 | 28 |
| Z2 | 0.363 | 23 |
| A3 | 0.209 | 24 |
| B3 | 0.214 | 22 |
| C3 | 0.178 | 18 |
| D3 | 0.212 | 18 |
| E3 | 0.261 | 18 |
| F3 | 0.534 | 16 |
| G3 | 0.407 | 14 |
| H3 | 0.255 | 14 |
| I3 | 0.422 | 14 |
| J3 | 0.324 | 13 |
| K3 | 0.505 | 13 |
| L3 | 0.378 | 12 |
| M3 | 0.280 | 12 |
| N3 | 0.422 | 12 |
| O3 | 0.558 | 12 |
| P3 | 0.290 | 12 |
| Q3 | 0.351 | 11 |
| R3 | 0.750 | 11 |

TABLE 1-continued

| Compound | EC50 (uM) | EC50 WS-3 Ratio |
|---|---|---|
| S3 | 0.386 | 10 |
| T3 | 0.422 | 10 |
| U3 | 0.432 | 10 |
| V3 | 0.489 | 9 |
| W3 | 0.371 | 9 |
| X3 | 0.461 | 9 |
| Y3 | 0.962 | 9 |
| Z3 | 0.515 | 8 |
| A4 | 0.599 | 8 |
| B4 | 0.408 | 7 |
| C4 | 1.235 | 3 |
| D4 | 1.786 | 3 |
| E4 | 0.537 | 7 |
| F4 | 0.858 | 7 |
| G4 | 0.614 | 7 |
| H4 | 0.734 | 6 |
| I4 | 0.813 | 6 |
| J4 | 0.622 | 6 |
| K4 | 0.877 | 6 |
| L4 | 0.828 | 6 |
| M4 | 0.892 | 5 |
| N4 | 0.908 | 5 |
| O4 | 0.712 | 5 |
| P4 | 0.693 | 5 |
| Q4 | 0.767 | 5 |
| R4 | 0.904 | 5 |
| S4 | 1.182 | 5 |
| T4 | 0.859 | 5 |
| U4 | 1.049 | 5 |
| V4 | 1.845 | 5 |
| W4 | 1.102 | 4 |
| X4 | 1.360 | 4 |
| Y4 | 0.625 | 4 |
| Z4 | 0.824 | 4 |
| A5 | 1.451 | 4 |
| B5 | 0.637 | 4 |
| C5 | 0.889 | 4 |
| D5 | 0.891 | 4 |
| E5 | 0.726 | 4 |
| F5 | 1.949 | 4 |
| G5 | 1.720 | 3 |
| H5 | 1.230 | 4 |
| I5 | 1.779 | 3 |
| G5 | 1.040 | 3 |
| K5 | 2.161 | 3 |
| L5 | 1.197 | 3 |
| M5 | 1.422 | 3 |
| N5 | 1.175 | 3 |
| O5 | 1.127 | 3 |
| P5 | 2.079 | 3 |
| Q5 | 3.810413 | 1 |
| R5 | 1.401 | 3 |
| S5 | 1.771 | 2 |
| T5 | 1.607 | 2 |
| U5 | 2.386 | 2 |
| V5 | 1.876 | 2 |
| W5 | 2.318 | 2 |
| X5 | 2.173 | 2 |
| Y5 | 2.375 | 2 |
| Z5 | 1.180 | 2 |
| A6 | 2.268 | 2 |
| B6 | 2.173 | 2 |
| C6 | 3.731 | 2 |
| D6 | 2.240 | 2 |
| E6 | 2.002 | 2 |
| F6 | 2.803 | 2 |
| G6 | 2.037 | 2 |
| H6 | 3.740 | 2 |
| I6 | 2.570 | 2 |
| J6 | 2.623 | 2 |
| K6 | 2.262 | 2 |
| L6 | 3.062 | 2 |
| M6 | 2.249 | 2 |
| N6 | 2.619 | 2 |
| O6 | 3.301 | 2 |
| P6 | 2.882 | 2 |
| Q6 | 1.671 | 2 |
| R6 | 2.593 | 1 |
| S6 | 3.444 | 1 |
| T6 | 2.405 | 1 |
| U6 | 2.997 | 1 |
| V6 | 3.289 | 1 |
| W6 | 3.751 | 1 |
| X6 | 3.216 | 1 |
| Y6 | 3.824 | 1 |
| Z6 | 4.629 | 1 |
| A7 | 4.660 | 1 |
| B7 | 3.703 | 1 |
| C7 | 3.470 | 1 |
| D7 | 0.124 | 53 |
| E7 | 5.516541 | 1 |
| F7 | 4.939072 | 1 |
| G7 | 4.285153 | 1 |
| H7 | 5.343864 | 1 |
| I7 | 5.11506 | 1 |
| J7 | 6.197407 | 1 |
| K7 | 4.238856 | 1 |
| L7 | 5.375403 | 1 |
| M7 | 10.98696 | 0.316 |
| N7 | 0.000011 | 1454336 |
| O7 | 0.000002 | 3531839 |
| P7 | 0.000004 | 1200594 |
| Q7 | 0.000006 | 817519 |
| R7 | 0.000026 | 182281 |
| S7 | 0.000266 | 32698 |
| T7 | 0.000397 | 24280 |
| U7 | 0.003001 | 9481 |
| V7 | 0.0007 | 6834 |
| W7 | 0.0018 | 4318 |
| X7 | 0.0011 | 2775 |
| Y7 | 0.0018 | 2799 |
| Z7 | 0.0016 | 2013 |
| A8 | 0.0014 | 1986 |
| B8 | 0.0039 | 813 |
| C8 | 0.0072 | 533 |
| D8 | 0.0082 | 425 |
| E8 | 0.0153 | 399 |
| F8 | 0.0166 | 336 |
| G8 | 0.0153 | 326 |
| H8 | 0.0232 | 183 |
| I8 | 0.0227 | 193 |
| J8 | 0.0313 | 146 |
| K8 | 0.0311 | 144 |
| L8 | 0.0369 | 109 |
| M8 | 0.0440 | 107 |
| N8 | 0.0466 | 87 |
| O8 | 0.0520 | 81 |
| P8 | 0.0405 | 77 |
| Q8 | 0.048 | 69 |
| R8 | 0.058 | 48 |
| S8 | 0.098 | 48 |
| T8 | 0.089 | 48 |
| U8 | 0.093 | 40 |
| V8 | 0.108 | 38 |
| W8 | 0.114 | 37 |
| X8 | 0.130 | 32 |
| Z8 | 0.140 | 32 |
| A9 | 0.157 | 27 |
| B9 | 0.172 | 30 |
| C9 | 0.122 | 27 |
| D9 | 0.151 | 25 |
| E9 | 0.191 | 22 |
| F9 | 0.232 | 22 |
| G9 | 0.259 | 17 |
| H9 | 0.286 | 16 |
| I9 | 0.293 | 13 |
| J9 | 0.352 | 12 |
| K9 | 0.419 | 11 |
| L9 | 0.455 | 12 |
| M9 | 0.361 | 11 |
| N9 | 0.631 | 10 |
| O9 | 0.446 | 9 |
| P9 | 0.560 | 9 |
| Q9 | 0.729 | 8 |

TABLE 1-continued

| Compound | EC50 (uM) | EC50 WS-3 Ratio |
|---|---|---|
| R9 | 0.750 | 6 |
| S9 | 0.919 | 5 |
| T9 | 0.958 | 5 |
| U9 | 1.040 | 5 |
| V9 | 0.821 | 5 |
| W9 | 0.986 | 5 |
| X9 | 0.931 | 5 |
| Y9 | 1.949 | 4 |
| Z9 | 1.165 | 4 |
| A10 | 1.231 | 4 |
| B10 | 1.227 | 4 |
| C10 | 1.431 | 3 |
| D10 | 0.0535 | 75 |
| E10 | 1.694853 | 3 |
| F10 | 2.161292 | 3 |
| G10 | 2.356718 | 3 |
| H10 | 1.632536 | 3 |
| I10 | 2.916701 | 3 |
| J10 | 1.846245 | 2 |
| K10 | 2.904192 | 2 |
| L10 | 1.924198 | 2 |
| M10 | 1.379 | 3 |
| N10 | 1.985332 | 2 |
| O10 | 3.740034 | 2 |
| P10 | 4.588583 | 1 |
| Q10 | 3.23947 | 1 |
| R10 | 3.035896 | 1 |
| S10 | 6.42262 | 1 |
| T10 | 6.906322 | 1 |
| U10 | 4.85575 | 1 |

Sensory Studies

Two typical sensory studies are described below followed by a table summarizing sensory results of selected compounds of the invention (Table 6).

Cool Line Scale Test with Example 26 (15 µM)

Formulation

All samples made with Low Sodium Buffer (LSB) pH ~7.1 and contain 0.1% ethanol.

General Protocol:

Compounds are rated on a 15 point line scale where 45 µM WS-3 (N-Ethyl-p-menthane-3-carboxamide) is ranked as a 5 in cool intensity. In most cases our compounds are tested to determine at what concentration the cooling intensity is equivalent to 45 µM WS-3. In each test, the panelist is presented with a 0 µM control sample, a 45 µM WS-3 control sample and the experimental compound sample and asked to rate the cooling intensity of each sample. Panelists are also asked to rate bitterness. In the table below there was no significant bitterness detected unless otherwise noted. Also, in the table below, n represents the number of tests completed for a given experiment (#panelists x #repetitions).

Conclusions:

Panelists found 15 µM Compound Z1 was significantly more cooling than 0 µM WS-3 (p<0.05) and not significantly different in cooling than 45 µM WS-3 (p>0.05). There were no significant bitter offtastes in any of the samples (p>0.05). Analytical for 15 µM Compound Z1 from a sample cup from the test was 70% of the expected value, while analytical from the bottle of solution was within the expected range.

TABLE 2

Average Cooling, n = 30 (15 Panelists × 2 rep). Tukey's Value = 1.103 (α = 0.05).

| Treatment | Average | SD | St Er | Tukey (5%) |
|---|---|---|---|---|
| 0 µM WS-3 | 2.1 | 2.2 | 0.4 | a |
| 15 µM Compound Z1 | 3.4 | 2.1 | 0.4 | b |
| 45 µM WS-3 | 3.8 | 1.9 | 0.3 | b |

TABLE 3

Average Bitterness, n = 30 (15 Panelists × 2 rep). Tukey's Value = 0.442 (α = 0.05).

| Treatment | Average | SD | St Er | Tukey (5%) |
|---|---|---|---|---|
| 0 µM WS-3 | 0.1 | 0.3 | 0.0 | a |
| 15 µM Compound Z1 | 0.3 | 0.6 | 0.1 | a |
| 45 µM WS-3 | 0.3 | 1.0 | 0.2 | a |

Cool Line Scale Test with Compound F1 (3 µM in LSB):

Formulation:

All samples were prepared with Low Sodium Buffer (LSB) pH ~7.1 and contain 0.1% ethanol Conclusions:

Panelists found 3 µM Compound F1 was significantly more cooling than 0 µM WS-3 (p<0.05) and not significantly different in cooling than 45 µM WS-3 (p>0.05). There were no significant bitter offtastes in any of the samples (p>0.05).

TABLE 4

Average Cooling, n = 28 (14 Panelists × 2 rep). Tukey's Value = 1.359 (α = 0.05).

| Treatment | Average | SD | St Er | Tukey (5%) |
|---|---|---|---|---|
| 0 µM WS-3 | 1.9 | 2.8 | 0.5 | a |
| 3 µM Compound F1 | 5.1 | 1.4 | 0.3 | b |
| 45 µM WS-3 | 5.2 | 2.1 | 0.4 | b |

TABLE 5

Average Bitterness, n = 28 (14 Panelists × 2 rep). Tukey's Value = 0.517 (α = 0.05), 0.449 (α = 0.10).

| Treatment | Average | SD | St Er | Tukey (5%) |
|---|---|---|---|---|
| 45 µM WS-3 | 0.3 | 0.8 | 0.1 | a |
| 3 µM Compound F1 | 0.4 | 0.6 | 0.1 | a |
| 0 µM WS-3 | 0.5 | 1.1 | 0.2 | a |

TABLE 6

Selected sensory results for compounds of the invention.

| Compound | Sensory Results | n |
|---|---|---|
| E1 | Panelists found 2 µM Compound E1 was significantly more cooling than 0 µM WS-3 and significantly less cooling than 45 µM. | 26 |

TABLE 6-continued

Selected sensory results for compounds of the invention.

| Compound | Sensory Results | n |
|---|---|---|
| F1 | Panelists found 3 μM Compound F1 was significantly more cooling than 0 μM WS-3 ($p < 0.05$) and not significantly different in cooling than 45 μM WS-3 ($p > 0.05$). | 28 |
| J1 | Panelists found 3 μM Compound J1 was significantly more cooling than 0 μM WS-3 ($p < 0.05$) and not significantly different in cooling than 45 μM WS-3 ($p > 0.05$). | 28 |
| N1 | Panelists found 5 μM Compound N1 was not significantly different in cooling than 0 μM WS-3 and 45 μM WS-3 ($p > 0.05$), but had an average score between 0 μM WS-3 and 45 μM WS-3. Panelists found 5 μM Compound N1 had a significant bitter offtaste ($p < 0.05$). | 22 |
| V1 | Panelists found 5 μM Compound V1 was significantly more cooling than 0 μM WS-3 ($p < 0.05$) and not significantly different in cooling than 45 μM WS-3 ($p > 0.05$). | 28 |
| U1 | Panelists found 5 μM Compound U1 was significantly more cooling than 0 μM WS-3 ($p < 0.05$) and not significantly different in cooling than 45 μM WS-3 ($p > 0.05$). | 24 |
| W1 | Panelists found 5 μM Compound W1 was significantly more cooling than 0 μM WS-3 ($p < 0.05$) and not significantly different in cooling than 45 μM WS-3 ($p > 0.05$). | 22 |
| Z1 | Panelists found 15 μM Compound Z1 was significantly more cooling than 0 μM WS-3 ($p < 0.05$) and not significantly different in cooling than 45 μM WS-3 ($p > 0.05$). There were no significant bitter offtastes in any of the samples ($p > 0.05$). | 30 |
| B1 | Panelists found 5 μM Compound B2 was significantly more cooling than 0 μM WS-3 and significantly less cooling than 45 μM WS-3 ($p < 0.05$). There were no significant bitter offtastes in any of the samples ($p > 0.05$). | 26 |
| L2 | Panelists found 15 μM Compound L2 was significantly more cooling than 0 μM WS-3 and significantly less cooling than 45 μM WS-3 ($p < 0.05$). T | 28 |
| M2 | Panelists found 5 μM Compound M2 was significantly more cooling than 0 μM WS-3 ($p < 0.05$) and not significantly different in cooling than 45 μM WS-3 ($p > 0.05$). | 30 |
| T2 | Panelists found 16.7 μM Compound T2 was significantly more cooling than 0 μM WS-3 ($p < 0.05$) and not significantly different in cooling than 45 μM WS-3 ($p > 0.05$). | 28 |
| W2 | Panelists found 5 μM Compound W2 was significantly more cooling than 0 μM WS-3 ($p < 0.05$) and not significantly different in cooling than 45 μM WS-3 ($p > 0.05$). | 30 |
| A3 | Panelists found 15 μM Compound A3 was significantly more cooling than 0 μM WS-3 ($p < 0.05$) and not significantly different in cooling than 45 μM WS-3 ($p > 0.05$). | 30 |
| I3 | Panelists found 5 μM Compound I3 was not significantly different in cooling than 0 μM WS-3 ($p > 0.05$) and significantly less cooling than 45 μM WS-3 ($p < 0.05$). | 30 |
| K3 | Panelists found 15 μM Compound K3 was significantly more cooling than 0 μM WS-3 ($p < 0.05$) and not significantly different in cooling than 45 μM WS-3 ($p > 0.05$). | 30 |
| V3 | Panelists found 15 μM Compound V3 was significantly more cooling than 0 μM WS-3 ($p < 0.05$) and not significantly different in cooling than 45 μM WS-3 ($p > 0.05$). | 30 |
| P6 | Panelists found 90 μM Compound P6 was not significantly different in cooling than 45 μM WS-3 ($p > 0.05$) and significantly more cooling than 0 μM WS-3 ($p < 0.05$). | 16 |
| P7 | Panelists found 3 μM Compound P7 was significantly more cooling than 0 μM WS-3 ($p < 0.05$) and not significantly different in cooling than 45 μM WS-3 ($p > 0.05$). | 30 |
| Y7 | Panelists found 3 μM Compound Y7 was significantly more cooling than 0 μM WS-3 ($p < 0.05$) and not significantly different in cooling than 45 μM WS-3 ($p > 0.05$). | 26 |
| Q7 | Panelists found 3 μM Q7 was significantly more cooling than 0 μM WS-3 ($p < 0.05$) and not significantly different in cooling than 45 μM WS-3 ($p > 0.05$). | 26 |

Biological test results of various compounds have also indicated that the present compounds wherein the hAr is a five-membered heteroaryl are surprisingly much more potent than those compounds wherein the hAr is an aryl or heteroaryl which is not five-membered. Exemplifying data are provided in Tables 7 and 8 below.

TABLE 7

(T7)

R—⟨phenyl⟩—O—CH$_2$—C(O)—N(R$_1$)—CH$_2$—hAr

| R | R1 | Ar | EC$_{50}$ (μM) | EC$_{50}$ Ration (WS-3) |
|---|---|---|---|---|
| H | Ethyl | Phenyl | 9.2100 | 0.5 |
| H | Ethyl | Thienyl | 1.4500 | 4.1 |
| 4-Me | Ethyl | Phenyl | 0.7755 | 4.2 |
| 4-Me | Ethyl | Thienyl | 0.0069 | 490.0 |
| 4-Me | 2-Pyridyl | Phenyl | 4.7239 | 0.6 |
| 4-Me | 2-Pyridyl | Thienyl | 0.5053 | 25.4 |
| 4-Me | Methyl | Phenyl | >100 | NA* |
| 4-Me | Methyl | Thienyl | 0.3694 | 14.5 |
| 4-Cl | 2-Pyridyl | Phenyl | NA | NA** |
| 4-Cl | 2-Pyridyl | Thienyl | 2.3182 | 2.4 |
| 4-Br | 2-Pyridyl | Phenyl | 15.5660 | 0.2 |
| 4-Br | 2-Pyridyl | Thienyl | 2.2679 | 2.3 |

*10% at 100 μM.
**22% at 25 μM.

TABLE 8

(T8)

R—⟨phenyl⟩—CH=CH—C(O)—N(R$_1$)—CH$_2$—hAr

| R | R1 | Ar | EC$_{50}$ (μM) | EC$_{50}$ Ration (WS-3) |
|---|---|---|---|---|
| 3,4-methylenedioxy | Ethyl | Phenyl | 1.5000* | nd |
| 3,4-methylenedioxy | Ethyl | Thienyl | >0.001 | 6833.8 |

*According to WO2011/061330 A2 E Table C 3-14.

Preparation and Examples

Standard procedures and chemical transformation and related methods are well known to one skilled in the art, and such methods and procedures have been described, for example, in standard references such as Fiesers' Reagents for Organic Synthesis, John Wiley and Sons, New York, N.Y., 2002; Organic Reactions, vols. 1-83, John Wiley and Sons, New York, N.Y., 2006; March J. and Smith M., Advanced Organic Chemistry, 6th ed., John Wiley and Sons, New York, N.Y.; and Larock R. C., Comprehensive Organic Transformations, Wiley-VCH Publishers, New York, 1999. All texts and references cited herein are incorporated by reference in their entirety.

Reactions using compounds having functional groups may be performed on compounds with functional groups that may be protected. A "protected" compound or derivatives means derivatives of a compound where one or more reactive site or sites or functional groups are blocked with protecting groups. Protected derivatives are useful in the preparation of the compounds of the present invention or in themselves; the protected derivatives may be the biologically active agent. An example of a comprehensive text listing suitable protecting groups may be found in T. W. Greene, Protecting Groups in Organic Synthesis, 3rd edition, John Wiley & Sons, Inc. 1999.

Synthesis of the examples of presented compounds is illustrated in the following schemes and procedures. The general synthetic schemes and related procedures used for the preparation of the examples compounds are given hereinafter.

Scheme 1

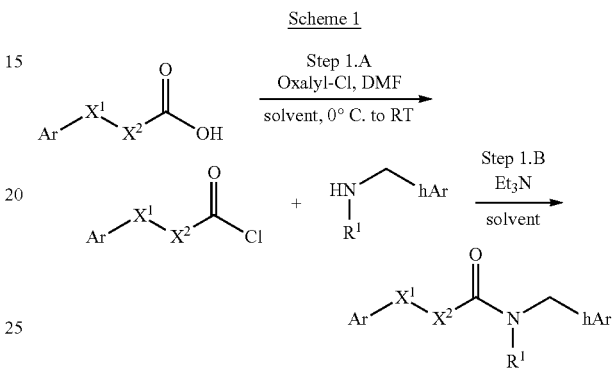

If not commercially available or differently described, all the secondary amines were prepared by reductive amination in a similar manner to example 6a or 21b utilizing one of the standard reducing agents and general conditions known to those skilled in the art such as: NaBH$_4$, LiAlH$_4$, Na(OAc)$_3$BH (STAB), Na(CN)BH$_3$, 2-picoline borane complex, 5-ethyl-2-methylpyridine borane (PEMB) or their equivalent, and DCM (dichloromethane), DCE (dichloroethane), Et$_2$O (diethyl ether), THF (tetrahydrofuran), dioxane, MeOH, EtOH, MeCN, AcOH alone or in binary or tertiary combinations thereof. One skilled in the art can readily derive the synthesis of the present compounds from the following descriptions according to the methods and principles discussed above. When commercially available, screened compounds were purchased from one from the following vendors: Enamine, Chemidiv, Princeton, Chembridge.

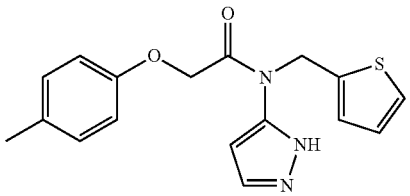 [SMILES: Cc1ccc(OCC(=O)N(Cc2cccs2)c2ccn[nH]2)cc1]

N-(1H-pyrazol-5-yl)-N-(thiophen-2-ylmethyl)-2-(p-tolyloxy)acetamide; Example 6

2-(p-tolyloxy)acetyl chloride (500 mg, 2.68 mmol. 2.0 eq) was added to a solution of pyridine (0.217 mL, 2.68 mmol, 2.0 eq) in dichloromethane. N-(thiophen-2-ylmethyl)-1H-pyrazol-5-amine (240 mg, 1.34 mmol, 1.0 eq) was added to the stirring mixture at room temperature. The reaction was allowed to stir overnight at room temperature. The mixture was diluted with dichloromethane and washed with water and brine followed by drying over sodium sulfate. The salts were filtered and washed with dichloromethane. The filtrate was concentrated and the residue was re-diluted in ethanol. Sodium hydroxide (pellets, 268 mg, 6.7 mmol, 5.0 eq) was added. The mixture was stirred at room temperature. Upon completion by LC-MS, the volatiles were removed and the residue was re-dissolved in ethyl acetate and washed with water and brine. The organic layer was dried over sodium sulfate. The crude was purified by column chromatography (ethyl acetate in hexanes) to yield 126 mg of product. The procedure was repeated on the same scale and yield 241 mg after column chromatography. The two batches were combined and re-purified via HPLC (acetonitrile in water). The collected fractions were combined and the volatiles were removed via rotary evaporation. The residue was dried three times in ethanol (10 mL, 200 proof) resulting in 288 mg (0.8796 mmol) of white solids as the desired product. Yield 16%. $^1$H NMR (400 MHz, DMSO-d6) δ 2.21 (s, 3H), 4.59 (br s, 2H), 4.98 (br s, 2H), 6.23 (br s, 1H), 6.67 (br d, J=8.5 Hz, 2H), 6.91 (br m, 2H), 7.04 (br d, J=8.1 Hz, 2H), 7.41 (m, 1H), 7.78 (br s, 1H), 12.88 (br s, 1H); M+H (328.1).

N-(thiophen-2-ylmethyl)-1H-pyrazol-5-amine; Example 6a 1H-pyrazol-5-amine (2.0 g, 1.0 eq, 24.07 mmol) and thiophene-2-carbaldehyde (2.23 mL, 1.0 eq, 24.07 mmol) were combined in methanol and stirred at room temperature with magnesium perchlorate (0.5 eq, 2.69 g) overnight. The volatiles were removed thereafter via rotary evaporation and the residue was re-diluted in ethyl acetate and washed with water then subsequently with brine, followed by drying over sodium sulfate. The salts were filtered and washed with ethyl acetate. The filtrate was concentrated to dryness followed by high vacuum treatment. The dried residue was re-dissolved in anhydrous dichloromethane (30 mL) and the system was flushed with nitrogen and sealed. The solution was chilled to 0° C. in an ice bath. LiAlH$_4$ (1.0 M in diethyl ether, 24.07 mmol, 24.07 mL, 1.0 eq) was added to the solution slowly, changing the solution color from yellow to orange. The mixture was allowed to stir overnight as the temperature increases to room temperature. The reaction was quenched with 1.0 N aqueous sodium hydroxide solution at 0° C. Majority of the volatiles were evaporated and the remaining aqueous layer was extracted with ethyl acetate. The organic layer was washed with brine and then dried over sodium sulfate. The crude was purified by column chromatography (ethyl acetate and hexanes) to give 1.97 g of yellow oil as the desired intermediate, N-(thiophen-2-ylmethyl)-1H-pyrazol-5-amine. $^1$H NMR (400 MHz, CDCl$_3$) δ 4.55 (s, 2H), 6.95 (dd, J=5.1, 3.5 Hz, 1H), 6.99-7.01 (m, 1H), 7.20 (dd, J=5.1, 1.3 Hz, 1H), 7.33 (d, J=2.4 Hz, 1H).

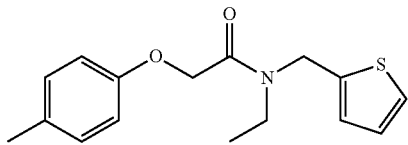 [SMILES: CCN(Cc1cccs1)C(=O)COc1ccc(C)cc1]

N-ethyl-N-(thiophen-2-ylmethyl)-2-(p-tolyloxy)acetamide; Example 21

To a round bottomed flask was added N-(thiophen-2-ylmethyl)ethanamine (0.92 g, 5 mmol), in dichloromethane (20 mL), followed by 2-(p-tolyloxy)acetyl chloride (0.93 g, 5 mmol) in 5 mL of dichloromethane and triethylamine (0.84 mL, 6 mmol). The reaction mixture was poured in water, extracted with dichloromethane (×3), washed with 1M NaOH, 1M HCl and brine, dried over MgSO$_4$ and evaporated in vacuo. The compound was purified on the biotage (dichloromethane:ethyl acetate 0-20% gradient); clean fractions were combined and concentrated. Final compound was then concentrated 3 times from ethanol. 1.259 g (4.35 mmol, 87%) of compound were obtained in purity greater than 97%. $^1$H NMR (400 MHz, DMSO-d$_6$, T=80° C.) δ $^1$H NMR (400 MHz, DMSO) δ 1.11 (br s, 3H), 2.24 (s, 3H), 3.37 (q, J=7.1 Hz, 2H), 4.71 (br s, 2H), 4.76 (s, 2H), 6.82 (d, J=8.5 Hz, 2H), 6.97 (br s, 1H), 7.04 (br s, 1H), 7.07 (d, J=8.5 Hz, 2H), 7.40 (br s, 1H); M+H (290.1).

2-(p-tolyloxy)acetyl chloride; Example 21a

To a 0° C. stirring suspension of 4.00 g of the acid (24.07 mmol; 1.0 eqmol) in 40.0 mL of dichloromethane, it was added 2.20 mL of oxalyl chloride (25.27 mmol; 1.05 eqmol) and then 56 uL of dimethylformamide (0.7221 mmol; 0.03 eqmol). The ice bath was removed and the reaction was allowed to stir at room temperature until gas evolution ceased (bubbler monitor). All the volatiles were then evaporated in vacuo. The obtained crude liquid contained some very fine precipitate, so the neat liquid was passed over a Celite pad which was flushed with hexanes. Once again, all the volatiles were then evaporated in vacuo, to obtain a clear liquid which showed only one compound at the $^1$H-NMR analysis. The obtained 4.129 g (22.36 mmol; 93%) were used in the next step without further purification. $^1$H NMR (400 MHz; CDCl$_3$) δ 2.30 (s, 3H), 4.92 (s, 2H), 6.84-6.76 (m, 2H), 7.15-7.08 (m, 2H).

N-(thiophen-2-ylmethyl)ethanamine; Example 21b

To a 0° C. chilled round bottom flask was added ethyl amine hydrochloride (4.58 g, 56.17 mmol) and thiophene-2-carbaldehyde (5.0 mL, 53.50 mmol) in methanol (20.0 mL), followed by triethylamine (7.83 mL, 56.17 mmol) and the reaction was stirred for 30 minutes. Sodiumtriacetoxyborohydride (15.87 g, 74.90 mmol) was added in one portion under vigorous stirring. The ice bath was removed and the flask was attached to a bubbler to allow gas evolution and expansion. The reaction was stirred overnight at room temp. Most of the volatiles were evaporated in vacuo. The reaction mixture was quenched by adding 1 N NaOH, and the product was extracted with dichloromethane. The organic extract was washed with brine and dried over MgSO$_4$. The volatiles were evaporated to give the crude free base N-(thiophen-2-ylmethyl)ethanamine (5.85 g, 41.42 mmol, 77%), which resulted of a purity grade >97% by $^1$H-NMR analysis, therefore it was used in the next step without any further purification. $^1$H NMR (400 MHz, CDCl$_3$) δ 1.13 (t, J=7.1 Hz, 3H), 2.71 (q, J=7.2 Hz, 2H), 4.00 (d, J=0.7 Hz, 2H), 6.90-6.97 (m, 2H), 7.21 (dd, J=5.0, 1.3 Hz, 1H).

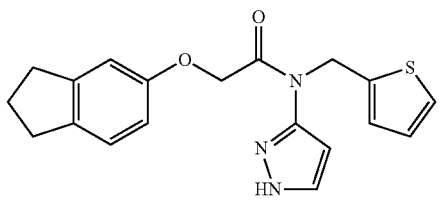 [SMILES: O=C(COc1ccc2c(c1)CCC2)N(Cc1cccs1)c1cc[nH]n1]

2-(2,3-dihydro-1H-inden-5-yloxy)-N-(1H-pyrazol-3-yl)-N-(thiophen-2-ylmethyl)acetamide; Example 1

Prepared in a similar manner to example 6 from 2-(2,3-dihydro-1H-inden-5-yloxy)acetyl chloride and N-(thiophen- 2-ylmethyl)-1H-pyrazol-4-amine. Yield: 27%. ¹H NMR (400 MHz, CDCl₃) δ 2.04 (m, 2H), 2.81 (m, 4H), 4.59 (br s, 2H), 5.07 (br s, 2H), 6.09 (br s, 1H), 6.62 (br d, J=8.4 Hz, 1H), 6.71 (br s, 1H), 6.91 (m, 2H), 7.05 (br d, J=8.2 Hz, 1H), 7.21 (dd, J=5.0, 1.3 Hz, 1H), 7.53 (d, J=2.4 Hz, 1H), 10.16 (br s, 1H); M+H (354.1).

azol-2-amine. ¹H NMR (400 MHz, CDCl₃) δ 2.27 (s, 3H), 5.01 (s, 2H), 5.25 (s, 2H), 6.76-6.70 (m, 2H), 6.91 (dd, J=5.1, 3.5 Hz, 1H), 7.08-7.01 (m, 3H), 7.21 (dd, J=5.1, 1.2 Hz, 1H), 7.52 (d, J=1.0 Hz, 1H); M+H (329.1).

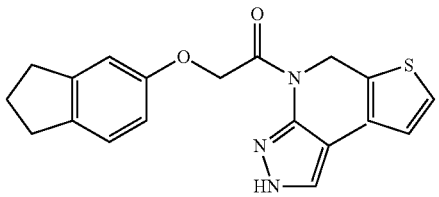 [SMILES: Cc1c[nH]nc1N(Cc1cccs1)C(=O)COc1ccc2c(c1)CCC2]

2-(2,3-dihydro-1H-inden-5-yloxy)-N-(4-methyl-1H-pyrazol-3-yl)-N-(thiophen-2-ylmethyl)acetamide; Example 2

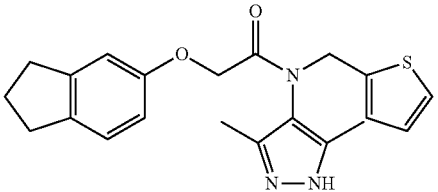

2-(2,3-dihydro-1H-inden-5-yloxy)-N-(3,5-dimethyl-1H-pyrazol-4-yl)-N-(thiophen-2-ylmethyl)acetamide; Example 7

Prepared in a similar manner to example 6 from 2-(2,3-dihydro-1H-inden-5-yloxy)acetyl chloride and 4-methyl-N-(thiophen-2-ylmethyl)-1H-pyrazol-5-amine. Yield: 48%. ¹H NMR (400 MHz, CDCl₃) δ 1.97 (s, 3H), 2.00-2.09 (m, 2H), 2.82 (m, 5H), 4.32 (br s, 2H), 4.92 (br s, 2H), 6.60 (br dd, J=8.2, 2.5 Hz, 1H), 6.68 (br d, J=2.4 Hz, 1H), 6.86 (br dd, J=3.4, 1.2 Hz, 1H), 6.91 (dd, J=5.1, 3.4 Hz, 1H), 7.06 (br d, J=8.2 Hz, 1H), 7.24 (dd, J=5.1, 1.2 Hz, 1H), 7.32 (br s, 1H), 9.98 (br s, 1H); M+H (368.1).

Prepared in a similar manner to example 6 from 2-(2,3-dihydro-1H-inden-5-yloxy)acetyl chloride and 3,5-dimethyl-N-(thiophen-2-ylmethyl)-1H-pyrazol-4-amine. Yield 54%. ¹H NMR (400 MHz, CDCl₃) δ 1.91 (s, 6H), 2.01-2.10 (m, 2H), 2.82 (m, 4H), 4.25 (s, 2H), 4.89 (br s, 2H), 6.60 (dd, J=8.2, 2.5 Hz, 1H), 6.68 (d, J=2.3 Hz, 1H), 6.84-6.87 (m, 1H), 6.90 (dd, J=5.1, 3.5 Hz, 1H), 7.06 (d, J=8.2 Hz, 1H), 7.24 (dd, J=5.1, 1.2 Hz, 1H); M+H (382.2).

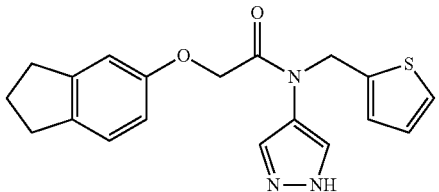 [SMILES: O=C(COc1ccc2c(c1)CCC2)N(Cc1cccs1)c1cn[nH]c1]

2-(2,3-dihydro-1H-inden-5-yloxy)-N-(1H-pyrazol-4-yl)-N-(thiophen-2-ylmethyl)acetamide; Example 3

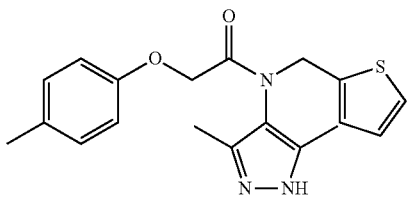

N-(3,5-dimethyl-1H-pyrazol-4-yl)-N-(thiophen-2-ylmethyl)-2-(p-tolyloxy)acetamide; Example 8

Prepared in a similar manner to example 6 from 2-(2,3-dihydro-1H-inden-5-yloxy)acetyl chloride and N-(thiophen-2-ylmethyl)-1H-pyrazol-4-amine. Yield: 40%. ¹H NMR (400 MHz, DMSO-d6) δ 1.98 (m, 2H), 2.77 (m, 4H), 4.49 (s, 2H), 4.87 (s, 2H), 6.54 (br dd, J=8.2, 2.5 Hz, 1H), 6.64 (br d, J=2.0 Hz, 1H), 6.88 (br d, J=2.4 Hz, 1H), 6.94 (dd, J=5.1, 3.4 Hz, 1H), 7.06 (br d, J=8.2 Hz, 1H), 7.45 (dd, J=5.1, 1.2 Hz, 1H), 7.62 (br s, 2H), 12.98 (br s, 1H); M+H (354.1).

Prepared in a similar manner to example 6 from 2-(p-tolyloxy)acetyl chloride and 3,5-dimethyl-N-(thiophen-2-ylmethyl)-1H-pyrazol-4-amine. Yield 83%. ¹H NMR (400 MHz, DMSO-d6) δ 1.79 (s, 6H), 4.23 (br s, 2H), 4.67 (br s, 1H), 4.84 (br s, 1H), 6.61-6.70 (m, 2H), 6.80 (dd, J=3.4, 1.2 Hz, 1H), 6.91 (dd, J=5.1, 3.4 Hz, 1H), 7.03 (m, 2H), 7.46 (dd, J=5.1, 1.2 Hz, 1H), 12.36 (br s, 1H); M+H (356.1).

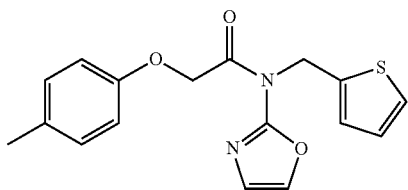 [SMILES: Cc1ccc(OCC(=O)N(Cc2cccs2)c2ncco2)cc1]

N-(oxazol-2-yl)-N-(thiophen-2-ylmethyl)-2-(p-tolyloxy)acetamide; Example 4

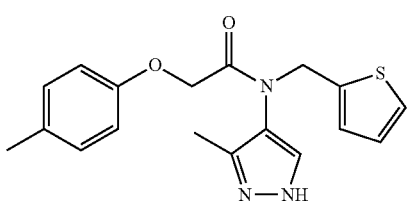 [SMILES: Cc1ccc(OCC(=O)N(Cc2cccs2)c2c[nH]nc2C)cc1]

N-(3-methyl-1H-pyrazol-4-yl)-N-(thiophen-2-ylmethyl)-2-(p-tolyloxy)acetamide; Example 9

Prepared in a similar manner to example 21 from 2-(p-tolyloxy)acetyl chloride and N-(thiophen-2-ylmethyl)ox- Prepared in a similar manner to example 6 from 2-(p-tolyloxy)acetyl chloride and 3-methyl-N-(thiophen-2-ylmethyl)-1H-pyrazol-4-amine. ¹H NMR (400 MHz, DMSO) δ ¹H NMR (400 MHz, CDCl₃) δ 1.96 (s, 3H), 2.24 (s, 3H), 4.32 (br s, 2H), 4.91 (br s, 2H), 6.69 (d, J=8.6 Hz, 2H), 6.84-6.87 (m, 1H), 6.89 (dd, J=5.1, 3.5 Hz, 1H), 7.01 (d, J=8.6 Hz, 2H), 7.22 (dd, J=5.1, 1.2 Hz, 1H), 7.31 (br s, 1H); M+H (342.1).

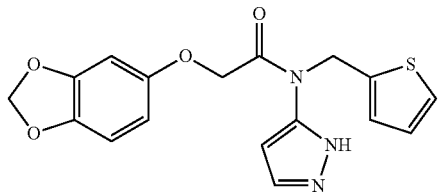 [SMILES: O=C(COc1ccc2c(c1)OCO2)N(Cc1cccs1)c1ccn[nH]1]

2-(benzo[d][1,3]dioxol-5-yloxy)-N-(1H-pyrazol-5-yl)-N-(thiophen-2-ylmethyl)acetamide; Example 12

Prepared in a similar manner to example 6 from 2-(benzo[d][1,3]dioxol-5-yloxy)acetyl chloride and N-(thiophen-2-ylmethyl)-1H-pyrazol-5-amine. Yield 28%. $^1$H NMR (400 MHz, CDCl$_3$) δ 4.53 (s, 2H), 5.06 (s, 2H), 5.86 (s, 2H), 6.05 (br d, J=2.1 Hz, 1H), 6.21 (dd, J=8.5, 2.5 Hz, 1H), 6.44 (d, J=2.5 Hz, 1H), 6.60 (d, J=8.5 Hz, 1H), 6.90 (m, 2H), 7.20 (dd, J=5.0, 1.3 Hz, 1H), 7.50 (d, J=2.4 Hz, 1H), 10.96 (br s, 1H); M+H (358.1).

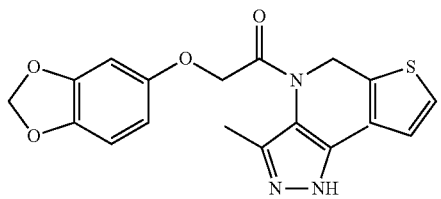 [SMILES: Cc1n[nH]c(C)c1N(Cc1cccs1)C(=O)COc1ccc2c(c1)OCO2]

2-(benzo[d][1,3]dioxol-5-yloxy)-N-(3,5-dimethyl-1H-pyrazol-4-yl)-N-(thiophen-2-ylmethyl)acetamide; Example 13

Prepared in a similar manner to example 6 from 2-(benzo[d][1,3]dioxol-5-yloxy)acetyl chloride and 3,5-dimethyl-N-(thiophen-2-ylmethyl)-1H-pyrazol-4-amine. $^1$H NMR (400 MHz, CDCl$_3$) δ 1.91 (s, 6H), 4.21 (s, 2H), 4.88 (br s, 2H), 5.90 (s, 2H), 6.20 (dd, J=8.5, 2.6 Hz, 1H), 6.45 (d, J=2.5 Hz, 1H), 6.64 (d, J=8.5 Hz, 1H), 6.85 (br dd, J=2.0, 1.4 Hz, 1H), 6.90 (dd, J=5.1, 3.4 Hz, 1H), 7.24 (dd, J=5.1, 1.3 Hz, 1H), 9.91 (br s, 1H); M+H (386.1).

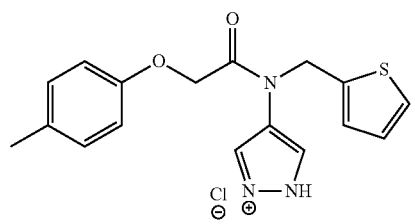 [SMILES: Cc1ccc(OCC(=O)N(Cc2cccs2)c2c[nH][nH+]c2)cc1 ; [Cl-]]

4-(N-(thiophen-2-ylmethyl)-2-(p-tolyloxy)acetamido)-1H-pyrazol-2-ium chloride; Example 14

257 mg of N-(1H-pyrazol-4-yl)-N-(thiophen-2-ylmethyl)-2-(p-tolyloxy)acetamide from example 15 were dissolved in EtOH (2.0 mL) and then a 2.0 M solution of HCl in Et$_2$O was added: a white solid crashed out of solution. After decanting, the liquids were taken away with a pipette and the obtained salt was washed with three aliquots of Et$_2$O. The crystals were then dissolved in EtOH (nearly 5.0 mL) and concentrated at the rotavap. This step was repeated for a total of three times. The solids were left overnight under high vacuum. In this way, 120 mg of desired product were obtained. $^1$H NMR (400 MHz, DMSO-d6, T=80° C.) δ 2.22 (s, 3H), 4.51 (s, 2H), 4.91 (s, 2H), 5.85 (m, 2H), 6.70 (br d, J=7.7, 2H), 6.90 (br s, 1H), 6.94 (m, 1H), 7.04 (br d, J=7.7, 2H), 7.39 (dt, J=1.1, 5.0, 1H), 7.57 (br s, 2H); M+H (328.1).

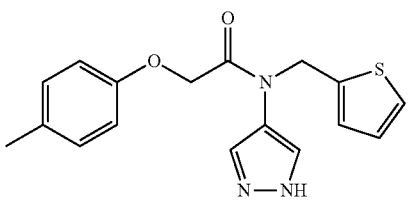

N-(1H-pyrazol-4-yl)-N-(thiophen-2-ylmethyl)-2-(p-tolyloxy)acetamide; Example 15

Prepared in a similar manner to example 6 from 2-(p-tolyloxy)acetyl chloride and N-(thiophen-2-ylmethyl)-1H-pyrazol-4-amine. Yield 60%. $^1$H NMR (400 MHz, CDCl$_3$) δ 2.25 (s, 3H), 4.42 (s, 2H), 4.95 (s, 2H), 6.71 (d, J=8.2 Hz, 2H), 6.88 (d, J=2.4 Hz, 1H), 6.92 (dd, J=5.1, 3.5 Hz, 1H), 7.03 (br d, J=8.2 Hz, 2H), 7.24 (dd, J=5.1, 1.2 Hz, 1H), 7.41 (br s, 2H). M+H (328.1).

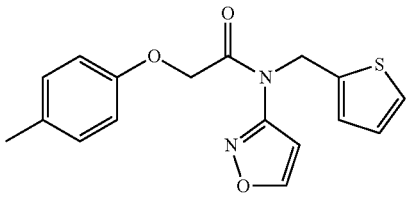 [SMILES: Cc1ccc(OCC(=O)N(Cc2cccs2)c2ccon2)cc1]

N-(isoxazol-3-yl)-N-(thiophen-2-ylmethyl)-2-(p-tolyloxy)acetamide; Example 16

Prepared in a similar manner to example 21 from 2-(p-tolyloxy)acetyl chloride and N-(thiophen-2-ylmethyl)isoxazol-3-amine. Yield 60%. $^1$H NMR (400 MHz, DMSO-d6) δ 2.21 (s, 3H), 4.96 (br s, 2H), 5.19 (br s, 2H), 6.71 (d, J=8.6 Hz, 2H), 6.94 (m, 2H), 7.05 (m, 3H), 7.45 (dd, J=5.1, 1.3 Hz, 1H), 8.95 (d, J=1.9 Hz, 1H); M+H (329.1).

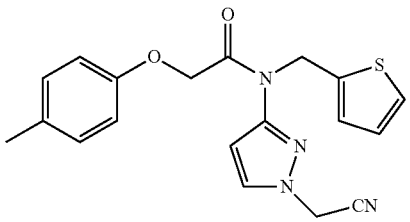 [SMILES: Cc1ccc(OCC(=O)N(Cc2cccs2)c2ccn(CC#N)n2)cc1]

N-(1-(cyanomethyl)-1H-pyrazol-3-yl)-N-(thiophen-2-ylmethyl)-2-(p-tolyloxy)acetamide; Example 17

N-(oxazol-2-yl)-N-(thiophen-2-ylmethyl)-2-(p-tolyloxy)acetamide (example 4) (430 mgs, 1.313 mmol) was dissolved in N, N-dimethylformamide. Sodium hydride (60% in mineral oil, 55 mgs, 1.38 mmol) was added at 0° C. and a bubbler was attached to observe gas evolution. The reaction was stirred with gradual warming to room temperature until gas evolution ceased. 2-bromoacetonitrile (92 μL, 1.38 mmol) was added at room temperature and the reaction was allowed to stir overnight. Upon completion by TLC (5:5 ethyl acetate:hexanes), the reaction was carefully quenched with water at 0° C. The reaction mixture was concentrated via rotary evaporation. The residue was taken up in water and extracted with ethyl acetate. The organic layer was washed with brine and dried over sodium sulfate. The crude material was purified by column chromatography (ethyl acetate and hexanes). (Yield 64%, the other possible isomer of N-alkylation was obtained as a minor product; data not reported). $^1$H NMR (400 MHz, DMSO-d6) δ 2.26 (s, 3H), 4.65 (broad, s, 2H), 4.96 (s, 2H), 5.05 (s, 2H), 6.09 (broad, s, 1H), 6.73 (d, 2H, J=8.8 Hz), 6.91 (m, 2H), 7.03 (d, 2H, J=8.4 Hz), 7.21 (dd, 1H, J1=4.8 Hz, J2=1.2 Hz), 7.50 (broad, s, 1H). Further two-dimensional NMR studies confirmed the structure assignment as the correct isomer; M+H (329.1).

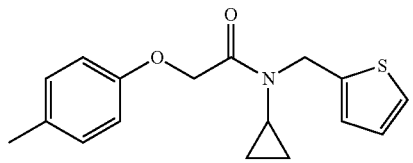

N-cyclopropyl-N-(thiophen-2-ylmethyl)-2-(p-tolyloxy)acetamide; Example 22

Prepared in a similar manner to example 21 from 2-(p-tolyloxy)acetyl chloride and N-(thiophen-2-ylmethyl)cyclopropanamine. $^1$H NMR (400 MHz, DMSO-d$_6$, T=50° C.) δ 0.87 (m, 4H), 2.23 (s, 3H), 2.72 (br m, 1H), 4.66 (br s, 2H), 4.93 (br s, 2H), 6.79-6.72 (m, 2H), 6.98 (br m, 2H), 7.09-7.02 (m, 2H), 7.42 (br dd, J=5.0, 1.0 Hz, 1H); M+H (302.1).

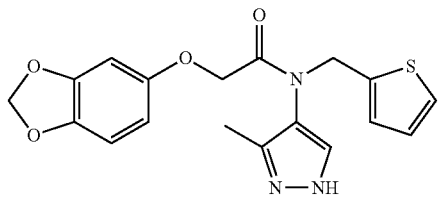 [SMILES: Cc1n[nH]cc1N(Cc1cccs1)C(=O)COc1ccc2c(c1)OCO2]

2-(benzo[d][1,3]dioxol-5-yloxy)-N-(3-methyl-1H-pyrazol-4-yl)-N-(thiophen-2-ylmethyl)acetamide; Example 18

Prepared in a similar manner to example 6 from 2-(benzo[d][1,3]dioxol-5-yloxy)acetyl chloride and 3-methyl-N-(thiophen-2-ylmethyl)-1H-pyrazol-4-amine. $^1$H NMR (400 MHz, CDCl$_3$) δ 1.96 (s, 3H), 4.28 (br s, 2H), 4.91 (br s, 2H), 5.87 (s, 2H), 6.18 (dd, J=8.5, 2.6 Hz, 1H), 6.42 (d, J=2.5 Hz, 1H), 6.62 (d, J=8.5 Hz, 1H), 6.83-6.86 (m, 1H), 6.89 (dd, J=5.1, 3.5 Hz, 1H), 7.22 (dd, J=5.1, 1.3 Hz, 1H), 7.31 (br s, 1H); M+H (372.1).

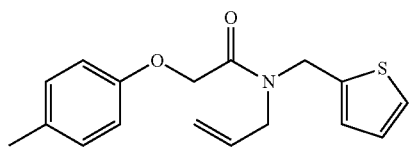

N-allyl-N-(thiophen-2-ylmethyl)-2-(p-tolyloxy)acetamide; Example 23

Prepared in a similar manner to example 21 from 2-(p-tolyloxy)acetyl chloride and N-(thiophen-2-ylmethyl)prop-2-en-1-amine. $^1$H NMR (400 MHz, DMSO-d$_6$, T=80° C.) δ 2.24 (s, 3H), 3.98 (d, J=5.5 Hz, 2H), 4.68 (br s, 2H), 4.77 (br s, 2H), 5.18 (d, J=15.3 Hz, 2H), 5.80 (br s, 1H), 6.78-6.83 (m, 2H), 6.95-7.00 (br m, 1H), 7.03 (br s, 1H), 7.05-7.10 (m, 2H), 7.42 (br d, J=4.6 Hz, 1H); M+H (302.1).

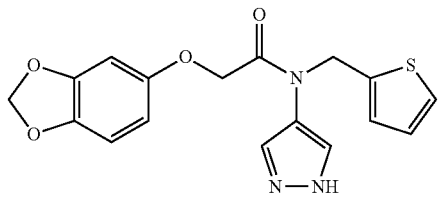 [SMILES: O=C(COc1ccc2c(c1)OCO2)N(Cc1cccs1)c1cn[nH]c1]

2-(benzo[d][1,3]dioxol-5-yloxy)-N-(1H-pyrazol-4-yl)-N-(thiophen-2-ylmethyl)acetamide; Example 20

Prepared in a similar manner to example 6 from 2-(benzo[d][1,3]dioxol-5-yloxy)acetyl chloride and N-(thiophen-2-ylmethyl)-1H-pyrazol-4-amine. Yield 73%. $^1$H NMR (400 MHz, CDCl$_3$) δ 4.38 (s, 2H), 4.94 (br s, 2H), 5.90 (s, 2H), 6.21 (dd, J=8.5, 2.6 Hz, 1H), 6.45 (d, J=2.5 Hz, 1H), 6.64 (d, J=8.5 Hz, 1H), 6.88 (br s, 1H), 6.92 (dd, J=5.1, 3.5 Hz, 1H), 7.24 (dd, J=5.1, 1.3 Hz, 1H), 7.41 (br s, 2H), 10.37 (br s, 1H); M+H (358.1).

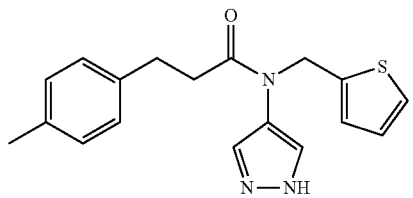 [SMILES: Cc1ccc(CCC(=O)N(Cc2cccs2)c2cn[nH]c2)cc1]

N-(1H-pyrazol-4-yl)-N-(thiophen-2-ylmethyl)-3-p-tolylpropanamide; Example 24

Prepared in a similar manner to example 21 from 3-p-tolylpropanoyl chloride and N-(thiophen-2-ylmethyl)-1H-pyrazol-4-amine. Yield 76%. $^1$H NMR (400 MHz, DMSO-d6) δ 2.22 (s, 3H), 2.36 (t, J=7.8 Hz, 2H), 2.72 (t, J=7.8 Hz, 2H), 4.84 (s, 2H), 6.78-6.85 (m, 1H), 6.91 (dd, J=5.1, 3.4 Hz, 1H), 6.97 (d, J=8.1 Hz, 2H), 7.02 (d, J=7.9 Hz, 2H), 7.24 (d, J=1.7 Hz, 1H), 7.41 (dd, J=5.1, 1.2 Hz, 1H), 7.57 (s, 1H), 12.89 (s, 1H); M+H (326.1).

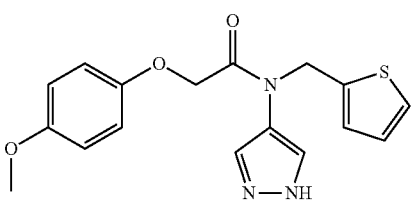 [SMILES: COc1ccc(OCC(=O)N(Cc2cccs2)c2cn[nH]c2)cc1]

2-(4-methoxyphenoxy)-N-(1H-pyrazol-4-yl)-N-(thiophen-2-ylmethyl)acetamide; Example 25

Prepared in a similar manner to example 6 from 2-(4-methoxyphenoxy)acetyl chloride and 2-(4-methoxyphenoxy)acetyl chloride. ¹H NMR (400 MHz, CDCl₃) δ 3.74 (br s, 3H), 4.40 (br s, 2H), 4.95 (br s, 2H), 6.78 (br s, 3H), 6.88 (br m, 1H), 6.92 (dd, J=5.1, 3.5 Hz, 1H), 7.24 (dd, J=5.1, 1.3 Hz, 1H), 7.41 (s, 2H); M+H (344.1).

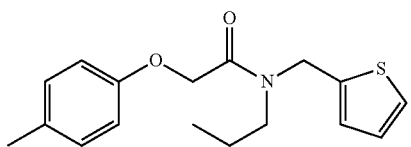 [SMILES: CCCN(Cc1cccs1)C(=O)COc1ccc(C)cc1]

N-propyl-N-(thiophen-2-ylmethyl)-2-(p-tolyloxy)acetamide; Example 28

Prepared in a similar manner to example 21 from 2-(p-tolyloxy)acetyl chloride and N-(thiophen-2-ylmethyl)propan-1-amine. ¹H NMR (400 MHz, DMSO-d₆, T=80° C.) δ 0.84 (t, J=7.4 Hz, 3H), 1.55 (br s, 2H), 2.24 (s, 3H), 3.25-3.31 (br m, 2H), 4.71 (br s, 2H), 4.76 (s, 2H), 6.81 (d, J=8.6 Hz, 2H), 6.97 (br s, 1H), 7.04 (br s, 1H), 7.05-7.10 (m, 2H), 7.40 (br s, 1H); M+H (304.1).

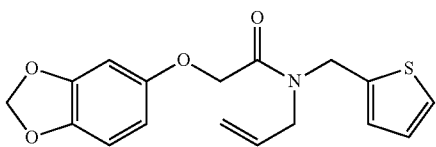 [SMILES: C=CCN(Cc1cccs1)C(=O)COc1ccc2c(c1)OCO2]

N-allyl-2-(benzo[d][1,3]dioxol-5-yloxy)-N-(thiophen-2-ylmethyl)acetamide; Example 30

This compound was Purchased from Enamine. M+H (332.1).

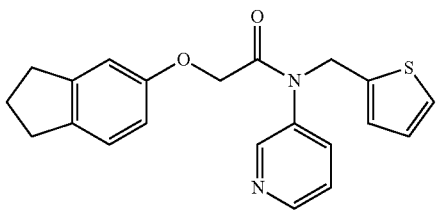 [SMILES: O=C(COc1ccc2c(c1)CCC2)N(Cc1cccs1)c1cccnc1]

2-(2,3-dihydro-1H-inden-5-yloxy)-N-(pyridin-3-yl)-N-(thiophen-2-ylmethyl)acetamide; Example 34

Prepared in a similar manner to example 21 from 2-(2,3-dihydro-1H-inden-5-yloxy)acetyl chloride and N-(thiophen-2-ylmethyl)pyridin-3-amine. ¹H NMR (400 MHz, DMSO-d6) δ 1.98 (m, 2H), 2.68-2.83 (m, 5H), 4.45 (br s, 2H), 5.04 (br s, 2H), 6.48 (br s, 1H), 6.60 (br s, 1H), 6.84 (br s, 1H), 6.91 (dd, J=5.1, 3.4 Hz, 1H), 7.05 (br d, J=8.1 Hz, 1H), 7.36-7.50 (m, 2H), 7.70 (ddd, J=8.1, 2.5, 1.5 Hz, 1H), 8.44 (dd, J=2.6, 0.6 Hz, 1H), 8.53 (br s, 1H); M+H (365.1).

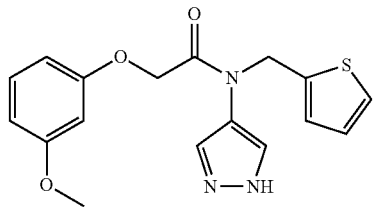 [SMILES: COc1cccc(OCC(=O)N(Cc2cccs2)c2cn[nH]c2)c1]

2-(3-methoxyphenoxy)-N-(1H-pyrazol-4-yl)-N-(thiophen-2-ylmethyl)acetamide; Example 35

Prepared in a similar manner to example 6 from 2-(3-methoxyphenoxy)acetyl chloride and N-(thiophen-2-ylmethyl)-1H-pyrazol-4-amine. ¹H NMR (400 MHz, CDCl₃) δ 3.73 (s, 3H), 4.43 (s, 2H), 4.94 (s, 2H), 6.36 (ddd, J=8.2, 2.4, 0.7 Hz, 1H), 6.41 (t, J=2.4 Hz, 1H), 6.50 (ddd, J=8.3, 2.4, 0.7 Hz, 1H), 6.85-6.93 (m, 2H), 7.11 (t, J=8.2 Hz, 1H), 7.23 (dd, J=5.1, 1.3 Hz, 1H), 7.41 (s, 2H), 11.24 (br s, 1H); M+H (344.1).

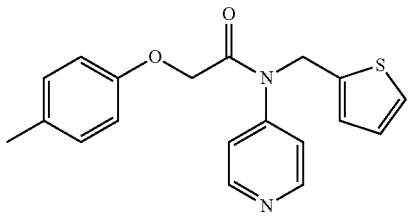 [SMILES: Cc1ccc(OCC(=O)N(Cc2cccs2)c2ccncc2)cc1]

N-(pyridin-4-yl)-N-(thiophen-2-ylmethyl)-2-(p-tolyloxy)acetamide; Example 36

Prepared in a similar manner to example 21 from 2-(p-tolyloxy)acetyl chloride and N-(thiophen-2-ylmethyl)pyridin-4-amine. ¹H NMR ¹H NMR (400 MHz, DMSO-d6) δ 2.20 (s, 3H), 4.66 (br s, 2H), 5.11 (s, 2H), 6.63 (d, J=8.6 Hz, 2H), 6.85-6.95 (m, 2H), 7.03 (d, J=8.6 Hz, 2H), 7.33-7.39 (m, 2H), 7.40-7.46 (m, 1H), 8.54-8.61 (m, 2H); M+H (339.1).

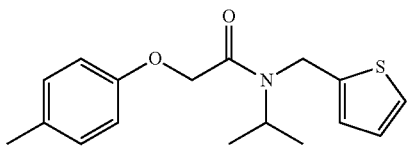 [SMILES: Cc1ccc(OCC(=O)N(Cc2cccs2)C(C)C)cc1]

N-isopropyl-N-(thiophen-2-ylmethyl)-2-(p-tolyloxy)acetamide; Example 38

Prepared in a similar manner to example 21 from 2-(p-tolyloxy)acetyl chloride and N-(thiophen-2-ylmethyl)propan-2-amine. Room temperature ¹H-NMR showed a mixture of rotamers in ~2:1 ratio: ¹H NMR (400 MHz, DMSO-d6) δ 1.12 (minor) (d, J=6.8 Hz, 6H), 1.17 (major) (d, J=6.6 Hz, 6H), 2.21 (minor) (s, 3H), 2.23 (major) (s, 3H), 4.20-4.06 (minor) (m, 1H), 4.50-4.34 (major) (m, 1H), 4.58 (major) (s, 2H), 4.66 (minor) (s, 2H), 4.72 (minor) (s, 2H), 4.82 (major) (s, 2H), 6.70 (minor) (d, J=8.1 Hz, 2H), 6.81 (major) (d, J=8.5 Hz, 2H), 6.89 (major) (dd, J=5.0, 3.5 Hz, 1H), 7.14-6.95 (m, 3H), 7.33 (major) (dd, J=5.1, 1.0 Hz, 1H), 7.48 (minor) (d, J=4.8 Hz, 1H); M+H (304.1).

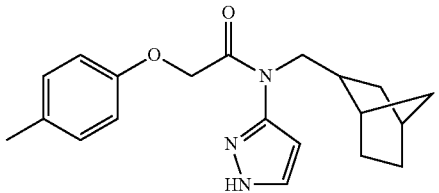 [SMILES: Cc1ccc(OCC(=O)N(CC2CC3CCC2C3)c2cc[nH]n2)cc1]

N-(bicyclo[2.2.1]heptan-2-ylmethyl)-N-(1H-pyrazol-3-yl)-2-(p-tolyloxy)acetamide; Example 39

Prepared in a similar manner to example 6 from 2-(p-tolyloxy)acetyl chloride and N-(bicyclo[2.2.1]heptan-2-ylmethyl)-1H-pyrazol-3-amine. Yield 18%. $^1$H NMR (400 MHz, CDCl$_3$) δ 0.81 (ddd, J=13.1, 5.2, 2.9 Hz, 1H), 0.96-1.06 (m, 1H), 1.26-1.51 (m, 5H), 1.70 (m, 1H), 1.76-1.86 (m, 1H), 2.10 (br t, J=4.0 Hz, 1H), 2.24 (s, 3H), 2.94 (br s, 1H), 4.34 (q, J=15.0 Hz, 2H), 4.52 (m, 1H), 6.21 (d, J=2.4 Hz, 1H), 6.71 (d, J=8.6 Hz, 2H), 7.01 (d, J=8.6 Hz, 2H), 7.62 (d, J=2.4 Hz, 1H); M+H (340.2).

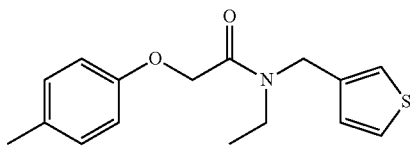 [SMILES: CCN(Cc1ccsc1)C(=O)COc1ccc(C)cc1]

N-ethyl-N-(thiophen-3-ylmethyl)-2-(p-tolyloxy)acetamide; Example 41

Prepared in a similar manner to example 21 from 2-(p-tolyloxy)acetyl chloride and N-(thiophen-3-ylmethyl)ethanamine. Room temperature $^1$H-NMR showed a mixture of rotamers in ~2:1 ratio: $^1$H NMR (400 MHz, DMSO-d6) δ 0.98 (minor) (t, J=7.1 Hz, 3H), 1.11 (major) (t, J=7.1 Hz, 3H), 2.21 (minor) (s, 3H), 2.23 (major) (s, 3H), 3.31-3.24 (m, 2H), 4.47 (major) (s, 2H), 4.54 (minor) (s, 1H), 4.75 (minor) (s, 1H), 4.80 (major) (s, 2H), 6.74 (minor) (d, J=8.5 Hz, 2H), 6.81 (major) (d, J=8.6 Hz, 2H), 6.97 (major) (dd, J=4.9, 1.1 Hz, 1H), 7.11-7.02 (m, 3H), 7.32 (major) (d, J=1.8 Hz, 1H), 7.42 (minor) (d, J=1.9 Hz, 1H), 7.48 (major) (dd, J=4.9, 3.0 Hz, 1H), 7.56 (minor) (dd, J=4.9, 3.0 Hz, 1H); M+H (290.1).

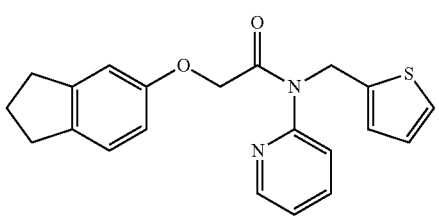 [SMILES: O=C(COc1ccc2c(c1)CCC2)N(Cc1cccs1)c1ccccn1]

N-(bicyclo[2.2.1]heptan-2-ylmethyl)-N-(1H-pyrazol-3-yl)-2-(p-tolyloxy)acetamide; Example 43

Prepared in a similar manner to example 21 from 2-(2,3-dihydro-1H-inden-5-yloxy)acetyl chloride and N-(thiophen-2-ylmethyl)pyridin-2-amine. $^1$H NMR (400 MHz, DMSO-d6) δ 1.89-2.06 (m, 2H), 2.75 (dd, J=15.7, 7.7 Hz, 4H), 4.76 (s, 2H), 5.20 (s, 2H), 6.47 (dd, J=8.2, 2.5 Hz, 1H), 6.58 (d, J=2.3 Hz, 1H), 6.86-6.95 (m, 2H), 7.03 (d, J=8.2 Hz, 1H), 7.31 (ddd, J=7.4, 4.9, 0.9 Hz, 1H), 7.39 (dd, J=4.9, 1.4 Hz, 1H), 7.46 (d, J=8.2 Hz, 1H), 7.88 (ddd, J=8.1, 7.5, 2.0 Hz, 1H), 8.46 (ddd, J=4.9, 1.9, 0.8 Hz, 1H); M+H (365.1).

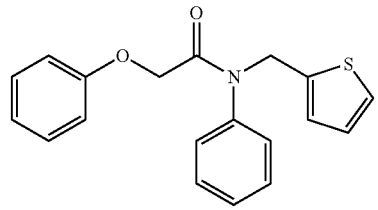 [SMILES: O=C(COc1ccccc1)N(Cc1cccs1)c1ccccc1]

2-phenoxy-N-phenyl-N-(thiophen-2-ylmethyl)acetamide; Example 45

Prepared in a similar manner to example 21 from 2-phenoxyacetyl chloride and N-(thiophen-2-ylmethyl)aniline. $^1$H NMR (400 MHz, DMSO-d6) δ 4.44 (br s, 2H), 5.01 (br s, 2H), 6.74 (br d, J=8.0 Hz, 2H), 6.84 (br s, 1H), 6.89-6.95 (m, 2H), 7.22-7.29 (m, 4H), 7.36-7.45 (m, 4H); M+H (324.1).

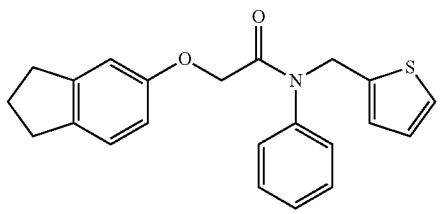 [SMILES: O=C(COc1ccc2c(c1)CCC2)N(Cc1cccs1)c1ccccc1]

2-(2,3-dihydro-1H-inden-5-yloxy)-N-phenyl-N-(thiophen-2-ylmethyl)acetamide; Example 47

Prepared in a similar manner to example 21 from 2-(2,3-dihydro-1H-inden-5-yloxy)acetyl chloride and N-(thiophen-2-ylmethyl)aniline. $^1$H NMR (400 MHz, DMSO-d6) δ 1.98 (m, 2H), 2.70-2.88 (m, 4H), 4.38 (br s, 2H), 5.00 (br s, 2H), 6.49 (br d, J=8.3 Hz, 1H), 6.59 (br s, 1H), 6.83 (br s, 1H), 6.91 (dd, J=5.0, 3.5 Hz, 1H), 7.05 (br d, J=8.2 Hz, 1H), 7.25 (d, J=7.1 Hz, 2H), 7.33-7.47 (m, 4H); M+H (364.1).

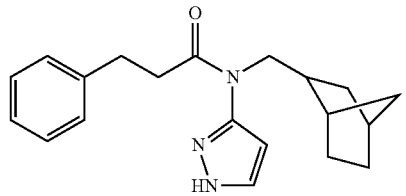 [SMILES: O=C(CCc1ccccc1)N(CC1CC2CCC1C2)c1cc[nH]n1]

N-(bicyclo[2.2.1]heptan-2-ylmethyl)-3-phenyl-N-(1H-pyrazol-3-yl)propanamide; Example 50

Prepared in a similar manner to example 6 from 3-phenylpropanoyl chloride and N-(bicyclo[2.2.1]heptan-2-ylmethyl)-1H-pyrazol-3-amine. Yield 9%. $^1$H NMR (400 MHz, CDCl$_3$) δ 0.71 (ddd, J=13.0, 5.3, 2.9 Hz, 1H), 0.90-1.01 (m, 1H), 1.24-1.50 (m, 6H), 1.62-1.78 (m, 3H), 2.05-2.09 (m, 1H), 2.33 (m, 2H), 2.84-2.93 (m, 3H), 4.41-4.50 (m, 1H), 6.01 (d, J=2.4 Hz, 1H), 7.05-7.12 (m, 2H), 7.19-7.12 (m, 1H), 7.25-7.19 (m, 2H), 7.54 (d, J=2.4 Hz, 1H); M+H (324.2).

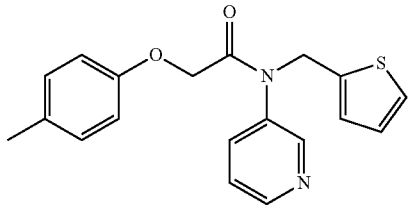 [SMILES: Cc1ccc(OCC(=O)N(Cc2cccs2)c2cccnc2)cc1]

N-(pyridin-3-yl)-N-(thiophen-2-ylmethyl)-2-(p-tolyloxy)acetamide; Example 51

Prepared in a similar manner to example 21 from 2-(p-tolyloxy)acetyl chloride and N-(thiophen-2-ylmethyl)pyridin-3-amine. ¹H NMR (400 MHz, DMSO-d6) δ 2.20 (s, 3H), 4.46 (br s, 2H), 5.04 (br s, 2H), 6.62 (br d, J=6.7 Hz, 2H), 6.84 (br s, 1H), 6.91 (dd, J=5.1, 3.4 Hz, 1H), 7.03 (br d, J=8.3 Hz, 2H), 7.41-7.49 (m, 2H), 7.71 (ddd, J=8.1, 2.5, 1.6 Hz, 1H), 8.47-8.42 (m, 1H), 8.54 (br d, J=3.5 Hz, 1H); M+H (339.1).

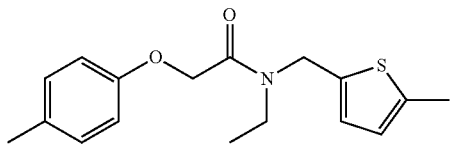

N-ethyl-N-((5-methylthiophen-2-yl)methyl)-2-(p-tolyloxy)acetamide; Example 54

Prepared in a similar manner to example 21 from 2-(p-tolyloxy)acetyl chloride and N-((5-methylthiophen-2-yl)methyl)ethanamine. Yield: 38%. Room temperature ¹H-NMR showed a mixture of rotamers in ~2:1 ratio: ¹H NMR (400 MHz, DMSO-d6) δ 1.00 (minor) (t, J=7.1 Hz, 3H), 1.13 (major) (t, J=7.1 Hz, 3H), 2.23 (s, 3H), 2.38 (major) (s, 3H), 2.41 (minor) (s, 3H), 3.29 (m, 2H), 4.54 (major) (s, 2H), 4.65 (minor) (s, 2H), 4.76 (s, 2H), 6.64-6.57 (major) (br m, 1H), 6.68 (minor) (br m, 1H), 6.84-6.75 (m, 3H), 6.87 (minor) (d, J=3.3 Hz, 1H), 7.07 (br d, J=8.5 Hz, 2H).

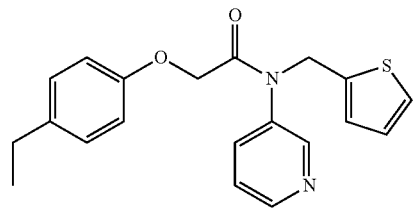

N 2-(4-ethylphenoxy)-N-(pyridin-3-yl)-N-(thiophen-2-ylmethyl)acetamide; Example 59

Prepared in a similar manner to example 21 from 2-(4-ethylphenoxy)acetyl chloride and N-(thiophen-2-ylmethyl) pyridin-3-amine. ¹H NMR (400 MHz, CDCl₃) δ 1.18 (t, J=7.6 Hz, 1H), 2.56 (q, J=7.6 Hz, 1H), 4.38 (s, 1H), 5.04 (s, 1H), 6.64 (d, J=8.3 Hz, 1H), 6.80 (dd, J=3.2, 0.8 Hz, 1H), 6.89 (dd, J=5.1, 3.5 Hz, 1H), 7.04 (d, J=8.4 Hz, 1H), 7.24 (dd, J=5.1, 1.2 Hz, 1H), 7.40-7.28 (m, 1H), 8.36 (s, 1H), 8.61 (s, 1H); M+H (353.1).

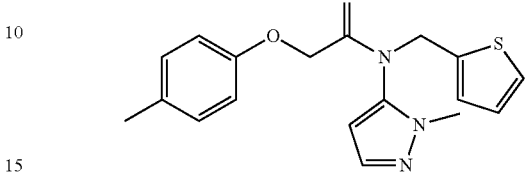

N-(1-methyl-1H-pyrazol-5-yl)-N-(thiophen-2-ylmethyl)-2-(p-tolyloxy)acetamide; Example 60

Prepared in a similar manner to example 6 from 2-(p-tolyloxy)acetyl chloride and 1-methyl-N-(thiophen-2-ylmethyl)-1H-pyrazol-5-amine. Yield 62%. ¹H NMR (400 MHz, DMSO-d6) δ 2.21 (s, 3H), 3.53 (s, 3H), 4.39 (br d, J=17.3, 2H), 4.77 (br d, J=14.9, 1H), 5.06 (br d, J=14.1, 1H), 6.15 (d, J=1.8, 1H), 6.67 (d, J=8.4, 2H), 6.90 (br d, J=2.7, 1H), 6.95 (dd, J=3.5, 5.1, 1H), 7.05 (d, J=8.4, 2H), 7.44 (d, J=1.8, 1H), 7.49 (dd, J=1.2, 5.1, 1H); M+H (324.2).

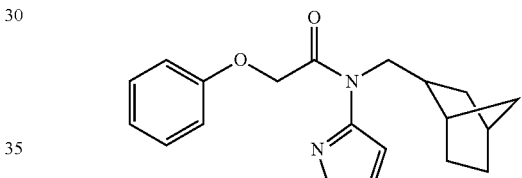

N-(bicyclo[2.2.1]heptan-2-ylmethyl)-2-phenoxy-N-(1H-pyrazol-3-yl)acetamide; Example 66

Prepared in a similar manner to example 6 from 2-phenoxyacetyl chloride and N-(bicyclo[2.2.1]heptan-2-ylmethyl)-1H-pyrazol-3-amine. Yield 18%. ¹H NMR (400 MHz, CDCl₃) δ 0.81 (ddd, J=13.2, 5.2, 3.0 Hz, 1H), 1.07-0.96 (m, 1H), 1.24-1.51 (m, 5H), 1.86-1.65 (m, 3H), 2.10 (br s, 1H), 2.94 (br s, 1H), 4.38 (q, J=15.1 Hz, 1H), 4.58-4.45 (m, 1H), 6.22 (d, J=2.4 Hz, 1H), 6.79-6.84 (m, 2H), 6.89-6.94 (m, 1H), 7.18-7.25 (m, 2H), 7.63 (d, J=2.4 Hz, 1H); M+H (326.1).

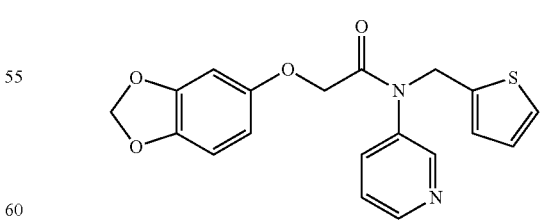

2-(benzo[d][1,3]dioxol-5-yloxy)-N-(pyridin-3-yl)-N-(thiophen-2-ylmethyl)acetamide; Example 70

Prepared in a similar manner to example 21 from 2-(benzo[d][1,3]dioxol-5-yloxy)acetyl chloride and N-(thiophen-2-ylmethyl)pyridin-3-amine. Yield 94%. ¹H NMR (400 MHz, DMSO-d6) δ 4.46 (br s, 2H), 5.05 (br s, 2H), 5.94 (s, 2H), 6.16 (br s, 1H), 6.45 (br s, 1H), 6.75 (d, J=8.5 Hz, 1H), 6.85 (br s, 1H), 6.91 (dd, J=5.1, 3.4 Hz, 1H), 7.45 (dd, J=5.1, 1.3 Hz, 1H), 7.53 (dd, J=8.2, 4.9 Hz, 1H), 7.80 (br d, J=8.1 Hz, 1H), 8.51 (br s, 1H), 8.58 (br d, J=3.7 Hz, 1H); M+H (369.1).

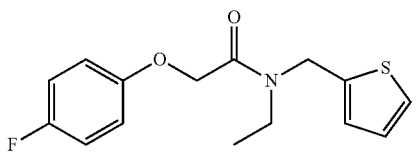 [SMILES: CCN(Cc1cccs1)C(=O)COc1ccc(F)cc1]

N-ethyl-2-(4-fluorophenoxy)-N-(thiophen-2-ylmethyl)acetamide; Example 72

Prepared in a similar manner to example 21 from 2-(4-fluorophenoxy)acetyl chloride and N-(thiophen-2-ylmethyl)ethanamine. Yield 66%. Room temperature ¹H-NMR showed a mixture of rotamers: ¹H NMR (400 MHz, DMSO-d6) δ 7.51-7.49 (minor) (m, 1H), 7.43-7.41 (major) (m, 1H), 7.14-7.09 (m, 2H), 7.07-7.00 (m, 1H), 6.97-6.87 (m, 3H), 4.84 (m, 2H), 4.75 (minor) (s, 2H), 4.64 (major) (s, 2H), 3.41-3.25 (m, 2H), 1.14 (major) (t, J=7.1 Hz, 3H), 1.03 (minor) (t, J=7.1 Hz, 3H); M+H (294.1).

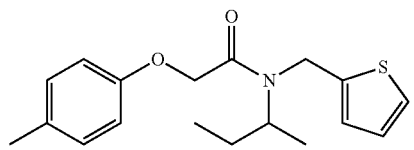 [SMILES: CCC(C)N(Cc1cccs1)C(=O)COc1ccc(C)cc1]

N-sec-butyl-N-(thiophen-2-ylmethyl)-2-(p-tolyloxy)acetamide; Example 79

Prepared in a similar manner to example 21 from 2-(p-tolyloxy)acetyl chloride and N-(thiophen-2-ylmethyl)butan-2-amine. Room temperature ¹H-NMR showed a mixture of rotamers in ~2:1 ratio: ¹H NMR (400 MHz, DMSO-d6) δ 0.74 (m, 3H), 1.14 (m, 3H), 1.39-1.79 (m, 2H), 2.22 (m, 3H), 3.73-4.28 (m, 1H), 4.42-4.85 (m, 4H), 6.69-6.81 (m, 2H), 6.88 (dd, J=5.1, 3.4 Hz, 1H), 6.97-7.13 (m, 3H), 7.41 (m, 1H); M+H (318.1).

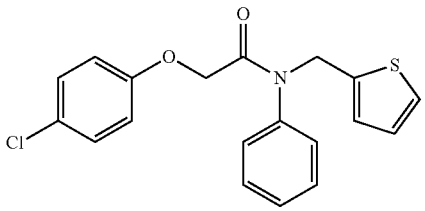 [SMILES: O=C(COc1ccc(Cl)cc1)N(Cc1cccs1)c1ccccc1]

2-(4-chlorophenoxy)-N-phenyl-N-(thiophen-2-ylmethyl)acetamide; Example 80

Prepared in a similar manner to example 21 from 2-(4-chlorophenoxy)acetyl chloride and N-(thiophen-2-ylmethyl)aniline. ¹H NMR (400 MHz, DMSO-d6) δ 4.44 (br s, 2H), 4.98 (br s, 2H), 6.72-6.84 (m, 3H), 6.89 (dd, J=4.8, 3.6 Hz, 1H), 7.26 (dd, J=8.1, 4.0 Hz, 4H), 7.31-7.45 (m, 4H); M+H (358.1).

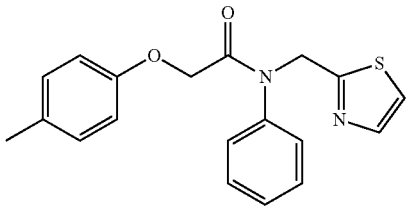 [SMILES: Cc1ccc(OCC(=O)N(Cc2nccs2)c2ccccc2)cc1]

N-phenyl-N-(thiazol-2-ylmethyl)-2-(p-tolyloxy)acetamide; Example 82

Prepared in a similar manner to example 21 from 2-(p-tolyloxy)acetyl chloride and N-(thiazol-2-ylmethyl)aniline. ¹H NMR (400 MHz, DMSO-d6) δ 2.19 (s, 3H), 4.44 (br s, 2H), 5.11 (br s, 2H), 6.62 (br d, J=7.6 Hz, 2H), 7.02 (d, J=8.3 Hz, 2H), 7.49-7.33 (m, 5H), 7.69 (br s, 2H); M+H (339.1).

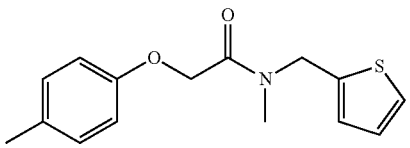 [SMILES: Cc1ccc(OCC(=O)N(C)Cc2cccs2)cc1]

N-methyl-N-(thiophen-2-ylmethyl)-2-(p-tolyloxy)acetamide; Example 85

Prepared in a similar manner to example 21 from 2-(p-tolyloxy)acetyl chloride and N-methyl-1-(thiophen-2-yl)methanamine. Room temperature ¹H-NMR showed a mixture of rotamers in ~3:1 ratio: ¹H NMR (400 MHz, DMSO-d6) δ 2.23 (br s, 3H), 2.83-2.97 (m, 3H), 4.64-4.83 (m, 4H), 6.79 (m, 2H), 6.97 (dd, J=5.1, 3.4 Hz, 1H), 7.01-7.11 (m, 3H), 7.42-7.54 (m, 1H); M+H (276.1).

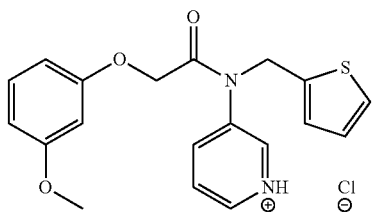 [SMILES: COc1cccc(OCC(=O)N(Cc2cccs2)c2ccc[nH+]c2)c1 ; [Cl-]]

3-(2-(3-methoxyphenoxy)-N-(thiophen-2-ylmethyl)acetamido)pyridinium chloride; Example 87

Prepared in a similar manner to example 14 from 2-(3-methoxyphenoxy)-N-(pyridin-3-yl)-N-(thiophen-2-ylmethyl)acetamide (example 99). ¹H NMR (400 MHz, DMSO-d6): δ, ppm: 3.70 (s, 3H), 4.58 (s, broad, 2H), 5.09 (s, broad, 2H), 6.31 (m, broad, 2H), 6.51 (dd, 1H, J1=8 Hz, J2=2 Hz), 6.88 (s, broad, 1H), 6.92 (m, 1H), 7.13 (t, 1H, J=8.4 Hz), 7.46 (dd, 1H, J1=5.2 Hz, J2=1.2 Hz), 7.68 (broad, 1H), 7.96 (broad, 1H), 8.66 (dd, 2H, J1=5.2 Hz, J2=1.2 Hz); M+H (355.1).

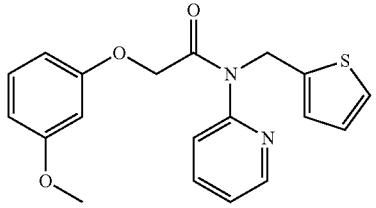 [SMILES: COc1cccc(OCC(=O)N(Cc2cccs2)c2ccccn2)c1]

2-(3-methoxyphenoxy)-N-(pyridin-2-yl)-N-(thiophen-2-ylmethyl)acetamide; Example 88

Prepared in a similar manner to example 21 from 2-(3-methoxyphenoxy)acetyl chloride and N-(thiophen-2-ylmethyl)pyridin-2-amine. Room temperature $^1$H NMR showed a mixture of rotamers: $^1$H NMR (400 MHz, CDCl$_3$) δ 3.74 (d, 3H), 4.80 (d, 2H), 5.28 (d, 2H), 6.29-6.51 (m, 4H), 6.86-6.93 (m, 2H), 7.08-7.20 (m, 2H), 7.32 (m, 1H), 7.82 (m, 1H), 8.51 (m, 1H); M+H (355.1).

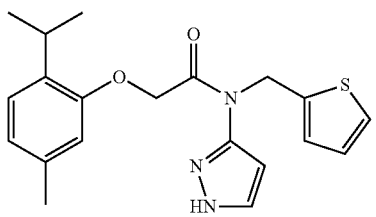 [SMILES: Cc1ccc(C(C)C)c(OCC(=O)N(Cc2cccs2)c2cc[nH]n2)c1]

2-(2-isopropyl-5-methylphenoxy)-N-(1H-pyrazol-3-yl)-N-(thiophen-2-ylmethyl)acetamide; Example 89

Prepared in a similar manner to example 21 from 2-(2-isopropyl-5-methylphenoxy)acetyl chloride and N-(thiophen-2-ylmethyl)-1H-pyrazol-5-amine. Yield 11%. $^1$H NMR (400 MHz, DMSO-d6) δ 1.12 (d, J=6.8 Hz, 6H), 2.21 (s, 3H), 2.99 (hept, J=6.8 Hz, 1H), 4.57 (br s, 2H), 4.98 (br s, 2H), 6.23 (br s, 1H), 6.56 (m, 2H), 6.92 (br d, J=4.1 Hz, 2H), 7.08 (d, J=8.5 Hz, 1H), 7.38-7.44 (m, 1H), 7.78 (br s, 1H), 12.90 (br s, 1H); M+H (370.2).

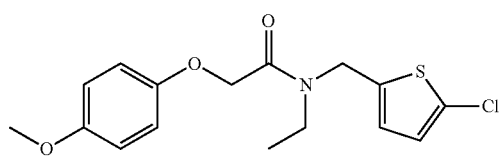 [SMILES: CCN(Cc1ccc(Cl)s1)C(=O)COc1ccc(OC)cc1]

N-((5-chlorothiophen-2-yl)methyl)-N-ethyl-2-(4-methoxyphenoxy)acetamide; Example 91

This compound was purchased from Enamine. M+H (340.1).

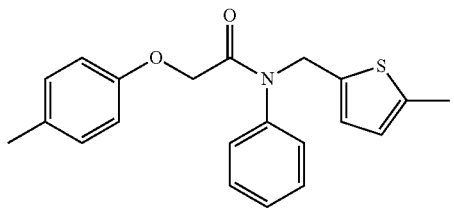

N-((5-methylthiophen-2-yl)methyl)-N-phenyl-2-(p-tolyloxy)acetamide; Example 92

Prepared in a similar manner to example 21 from 2-(p-tolyloxy)acetyl chloride and N-((5-methylthiophen-2-yl)methyl)aniline. Yield 57%. $^1$H NMR (400 MHz, CDCl$_3$) δ 2.25 (s, 3H), 2.43 (d, J=1.0 Hz, 3H), 4.33 (s, 2H), 4.94 (s, 2H), 6.51 (m, 1H), 6.57 (d, J=3.4 Hz, 1H), 6.67 (br d, J=8.6 Hz, 2H), 7.01 (br d, J=8.2 Hz, 2H), 7.05-7.12 (m, 2H), 7.33-7.44 (m, 3H); M+H (352.1).

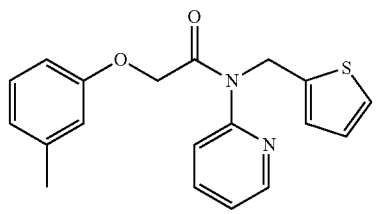 [SMILES: Cc1cccc(OCC(=O)N(Cc2cccs2)c2ccccn2)c1]

N-(pyridin-2-yl)-N-(thiophen-2-ylmethyl)-2-(m-tolyloxy)acetamide; Example 93

This compound was purchased from Chemdiv. M+H (339.1).

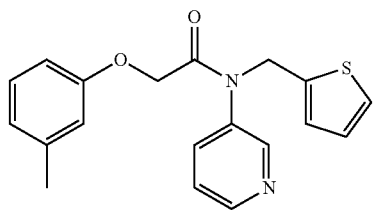 [SMILES: Cc1cccc(OCC(=O)N(Cc2cccs2)c2cccnc2)c1]

N-(pyridin-3-yl)-N-(thiophen-2-ylmethyl)-2-(m-tolyloxy)acetamide; Example 94

Prepared in a similar manner to example 21 from 2-(m-tolyloxy)acetyl chloride and N-(thiophen-2-ylmethyl)pyridin-3-amine. $^1$H NMR (400 MHz, CDCl$_3$) δ 2.28 (s, 3H), 4.40 (br s, 2H), 5.04 (br s, 2H), 6.52 (m, 2H), 6.76 (br d, J=7.4 Hz, 1H), 6.82-6.79 (m, 1H), 6.89 (dd, J=5.1, 3.5 Hz, 1H), 7.10 (t, J=7.9 Hz, 1H), 7.24 (dd, J=5.1, 1.2 Hz, 1H), 7.31-7.37 (m, 2H), 8.37 (br s, 1H), 8.61 (br dd, J=4.4, 1.5 Hz, 1H); M+H (339.1).

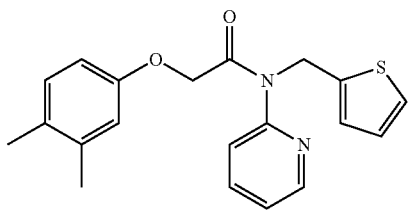 [SMILES: Cc1ccc(OCC(=O)N(Cc2cccs2)c2ccccn2)cc1C]

2-(3,4-dimethylphenoxy)-N-(pyridin-2-yl)-N-(thiophen-2-ylmethyl)acetamide; Example 96

This compound was purchased from Chemdiv. M+H (353.1).

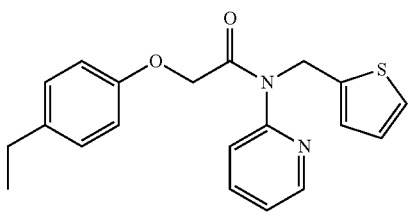 [SMILES: CCc1ccc(OCC(=O)N(Cc2cccs2)c2ccccn2)cc1]

2-(4-ethylphenoxy)-N-(pyridin-2-yl)-N-(thiophen-2-ylmethyl)acetamide; Example 98

Prepared in a similar manner to example 21 from 2-(4-ethylphenoxy)acetyl chloride and N-(thiophen-2-ylmethyl)pyridin-2-amine. $^1$H NMR (400 MHz, CDCl$_3$) δ 1.18 (t, J=7.6 Hz, 3H), 2.55 (q, J=7.6 Hz, 2H), 4.74 (s, 2H), 5.24 (s, 2H), 6.66 (d, J=8.7 Hz, 2H), 6.85-6.91 (m, 2H), 7.03 (d, J=8.7 Hz, 2H), 7.12-7.20 (m, 2H), 7.22-7.25 (m, 1H), 7.73 (ddd, J=8.1, 7.5, 2.0 Hz, 1H), 8.49 (ddd, J=4.9, 2.0, 0.8 Hz, 1H); M+H (353.1).

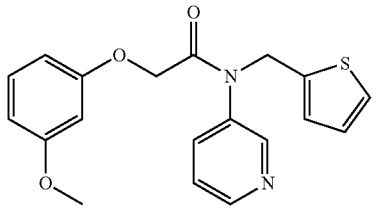 [SMILES: COc1cccc(OCC(=O)N(Cc2cccs2)c2cccnc2)c1]

2-(3-methoxyphenoxy)-N-(pyridin-3-yl)-N-(thiophen-2-ylmethyl)acetamide; Example 99

Prepared in a similar manner to example 21 from 2-(3-methoxyphenoxy)acetyl chloride and N-(thiophen-2-ylmethyl)pyridin-3-amine. $^1$H NMR (400 MHz, CDCl$_3$) δ 3.75 (s, 3H), 4.38 (s, 2H), 5.04 (s, 2H), 6.31 (s, 2H), 6.54-6.45 (m, 1H), 6.83-6.77 (m, 1H), 6.89 (dd, J=5.1, 3.5 Hz, 1H), 7.11 (t, J=8.6 Hz, 1H), 7.24 (dd, J=5.1, 1.2 Hz, 1H), 7.40-7.29 (m, 2H), 8.37 (s, 1H), 8.61 (d, J=3.1 Hz, 1H); M+H (355.1).

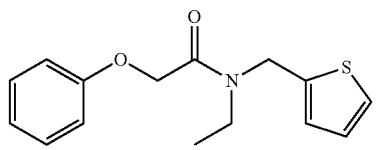 [SMILES: CCN(Cc1cccs1)C(=O)COc1ccccc1]

N-ethyl-3-phenyl-N-(thiophen-2-ylmethyl)propanamide; Example 101

Prepared in a similar manner to example 21 from 3-phenylpropanoyl chloride and N-(thiophen-2-ylmethyl)ethanamine. Room temperature $^1$H-NMR showed a mixture of rotamers in ~2:1 ratio: $^1$H NMR (400 MHz, DMSO-d6) δ 1.01 (m, 3H), 2.58-2.72 (m, 2H), 2.84 (m, 2H), 3.28 (m, 2H), 4.64 (m, 2H), 6.92-7.04 (m, 2H), 7.13-7.32 (m, 4H), 7.39-7.45 (m, 1H); M+H (274.1).

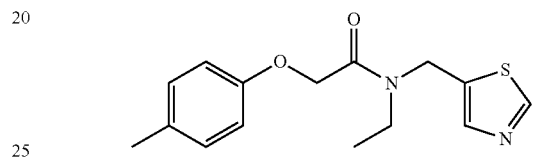

N-ethyl-N-(thiazol-5-ylmethyl)-2-(p-tolyloxy)acetamide; Example 102

Prepared in a similar manner to example 21 from 2-(p-tolyloxy)acetyl chloride and N-(thiazol-5-ylmethyl)ethanamine. Yield: 71%. Room temperature $^1$H-NMR showed a mixture of rotamers in ~3:1 ratio: $^1$H NMR (400 MHz, DMSO-d6) δ 0.97 (minor) (t, J=7.0 Hz, 3H), 1.12 (major) (t, J=7.1 Hz, 3H), 2.21 (s, 3H), 3.29-3.37 (m, 2H), 4.66 (s, 2H) (major), 4.77 (s, 2H), 4.81 (minor) (s, 1H), 6.77 (d, J=8.6 Hz, 2H), 7.05 (d, J=8.6 Hz, 2H), 7.85 (major) (d, J=0.6 Hz, 1H), 7.89 (minor) (br s, 1H), 8.97 (major) (d, J=0.7 Hz, 1H), 9.06 (minor) (br s, 1H); M+H (291.1).

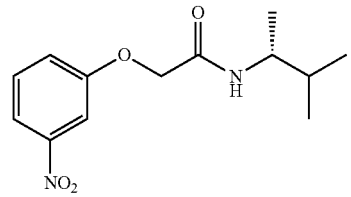 [SMILES: CC(C)[C@@H](C)NC(=O)COc1cccc([N+](=O)[O-])c1]

(R)—N-(3-methylbutan-2-yl)-2-(3-nitrophenoxy)acetamide; Example 103

This compound was prepared in a library format. M+H (267.1).

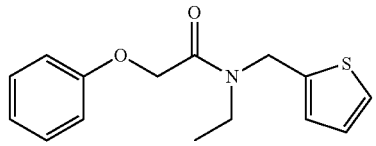 [SMILES: CCN(Cc1cccs1)C(=O)COc1ccccc1]

N-ethyl-2-phenoxy-N-(thiophen-2-ylmethyl)acetamide; Example 105

Prepared in a similar manner to example 21 from 2-phenoxyacetyl chloride and N-(thiophen-2-ylmethyl)ethanamine. Room temperature $^1$H-NMR showed a mixture of rotamers in ~2:1 ratio: $^1$H NMR (400 MHz, DMSO-d6) δ 1.01 (minor) (t, J=7.1 Hz, 3H), 1.14 (t, J=7.1 Hz, 3H), 3.29-3.37 (m, 2H), 4.65 (major) (br s, 2H), 4.77 (minor) (br s, 2H), 4.84 (br s, 2H), 6.93 (ddd, J=19.7, 11.9, 7.1 Hz, 3H), 7.02 (minor) (dd, J=5.0, 3.6 Hz, 1H), 7.05 (major) (d, J=2.7 Hz, 1H), 7.11 (minor) (d, J=2.8 Hz, 1H), 7.22-7.33 (m, 2H), 7.42 (major) (dd, J=5.1, 1.1 Hz, 1H), 7.51 (minor) (dd, J=5.0, 0.7 Hz, 1H); M+H (276.1).

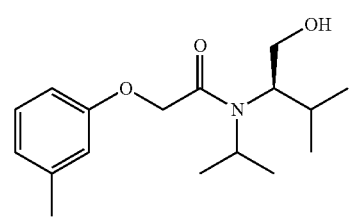 [SMILES: Cc1cccc(OCC(=O)N(C(C)C)[C@@H](CO)C(C)C)c1]

((R)—N-(1-hydroxy-3-methylbutan-2-yl)-N-isopropyl-2-(m-tolyloxy)acetamide; Example 106

This compound was prepared in a library format. M+H (294.2).

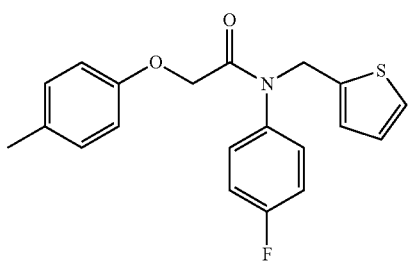 [SMILES: Cc1ccc(OCC(=O)N(Cc2cccs2)c2ccc(F)cc2)cc1]

N-(4-fluorophenyl)-N-(thiophen-2-ylmethyl)-2-(p-tolyloxy)acetamide; Example 109

This compound was purchased from Chemdiv. M+H (356.1).

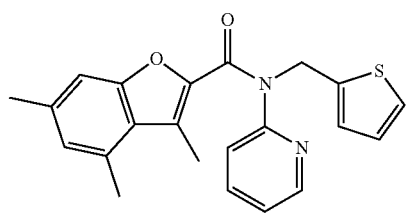

2 3,4,6-trimethyl-N-(pyridin-2-yl)-N-(thiophen-2-ylmethyl)benzofuran-2-carboxamide; Example 110

This compound was purchased from Princeton. M+H (377.1).

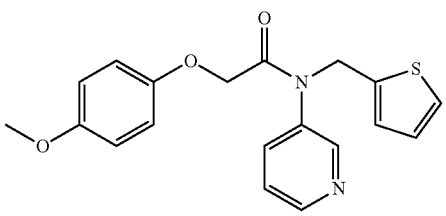 [SMILES: COc1ccc(OCC(=O)N(Cc2cccs2)c2cccnc2)cc1]

2-(4-methoxyphenoxy)-N-(pyridin-3-yl)-N-(thiophen-2-ylmethyl)acetamide; Example 111

Prepared in a similar manner to example 21 from 2-(4-methoxyphenoxy)acetyl chloride and N-(thiophen-2-ylmethyl)pyridin-3-amine. $^1$H NMR (400 MHz, CDCl$_3$) δ 3.74 (s, 3H), 4.36 (s, 2H), 5.04 (s, 2H), 6.67 (d, J=9.0 Hz, 2H), 6.82-6.73 (m, 3H), 6.89 (dd, J=5.1, 3.5 Hz, 1H), 7.24 (dd, J=5.1, 1.2 Hz, 1H), 7.39-7.28 (m, 2H), 8.35 (s, 1H), 8.61 (dd, J=4.4, 1.7 Hz, 1H); M+H (355.1).

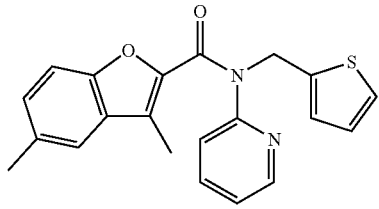 [SMILES: Cc1ccc2oc(C(=O)N(Cc3cccs3)c3ccccn3)c(C)c2c1]

3,5-dimethyl-N-(pyridin-2-yl)-N-(thiophen-2-ylmethyl)benzofuran-2-carboxamide; Example 115

This compound was purchased from Princeton. M+H (363.1).

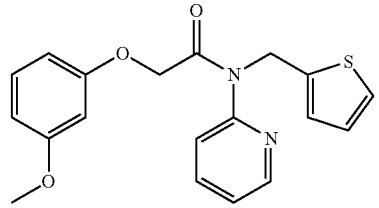 [SMILES: COc1cccc(OCC(=O)N(Cc2cccs2)c2ccccn2)c1]

2-(3-methoxyphenoxy)-N-(pyridin-2-yl)-N-(thiophen-2-ylmethyl)acetamide; Example 116

This compound was purchased from Chemdiv. M+H (355.1).

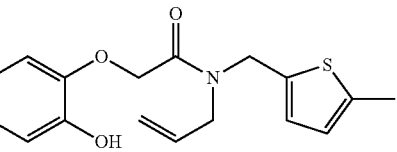

N-allyl-2-(2-hydroxyphenoxy)-N-((5-methylthiophen-2-yl)methyl)acetamide; Example 117

This compound was purchased from Chembridge. M+H (318.1).

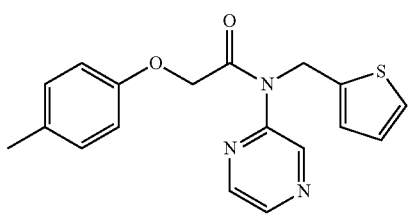 [SMILES: Cc1ccc(OCC(=O)N(Cc2cccs2)c2cnccn2)cc1]

N-(pyrazin-2-yl)-N-(thiophen-2-ylmethyl)-2-(p-tolyloxy)acetamide; Example 122

Prepared in a similar manner to example 21 from 2-(p-tolyloxy)acetyl chloride and N-(thiophen-2-ylmethyl)pyrazin-2-amine. $^1$H NMR (400 MHz, DMSO-d6) δ 2.20 (s, 3H), 4.90 (br s, 2H), 5.27 (br s, 2H), 6.59 (d, J=8.1 Hz, 2H), 6.91 (dd, J=5.1, 3.4 Hz, 1H), 6.96 (br d, J=2.5 Hz, 1H), 7.02 (d, J=8.1 Hz, 2H), 7.41 (dd, J=5.1, 1.3 Hz, 1H), 8.44-8.57 (m, 2H), 8.82 (d, J=1.1 Hz, 1H); M+H (340.1).

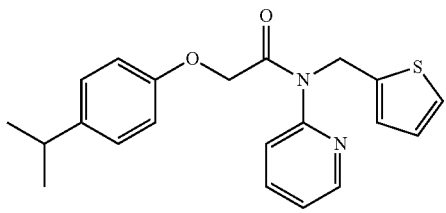

2-(4-isopropylphenoxy)-N-(pyridin-2-yl)-N-(thiophen-2-ylmethyl)acetamide; Example 123

This compound was purchased from Chemdiv. M+H (367.1).

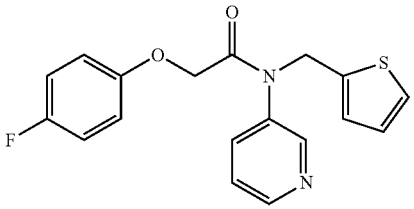

2-(4-fluorophenoxy)-N-(pyridin-3-yl)-N-(thiophen-2-ylmethyl)acetamide; Example 124

Prepared in a similar manner to example 21 from 2-(4-fluorophenoxy)acetyl chloride and N-(thiophen-2-ylmethyl)pyridin-3-amine. $^1$H NMR (400 MHz, CDCl$_3$) δ 4.37 (br s, 2H), 5.04 (br s, 2H), 6.68 (br dd, J=9.0, 4.1 Hz, 2H), 6.80 (dd, J=3.5, 1.1 Hz, 1H), 6.86-6.95 (m, 3H), 7.23-7.26 (m, 1H), 7.31-7.37 (m, 2H), 8.36 (br s, 1H), 8.62 (br dd, J=4.3, 1.9 Hz, 1H); M+H (343.1).

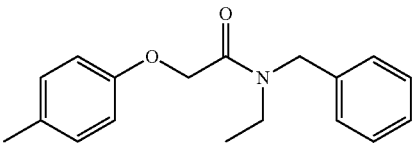 [SMILES: CCN(Cc1ccccc1)C(=O)COc1ccc(C)cc1]

N-benzyl-N-ethyl-2-(p-tolyloxy)acetamide; Example 127

Prepared in a similar manner to example 21 from 2-(p-tolyloxy)acetyl chloride and N-benzylethanamine. Room temperature $^1$H-NMR showed a mixture of rotamers in ~2:1 ratio: $^1$H NMR (400 MHz, DMSO-d6) δ 0.99 (minor) (t, J=7.1 Hz, 3H), 1.11 (major) (t, J=7.1 Hz, 3H), 2.21 (minor) (s, 3H), 2.23 (major) (s, 3H), 3.22-3.32 (m, 2H), 4.52 (major) (br s, 2H), 4.59 (minor) (br s, 2H), 4.72 (minor) (br s, 2H), 4.85 (major) (br s, 2H), 6.72 (minor) (d, J=8.6 Hz, 2H), 6.83 (d, J=8.6 Hz, 2H), 7.04 (minor) (d, J=8.3 Hz, 2H), 7.09 (d, J=8.2 Hz, 1H), 7.19-7.34 (m, 4H), 7.39 (br t, J=7.2 Hz, 1H); M+H (284.2).

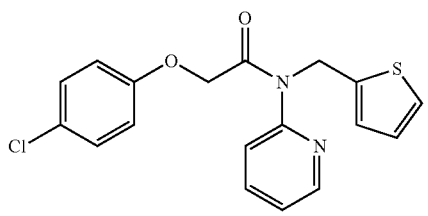

2-(4-chlorophenoxy)-N-(pyridin-2-yl)-N-(thiophen-2-ylmethyl)acetamide; Example 128

This compound was purchased from Chemdiv. M+H (359.1).

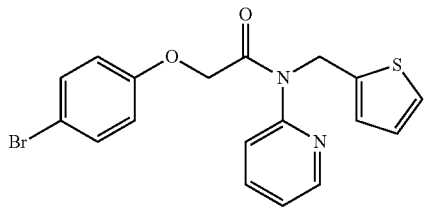 [SMILES: O=C(COc1ccc(Cl)cc1)N(Cc1cccs1)c1ccccn1]

2-(4-bromophenoxy)-N-(pyridin-2-yl)-N-(thiophen-2-ylmethyl)acetamide; Example 131

This compound was commercially available purchased from Princeton. M+H (405.0).

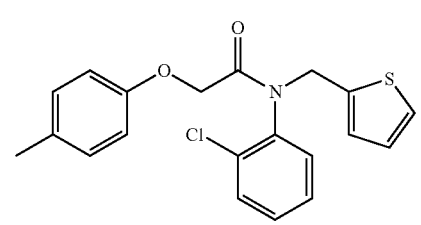 [SMILES: Cc1ccc(OCC(=O)N(Cc2cccs2)c2ccccc2Cl)cc1]

N-(2-chlorophenyl)-N-(thiophen-2-ylmethyl)-2-(p-tolyloxy)acetamide; Example 132

This compound was purchased from Chemdiv. M+H (372.1).

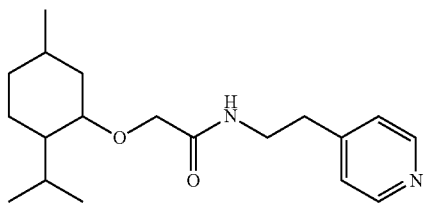 [SMILES: CC1CCC(C(C)C)C(OCC(=O)NCCc2ccncc2)C1]

2-(2-isopropyl-5-methylcyclohexyloxy)-N-(2-(pyridin-4-yl)ethyl)acetamide; Example 133

Prepared in a similar manner to example 21 from 2-(2-isopropyl-5-methylcyclohexyloxy)acetyl chloride and 2-(pyridin-4-yl)ethanamine. $^1$H NMR (400 MHz, DMSO-d6) δ 0.69 (d, J=6.9 Hz, 3H), 0.71-0.83 (m, 2H), 0.84 (d, J=7.1 Hz, 3H), 0.86 (d, J=6.6 Hz, 3H), 0.89-0.97 (m, 1H), 1.19 (ddt, J=13.4, 10.3, 3.1 Hz, 1H), 1.23-1.37 (m, 1H), 1.50-1.66 (m, 2H), 1.93-2.02 (m, 1H), 2.03-2.14 (m, 1H), 2.77 (t, J=7.0 Hz, 2H), 3.08 (td, J=10.6, 4.1 Hz, 1H), 3.39 (dd, J=13.1, 7.0 Hz, 2H), 3.75 (d, J=14.8 Hz, 1H), 3.89 (d, J=14.8 Hz, 1H), 7.22 (dd, J=4.4, 1.6 Hz, 2H), 7.51 (t, J=5.8 Hz, 1H), 8.45 (dd, J=4.4, 1.6 Hz, 2H); M+H (319.2).

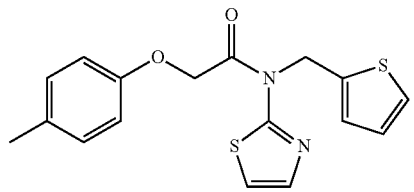 [SMILES: Cc1ccc(OCC(=O)N(Cc2cccs2)c2nccs2)cc1]

N-(thiazol-2-yl)-N-(thiophen-2-ylmethyl)-2-(p-tolyloxy)acetamide; Example 135

Prepared in a similar manner to example 21 from 2-(p-tolyloxy)acetyl chloride and N-(thiophen-2-ylmethyl)thiazol-2-amine. Yield 74%. $^1$H NMR (400 MHz, CDCl$_3$) δ 2.28 (s, 3H), 4.98 (br s, 2H), 5.71 (br s, 2H), 6.80 (br d, J=8.5 Hz, 2H), 6.95 (dd, J=5.1, 3.5 Hz, 1H), 7.00-7.14 (m, 3H), 7.23 (dd, J=5.1, 1.2 Hz, 1H), 7.57 (d, J=3.6 Hz, 1H); M+H (345.1).

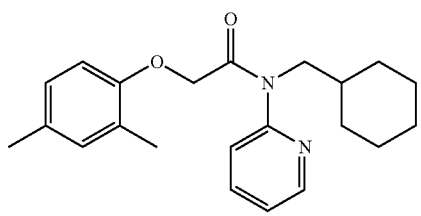 [SMILES: Cc1ccc(OCC(=O)N(CC2CCCCC2)c2ccccn2)c(C)c1]

N-(cyclohexylmethyl)-2-(2,4-dimethylphenoxy)-N-(pyridin-2-yl)acetamide; Example 137

This compound was purchased from Enamine. M+H (353.2).

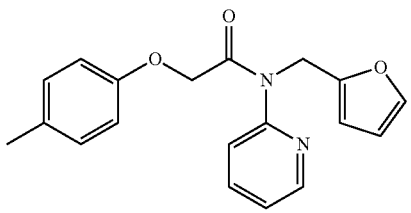

N-(furan-2-ylmethyl)-N-(pyridin-2-yl)-2-(p-tolyloxy)acetamide; Example 138

This compound was purchased from Princeton. M+H (323.1).

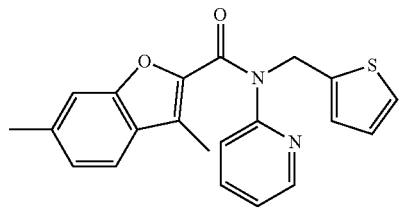 [SMILES: Cc1ccc2c(C)c(C(=O)N(Cc3cccs3)c3ccccn3)oc2c1]

3,6-dimethyl-N-(pyridin-2-yl)-N-(thiophen-2-ylmethyl)benzofuran-2-carboxamide; Example 139

This compound was purchased from Princeton. M+H (363.1).

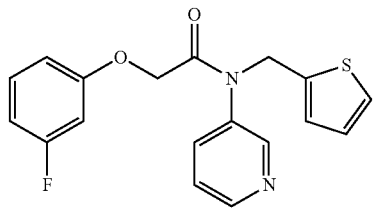 [SMILES: O=C(COc1cccc(F)c1)N(Cc1cccs1)c1cccnc1]

2-(3-fluorophenoxy)-N-(pyridin-3-yl)-N-(thiophen-2-ylmethyl)acetamide; Example 142

Prepared in a similar manner to example 21 from 2-(3-fluorophenoxy)acetyl chloride and N-(thiophen-2-ylmethyl)pyridin-3-amine. $^1$H NMR (400 MHz, CDCl$_3$) δ 4.39 (s, 2H), 5.05 (s, 2H), 6.44 (br d, 1H), 6.52 (br d, 1H), 6.66 (td, J=8.2, 2.0 Hz, 1H), 6.80 (dd, J=3.4, 1.0 Hz, 1H), 6.89 (dd, J=5.1, 3.5 Hz, 1H), 7.17 (m, 1H), 7.25 (dd, J=5.2, 1.3 Hz, 1H), 7.31-7.41 (m, 2H), 8.38 (br s, 1H), 8.63 (br dd, J=4.2, 1.9 Hz, 1H); M+H (343.1).

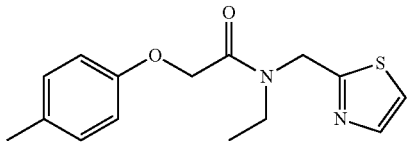

N-ethyl-N-(thiazol-2-ylmethyl)-2-(p-tolyloxy)acetamide; Example 143

Prepared in a similar manner to example 21 from 2-(p-tolyloxy)acetyl chloride and N-(thiazol-2-ylmethyl)ethanamine. Yield: 21%. Room temperature $^1$H-NMR showed a mixture of rotamers in ~2:1 ratio: $^1$H NMR (400 MHz, DMSO-d6) δ 1.01 (minor) (t, J=7.1 Hz, 3H), 1.15 (major) (t, J=7.1 Hz, 3H), 2.21 (minor) (s, 3H), 2.23 (major) (s, 3H), 3.34-3.39 (minor) (q, J=7.1 Hz, 2H), 3.45 (major) (q, J=7.1 Hz, 2H), 4.76 (major) (br s, 1H), 4.84 (major) (br s, 1H), 4.86 (minor) (br s, 2H), 4.92 (minor) (br s, 2H), 6.77 (minor) (br d, J=8.6 Hz, 2H), 6.81 (major) (br d, J=8.6 Hz, 2H), 7.06 (m, 2H), 7.66 (major) (d, J=3.3 Hz, 1H), 7.72 (major) (d, J=3.3 Hz, 1H), 7.74 (minor) (d, J=3.3 Hz, 1H), 7.83 (minor) (d, J=3.3 Hz, 1H); M+H (291.1).

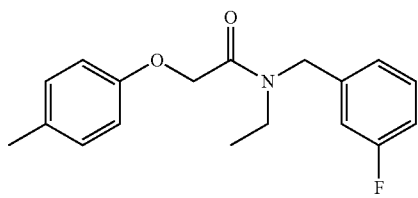 [SMILES: CCN(Cc1cccc(F)c1)C(=O)COc1ccc(C)cc1]

N-ethyl-N-(3-fluorobenzyl)-2-(p-tolyloxy)acetamide; Example 148

Prepared in a similar manner to example 21 from 2-(p-tolyloxy)acetyl chloride and N-(3-fluorobenzyl)ethanamine. Yield: 73%. Room temperature $^1$H-NMR showed a mixture of rotamers in ~2:1 ratio: $^1$H NMR (400 MHz, DMSO-d6) δ 0.99 (minor) (t, J=7.1 Hz, 3H), 1.12 (major) (t, J=7.1 Hz, 3H), 2.21 (minor) (s, 2H), 2.23 (major) (s, 2H), 3.30 (m, 2H), 4.53 (major) (br s, 2H), 4.61 (minor) (br s, 2H), 4.72 (minor) (br s, 2H), 4.88 (major) (br s, 2H), 6.72 (minor) (d, J=8.6 Hz, 2H), 6.83 (major) (d, J=8.6 Hz, 2H), 6.98-7.20 (m, 5H), 7.35 (td, J=7.9, 6.2 Hz, 1H), 7.43 (minor) (td, J=7.9, 6.2 Hz, 1H); M+H (302.1).

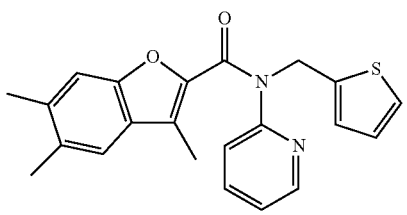 [SMILES: Cc1cc2oc(C(=O)N(Cc3cccs3)c3ccccn3)c(C)c2cc1C]

3,5,6-trimethyl-N-(pyridin-2-yl)-N-(thiophen-2-ylmethyl)benzofuran-2-carboxamide; Example 144

This compound was purchased from Princeton. M+H (377.1).

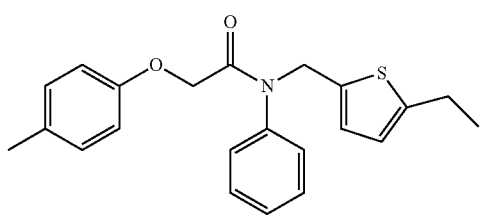 [SMILES: CCc1ccc(CN(C(=O)COc2ccc(C)cc2)c2ccccc2)s1]

N-((5-ethylthiophen-2-yl)methyl)-N-phenyl-2-(p-tolyloxy)acetamide; Example 151

Prepared in a similar manner to example 21 from 2-(p-tolyloxy)acetyl chloride and N-((5-ethylthiophen-2-yl)methyl)aniline. Yield 60%. $^1$H NMR (400 MHz, CDCl$_3$) δ 1.28 (t, J=7.5 Hz, 3H), 2.25 (s, 3H), 2.79 (qd, J=7.5, 1.0 Hz, 2H), 4.33 (s, 2H), 4.95 (s, 2H), 6.54 (dt, J=3.4, 1.1 Hz, 1H), 6.60 (d, J=3.4 Hz, 1H), 6.67 (br d, J=8.6 Hz, 2H), 7.01 (br d, J=8.2 Hz, 2H), 7.06-7.12 (m, 2H), 7.35-7.41 (m, 3H); M+H (366.1).

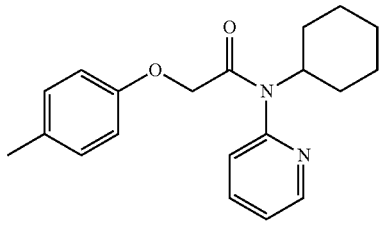 [SMILES: Cc1ccc(OCC(=O)N(c2ccccn2)C2CCCCC2)cc1]

N-((5-ethylthiophen-2-yl)methyl)-N-phenyl-2-(p-tolyloxy)acetamide; Example 157

Prepared in a similar manner to example 21 from 2-(p-tolyloxy)acetyl chloride and N-cyclohexylpyridin-2-amine. $^1$H NMR (400 MHz, DMSO-d6) δ 0.82-0.97 (m, 1H), 1.06-1.33 (m, 4H), 1.51 (br d, J=12.8 Hz, 1H), 1.66 (br d, J=13.3 Hz, 2H), 1.76 (br d, J=11.5 Hz, 2H), 2.17 (s, 3H), 4.11-4.36 (m, 3H), 6.58 (d, J=8.6 Hz, 2H), 7.00 (d, J=8.6 Hz, 2H), 7.39-7.47 (m, 2H), 7.93 (td, J=7.7, 2.0 Hz, 1H), 8.56 (ddd, J=4.8, 2.0, 0.8 Hz, 1H); M+H (325.2).

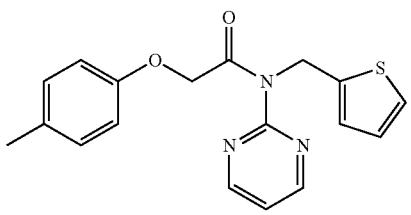 [SMILES: Cc1ccc(OCC(=O)N(Cc2cccs2)c2ncccn2)cc1]

N-(pyrimidin-2-yl)-N-(thiophen-2-ylmethyl)-2-(p-tolyloxy)acetamide; Example 159

Prepared in a similar manner to example 21 from 2-(p-tolyloxy)acetyl chloride and N-(thiophen-2-ylmethyl)pyrimidin-2-amine. $^1$H NMR (400 MHz, CDCl$_3$) δ 2.26 (s, 3H), 5.20 (s, 2H), 5.53 (s, 2H), 6.69 (d, J=8.6 Hz, 2H), 6.93-6.84 (m, 1H), 7.04 (ddd, J=17.3, 9.3, 6.5 Hz, 3H), 7.18-7.09 (m, 2H), 8.63 (d, J=4.8 Hz, 2H); M+H (340.1).

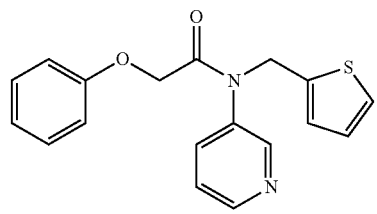 [SMILES: O=C(COc1ccccc1)N(Cc1cccs1)c1cccnc1]

2-phenoxy-N-(pyridin-3-yl)-N-(thiophen-2-ylmethyl)acetamide; Example 162

Prepared in a similar manner to example 21 from 2-phenoxyacetyl chloride and N-(thiophen-2-ylmethyl)pyridin-3-amine. $^1$H NMR (400 MHz, CDCl$_3$) δ 4.41 (br s, 2H), 5.04

(br s, 2H), 6.72 (d, J=8.1 Hz, 2H), 6.78-6.82 (m, 1H), 6.88 (dd, J=5.1, 3.5 Hz, 1H), 6.94 (t, J=7.3 Hz, 1H), 7.18-7.25 (m, 3H), 7.30-7.40 (m, 2H), 8.37 (br s, 1H), 8.61 (br s, 1H); M+H (325.1).

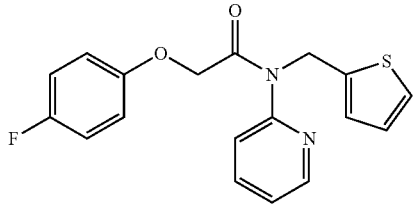 [SMILES: O=C(COc1ccc(F)cc1)N(Cc1cccs1)c1ccccn1]

2-(4-fluorophenoxy)-N-(pyridin-2-yl)-N-(thiophen-2-ylmethyl)acetamide; Example 163

This compound was purchased from Chemdiv. M+H (343.1).

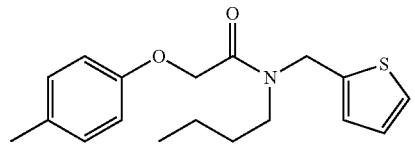 [SMILES: CCCCN(Cc1cccs1)C(=O)COc1ccc(C)cc1]

N-(thiophen-2-ylmethyl)butan-1-amine; Example 165

Prepared in a similar manner to example 21 from 2-(p-tolyloxy)acetyl chloride and N-cyclohexylpyridin-2-amine. Room temperature $^1$H-NMR showed a mixture of rotamers in ~2:1 ratio: $^1$H NMR (400 MHz, DMSO-d6) δ 0.83 (m, 3H), 1.16-1.28 (m, 2H), 1.35-1.57 (m, 2H), 2.20 (m, 3H), 3.20-3.28 (m, 2H), 4.60-4.80 (m, 4H), 6.71-6.80 (m, 2H), 6.90-7.10 (m, 4H), 7.38-7.50 (m, 1H); M+H (318.1).

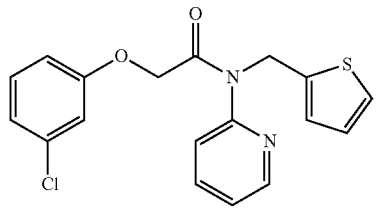

2-(3-chlorophenoxy)-N-(pyridin-2-yl)-N-(thiophen-2-ylmethyl)acetamide; Example 166

This compound was purchased from Chemdiv. M+H (359.1).

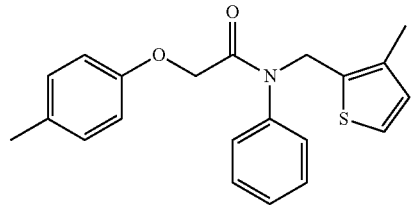 [SMILES: Cc1ccc(OCC(=O)N(Cc2sccc2C)c2ccccc2)cc1]

N-((3-methylthiophen-2-yl)methyl)-N-phenyl-2-(p-tolyloxy)acetamide; Example 168

Prepared in a similar manner to example 21 from 2-(p-tolyloxy)acetyl chloride and N-((3-methylthiophen-2-yl)

methyl)aniline. Yield 55%. $^1$H NMR (400 MHz, CDCl$_3$) δ 1.87 (s, 3H), 2.25 (s, 3H), 4.33 (s, 5H), 5.02 (s, 3H), 6.65-6.72 (m, 3H), 6.95-7.08 (m, 4H), 7.11 (d, J=5.1 Hz, 1H), 7.34-7.40 (m, 3H); M+H (352.1).

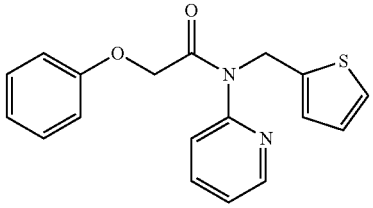 [SMILES: O=C(COc1ccccc1)N(Cc1cccs1)c1ccccn1]

2-phenoxy-N-(pyridin-2-yl)-N-(thiophen-2-ylmethyl)acetamide; Example 169

This compound was purchased from Chemdiv. M+H (325.1).

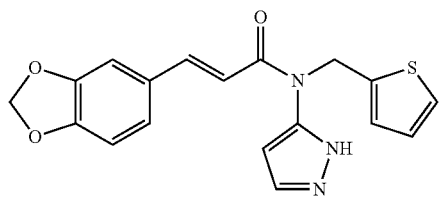 [SMILES: O=C(/C=C/c1ccc2c(c1)OCO2)N(Cc1cccs1)c1ccn[nH]1]

(E)-3-(benzo[d][1,3]dioxol-5-yl)-N-(1H-pyrazol-5-yl)-N-(thiophen-2-ylmethyl)acrylamide; Example 171

Prepared in a similar manner to example 6 from (E)-3-(benzo[d][1,3]dioxol-5-yl)acryloyl chloride and N-(thiophen-2-ylmethyl)-1H-pyrazol-5-amine. $^1$H NMR (400 MHz, CDCl$_3$) δ 5.18 (br s, 2H), 5.96 (s, 2H), 6.09 (br s, 1H), 6.37 (br d, J=14.1 Hz, 1H), 6.75 (d, J=8.0 Hz, 1H), 6.84 (br s, 1H), 6.87-6.98 (m, 3H), 7.19 (dd, J=5.1, 1.2 Hz, 1H), 7.55 (d, J=2.4 Hz, 1H), 7.67 (d, J=15.4 Hz, 1H), 10.16 (br s, 1H); M+H (354.1).

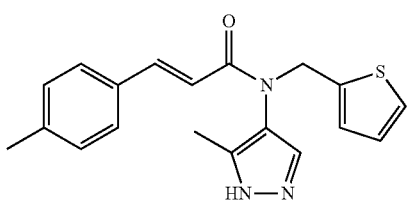 [SMILES: Cc1ccc(/C=C/C(=O)N(Cc2cccs2)c2cn[nH]c2C)cc1]

(E)-N-(5-methyl-1H-pyrazol-4-yl)-N-(thiophen-2-ylmethyl)-3-p-tolylacrylamide; Example 172

Prepared in a similar manner to example 6 from (E)-3-p-tolylacryloyl chloride and 5-methyl-N-(thiophen-2-ylmethyl)-1H-pyrazol-4-amine. $^1$H NMR (400 MHz, CDCl$_3$) δ 1.92 (s, 3H), 2.32 (s, 3H), 5.01 (br s, 2H), 6.36 (d, J=15.6 Hz, 1H), 6.83-6.91 (m, 2H), 7.09 (d, J=8.0 Hz, 2H), 7.21 (dd, J=5.0, 1.4 Hz, 1H), 7.25 (d, J=8.3 Hz, 2H), 7.38 (s, 1H), 7.75 (d, J=15.6 Hz, 1H); M+H (338.1).

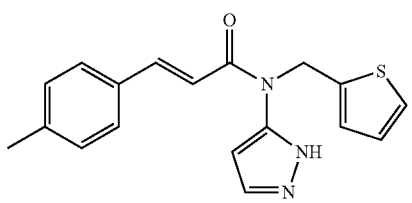 [SMILES: Cc1ccc(/C=C/C(=O)N(Cc2cccs2)c2ccn[nH]2)cc1]

(E)-N-(1H-pyrazol-5-yl)-N-(thiophen-2-ylmethyl)-3-p-tolylacrylamide; Example 173

Prepared in a similar manner to example 6 from (E)-3-p-tolylacryloyl chloride and N-(thiophen-2-ylmethyl)-1H-pyrazol-5-amine. $^1$H NMR (400 MHz, DMSO-d6) δ 2.29 (s, 3H), 5.06 (br s, 2H), 6.13 (br s, 1H), 6.52 (br d, J=15.8 Hz, 1H), 6.90 (m, 2H), 7.18 (d, J=7.7 Hz, 2H), 7.24-7.44 (m, 3H), 7.55 (d, J=15.6 Hz, 1H), 7.78 (br s, 1H), 12.85 (br s, 1H); M+H (324.1).

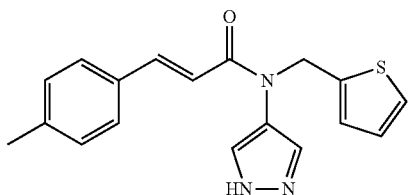 [SMILES: Cc1ccc(/C=C/C(=O)N(Cc2cccs2)c2cn[nH]c2)cc1]

(E)-N-(1H-pyrazol-4-yl)-N-(thiophen-2-ylmethyl)-3-p-tolylacrylamide; Example 174

To a 0° C. stirring solution of (E)-3-p-tolylacryloyl chloride (362 mg, 2.000 mmol) in DCM (4.0 mL) was added pyridine (162 uL, 2.000 mmol) and then N-(thiophen-2-ylmethyl)-1H-pyrazol-4-amine (179 mg, 1.000 mmol). The ice bath was removed and the reaction was stirred until completion. All the volatiles were evaporated under vacuum and the residue was taken up in EtOH (15.0 mL) and THF (5.0 mL). To this mixture was added 1.0 M NaOH (6.0 mL; 6.000 mmol) and the reaction was stirred overnight.

All the volatiles were evaporated under vacuum and the residue was taken up in DCM. The obtained organic layer was washed with water and then brine. The resulting organic solution was dried over MgSO$_4$ and concentrated. The obtained crude product was absorbed under vacuum on Florisil with the aid of DCM (dry load). The obtained dispersion was purified on the biotage (DCM:MeOH 1-15% gradient over 40 CV, 40 g Silicycle column).

The collected fractions were evaporated to afford (E)-N-(1H-pyrazol-4-yl)-N-(thiophen-2-ylmethyl)-3-p-tolylacrylamide (267 mg, 0.8256 mmol; 83%) as a white solid, which was judged less than 97% pure by $^1$H-NMR and LC-MS analysis.

The said material was then completely dissolved in hot mixture of EtOH (5.0 mL) and DCM (2.0 mL). Upon cooling thick white needles started to form and the process was allowed to happen overnight. After decanting, the liquids were taken away with a pipette and the obtained solid was washed with three aliquots of cold EtOH. The obtained crystals were then heated in hot ethanol and the volatiles were then evaporated at the rotavap. This step was repeated 3 times in order to get rid of traces of DCM. The solids were then left overnight under high vacuum.

In this way, 169 mg (0.5226 mmol, 52%) were obtained in purity judged more than 97% pure by $^1$H-NMR and LC-MS analysis. $^1$H NMR (400 MHz, DMSO-d6, T=80° C.) δ 2.30 (s, 3H), 5.03 (s, 2H), 6.58 (s, 1H), 6.98-6.85 (m, 2H), 7.17 (d, J=8.1 Hz, 2H), 7.40 (ddd, J=41.4, 19.2, 11.8 Hz, 6H); M+H (324.1).; Example 174a (E)-3-p-tolylacryloyl chloride To a 0° C. stirring suspension of 4.22 g of the acid (26.02 mmol; 1.0 eqmol) in 50.0 mL of DCM, it was added 2.38 mL of oxalyl chloride (27.32 mmol; 1.05 eqmol) and then 60 uL of DMF (0.7806 mmol; 0.03 eqmol). The ice bath was removed and the reaction was allowed to stir at room temperature until gas evolution ceased (bubbler monitor).

All the volatiles were then evaporated at the rotavap under high vacuum. 4.723 g (26.14 mmol; quant.) of a white solid were recovered. This material was used in the next step without any further purification.

Example 174b;
N-(thiophen-2-ylmethyl)-1H-pyrazol-4-amine

To a 0° C. stirring mixture of 1H-pyrazol-4-amine (250 mg, 3.008 mmol) and thiophene-2-carbaldehyde (281 uL, 3.008 mmol) in methanol and acetic acid (5.0 ml, 10:1 ratio) was added 5-ethyl-2-methylpyridine borane complex (444 uL, 3.008 mmol). The ice bath was removed and the flask was attached to a bubbler to allow gas evolution and expansion. The reaction was stirred overnight at room temp. Most of the volatiles were evaporated in vacuo. With the aid of a 0° C. chilling bath, a 10 M solution of NaOH in water was carefully added. The ice bath was removed and stirring was continued for nearly 1 hour. The aqueous layer was extracted with DCM (3×), washed with brine, and dried over MgSO$_4$ and concentrated. The obtained crude product was left under vacuum to remove the volatiles. The obtained viscous oil was diluted with DCM and evaporated under a gentle stream of nitrogen overnight. Solid crystals of the amine separated out and were washed with three aliquots of Hex:EtOAc=9:1. In this way, 391 mg (2.181 mmol; 72%) of the desired product were obtained in more than 97% purity by $^1$H-NMR analysis. $^1$H NMR (400 MHz, DMSO-d6) δ 4.21 (d, J=5.6 Hz, 1H), 4.92 (t, J=6.0 Hz, 1H), 6.94 (dd, J=5.1, 3.4 Hz, 1H), 7.10-6.99 (m, 3H), 7.36 (dd, J=5.1, 1.2 Hz, 1H), 12.05 (br s, 1H).

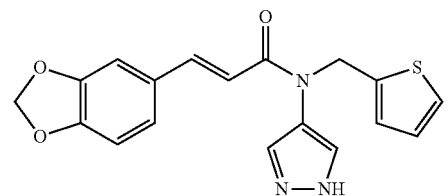 [SMILES: O=C(/C=C/c1ccc2c(c1)OCO2)N(Cc1cccs1)c1cn[nH]c1]

(E)-3-(benzo[d][1,3]dioxol-5-yl)-N-(1H-pyrazol-4-yl)-N-(thiophen-2-ylmethyl)acrylamide; Example 175

Prepared in a similar manner to example 6 from (E)-3-(benzo[d][1,3]dioxol-5-yl)acryloyl chloride and N-(thiophen-2-ylmethyl)-1H-pyrazol-4-amine. Yield 82%. $^1$H NMR (400 MHz, CDCl₃) δ 5.04 (br s, 2H), 5.95 (s, 2H), 6.33 (d, J=15.5 Hz, 1H), 6.75 (d, J=8.0 Hz, 1H), 6.81 (br d, J=1.3 Hz, 1H), 6.86-6.97 (m, 3H), 7.22 (dd, J=4.8, 1.5 Hz, 1H), 7.43 (br s, 2H), 7.66 (d, J=15.5 Hz, 1H); M+H (354.1).

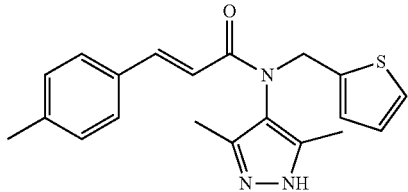 [SMILES: Cc1ccc(/C=C/C(=O)N(Cc2cccs2)c2c(C)n[nH]c2C)cc1]

(E)-N-(3,5-dimethyl-1H-pyrazol-4-yl)-N-(thiophen-2-ylmethyl)-3-p-tolylacrylamide; Example 176

Prepared in a similar manner to example 6 from (E)-3-p-tolylacryloyl chloride and 3,5-dimethyl-N-(thiophen-2-ylmethyl)-1H-pyrazol-4-amine. ¹H NMR (400 MHz, CDCl₃) δ 1.89 (s, 6H), 2.33 (s, 3H), 4.96 (br s, 2H), 6.28 (d, J=15.6 Hz, 1H), 6.83-6.86 (m, 1H), 6.89 (dd, J=5.1, 3.5 Hz, 1H), 7.10 (d, J=8.0 Hz, 2H), 7.22 (dd, J=5.1, 1.3 Hz, 1H), 7.25 (d, J=8.0 Hz, 2H), 7.75 (d, J=15.6 Hz, 1H); M+H (352.1).

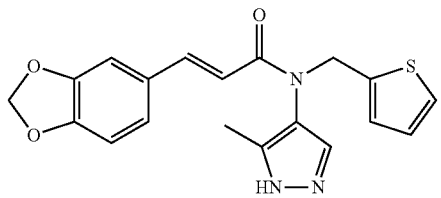 [SMILES: Cc1[nH]ncc1N(Cc1cccs1)C(=O)/C=C/c1ccc2c(c1)OCO2]

(E)-3-(benzo[d][1,3]dioxol-5-yl)-N-(5-methyl-1H-pyrazol-4-yl)-N-(thiophen-2-ylmethyl)acrylamide; Example 177

Prepared in a similar manner to example 6 from (E)-3-(benzo[d][1,3]dioxol-5-yl)acryloyl chloride and 5-methyl-N-(thiophen-2-ylmethyl)-1H-pyrazol-4-amine. ¹H NMR (400 MHz, CDCl₃) δ 1.91 (s, 3H), 4.99 (s, 2H), 5.96 (s, 2H), 6.21 (d, J=15.5 Hz, 1H), 6.75 (d, J=8.0 Hz, 1H), 6.80 (d, J=1.7 Hz, 1H), 6.93-6.83 (m, 3H), 7.22 (dd, J=5.1, 1.2 Hz, 1H), 7.36 (s, 1H), 7.68 (d, J=15.5 Hz, 1H); M+H (368.1).

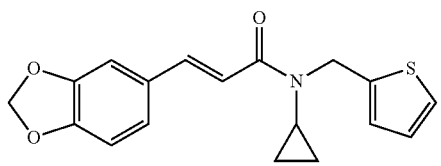 [SMILES: O=C(/C=C/c1ccc2c(c1)OCO2)N(Cc1cccs1)C1CC1]

(E)-3-(benzo[d][1,3]dioxol-5-yl)-N-cyclopropyl-N-(thiophen-2-ylmethyl)acrylamide; Example 178

This compound was commercially available. M+H (302.1).

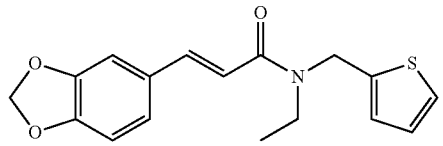

(E)-3-(benzo[d][1,3]dioxol-5-yl)-N-ethyl-N-(thiophen-2-ylmethyl)acrylamide; Example 179

Prepared in a similar manner to example 21 from (E)-3-(benzo[d][1,3]dioxol-5-yl)acryloyl chloride and N-(thiophen-2-ylmethyl)ethanamine. ¹H NMR (400 MHz, DMSO-d6, T=80° C.) δ 1.12 (t, J=7.1 Hz, 3H), 3.50 (br q, J=6.9 Hz, 2H), 4.81 (br s, 2H), 6.04 (d, J=0.5 Hz, 2H), 6.91 (d, J=8.0 Hz, 1H), 6.94-7.03 (m, 2H), 7.05 (br d, J=3.4 Hz, 1H), 7.12 (br dd, J=8.0, 1.5 Hz, 1H), 7.34 (br s, 1H), 7.38 (br d, J=5.1 Hz, 1H), 7.47 (d, J=15.3 Hz, 1H); M+H (316.1).

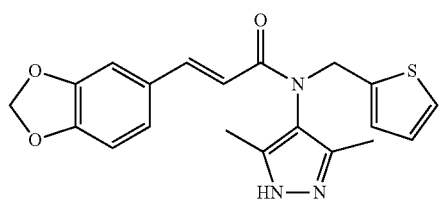 [SMILES: Cc1n[nH]c(C)c1N(Cc1cccs1)C(=O)/C=C/c1ccc2c(c1)OCO2]

(E)-3-(benzo[d][1,3]dioxol-5-yl)-N-(3,5-dimethyl-1H-pyrazol-4-yl)-N-(thiophen-2-ylmethyl)acrylamide; Example 180

Prepared in a similar manner to example 6 from (E)-3-(benzo[d][1,3]dioxol-5-yl)acryloyl chloride and 3,5-dimethyl-N-(thiophen-2-ylmethyl)-1H-pyrazol-4-amine. ¹H NMR (400 MHz, CDCl₃) δ 1.90 (s, 6H), 4.95 (br s, 2H), 5.93 (s, 2H), 6.17 (d, J=15.5 Hz, 1H), 6.72 (d, J=8.0 Hz, 1H), 6.79 (d, J=1.7 Hz, 1H), 6.81-6.91 (m, 3H), 7.20 (dd, J=5.1, 1.3 Hz, 1H), 7.69 (d, J=15.5 Hz, 1H); M+H (382.1).

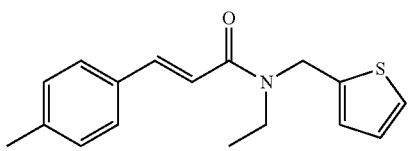

(E)-N-ethyl-N-(thiophen-2-ylmethyl)-3-p-tolylacrylamide; Example 181

Prepared in a similar manner to example 21 from (E)-3-p-tolylacryloyl chloride and N-(thiophen-2-ylmethyl)ethanamine. Yield 82%. ¹H NMR (400 MHz, DMSO-d6, T=80° C.) δ 1.13 (t, J=7.1 Hz, 3H), 2.33 (s, 3H), 3.51 (br q, J=7.1 Hz, 2H), 4.82 (br s, 2H), 6.97 (dd, J=5.0, 3.5 Hz, 1H), 7.01-7.11 (m, 2H), 7.21 (br d, J=8.0 Hz, 2H), 7.39 (dd, J=5.1, 1.2 Hz, 1H), 7.53 (br m, 3H) M+H (286.2).

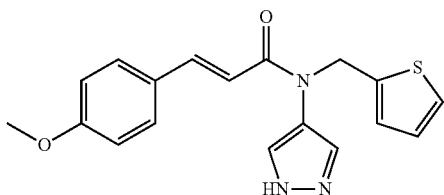 [SMILES: COc1ccc(/C=C/C(=O)N(Cc2cccs2)c2cn[nH]c2)cc1]

(E)-3-(4-methoxyphenyl)-N-(1H-pyrazol-4-yl)-N-(thiophen-2-ylmethyl)acrylamide; Example 183

Prepared in a similar manner to example 6 from (E)-3-(4-methoxyphenyl)acryloyl chloride and N-(thiophen-2-ylmethyl)-1H-pyrazol-4-amine. $^1$H NMR (400 MHz, DMSO-d6) δ 3.75 (s, 3H), 4.98 (s, 2H), 6.43 (d, J=15.6 Hz, 1H), 6.82-6.98 (m, 4H), 7.32-7.46 (m, 4H), 7.52 (d, J=15.6 Hz, 1H), 7.73 (br s, 1H), 12.98 (br s, 1H); M+H (340.1).

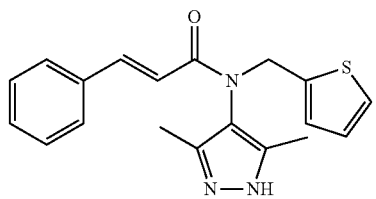

N-(3,5-dimethyl-1H-pyrazol-4-yl)-N-(thiophen-2-ylmethyl)cinnamamide; Example 186

Prepared in a similar manner to example 6 from cinnamoyl chloride and 3,5-dimethyl-N-(thiophen-2-ylmethyl)-1H-pyrazol-4-amine. Yield 67%. $^1$H NMR (400 MHz, DMSO-d6) δ 1.76 (s, 6H), 4.77-4.96 (br m, 2H), 6.33 (d, J=15.7 Hz, 1H), 6.83 (dd, J=3.4, 1.2 Hz, 1H), 6.92 (dd, J=5.1, 3.4 Hz, 1H), 7.35 (dd, J=6.2, 2.6 Hz, 3H), 7.43 (m, 3H), 7.59 (d, J=15.7 Hz, 1H), 12.36 (br s, 1H); M+H (338.1).

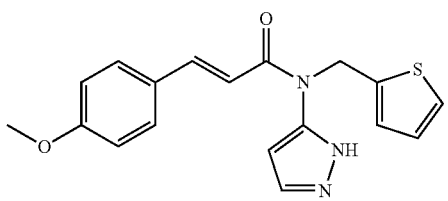 [SMILES: COc1ccc(/C=C/C(=O)N(Cc2cccs2)c2ccn[nH]2)cc1]

(E)-3-(4-methoxyphenyl)-N-(1H-pyrazol-5-yl)-N-(thiophen-2-ylmethyl)acrylamide; Example 184

Prepared in a similar manner to example 6 from (E)-3-(4-methoxyphenyl)acryloyl chloride and N-(thiophen-2-ylmethyl)-1H-pyrazol-5-amine. $^1$H NMR (400 MHz, CDCl$_3$) δ 3.79 (s, 3H), 5.18 (br s, 2H), 6.09 (br s, 1H), 6.41 (br d, J=15.2 Hz, 2H), 6.81 (d, J=8.7 Hz, 1H), 6.89 (dd, J=5.0, 3.5 Hz, 1H), 6.95 (br d, J=2.8 Hz, 1H), 7.19 (dd, J=5.1, 1.2 Hz, 1H), 7.32 (br d, J=8.4 Hz, 2H), 7.52 (d, J=2.4 Hz, 1H), 7.72 (d, J=15.5 Hz, 1H); M+H (340.1).

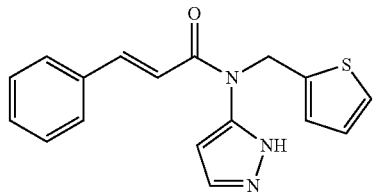 [SMILES: O=C(/C=C/c1ccccc1)N(Cc1cccs1)c1ccn[nH]1]

N-(1H-pyrazol-5-yl)-N-(thiophen-2-ylmethyl)cinnamamide; Example 187

Prepared in a similar manner to example 6 from cinnamoyl chloride and N-(thiophen-2-ylmethyl)-1H-pyrazol-5-amine. $^1$H NMR (400 MHz, CDCl$_3$) δ 5.19 (br s, 1H), 6.09 (br s, 2H), 6.54 (br d, J=15.0 Hz, 2H), 6.90 (dd, J=5.0, 3.5 Hz, 1H), 6.96 (br d, J=2.5 Hz, 1H), 7.20 (dd, J=5.1, 1.3 Hz, 1H), 7.30 (m, 3H), 7.37 (br s, 2H), 7.54 (d, J=2.4 Hz, 1H), 7.76 (d, J=15.6 Hz, 1H); M+H (310.1).

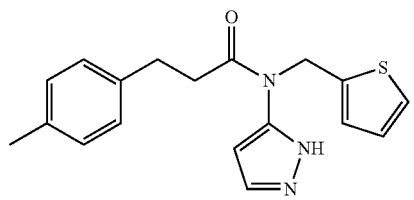

N-(1H-pyrazol-5-yl)-N-(thiophen-2-ylmethyl)-3-p-tolylpropanamide; Example 185

Prepared in a similar manner to example 6 from 3-p-tolylpropanoyl chloride and N-(thiophen-2-ylmethyl)-1H-pyrazol-5-amine. $^1$H NMR (400 MHz, CDCl$_3$) δ 2.28 (br s, 3H), 2.39-2.56 (m, 2H), 2.85-2.97 (m, 2H), 5.02 (br s, 2H), 5.91 (d, J=2.3 Hz, 1H), 6.81-6.91 (m, 2H), 6.93-7.06 (m, 4H), 7.15-7.22 (m, 1H), 7.45 (d, J=2.4 Hz, 1H), 10.17 (br s, 1H); M+H (326.1).

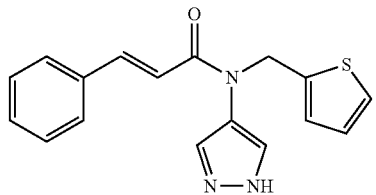 [SMILES: O=C(/C=C/c1ccccc1)N(Cc1cccs1)c1cn[nH]c1]

N-(1H-pyrazol-4-yl)-N-(thiophen-2-ylmethyl)cinnamamide; Example 190

Prepared in a similar manner to example 6 from cinnamoyl chloride and N-(thiophen-2-ylmethyl)-1H-pyrazol-4-amine. Yield 38%. Room temperature $^1$H NMR showed a mixture of rotamers: $^1$H NMR (400 MHz, acetone-d6) δ 2.82 (d, 2H), 5.05 (d, 2H), 6.68 (d, J=15.6 Hz, 1H), 6.93 (d, 2H), 7.26-7.72 (m, 9H), 12.24 (br s, 1H); M+H (310.1).

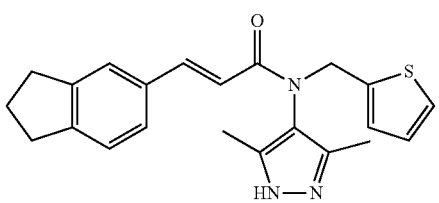 [SMILES: Cc1n[nH]c(C)c1N(Cc1cccs1)C(=O)/C=C/c1ccc2c(c1)CCC2]

(E)-3-(2,3-dihydro-1H-inden-5-yl)-N-(3,5-dimethyl-1H-pyrazol-4-yl)-N-(thiophen-2-ylmethyl)acrylamide; Example 192

Prepared in a similar manner to example 6 from (E)-3-(2,3-dihydro-1H-inden-5-yl)acryloyl chloride and 3,5-dimethyl-N-(thiophen-2-ylmethyl)-1H-pyrazol-4-amine. 1H NMR (400 MHz, CDCl$_3$) δ 1.90 (s, 6H), 2.05 (p, J=7.5 Hz, 2H), 2.86 (dd, J=12.8, 7.5 Hz, 4H), 4.96 (br s, 2H), 6.28 (d, J=15.6 Hz, 1H), 6.82-6.91 (m, 2H), 7.14 (br s, 2H), 7.18-7.25 (m, 2H), 7.77 (d, J=15.6 Hz, 1H); M+H (378.1).

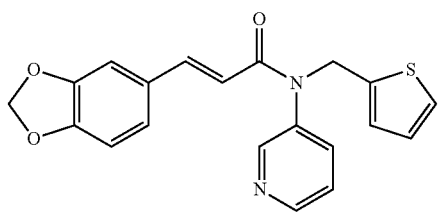 [SMILES: O=C(/C=C/c1ccc2c(c1)OCO2)N(Cc1cccs1)c1cccnc1]

((E)-3-(benzo[d][1,3]dioxol-5-yl)-N-(pyridin-3-yl)-N-(thiophen-2-ylmethyl)acrylamide; Example 195

Prepared in a similar manner to example 21 from (E)-3-(benzo[d][1,3]dioxol-5-yl)acryloyl chloride and N-(thiophen-2-ylmethyl)pyridin-3-amine. Yield 87%. Room temperature $^1$H NMR showed a mixture of rotamers: $^1$H NMR (400 MHz, CDCl$_3$) δ 5.15 (s, 2H), 5.95 (s, 2H), 6.01 (br d, 1H), 6.74 (m, 2H), 6.79-6.95 (m, 3H), 7.14-7.23 (m, 2H), 7.35 (m, 1H), 7.42 (m, 1H), 7.69 (m, 1H), 8.41 (dd, J=2.5, 0.7 Hz, 1H), 8.62 (dd, J=4.7, 1.6 Hz, 1H); M+H (365.1).

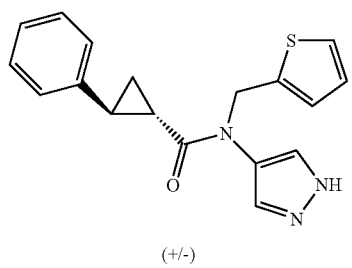 [SMILES: O=C([C@H]1C[C@@H]1c1ccccc1)N(Cc1cccs1)c1cn[nH]c1]

(+/−)

(+/−) (E)-2-phenyl-N-(1H-pyrazol-4-yl)-N-(thiophen-2-ylmethyl)cyclopropanecarboxamide; Example 196

Prepared in a similar manner to example 6 from (+/−) (E)-2-phenylcyclopropanecarbonyl chloride and N-(thiophen-2-ylmethyl)-1H-pyrazol-4-amine. Yield 88%. $^1$H NMR (400 MHz, DMSO-d6, T=80° C.) δ 1.19 (br m, 1H), 1.49 (m, 1H), 1.86 (br s, 1H), 2.38 (m, 1H), 4.95 (br s, 2H), 6.87 (br m, 1H), 6.96-6.90 (m, 1H), 7.02 (br d, J=7.2 Hz, 2H), 7.10-7.17 (m, 1H), 7.18-7.25 (m, 2H), 7.29 (br s, 1H), 7.36-7.37 (m, 1H), 7.58 (br s, 1H), 12.67 (br s, 1H); M+H (324.1).

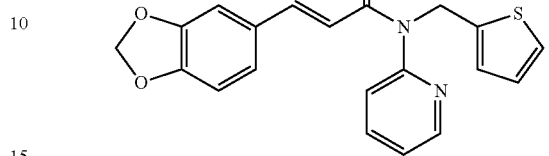

(E)-3-(benzo[d][1,3]dioxol-5-yl)-N-(pyridin-2-yl)-N-(thiophen-2-ylmethyl)acrylamide; Example 197

Prepared in a similar manner to example 21 from (E)-3-(benzo[d][1,3]dioxol-5-yl)acryloyl chloride and N-(thiophen-2-ylmethyl)pyridin-2-amine. $^1$H NMR (400 MHz, CDCl$_3$); δ 5.39 (d, J=0.5 Hz, 2H), 5.96 (s, 2H), 6.28 (d, J=15.4 Hz, 1H), 6.76 (d, J=8.0 Hz, 1H), 6.81 (d, J=1.7 Hz, 1H), 6.86 (dd, J=5.1, 3.5 Hz, 1H), 6.91 (m, 2H), 7.06 (br d, J=8.0 Hz, 1H), 7.16 (dd, J=5.1, 1.3 Hz, 1H), 7.23 (ddd, J=7.5, 4.9, 1.0 Hz, 1H), 7.61-7.75 (m, 2H), 8.59 (m, 1H); M+H (365.1).

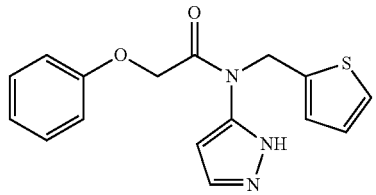 [SMILES: O=C(COc1ccccc1)N(Cc1cccs1)c1ccn[nH]1]

2-phenoxy-N-(1H-pyrazol-5-yl)-N-(thiophen-2-ylmethyl)acetamide; Example 199

Prepared in a similar manner to example 6 from 2-phenoxyacetyl chloride and N-(thiophen-2-ylmethyl)-1H-pyrazol-5-amine. $^1$H NMR (400 MHz, CDCl$_3$) δ 4.62 (br s, 2H), 5.07 (br s, 2H), 6.08 (br s, 1H), 6.83 (br d, J=8.0 Hz, 1H), 6.87-6.96 (m, 3H), 7.18-7.25 (m, 3H), 7.52 (d, J=2.5 Hz, 1H); M+H (314.1).

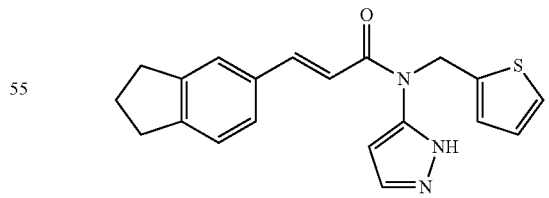

(E)-3-(2,3-dihydro-1H-inden-5-yl)-N-(1H-pyrazol-5-yl)-N-(thiophen-2-ylmethyl)acrylamide; Example 200

Prepared in a similar manner to example 6 from (E)-3-(2,3-dihydro-1H-inden-5-yl)acryloyl chloride and N-(thiophen-2-ylmethyl)-1H-pyrazol-5-amine. ¹H NMR (400 MHz, CDCl₃) δ 2.03 (p, J=7.5 Hz, 2H), 2.84 (m, 4H), 5.17 (s, 2H), 6.07 (br s, 1H), 6.48 (br d, J=15.5 Hz, 1H), 6.88 (br dd, J=5.0, 3.5 Hz, 1H), 6.93 (br d, J=2.7 Hz, 1H), 7.08-7.24 (m, 4H), 7.47 (d, J=2.4 Hz, 1H), 7.76 (d, J=15.5 Hz, 1H), 11.35 (br s, 1H); M+H (350.1).

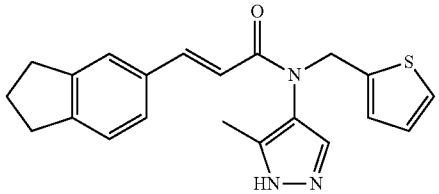 [SMILES: Cc1[nH]ncc1N(Cc1cccs1)C(=O)/C=C/c1ccc2c(c1)CCC2]

(E)-3-(2,3-dihydro-1H-inden-5-yl)-N-(5-methyl-1H-pyrazol-4-yl)-N-(thiophen-2-ylmethyl)acrylamide; Example 201

Prepared in a similar manner to example 6 from (E)-3-(2,3-dihydro-1H-inden-5-yl)acryloyl chloride and 5-methyl-N-(thiophen-2-ylmethyl)-1H-pyrazol-4-amine. ¹H NMR (400 MHz, CDCl₃) δ 1.93 (s, 3H), 2.03 (p, J=7.5 Hz, 2H), 2.85 (q, J=7.5 Hz, 4H), 5.01 (br s, 2H), 6.37 (d, J=15.5 Hz, 1H), 6.83-6.90 (m, 2H), 7.13 (br s, 2H), 7.17-7.23 (m, 2H), 7.40 (br s, 1H), 7.77 (d, J=15.6 Hz, 1H); M+H (364.1).

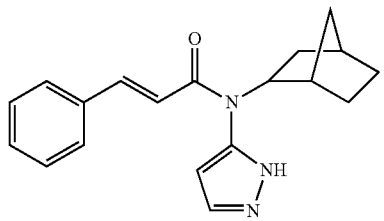 [SMILES: O=C(/C=C/c1ccccc1)N(c1ccn[nH]1)C1CC2CCC1C2]

N-(bicyclo[2.2.1]heptan-2-yl)-N-(1H-pyrazol-5-yl)cinnamamide; Example 203

Prepared in a similar manner to example 6 from cinnamoyl chloride and N-(bicyclo[2.2.1]heptan-2-yl)-1H-pyrazol-5-amine. ¹H NMR (400 MHz, CDCl₃) δ 0.80-0.87 (m, 1H), 1.00-1.08 (m, 1H), 1.30-1.35 (m, 1H), 1.35-1.48 (m, 1H), 1.54-1.48 (m, 1H), 1.68-1.78 (m, 1H), 1.89-1.78 (m, 1H), 2.10-2.13 (m, 1H), 2.92-2.99 (m, 1H), 4.60 (m, 1H), 6.18-6.25 (m, 2H), 7.21-7.33 (m, 5H), 7.59-7.69 (m, 2H); M+H (308.2).

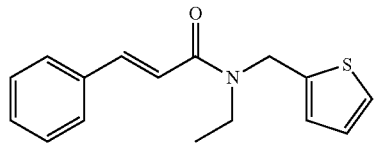 [SMILES: CCN(Cc1cccs1)C(=O)/C=C/c1ccccc1]

N-ethyl-N-(thiophen-2-ylmethyl)cinnamamide; Example 204

Prepared in a similar manner to example 21 from cinnamoyl chloride and N-(thiophen-2-ylmethyl)ethanamine. Room temperature ¹H-NMR showed a mixture of rotamers in ~2:1 ratio: ¹H NMR (400 MHz, DMSO-d6) δ 1.10 (m, 3H), 3.41 (minor) (br q, J=7.0 Hz, 2H), 3.54 (major) (br q, J=6.9 Hz, 2H), 4.73 (major) (br s, 2H), 4.97 (minor) (br s, 2H), 6.93-7.01 (m, 1H), 7.08 (m, 1H), 7.13 (major) (d, J=15.4 Hz, 1H), 7.28 (minor) (d, J=15.4 Hz, 1H), 7.42 (m, 4H), 7.56 (m, 1H), 7.71 (m, 2H); M+H (272.1).

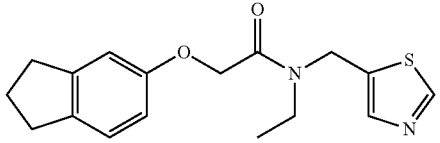 [SMILES: CCN(Cc1cncs1)C(=O)COc1ccc2c(c1)CCC2]

2-(2,3-dihydro-1H-inden-5-yloxy)-N-ethyl-N-(thiazol-5-ylmethyl)acetamide; Example 205

Prepared in a similar manner to example 21 from 2-(2,3-dihydro-1H-inden-5-yloxy)acetyl chloride and N-(thiazol-5-ylmethyl)ethanamine. Room temperature ¹H-NMR showed a mixture of rotamers in ~4:1 ratio: ¹H NMR (400 MHz, DMSO-d6) δ 0.99 (minor) (t, J=7.0 Hz, 3H), 1.14 (major) (t, J=7.1 Hz, 3H), 1.99 (p, J=7.4 Hz, 2H), 2.70-2.86 (m, 4H), 3.22-3.41 (m, 2H), 4.68 (major) (br s, 2H), 4.77 (br s, 2H), 4.83 (minor) (br s, 2H), 6.66 (dd, J=8.2, 2.5 Hz, 1H), 6.76 (br s, 1H), 7.09 (d, J=8.2 Hz, 1H), 7.86 (major) (s, 1H), 7.91 (minor) (s, 1H), 8.99 (major) (s, 1H), 9.09 (minor) (s, 1H); M+H (317.1).

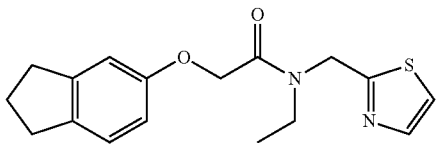

2-(2,3-dihydro-1H-inden-5-yloxy)-N-ethyl-N-(thiazol-5-ylmethyl)acetamide; Example 212

Prepared in a similar manner to example 21 from 2-(2,3-dihydro-1H-inden-5-yloxy)acetyl chloride and N-(thiazol-2-ylmethyl)ethanamine. Room temperature ¹H-NMR showed a mixture of rotamers in ~2:1 ratio: ¹H NMR (400 MHz, DMSO-d6) δ 1.01 (minor) (t, J=7.1 Hz, 3H), 1.15 (major) (t, J=7.1 Hz, 3H), 1.99 (m, 2H), 2.67-2.88 (m, 4H), 3.36 (minor) (q, J=7.1 Hz, 2H), 3.46 (major) (q, J=7.1 Hz, 2H), 4.77 (major) (br s, 2H), 4.83 (major) (br s, 2H), 4.85 (minor) (br s, 2H), 4.92 (minor) (s, 1H), 6.63 (minor) (dd, J=8.2, 2.3 Hz, 1H), 6.67 (major) (dd, J=8.2, 2.5 Hz, 1H), 6.75 (minor) (br d, J=1.8 Hz, 1H), 6.78 (major) (br d, J=2.0 Hz, 1H), 7.08 (t, J=8.3 Hz, 1H), 7.67 (major) (d, J=3.3 Hz, 1H), 7.72 (major) (d, J=3.3 Hz, 1H), 7.74 (minor) (d, J=3.3 Hz, 1H), 7.83 (minor) (d, J=3.2 Hz, 1H); M+H (317.1).

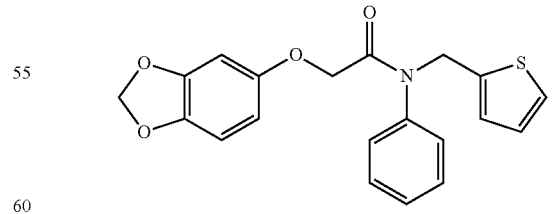

2-(benzo[d][1,3]dioxol-5-yloxy)-N-phenyl-N-(thiophen-2-ylmethyl)acetamide; Example 217

Prepared in a similar manner to example 21 from 2-(benzo[d][1,3]dioxol-5-yloxy)acetyl chloride and N-(thiophen-2-ylmethyl)aniline. ¹H NMR (400 MHz, CDCl₃) δ 5.93 (s, 2H), 6.10 (d, J=15.5 Hz, 1H), 6.73 (dd, J=4.8, 3.2 Hz, 2H), 6.87 (m, 3H), 7.05-7.14 (m, 2H), 7.21 (dd, J=5.1, 1.2 Hz, 1H), 7.33-7.44 (m, 3H), 7.65 (d, J=15.5 Hz, 1H); M+H (368.1).

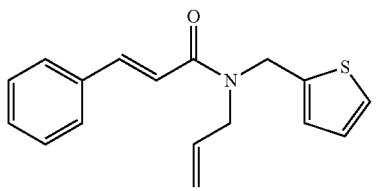 [SMILES: C=CCN(Cc1cccs1)C(=O)/C=C/c1ccccc1]

N-allyl-N-(thiophen-2-ylmethyl)cinnamamide; Example 218

This compound was purchased from Enamine. M+H (284.1).

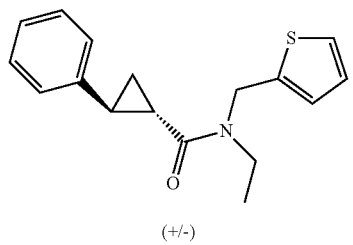 [SMILES: CCN(Cc1cccs1)C(=O)[C@H]1C[C@@H]1c1ccccc1]

(+/−)

(+/−) (E)-N-ethyl-2-phenyl-N-(thiophen-2-ylmethyl) cyclopropanecarboxamide; Example 220

Prepared in a similar manner to example 6 from (+/−) (E)-2-phenylcyclopropanecarbonyl chloride and N-(thiophen-2-ylmethyl)ethanamine. ¹H NMR (400 MHz, DMSO-d6, T=80° C.) δ 1.19 (br m, 1H), 1.49 (m, 1H), 1.86 (br s, 1H), 2.34-2.42 (m, 1H), 4.95 (br s, 2H), 6.87 (br d, J=3.4 Hz, 1H), 6.90-6.96 (m, 1H), 7.02 (br d, J=7.2 Hz, 2H), 7.10-7.17 (m, 1H), 7.18-7.25 (m, 2H), 7.30 (br s; 1H), 7.35-7.39 (m, 1H), 7.58 (s, 1H), 12.67 (br s, 1H); M+H (286.1).

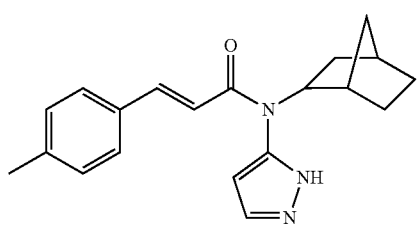 [SMILES: Cc1ccc(/C=C/C(=O)N(c2ccn[nH]2)C2CC3CCC2C3)cc1]

(E)-N-(bicyclo[2.2.1]heptan-2-yl)-N-(1H-pyrazol-5-yl)-3-p-tolylacrylamide; Example 223

Prepared in a similar manner to example 6 from (E)-3-p-tolylacryloyl chloride and N-(bicyclo[2.2.1]heptan-2-yl)-1H-pyrazol-5-amine. ¹H NMR (400 MHz, CDCl₃) δ 0.84 (m, 1H), 1.08-0.99 (m, 1H), 1.25-1.54 (m, 4H), 1.64-1.78 (m, 1H), 1.78-1.89 (m, 1H), 2.10 (br s, 1H), 2.30 (s, 3H), 2.95 (br s, 1H), 4.51-4.68 (m, 1H), 6.17 (d, J=15.5 Hz, 1H), 6.21 (d, J=2.3 Hz, 1H), 7.05 (d, J=8.1 Hz, 2H), 7.19 (d, J=8.1 Hz, 2H), 7.58-7.67 (m, 2H); M+H (321.2).

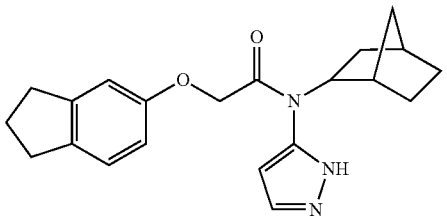 [SMILES: O=C(COc1ccc2c(c1)CCC2)N(c1ccn[nH]1)C1CC2CCC1C2]

N-(bicyclo[2.2.1]heptan-2-yl)-2-(2,3-dihydro-1H-inden-5-yloxy)-N-(1H-pyrazol-5-yl)acetamide; Example 229

Prepared in a similar manner to example 6 from 2-(2,3-dihydro-1H-inden-5-yloxy)acetyl chloride and N-(bicyclo[2.2.1]heptan-2-yl)-1H-pyrazol-5-amine. ¹H NMR (400 MHz, CDCl₃) δ 0.78-0.88 (m, 1H), 0.94-1.09 (m, 1H), 1.27-1.50 (m, 4H), 1.62-1.77 (m, 1H), 1.77-1.89 (m, 1H), 1.96-2.03 (m, 2H), 2.09 (br s, 1H), 2.78 (m, 4H), 2.95 (br s, 1H), 4.36 (m, 2H), 4.46-4.60 (m, 1H), 6.19 (d, J=2.4 Hz, 1H), 6.58 (dd, J=8.2, 2.5 Hz, 1H), 6.68 (br d, J=2.3 Hz, 1H), 7.01 (d, J=8.2 Hz, 1H), 7.59 (d, J=2.4 Hz, 1H), 11.11 (br s, 1H); M+H (351.2).

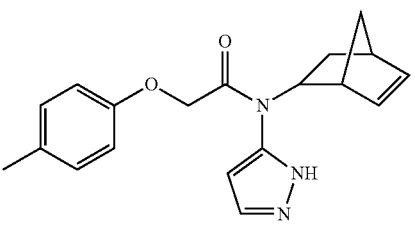

endo/exo mixture

N-(bicyclo[2.2.1]hept-5-en-2-ylmethyl)-N-(1H-pyrazol-5-yl)-2-(p-tolyloxy)acetamide; Example 230

Prepared in a similar manner to example 6 from 2-(p-tolyloxy)acetyl chloride and N-(bicyclo[2.2.1]hept-5-en-2-ylmethyl)-1H-pyrazol-5-amine (endo and exo mixture). ¹H NMR (400 MHz, CDCl₃) δ 0.53 (m, 1H), 1.04-1.50 (m, 3H), 1.57-1.82 (m, 1H), 2.22 (s, 3H), 2.32-2.43 (m, 1H), 2.73 (br s, 1H), 2.80 (br s, 1H), 3.44-3.89 (m, 2H), 4.53-4.57 (m, 2H), 5.78-5.86 (m, 1H), 5.96-6.05 (m, 1H), 6.05-6.13 (m, 1H), 6.13-6.22 (m, 1H), 6.71 (m, 2H), 6.99 (d, J=8.3 Hz, 2H), 7.53-7.57 (m, 1H), 11.17 (br s, 1H); M+H (338.2).

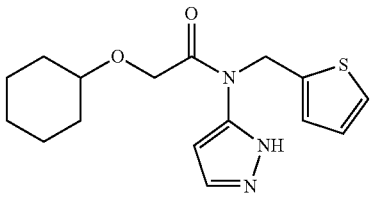 [SMILES: O=C(COC1CCCCC1)N(Cc1cccs1)c1ccn[nH]1]

2-(cyclohexyloxy)-N-(1H-pyrazol-5-yl)-N-(thiophen-2-ylmethyl)acetamide; Example 232

Prepared in a similar manner to example 6 from 2-(cyclohexyloxy)acetyl chloride and N-(thiophen-2-ylmethyl)-

1H-pyrazol-5-amine. ¹H NMR (400 MHz, CDCl₃) δ 1.09-1.33 (m, 6H), 1.69 (m, 2H), 1.87 (m, 2H), 3.29 (br s, 1H), 4.07 (br s, 2H), 5.04 (br s, 2H), 6.03 (br s, 1H), 6.86-6.94 (m, 2H), 7.19 (dd, J=5.0, 1.3 Hz, 1H), 7.51 (d, J=2.4 Hz, 1H); M+H (320.1).

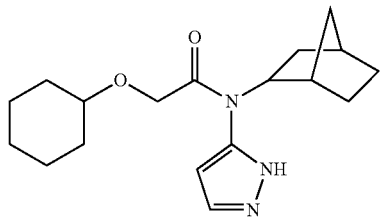 [SMILES: O=C(COC1CCCCC1)N(c1ccn[nH]1)C1CC2CCC1C2]

N-(bicyclo[2.2.1]heptan-2-yl)-2-(cyclohexyloxy)-N-(1H-pyrazol-5-yl)acetamide; Example 233

Prepared in a similar manner to example 6 from 2-(cyclohexyloxy)acetyl chloride and N-(bicyclo[2.2.1]heptan-2-yl)-1H-pyrazol-5-amine. ¹H NMR (400 MHz, CDCl₃) δ 0.76 (ddd, J=13.1, 5.2, 2.9 Hz, 1H), 0.93-1.03 (m, 1H), 1.07-1.54 (m, 10H), 1.60-1.92 (m, 6H), 2.08 (br s, 1H), 2.93 (br s, 1H), 3.19-3.29 (m, 1H), 3.78-3.93 (m, 2H), 4.43-4.54 (m, 1H), 6.15 (d, J=2.4 Hz, 1H), 7.61 (d, J=2.4 Hz, 1H); M+H (318.2).

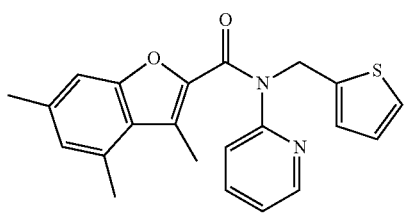 [SMILES: Cc1cc(C)c2c(C)c(C(=O)N(Cc3cccs3)c3ccccn3)oc2c1]

3,4,6-trimethyl-N-(pyridin-2-yl)-N-(thiophen-2-ylmethyl)benzofuran-2-carboxamide; Example 235

This compound was purchased from Princeton. M+H (377.1).

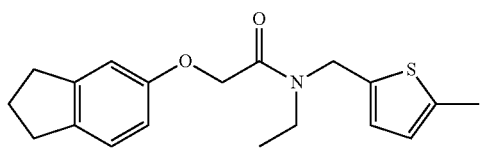 [SMILES: CCN(Cc1ccc(C)s1)C(=O)COc1ccc2c(c1)CCC2]

2-(2,3-dihydro-1H-inden-5-yloxy)-N-ethyl-N-((5-methylthiophen-2-yl)methyl)acetamide; Example 236

Prepared in a similar manner to example 21 from 2-(2,3-dihydro-1H-inden-5-yloxy)acetyl chloride and N-((5-methylthiophen-2-yl)methyl)ethanamine. Room temperature ¹H-NMR showed a mixture of rotamers in ~2:1 ratio: ¹H NMR (400 MHz, DMSO-d6) δ 1.00 (minor) (t, J=7.1 Hz, 3H), 1.13 (major) (t, J=7.1 Hz, 3H), 1.92-2.09 (m, 2H), 2.38 (major) (s, 2H), 2.41 (minor) (s, 3H), 2.78 (m, 4H), 3.25-3.38 (m, 2H), 4.54 (major) (br s, 2H), 4.65 (minor) (br s, 2H), 4.75 (br s, 2H), 6.56-6.71 (m, 2H), 6.73 (minor) (d, J=1.6 Hz, 1H), 6.77 (major) (d, J=2.0 Hz, 1H), 6.81 (major) (d, J=3.3 Hz, 1H), 6.87 (minor) (d, J=3.3 Hz, 1H), 7.09 (m, 1H); M+H (330.1).

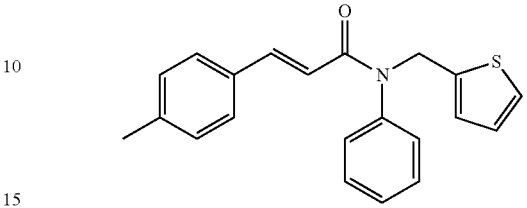

(E)-N-phenyl-N-(thiophen-2-ylmethyl)-3-p-tolylacrylamide; Example 237

Prepared in a similar manner to example 21 from (E)-3-p-tolylacryloyl chloride and N-(thiophen-2-ylmethyl)aniline. ¹H NMR (400 MHz, CDCl₃) δ 2.31 (s, 3H), 5.14 (s, 2H), 6.23 (d, J=15.6 Hz, 1H), 6.82-6.92 (m, 2H), 7.05-7.13 (m, 4H), 7.16-7.24 (m, 3H), 7.33-7.44 (m, 3H), 7.72 (d, J=15.6 Hz, 1H); M+H (334.1).

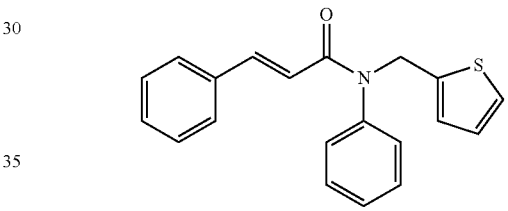

N-phenyl-N-(thiophen-2-ylmethyl)cinnamamide; Example 238

Prepared in a similar manner to example 21 from cinnamoyl chloride and N-(thiophen-2-ylmethyl)aniline. ¹H NMR (400 MHz, DMSO-d6) δ 5.14 (br s, 2H), 6.29 (br d, J=15.4 Hz, 1H), 6.84 (m, 1H), 6.89 (dd, J=5.1, 3.4 Hz, 1H), 7.14-7.23 (m, 2H), 7.30-7.51 (m, 9H), 7.60 (d, J=15.6 Hz, 1H); M+H (320.1).

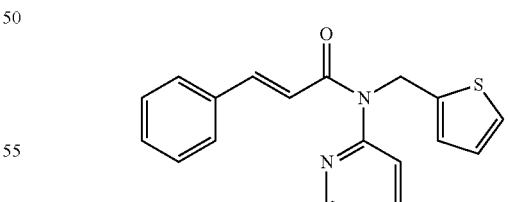

N-(pyridin-2-yl)-N-(thiophen-2-ylmethyl)cinnamamide; Example 239

Prepared in a similar manner to example 21 from cinnamoyl chloride and N-(thiophen-2-ylmethyl)pyridin-2-amine. ¹H NMR (400 MHz, DMSO-d6) δ 5.34 (br s, 2H), 6.64 (br d, J=15.5 Hz, 1H), 6.88 (dd, J=5.0, 3.5 Hz, 1H), 6.92

(br dd, J=3.4, 1.2 Hz, 1H), 7.28-7.41 (m, 6H), 7.48-7.55 (m, 2H), 7.62 (d, J=15.5 Hz, 1H), 7.83-7.91 (m, 1H), 8.53 (ddd, J=4.8, 1.9, 0.9 Hz, 1H); M+H (321.1).

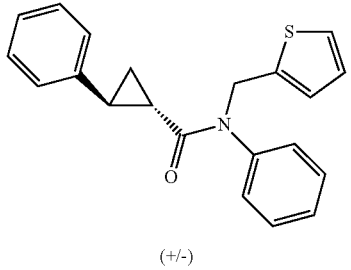 [SMILES: O=C([C@H]1C[C@@H]1c1ccccc1)N(Cc1cccs1)c1ccccc1]

(+/−)

(+/−) (E)-N,2-diphenyl-N-(thiophen-2-ylmethyl)cyclopropanecarboxamide; Example 240

Prepared in a similar manner to example 21 from (+/−) (E)-2-phenylcyclopropanecarbonyl chloride and N-(thiophen-2-ylmethyl)aniline. $^1$H NMR (400 MHz, CDCl$_3$) δ 1.07 (m, 1H), 1.57-1.64 (m, 1H), 1.69 (m, 1H), 2.58 (m, 1H), 5.06 (s, 2H), 7.04-7.24 (m, 5H), 7.26-7.32 (m, 3H); M+H (334.1).

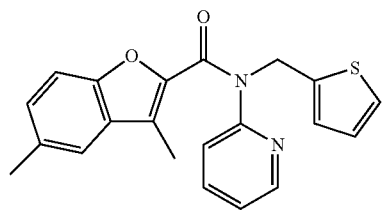 [SMILES: Cc1ccc2oc(C(=O)N(Cc3cccs3)c3ccccn3)c(C)c2c1]

3,5-dimethyl-N-(pyridin-2-yl)-N-(thiophen-2-ylmethyl)benzofuran-2-carboxamide; Example 241

This compound was purchased from Princeton. M+H (363.1).

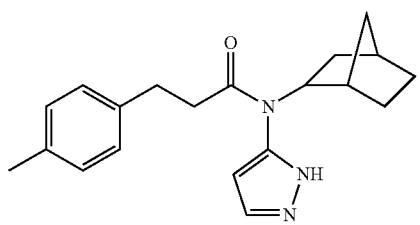 [SMILES: Cc1ccc(CCC(=O)N(c2ccn[nH]2)C2CC3CCC2C3)cc1]

N-(bicyclo[2.2.1]heptan-2-yl)-N-(1H-pyrazol-5-yl)-3-p-tolylpropanamide; Example 242

Prepared in a similar manner to example 6 from 3-p-tolylpropanoyl chloride and N-(bicyclo[2.2.1]heptan-2-yl)-1H-pyrazol-5-amine. $^1$H NMR (400 MHz, CDCl$_3$) δ 0.72 (m, 1H), 0.91-1.00 (m, 1H), 1.24-1.49 (m, 5H), 1.57-1.78 (m, 2H), 2.06 (m, 1H), 2.26 (s, 3H), 2.28-2.37 (m, 2H), 2.76-2.90 (m, 3H), 4.41-4.52 (m, 1H), 6.02 (d, J=2.4 Hz, 2H), 6.95 (d, J=8.1 Hz, 2H), 7.00 (d, J=7.9 Hz, 1H), 7.53 (d, J=2.4 Hz, 1H), 11.40 (br s, 1H); M+H (324.2).

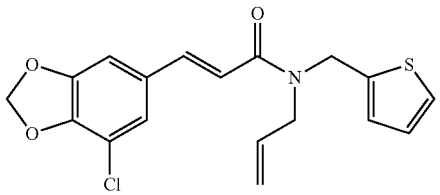 [SMILES: C=CCN(Cc1cccs1)C(=O)/C=C/c1cc(Cl)c2c(c1)OCO2]

(E)-N-allyl-3-(7-chlorobenzo[d][1,3]dioxol-5-yl)-N-(thiophen-2-ylmethyl)acrylamide; Example 243

This compound was purchased from Enamine. M+H (362.1).

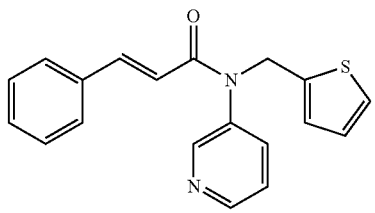 [SMILES: O=C(/C=C/c1ccccc1)N(Cc1cccs1)c1cccnc1]

N-(pyridin-3-yl)-N-(thiophen-2-ylmethyl)cinnamamide; Example 244

Prepared in a similar manner to example 21 from cinnamoyl chloride and N-(thiophen-2-ylmethyl)pyridin-3-amine. $^1$H NMR (400 MHz, DMSO-d6) δ 5.19 (br s, 2H), 6.32 (br s, 1H), 6.81-6.97 (m, 2H), 7.28-7.39 (m, 3H), 7.39-7.52 (m, 4H), 7.59-7.68 (m, 2H), 8.37 (br d, J=2.3 Hz, 1H), 8.55 (br d, J=3.6 Hz, 1H); M+H (321.1).

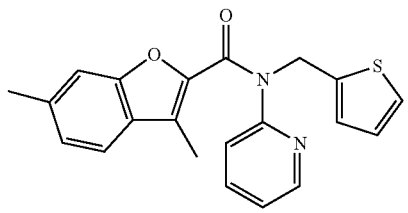 [SMILES: Cc1ccc2c(C)c(C(=O)N(Cc3cccs3)c3ccccn3)oc2c1]

3,6-dimethyl-N-(pyridin-2-yl)-N-(thiophen-2-ylmethyl)benzofuran-2-carboxamide; Example 249

This compound was purchased from Princeton. M+H (363.1).

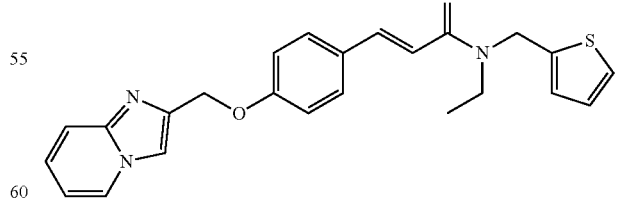

(E)-N-ethyl-3-(4-(imidazo[1,2-a]pyridin-2-ylmethoxy)phenyl)-N-(thiophen-2-ylmethyl)acrylamide; Example 254

This compound was purchased from Enamine. M+H (418.2).

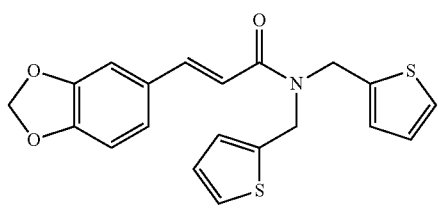 [SMILES: O=C(/C=C/c1ccc2c(c1)OCO2)N(Cc1cccs1)Cc1cccs1]

(E)-3-(benzo[d][1,3]dioxol-5-yl)-N,N-bis(thiophen-2-ylmethyl)acrylamide; Example 255

This compound was purchased from Enamine. M+H (384.1).

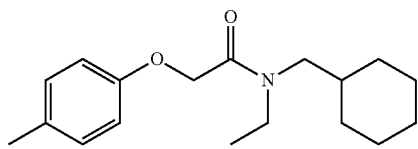 [SMILES: CCN(CC1CCCCC1)C(=O)COc1ccc(C)cc1]

N-(cyclohexylmethyl)-N-ethyl-2-(p-tolyloxy)acetamide; Example 256

Prepared in a similar manner to example 21 from 2-(p-tolyloxy)acetyl chloride and N-(cyclohexylmethyl)ethanamine. Room temperature $^1$H-NMR showed a mixture of rotamers in ~2:1 ratio: $^1$H NMR (400 MHz, DMSO-d6) δ 0.78-1.28 (m, 8H), 1.53-1.69 (m, 6H), 2.22 (s, 3H), 3.11 (t, J=6.8 Hz, 2H), 3.22-3.38 (m, 2H), 4.67 (minor) (s, 2H), 4.74 (major) (s, 2H), 6.74-6.82 (m, 2H), 7.02-7.11 (m, 2H); M+H (290.2).

Scheme 2

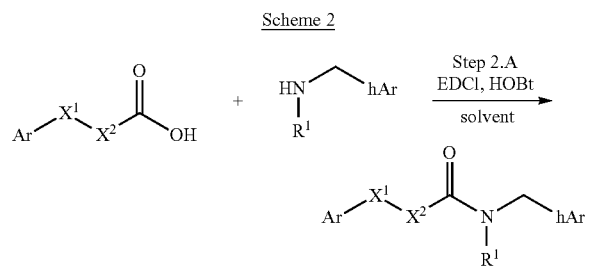

If not commercially available or differently described, all the secondary amines were prepared by reductive amination in a similar manner to example 6a or 21b utilizing one of the standard reducing agents and general conditions known to those skilled in the art such as: NaBH$_4$, LiAlH$_4$, Na(OAc)$_3$BH (STAB), Na(CN)BH$_3$, 2-picoline borane complex, 5-ethyl-2-methylpyridine borane (PEMB) or their equivalent, and DCM (dichloromethane), DCE (dichloroethane), Et$_2$O (diethyl ether), THF (tetrahydrofuran), dioxane, MeOH, EtOH, MeCN, AcOH alone or in binary or tertiary combinations thereof. All the employed acids were commercially available. The condensation between acid and amine was mediated by a condensing reagent such as EDCI (1-ethyl-3-(3-dimethylaminopropyl) carbodiimide)), DCC (N,N'-dicyclohexylcarbodiimide), DIC (N,N'-diisopropylcarbodiimide), HATU (2-(1H-7-azabenzotriazol-1-yl)-1,1,3,3-tetramethyl uronium hexafluorophosphate Methanaminium), PyBOP (benzotriazol-1-yl-oxytripyrrolidinophosphonium hexafluorophosphate), CDI (carbonyldiimidazole), 2-chloro-1-methylpyridinium iodide, T3P (propylphosphonic anhydride), according to synthetic protocols well established in the literature. One skilled in the art can readily derive the synthesis of the present compounds from the following descriptions according to the methods and principles discussed above.

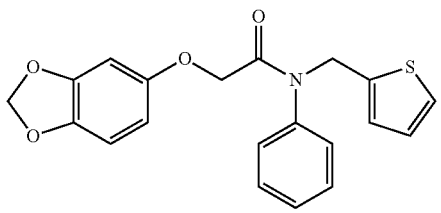 [SMILES: O=C(COc1ccc2c(c1)OCO2)N(Cc1cccs1)c1ccccc1]

2-(benzo[d][1,3]dioxol-5-yloxy)-N-phenyl-N-(thiophen-2-ylmethyl)acetamide; Example 5

To a microwave vial was added 2-(benzo[d][1,3]dioxol-5-yloxy)acetic acid (195 mg, 1.0 mmol) in DCM (1.0 mL), followed by N-(thiophen-2-ylmethyl)aniline (190 mg, 1.0 mmol), EDC (230 mg, 1.2 mmol) and HOBt (270 mg, 2.0 mmol) in DCM (2.0 mL) and DMF (2.0 mL). The microwave vial was capped and reacted under microwave irradiation (Emrys Optimizer reactor) at 100° C. for 10 minutes. The compound was purified on HPLC; clean fractions were combined and concentrated. Final compound was recrystallized from ethanol and water, affording 169 mg (0.46 mmol, 46%). $^1$H NMR (400 MHz, DMSO-d6) δ 4.36 (s, 2H), 5.00 (s, 2H), 5.94 (s, 2H), 6.15 (br d, J=6.2 Hz, 1H), 6.45 (br s, 1H), 6.75 (d, J=8.5 Hz, 1H), 6.83 (br s, 1H), 6.90 (dd, J=5.1, 3.4 Hz, 1H), 7.22-7.29 (m, 2H), 7.33-7.46 (m, 4H); M+H (368.1).

N-(thiophen-2-ylmethyl)aniline; Example 5a

To a 0° C. chilled round bottom flask was added aniline (3.0 g, 30 mmol) and thiophene-2-carbaldehyde (3.4 g, 30 mmol) in methanol and acetic acid (30.0 ml, 10:1), followed by 2-picoline borane complex (3.2 g, 30 mmol). The ice bath was removed and the flask was attached to a bubbler to allow gas evolution and expansion. The reaction was stirred overnight at room temp. Most of the volatiles were evaporated in vacuo. With the aid of a 0° C. chilling bath, 10% HCl (150 mL) was added to the residue and stirred for 2 hours at room temp. Around 60 mL of a 10 M solution of NaOH in water was added under cooling to make the solution alkaline. Aqueous layer was extracted with DCM (3 times), washed with brine, and dried over MgSO$_{4(s)}$ and concentrated. The obtained crude was absorbed under vacuum on Florisil with the aid of DCM (dry load). The obtained dispersion was purified by column chromatography (Biotage system; hex:EtOAc 25-100% gradient over 30 CV, 80 g Silicycle silica column). The collected fractions were evaporated to afford 5.68 g (29.87 mmol; 99%), which was judged more than 97% pure by $^1$H-NMR analysis.

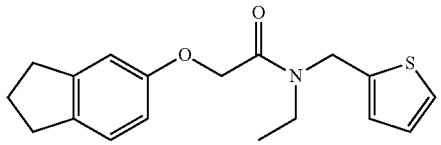 [SMILES: CCN(Cc1cccs1)C(=O)COc1ccc2c(c1)CCC2]

2-(2,3-dihydro-1H-inden-5-yloxy)-N-ethyl-N-(thiophen-2-ylmethyl)acetamide; Example 10

Prepared in a similar manner to example 5 from 2-(2,3-dihydro-1H-inden-5-yloxy)acetic acid and N-(thiophen-2- ylmethyl)ethanamine. $^1$H NMR (400 MHz, DMSO-d6) δ 1.98 (p, J=7.4 Hz, 2H), 2.77 (dt, J=14.6, 7.4 Hz, 4H), 4.49 (s, 2H), 4.87 (s, 2H), 6.54 (dd, J=8.2, 2.5 Hz, 1H), 6.64 (d, J=2.0 Hz, 1H), 6.88 (d, J=2.4 Hz, 1H), 6.94 (dd, J=5.1, 3.4 Hz, 1H), 7.06 (d, J=8.2 Hz, 1H), 7.45 (dd, J=5.1, 1.2 Hz, 1H), 7.62 (s, 2H), 12.98 (s, 1H); M+H (316.1).

NMR (400 MHz, DMSO-d6) δ 2.20 (s, 3H), 4.39 (s, 2H), 5.00 (s, 2H), 6.63 (br d, J=8.2 Hz, 2H), 6.83 (br s, 1H), 6.91 (dd, J=5.1, 3.4 Hz, 1H), 7.03 (d, J=8.2 Hz, 2H), 7.20-7.31 (m, 2H), 7.33-7.49 (m, 4H); M+H (338.1).

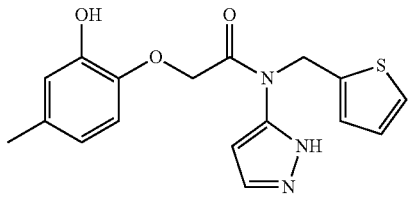 [SMILES: Cc1ccc(OCC(=O)N(Cc2cccs2)c2ccn[nH]2)c(O)c1]

2-(2-hydroxy-4-methylphenoxy)-N-(1H-pyrazol-5-yl)-N-(thiophen-2-ylmethyl)-acetamide; Example 11

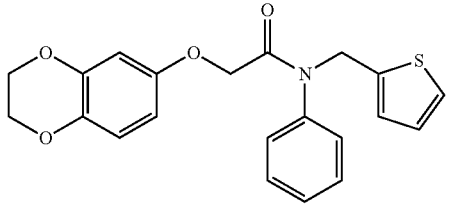

2-(2,3-dihydrobenzo[b][1,4]dioxin-6-yloxy)-N-phenyl-N-(thiophen-2-ylmethyl)acetamide; Example 29

Prepared in a similar manner to example 5 from 2-(2-hydroxy-4-methylphenoxy)acetic acid and N-(thiophen-2-ylmethyl)-1H-pyrazol-5-amine. Yield 10%. $^1$H NMR (400 MHz, DMSO-d6) δ 12.88 (s, 1H), 9.01 (s, 1H), 7.77 (s, 1H), 7.45-7.35 (m, 1H), 6.93-6.90 (m, 2H), 6.65-6.62 (m, 1H), 6.60-6.59 (m, 1H) 6.48-6.45 (m, 1H), 6.21 (s, 1H), 4.98 (s, 2H), 4.56 (s, 2H), 2.14 (s, 3H); M+H (344.1).

Prepared in a similar manner to example 5 from 2-(2,3-dihydrobenzo[b][1,4]dioxin-6-yloxy)acetic acid and N-(thiophen-2-ylmethyl)aniline. $^1$H NMR (400 MHz, DMSO-d6) δ 4.16 (tdd, J=5.6, 3.6, 2.2 Hz, 4H), 4.33 (s, 2H), 5.00 (s, 2H), 6.23 (d, J=9.0 Hz, 2H), 6.70 (d, J=8.6 Hz, 1H), 6.82 (s, 1H), 6.90 (dd, J=5.1, 3.4 Hz, 1H), 7.28-7.21 (m, 2H), 7.47-7.34 (m, 4H); M+H (382.1).

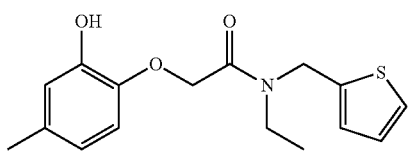 [SMILES: CCN(Cc1cccs1)C(=O)COc1ccc(C)cc1O]

N-ethyl-2-(2-hydroxy-4-methylphenoxy)-N-(thiophen-2-ylmethyl)acetamide; Example 19

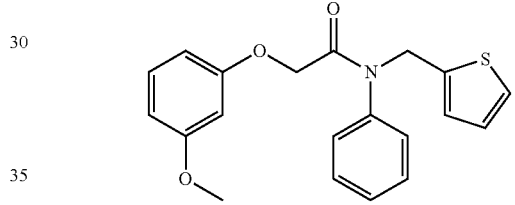

2-(3-methoxyphenoxy)-N-phenyl-N-(thiophen-2-ylmethyl)acetamide; Example 31

Prepared in a similar manner to example 5 from 2-(2-hydroxy-4-methylphenoxy)acetic acid and N-(thiophen-2-ylmethyl)ethanamine Yield 59%. $^1$H NMR (400 MHz, DMSO-d6) δ 9.28 (major) (s, 1H), 9.27 (minor) (s, 1H), 7.49 (minor) (dd, J=5.1, 1.2 Hz, 1H), 7.42 (major) (dd, J=5.1, 1.2 Hz, 1H), 7.09-7.06 (minor) (m, 1H), 7.06-7.05 (major) (m, 1H), 7.02-7.00 (minor) (m, 1H), 6.96-6.94 (major) (m, 1H), 6.78 (major) (d, J=8.1 Hz, 1H), 6.74 (minor) (d, J=8.1 Hz, 1H), 6.63-6.62 (m, 1H), 6.52-6.50 (m, 1H), 4.80 (minor) (s, 2H), 4.79 (major) (s, 2H), 4.74 (minor) (s, 2H), 4.65 (major) (s, 2H), 3.35-3.28 (m, 2H), 2.16 (s, 3H), 1.11 (major) (t, J=7.2 Hz, 3H), 1.01 (minor) (t, J=7.2 Hz, 3H); M+H (306.1).

Prepared in a similar manner to example 5 from 2-(3-methoxyphenoxy)acetic acid and N-(thiophen-2-ylmethyl) aniline. $^1$H NMR (400 MHz, DMSO-d6) δ 3.69 (s, 3H), 4.42 (s, 2H), 5.01 (s, 2H), 6.31 (m, 2H), 6.50 (dd, J=8.2, 1.7 Hz, 1H), 6.83 (br s, 1H), 6.91 (dd, J=5.1, 3.4 Hz, 1H), 7.13 (t, J=8.1 Hz, 1H), 7.21-7.32 (m, 2H), 7.33-7.52 (m, 4H); M+H (354.1).

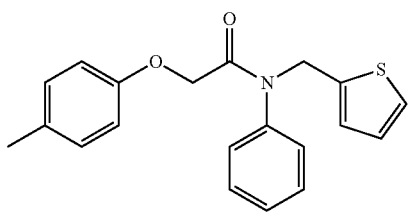 [SMILES: Cc1ccc(OCC(=O)N(Cc2cccs2)c2ccccc2)cc1]

N-phenyl-N-(thiophen-2-ylmethyl)-2-(p-tolyloxy) acetamide; Example 26

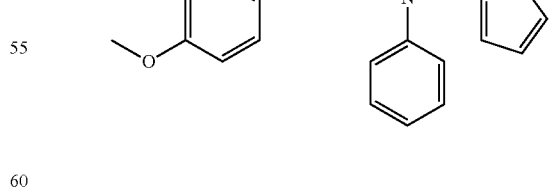

2-(4-methoxyphenoxy)-N-phenyl-N-(thiophen-2-ylmethyl)acetamide; Example 33

Prepared in a similar manner to example 5 from 2-(p-tolyloxy)acetic acid and N-(thiophen-2-ylmethyl)aniline. $^1$H Prepared in a similar manner to example 5 from 2-(4-methoxyphenoxy)acetic acid and N-(thiophen-2-ylmethyl) aniline. $^1$H NMR (400 MHz, DMSO-d6) δ 3.67 (s, 3H), 4.36 (s, 2H), 5.00 (s, 2H), 6.68 (br d, J=8.7 Hz, 2H), 6.77-6.85 (m, 3H), 6.91 (dd, J=5.1, 3.4 Hz, 1H), 7.23-7.29 (m, 2H), 7.33-7.44 (m, 4H); M+H (354.1).

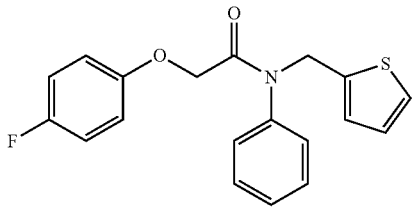 [SMILES: O=C(COc1ccc(F)cc1)N(Cc1cccs1)c1ccccc1]

2-(4-fluorophenoxy)-N-phenyl-N-(thiophen-2-ylmethyl)acetamide; Example 37

Prepared in a similar manner to example 5 from 2-(4-fluorophenoxy)acetic acid and N-(thiophen-2-ylmethyl)aniline. $^1$H NMR (400 MHz, DMSO-d6) δ 4.43 (s, 2H), 5.00 (s, 2H), 6.72-6.87 (m, 3H), 6.91 (dd, J=5.1, 3.4 Hz, 1H), 7.01-7.14 (m, 2H), 7.23-7.31 (m, 2H), 7.34-7.47 (m, 4H); M+H (342.1).

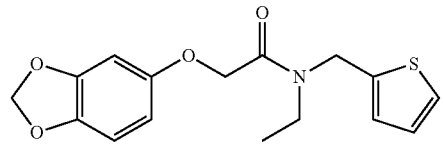 [SMILES: CCN(Cc1cccs1)C(=O)COc1ccc2c(c1)OCO2]

2-(benzo[d][1,3]dioxol-5-yloxy)-N-ethyl-N-(thiophen-2-ylmethyl)acetamide; Example 40

Prepared in a similar manner to example 5 from 2-(benzo[d][1,3]dioxol-5-yloxy)acetic acid and N-(thiophen-2-ylmethyl)ethanamine. Room temperature $^1$H NMR showed a mixture of rotamers in a ~2:1 ratio: $^1$H NMR (400 MHz, DMSO-d6) δ 0.98-1.14 (m, 3H), 3.22-3.37 (m, 3H), 4.59-4.80 (m, 4H), 5.96 (s, 2H), 6.29-6.39 (m, 1H), 6.59-6.63 (m, 1H), 6.78-6.81 (m, 1H), 6.95 (dd, J=5.1, 3.4 Hz, 1H), 7.01-7.10 (m, 2H), 7.41-7.51 (m, 1H); M+H (320.1).

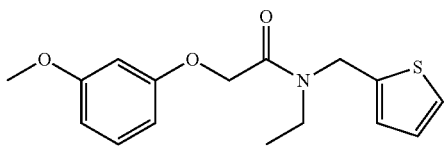 [SMILES: CCN(Cc1cccs1)C(=O)COc1cccc(OC)c1]

N-ethyl-2-(3-methoxyphenoxy)-N-(thiophen-2-ylmethyl)acetamide; Example 42

Prepared in a similar manner to example 5 from 2-(3-methoxyphenoxy)acetic acid and N-(thiophen-2-ylmethyl)ethanamine. Room temperature $^1$H NMR showed a mixture of rotamers in a ~2:1 ratio: $^1$H NMR (400 MHz, DMSO-d6) δ 0.98-1.14 (m, 3H), 3.25-3.36 (m, 2H), 3.69 (m, 3H), 4.61-4.76 (m, 2H), 4.80 (br s, 2H), 6.38-6.56 (m, 3H), 6.88-7.22 (m, 3H), 7.37-7.53 (m, 1H); M+H (306.1).

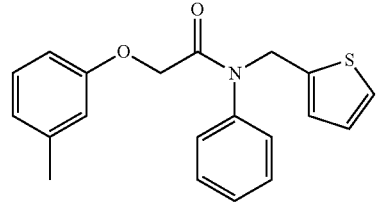 [SMILES: Cc1cccc(OCC(=O)N(Cc2cccs2)c2ccccc2)c1]

N-phenyl-N-(thiophen-2-ylmethyl)-2-(m-tolyloxy)acetamide; Example 46

Prepared in a similar manner to example 5 from 2-(m-tolyloxy)acetic acid and N-(thiophen-2-ylmethyl)aniline. $^1$H NMR (400 MHz, DMSO-d6) δ 2.22 (s, 3H), 4.39 (s, 2H), 4.99 (s, 2H), 6.51 (br d, J=12.5 Hz, 2H), 6.71 (br d, J=7.5 Hz, 1H), 6.82 (br s, 1H), 6.89 (dd, J=5.1, 3.4 Hz, 1H), 7.09 (t, J=7.8 Hz, 1H), 7.22-7.27 (m, 2H), 7.33-7.52 (m, 4H); M+H (338.1).

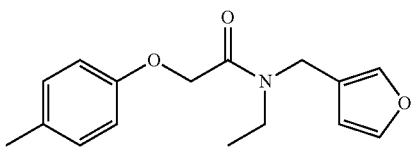 [SMILES: CCN(Cc1ccoc1)C(=O)COc1ccc(C)cc1]

N-ethyl-N-(furan-3-ylmethyl)-2-(p-tolyloxy)acetamide; Example 48

Prepared in a similar manner to example 5 from 2-(p-tolyloxy)acetic acid and N-(furan-3-ylmethyl)ethanamine. Room temperature $^1$H NMR showed a mixture of rotamers in a ~2:1 ratio: $^1$H NMR (400 MHz, DMSO-d6) δ 1.06 (m, 3H), 2.22 (br d, 3H), 3.18-3.32 (m, 2H), 4.34 (m, 2H), 4.78 (s, 2H), 6.3-6.50 (m, 1H), 6.78 (m, 2H), 7.07 (br dd, J=8.3, 3.8 Hz, 2H), 7.59 (br d, J=1.4 Hz, 1H), 7.62-7.72 (m, 1H); M+H (266.1).

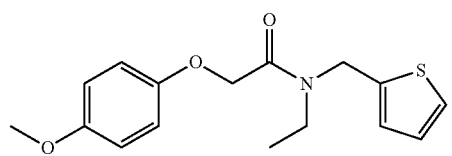 [SMILES: CCN(Cc1cccs1)C(=O)COc1ccc(OC)cc1]

N-ethyl-2-(4-methoxyphenoxy)-N-(thiophen-2-ylmethyl)acetamide; Example 49

Prepared in a similar manner to example 5 from 2-(4-methoxyphenoxy)acetic acid and N-(thiophen-2-ylmethyl)ethanamine. Room temperature $^1$H NMR showed a mixture of rotamers in a ~2:1 ratio: $^1$H NMR (400 MHz, DMSO-d6) δ 0.95-1.14 (m, 3H), 3.24-3.38 (m, 2H), 3.66-3.68 (m, 3H), 4.61-4.75 (m, 4H), 6.80-6.84 (m, 4H), 6.89-7.10 (m, 2H), 7.33-7.52 (m, 1H); M+H (306.1).

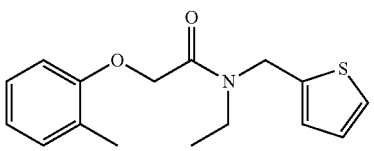 [SMILES: CCN(Cc1cccs1)C(=O)COc1ccccc1C]

N-ethyl-N-(thiophen-2-ylmethyl)-2-(o-tolyloxy)acetamide; Example 52

This compound was prepared in a library format. M+H (290.1).

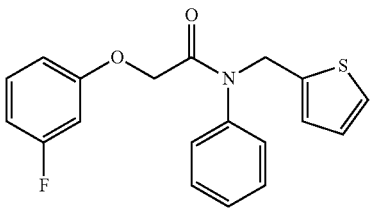

2-(3-fluorophenoxy)-N-phenyl-N-(thiophen-2-ylmethyl)acetamide; Example 53

Prepared in a similar manner to example 5 from 2-(3-fluorophenoxy)acetic acid and N-(thiophen-2-ylmethyl)aniline. $^1$H NMR (400 MHz, DMSO-d6) δ 4.48 (br s, 2H), 5.00 (br s, 2H), 6.62 (m, 2H), 6.75 (td, J=8.3, 2.0 Hz, 1H), 6.84 (br s, 1H), 6.91 (dd, J=5.1, 3.4 Hz, 1H), 7.22-7.32 (m, 3H), 7.34-7.50 (m, 4H); M+H (342.1).

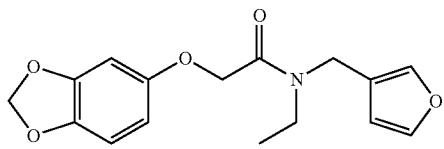 [SMILES: CCN(Cc1ccoc1)C(=O)COc1ccc2c(c1)OCO2]

2-(benzo[d][1,3]dioxol-5-yloxy)-N-ethyl-N-(furan-3-ylmethyl)acetamide; Example 56

Prepared in a similar manner to example 5 from 2-(benzo[d][1,3]dioxol-5-yloxy)acetic acid and N-(furan-3-ylmethyl)ethanamine. Room temperature $^1$H NMR showed a mixture of rotamers in a ~2:1 ratio $^1$H NMR (400 MHz, DMSO-d6) δ 0.97-1.13 (m, 3H), 3.27 (m, 2H), 4.30-4.36 (m, 2H), 4.74 (br s, 2H), 5.95 (m, 2H), 6.28-6.50 (m, 2H), 6.61 (m, 1H), 6.79 (m, 1H), 7.59 (br d, J=1.4 Hz, 1H), 7.63-7.73 (m, 1H); M+H (304.1).

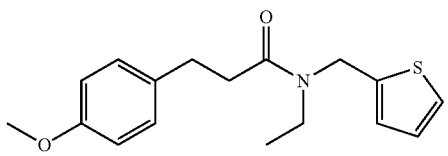 [SMILES: CCN(Cc1cccs1)C(=O)CCc1ccc(OC)cc1]

N-ethyl-3-(4-methoxyphenyl)-N-(thiophen-2-ylmethyl)propanamide; Example 57

Prepared in a similar manner to example 5 from 3-(4-methoxyphenyl)propanoic acid and N-(thiophen-2-ylmethyl)ethyl)ethanamine. Room temperature $^1$H NMR showed a mixture of rotamers in a ~2:1 ratio: $^1$H NMR (400 MHz, DMSO-d6) δ 0.96-1.05 (m, 3H), 2.55-2.65 (m, 2H), 2.71-2.81 (m, 2H), 3.21-3.31 (m, 2H), 3.70 (s, 3H), 4.60-4.68 (m, 2H), 6.81 (d, J=8.7 Hz, 2H), 6.90-7.02 (m, 2H), 7.07-7.20 (m, 2H), 7.38-7.46 (m, 1H); M+H (304.1).

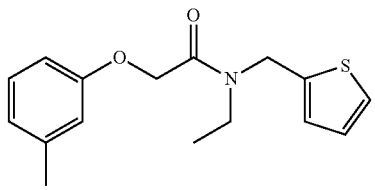 [SMILES: CCN(Cc1cccs1)C(=O)COc1cccc(C)c1]

N-ethyl-N-(thiophen-2-ylmethyl)-2-(m-tolyloxy)acetamide; Example 58

Prepared in a similar manner to example 5 from 2-(m-tolyloxy)acetic acid and N-(thiophen-2-ylmethyl)ethanamine. Room temperature 1H NMR showed a mixture of rotamers in a ~2:1 ratio: $^1$H NMR (400 MHz, DMSO-d6) δ 1.01 (minor) (t, J=7.1 Hz, 3H), 1.14 (major) (t, J=7.1 Hz, 3H), 2.25 (minor) (s, 3H), 2.26 (major) (s, 3H), 3.27-3.45 (m, 2H), 4.65 (major) (s, 2H), 4.76 (minor) (s, 2H), 4.81 (s, 2H), 6.63-6.81 (m, 3H), 6.92-7.20 (m, 3H), 7.55-7.38 (m, 1H); M+H (290.1).

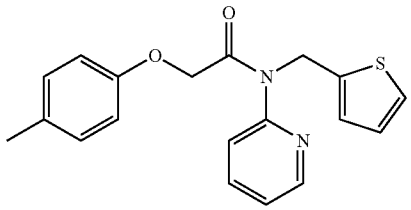 [SMILES: Cc1ccc(OCC(=O)N(Cc2cccs2)c2ccccn2)cc1]

N-(pyridin-2-yl)-N-(thiophen-2-ylmethyl)-2-(p-tolyloxy)acetamide; Example 61

Prepared in a similar manner to example 5 from 2-(p-tolyloxy)acetic acid and N-(thiophen-2-ylmethyl)pyridin-2-amine. $^1$H NMR (400 MHz, DMSO-d6) δ 2.18 (s, 3H), 4.75 (s, 2H), 5.19 (s, 2H), 6.58-6.61 (m, 2H), 6.86-6.89 (m, 2H), 7.00 (m, 2H), 7.29 (ddd, J=7.4, 4.9, 0.9 Hz, 1H), 7.37 (dd, J=4.8, 1.5 Hz, 1H), 7.45 (br d, J=8.1 Hz, 1H), 7.85 (ddd, J=8.1, 7.5, 2.0 Hz, 1H), 8.44 (ddd, J=4.9, 1.9, 0.8 Hz, 1H); M+H (339.1).

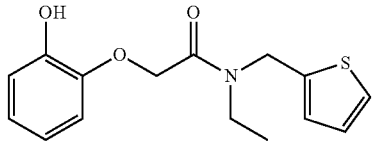 [SMILES: CCN(Cc1cccs1)C(=O)COc1ccccc1O]

N-ethyl-2-(2-hydroxyphenoxy)-N-(thiophen-2-ylmethyl)acetamide; Example 62

Prepared in a similar manner to example 5 from 2-(2-hydroxyphenoxy)acetic acid and N-(thiophen-2-ylmethyl)ethanamine. Yield 33%. Room temperature $^1$H NMR showed a mixture of rotamers in a ~2:1 ratio: $^1$H NMR (400 MHz, DMSO-d6) δ 9.31 (s, 1H), 7.50 (minor) (dd, J=5.2, 1.2

Hz, 1H), 7.42 (major) (dd, J=5.2, 1.2 Hz, 1H), 7.11-7.10 (minor) (m, 1H), 7.06-7.05 (major) (m, 1H), 7.03-7.01 (minor) (m, 1H), 6.96-6.94 (major) (m, 1H), 6.89-6.79 (m, 3H), 6.73-6.69 (m, 1H), 4.85 (minor) (s, 2H), 4.84 (major) (s, 2H), 4.76 (minor) (s, 2H), 4.66 (major) (s, 2H), 3.37-3.27 (m, 2H), 1.13 (major) (t, J=7.0 Hz, 3H), 1.01 (t, J=7.0 Hz, 3H); M+H (292.1).

ethyl)pyridin-2-amine. ¹H NMR (400 MHz, DMSO-d6) δ 4.74 (br s, 2H), 5.20 (br s, 2H), 5.94 (s, 2H), 6.16 (dd, J=8.5, 2.6 Hz, 1H), 6.42 (d, J=2.5 Hz, 1H), 6.74 (d, J=8.5 Hz, 1H), 6.89 (m, 2H), 7.31 (ddd, J=7.4, 4.9, 0.9 Hz, 1H), 7.38 (dd, J=4.8, 1.5 Hz, 1H), 7.47 (d, J=8.1 Hz, 1H), 7.78-7.95 (m, 1H), 8.46 (ddd, J=4.8, 1.9, 0.7 Hz, 1H); M+H (369.1).

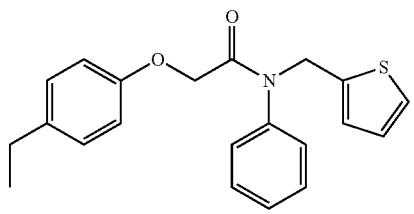 [SMILES: CCc1ccc(OCC(=O)N(Cc2cccs2)c2ccccc2)cc1]

2-(4-ethylphenoxy)-N-phenyl-N-(thiophen-2-ylmethyl)acetamide; Example 63

Prepared in a similar manner to example 5 from 2-(4-ethylphenoxy)acetic acid and N-(thiophen-2-ylmethyl)aniline. ¹H NMR (400 MHz, DMSO-d6) δ 1.12 (t, J=7.6 Hz, 3H), 2.53 (q, J=7.6 Hz, 2H), 4.39 (br s, 2H), 5.00 (br s, 2H), 6.65 (br d, J=8.2 Hz, 2H), 6.83 (br s, 1H), 6.91 (dd, J=5.1, 3.4 Hz, 1H), 7.06 (d, J=8.6 Hz, 2H), 7.22-7.31 (m, 2H), 7.33-7.49 (m, 4H); M+H (352.1).

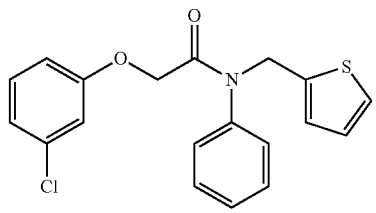

2-(3-chlorophenoxy)-N-phenyl-N-(thiophen-2-ylmethyl)acetamide; Example 68

Prepared in a similar manner to example 5 from 2-(3-chlorophenoxy)acetic acid and N-(thiophen-2-ylmethyl)aniline. ¹H NMR (400 MHz, DMSO-d6) δ 4.50 (br s, 2H), 5.00 (br s, 2H), 6.74 (br d, J=7.5 Hz, 1H), 6.83 (br s, 2H), 6.91 (dd, J=5.1, 3.4 Hz, 1H), 6.98 (ddd, J=7.9, 1.9, 0.8 Hz, 1H), 7.21-7.31 (m, 3H), 7.33-7.51 (m, 4H); M+H (358.1).

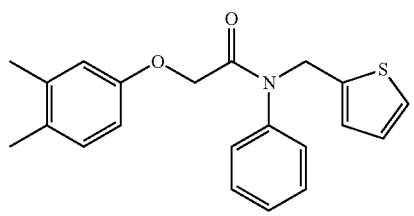 [SMILES: Cc1ccc(OCC(=O)N(Cc2cccs2)c2ccccc2)cc1C]

2-(3,4-dimethylphenoxy)-N-phenyl-N-(thiophen-2-ylmethyl)acetamide; Example 65

Prepared in a similar manner to example 5 from 2-(3,4-dimethylphenoxy)acetic acid and N-(thiophen-2-ylmethyl) aniline. ¹H NMR (400 MHz, DMSO-d6) δ 2.11 (s, 3H), 2.14 (s, 3H), 4.36 (br s, 2H), 5.00 (br s, 2H), 6.44 (br d, J=7.6 Hz, 1H), 6.53 (br s, 1H), 6.83 (s, 1H), 6.91 (dd, J=5.1, 3.4 Hz, 1H), 6.97 (d, J=8.2 Hz, 1H), 7.23-7.28 (m, 2H), 7.35-7.47 (m, 4H); M+H (352.1).

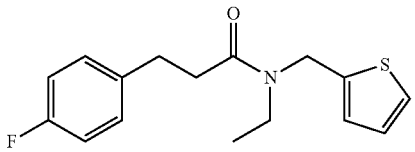

N-ethyl-3-(4-fluorophenyl)-N-(thiophen-2-ylmethyl)propanamide; Example 69

Prepared in a similar manner to example 5 from 3-(4-fluorophenyl)propanoic acid and N-(thiophen-2-ylmethyl) ethanamine. Room temperature ¹H NMR showed a mixture of rotamers in a ~2:1 ratio: ¹H NMR (400 MHz, DMSO-d6) δ 1.12-0.93 (m, 3H), 2.57-2.70 (m, 2H), 2.83 (br dd, J=16.5, 8.7 Hz, 2H), 3.22-3.33 (m, 2H), 4.61 (major) (br s, 2), 4.68 (minor) (br s, 12), 6.89-7.02 (m, 2H), 7.02-7.12 (m, 2H), 7.18-7.33 (m, 2H), 7.36-7.47 (m, 1H); M+H (292.1).

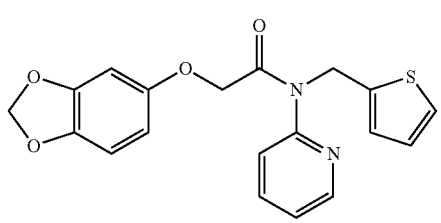 [SMILES: O=C(COc1ccc2c(c1)OCO2)N(Cc1cccs1)c1ccccn1]

2-(benzo[d][1,3]dioxol-5-yloxy)-N-(pyridin-2-yl)-N-(thiophen-2-ylmethyl)acetamide; Example 67

Prepared in a similar manner to example 5 from 2-(benzo[d][1,3]dioxol-5-yloxy)acetic acid and N-(thiophen-2-ylm-

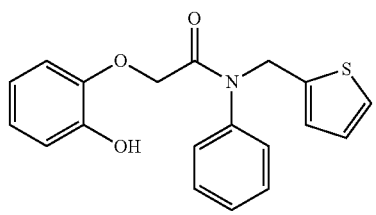 [SMILES: O=C(COc1ccccc1O)N(Cc1cccs1)c1ccccc1]

2-(2-hydroxyphenoxy)-N-phenyl-N-(thiophen-2-ylmethyl)acetamide; Example 71

Prepared in a similar manner to example 5 from 2-(2-hydroxyphenoxy)acetic acid and N-(thiophen-2-ylmethyl) aniline. ¹H NMR (400 MHz, DMSO-d6) δ 4.39 (br s, 2H), 5.02 (br s, 2H), 6.63-6.86 (m, 5H), 6.91 (dd, J=5.1, 3.4 Hz, 1H), 7.26 (m, 2H), 7.35-7.46 (m, 4H), 9.15 (s, 1H); M+H (340.1).

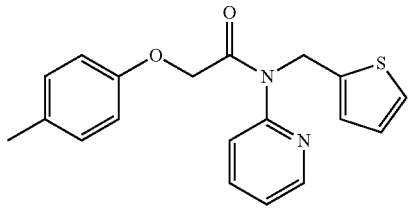 [SMILES: Cc1ccc(OCC(=O)N(Cc2cccs2)c2ccccn2)cc1]

N-(pyridin-2-yl)-N-(thiophen-2-ylmethyl)-2-(p-tolyloxy)acetamide; Example 73

Prepared in a similar manner to example 5 from 2-(p-tolyloxy)acetic acid and N-(thiophen-2-ylmethyl)pyridin-2-amine. $^1$H NMR (400 MHz, DMSO-d6) δ 2.20 (s, 3H), 4.77 (br s, 2H), 5.03 (br s, 2H), 6.61 (d, J=8.1 Hz, 2H), 6.95 (dd, J=5.0, 1.3 Hz, 1H), 7.02 (d, J=8.1 Hz, 2H), 7.25 (br dd, J=2.9, 1.1 Hz, 1H), 7.30 (ddd, J=7.4, 4.9, 0.9 Hz, 1H), 7.42-7.48 (m, 2H), 7.81-7.90 (m, 1H), 8.45 (ddd, J=4.8, 1.9, 0.8 Hz, 1H); M+H (339.1).

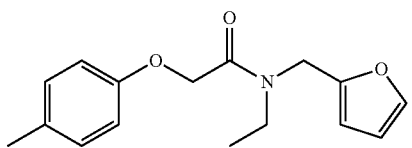

N-ethyl-N-(furan-2-ylmethyl)-2-(p-tolyloxy)acetamide; Example 74

Prepared in a similar manner to example 5 from 2-(p-tolyloxy)acetic acid and N-(furan-2-ylmethyl)ethanamine. Room temperature $^1$H NMR showed a mixture of rotamers in a ~1:1 ratio $^1$H NMR (400 MHz, DMSO-d6) δ 0.91-1.09 (m, 3H), 2.20 (s, 3H), 3.24-3.34 (m, 2H), 4.49-4.54 (m, 2H), 4.76-4.84 (m, 2H), 6.28-6.39 (m, 1H), 6.43 (br d, J=1.3 Hz, 1H), 6.84-6.70 (m, 2H), 7.05 (br d, J=7.9 Hz, 2H), 7.56-7.66 (m, 1H); M+H (274.1).

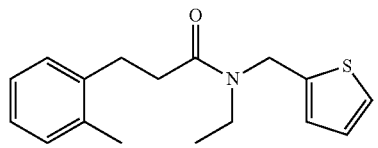 [SMILES: CCN(Cc1cccs1)C(=O)CCc1ccccc1C]

N-ethyl-N-(thiophen-2-ylmethyl)-3-o-tolylpropanamide; Example 77

Prepared in a similar manner to example 5 from 3-o-tolylpropanoic acid and N-(thiophen-2-ylmethyl)ethanamine. Room temperature $^1$H NMR showed a mixture of rotamers in a ~2:1 ratio: $^1$H NMR (400 MHz, DMSO-d6) δ 1.02 (m, 3H), 2.21 (minor) (s, 3H) 2.28 (major) (s, 3H), 2.52-2.65 (m, 2H), 2.75-2.88 (m, 2H), 3.23-3.32 (m, 2H), 4.62 (major) (s, 2H), 4.68 (minor) (br s, 2H), 6.89-7.04 (m, 2H), 7.04-7.20 (m, 4H), 7.37-7.48 (m, 1H); M+H (288.1).

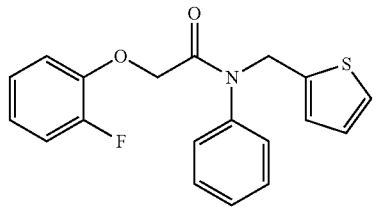 [SMILES: O=C(COc1ccccc1F)N(Cc1cccs1)c1ccccc1]

2-(2-fluorophenoxy)-N-phenyl-N-(thiophen-2-ylmethyl)acetamide; Example 78

Prepared in a similar manner to example 5 from 2-(2-fluorophenoxy)acetic acid and N-(thiophen-2-ylmethyl)aniline. $^1$H NMR (400 MHz, DMSO-d6) δ 4.53 (br s, 2H), 5.00 (br s, 2H), 6.82-6.95 (m, 4H), 7.06 (m, 1H), 7.18 (ddd, J=11.8, 8.0, 1.6 Hz, 1H), 7.26-7.31 (m, 2H), 7.36-7.47 (m, 4H); M+H (342.1).

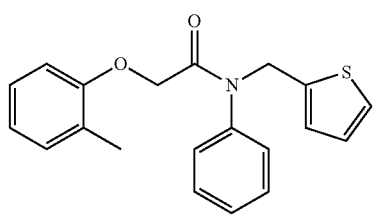 [SMILES: Cc1ccccc1OCC(=O)N(Cc1cccs1)c1ccccc1]

N-phenyl-N-(thiophen-2-ylmethyl)-2-(o-tolyloxy)acetamide; Example 81

Prepared in a similar manner to example 5 from 2-(o-tolyloxy)acetic acid and N-(thiophen-2-ylmethyl)aniline. $^1$H NMR (400 MHz, DMSO-d6) δ 2.06 (s, 3H), 4.46 (br s, 2H), 4.99 (br s, 2H), 6.57 (br d, J=7.9 Hz, 1H), 6.80 (m, 2H), 6.89 (dd, J=5.1, 3.4 Hz, 1H), 7.06 (m, 2H), 7.20-7.29 (m, 2H), 7.32-7.46 (m, 4H); M+H (338.1).

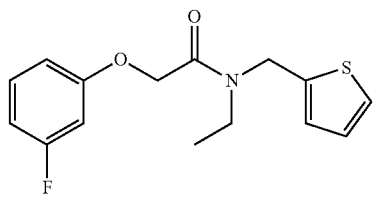 [SMILES: CCN(Cc1cccs1)C(=O)COc1cccc(F)c1]

N-ethyl-2-(3-fluorophenoxy)-N-(thiophen-2-ylmethyl)acetamide; Example 84

Prepared in a similar manner to example 5 from 2-(3-fluorophenoxy)acetic acid and N-(thiophen-2-ylmethyl)ethanamine. Room temperature $^1$H NMR showed a mixture of rotamers in a ~2:1 ratio: $^1$H NMR (400 MHz, DMSO-d6) δ 1.01 (minor) (t, J=7.1 Hz, 3H), 1.14 (major) (t, J=7.1 Hz, 3H), 3.27-3.38 (m, 2H), 4.65 (major) (br s, 2H), 4.76 (minor) (br s, 2H), 4.88 (minor) (br s, 2H), 4.90 (major) (br s, 2H), 6.70-6.83 (m, 3H), 6.95 (major) (dd, J=5.1, 3.4 Hz, 1H), 7.03 (minor) (dd, J=5.0, 3.5 Hz, 1H), 7.05 (major) (dd, J=3.4, 1.0 Hz, 1H), 7.12 (minor) (d, J=2.6 Hz, 1H), 7.30 (m, 1H), 7.42 (major) (dd, J=5.1, 1.2 Hz, 1H), 7.51 (minor) (dd, J=5.1, 1.1 Hz, 1H); M+H (294.1).

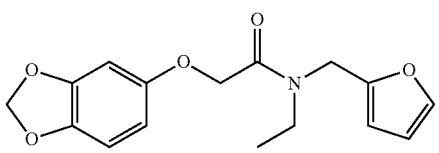 [SMILES: CCN(Cc1ccco1)C(=O)COc1ccc2c(c1)OCO2]

2-(benzo[d][1,3]dioxol-5-yloxy)-N-ethyl-N-(furan-2-ylmethyl)acetamide; Example 86

Prepared in a similar manner to example 5 from 2-(benzo[d][1,3]dioxol-5-yloxy)acetic acid and N-(furan-2-ylmethyl)ethanamine. Room temperature $^1$H NMR showed a mixture of rotamers in a ~1:1 ratio $^1$H NMR (400 MHz, DMSO-d6) δ 0.93-1.10 (m, J=56.3, 7.1 Hz, 3H), 3.25-3.34 (m, 2H), 4.50-4.54 (m, 2H), 4.75-4.82 (m, 2H), 5.95 (s, 2H), 6.30-6.45 (m, 3H), 6.61 (dd, J=9.5, 2.5 Hz, 1H), 6.80 (d, J=8.5 Hz, 1H), 7.57-7.68 (m, 1H); M+H (304.1).

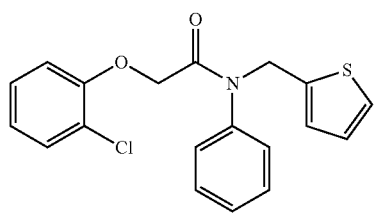

2-(2-chlorophenoxy)-N-phenyl-N-(thiophen-2-ylmethyl)acetamide; Example 95

Prepared in a similar manner to example 5 from 2-(2-chlorophenoxy)acetic acid and N-(thiophen-2-ylmethyl)aniline. $^1$H NMR (400 MHz, DMSO-d6) δ 4.57 (br s, 2H), 5.00 (br s, 2H), 6.84 (br s, 2H), 6.88-6.97 (m, 2H), 7.21-7.27 (m, 1H), 7.28-7.33 (m, 2H), 7.36-7.47 (m, 5H); M+H (358.1).

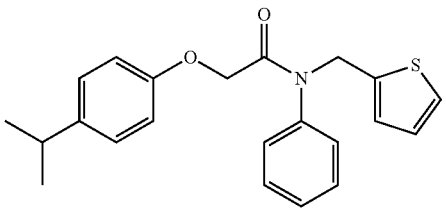 [SMILES: CC(C)c1ccc(OCC(=O)N(Cc2cccs2)c2ccccc2)cc1]

2-(4-isopropylphenoxy)-N-phenyl-N-(thiophen-2-ylmethyl)acetamide; Example 97

Prepared in a similar manner to example 5 from 2-(4-isopropylphenoxy)acetic acid and N-(thiophen-2-ylmethyl)aniline. $^1$H NMR (400 MHz, DMSO-d6) δ 1.15 (d, J=6.9 Hz, 6H), 2.80 (sept, J=6.9 Hz, 1H), 4.39 (br s, 2H), 5.00 (br s, 2H), 6.66 (br d, J=8.4 Hz, 2H), 6.83 (br s, 1H), 6.91 (dd, J=5.1, 3.4 Hz, 1H), 7.10 (d, J=8.6 Hz, 2H), 7.24-7.30 (m, 2H), 7.35-7.47 (m, 4H); M+H (366.1).

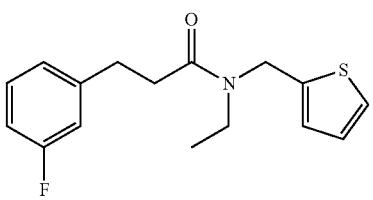 [SMILES: CCN(Cc1cccs1)C(=O)CCc1cccc(F)c1]

N-ethyl-3-(3-fluorophenyl)-N-(thiophen-2-ylmethyl)propanamide; Example 100

Prepared in a similar manner to example 5 from 3-(3-fluorophenyl)propanoic acid and N-(thiophen-2-ylmethyl)ethanamine. Room temperature $^1$H NMR showed a mixture of rotamers in a ~2:1 ratio: $^1$H NMR (400 MHz, DMSO-d6) δ 0.96-1.08 (m, 3H), 2.58-2.73 (m, 2H), 2.86 (br dd, J=16.4, 8.4 Hz, 2H), 3.23-3.31 (m, 2H), 4.60-4.71 (m, 2H), 6.91-7.03 (m, 2H), 7.07-7.17 (m, 2H), 7.20-7.37 (m, 2H), 7.36-7.48 (m, 1H); M+H (292.1).

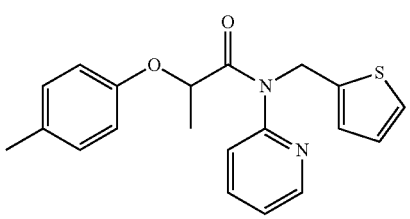 [SMILES: Cc1ccc(OC(C)C(=O)N(Cc2cccs2)c2ccccn2)cc1]

N-(pyridin-2-yl)-N-(thiophen-2-ylmethyl)-2-(p-tolyloxy)propanamide; Example 104

Prepared in a similar manner to example 5 from 2-(p-tolyloxy)propanoic acid and N-(thiophen-2-ylmethyl)pyridin-2-amine. $^1$H NMR (400 MHz, CDCl$_3$) δ 1.53 (d, J=6.6 Hz, 3H), 2.24 (s, 3H), 5.00 (q, J=6.6 Hz, 1H), 5.23 (br s, 2H), 6.57-6.64 (m, 2H), 6.85-6.87 (m, 2H), 6.97 (br d, J=8.2 Hz, 2H), 7.04 (br d, J=8.0 Hz, 1H), 7.16-7.24 (m, 2H), 7.65-7.73 (m, 1H), 8.47 (dd, J=5.0, 1.3 Hz, 1H); M+H (353.1).

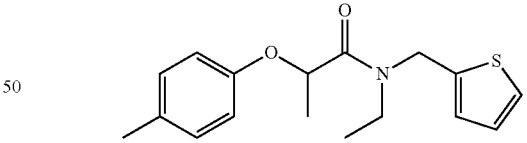

N-ethyl-N-(thiophen-2-ylmethyl)-2-(p-tolyloxy)propanamide; Example 107

Prepared in a similar manner to example 5 from 2-(p-tolyloxy)propanoic acid and N-(thiophen-2-ylmethyl)ethanamine. $^1$H NMR showed a mixture of rotamers in a ~2:1 ratio: $^1$H NMR (400 MHz, DMSO-d6) δ 0.95 (minor) (t, J=7.0 Hz, 3H), 1.10 (major) (t, J=7.1 Hz, 3H), 1.36-1.43 (m, 3H), 2.20 (minor) (s, 3H), 2.22 (major) (s, 3H), 3.21 (minor) (q, J=7.0 Hz, 2H), 3.38 (major) (q, J=7.0 Hz, 2H), 4.61 (major) (d, J=15.1 Hz, 1H), 4.67 (minor) (d, J=15.0 Hz, 1H), 4.78 (major) (d, J=16.5 Hz, 1H), 4.86 (minor) (d, J=16.4 Hz, 1H), 5.15 (major) (q, J=6.4 Hz, 1H), 5.22 (minor) (q, J=6.3

Hz, 1H), 6.69 (minor) (d, J=8.6 Hz, 2H), 6.75 (major) (d, J=8.6 Hz, 2H), 6.89-7.12 (m, 4H), 7.41 (major) (dd, J=5.1, 1.3 Hz, 1H), 7.51 (minor) (dd, J=5.1, 1.3 Hz, 1H); M+H (353.1).

2H), 6.89-7.06 (m, 5H), 7.14 (br t, J=7.4 Hz, 1H), 7.39 (major) (dd, J=5.1, 1.3 Hz, 1H), 7.45 (minor) (dd, J=4.8, 1.6 Hz, 1H); M+H (288.1).

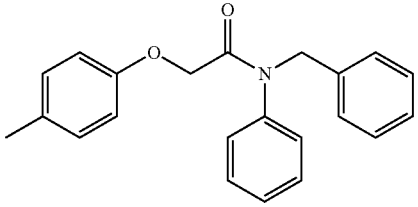 [SMILES: Cc1ccc(OCC(=O)N(Cc2ccccc2)c2ccccc2)cc1]

N-benzyl-N-phenyl-2-(p-tolyloxy)acetamide; Example 108

Prepared in a similar manner to example 5 from 2-(p-tolyloxy)acetic acid and N-benzylaniline. ¹H NMR (400 MHz, DMSO-d6) δ 2.19 (s, 3H), 4.43 (br s, 2H), 4.86 (br s, 2H), 6.63 (d, J=8.2 Hz, 2H), 7.02 (d, J=8.2 Hz, 2H), 7.14-7.40 (m, 10H); M+H (332.1).

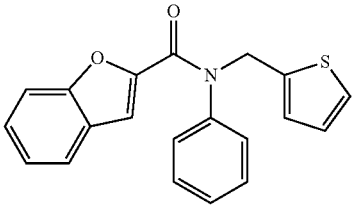

N-phenyl-N-(thiophen-2-ylmethyl)benzofuran-2-carboxamide; Example 114

Prepared in a similar manner to example 5 from benzofuran-2-carboxylic acid and N-(thiophen-2-ylmethyl)aniline. ¹H NMR (400 MHz, DMSO-d6) δ 5.21 (br s, 2H), 6.44 (br s, 1H), 6.87-6.90 (m, 1H), 6.91 (dd, J=5.0, 3.5 Hz, 1H), 7.16-7.25 (m, 3H), 7.33-7.41 (m, 4H), 7.42-7.46 (m, 2H), 7.54-7.60 (m, 1H); M+H (334.1).

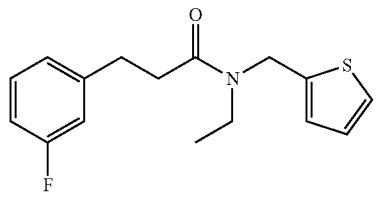 [SMILES: CCN(Cc1cccs1)C(=O)CCc1cccc(F)c1]

N-ethyl-3-(3-fluorophenyl)-N-(thiophen-2-ylmethyl)propanamide; Example 112

Prepared in a similar manner to example 5 from 3-(3-fluorophenyl)propanoic acid and N-(thiophen-2-ylmethyl)ethanamine. ¹H NMR showed a mixture of rotamers in a ~2:1 ratio: ¹H NMR (400 MHz, DMSO-d6) δ 1.01 (m, 3H), 2.60-2.74 (m, 2H), 2.81-2.91 (m, 2H), 3.23-3.33 (m, 2H), 4.61 (major) (br s, 2H), 4.69 (minor) (br s, 2H), 6.91-7.15 (m, 4H), 7.24-7.34 (m, 1H), 7.39 (major) (dd, J=5.1, 1.2 Hz, 1H), 7.45 (minor) (dd, J=3.8, 2.5 Hz, 1H); M+H (292.1).

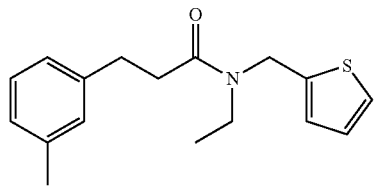 [SMILES: CCN(Cc1cccs1)C(=O)CCc1cccc(C)c1]

N-ethyl-N-(thiophen-2-ylmethyl)-3-m-tolylpropanamide; Example 113

Prepared in a similar manner to example 5 from 3-m-tolylpropanoic acid and N-(thiophen-2-ylmethyl)ethanamine. ¹H NMR showed a mixture of rotamers in a ~2:1 ratio: ¹H NMR (400 MHz, DMSO-d6) δ 0.96-1.06 (m, 3H), 2.25 (s, 3H), 2.56-2.69 (m, 2H), 2.72-2.86 (m, 2H), 3.21-3.31 (m, 2H), 4.61 (major) (br s, 2H), 4.67 (minor) (br s, N-(2-ethylhexyl)-3-(4-hydroxyphenyl)propanamide; Example 118

Prepared in a similar manner to example 5 from 3-(4-hydroxyphenyl)propanoic acid and 2-ethylhexan-1-amine. ¹H NMR (400 MHz, DMSO-d6) δ 0.79 (t, J=7.4 Hz, 3H), 0.86 (t, J=6.9 Hz, 3H), 1.06-1.39 (m, 10H), 2.30 (dd, J=8.5, 6.9 Hz, 2H), 2.67 (t, J=7.7 Hz, 2H), 2.89-3.01 (m, 2H), 6.63 (d, J=8.5 Hz, 2H), 6.96 (d, J=8.6 Hz, 2H), 7.64 (t, J=5.8 Hz, 1H), 9.11 (s, 1H); M+H (278.2).

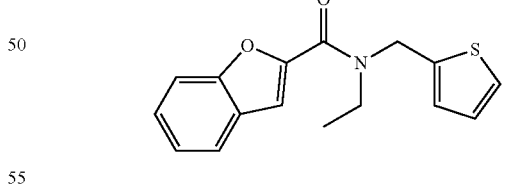

N-ethyl-N-(thiophen-2-ylmethyl)benzofuran-2-carboxamide; Example 119

Prepared in a similar manner to example 5 from benzofuran-2-carboxylic acid and N-(thiophen-2-ylmethyl)ethanamine. ¹H NMR (400 MHz, DMSO-d6) δ 1.23 (br s, 3H), 3.53 (br s, 2H), 4.84 (br s, 2H), 7.00 (dd, J=5.1, 3.4 Hz, 1H), 7.14 (br s, 1H), 7.31-7.37 (m, 1H), 7.42-7.52 (m, 3H), 7.66 (br dd, J=8.3, 0.8 Hz, 1H), 7.76 (ddd, J=7.8, 1.3, 0.7 Hz, 1H); M+H (286.1).

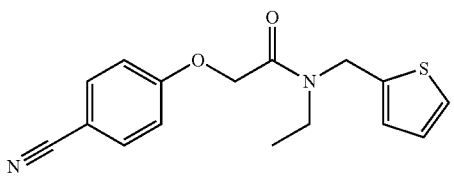 [SMILES: CCN(Cc1cccs1)C(=O)COc1ccc(C#N)cc1]

2-(4-cyanophenoxy)-N-ethyl-N-(thiophen-2-ylm-ethyl)acetamide; Example 120

Prepared in a similar manner to example 5 from 2-(4-cyanophenoxy)acetic acid and N-(thiophen-2-ylmethyl)ethanamine. $^1$H NMR showed a mixture of rotamers in a ~2:1 ratio: $^1$H NMR (400 MHz, DMSO-d6) δ 1.01 (minor) (t, J=7.1 Hz, 3H), 1.15 (major) (t, J=7.1 Hz, 3H), 3.30-3.34 (m, 2H), 4.65 (major) (br s, 2H), 4.76 (minor) (br s, 2H), 4.96 (minor) (br s, 2H), 4.99 (major) (br s, 2H), 6.95 (major) (dd, J=5.1, 3.4 Hz, 1H), 7.03 (minor) (dd, J=5.1, 3.5 Hz, 1H), 7.06 (major) (dd, J=3.4, 1.0 Hz, 1H), 7.13 (minor) (d, J=2.5 Hz, 1H), 7.22-7.31 (m, 1H), 7.34-7.45 (m, 2H), 7.45-7.56 (m, 1H); M+H (301.1).

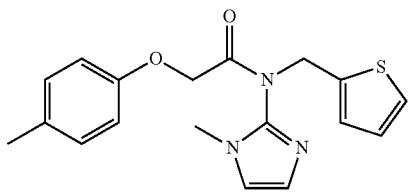

N-(1-methyl-1H-imidazol-2-yl)-N-(thiophen-2-ylm-ethyl)-2-(p-tolyloxy)acetamide; Example 121

Prepared in a similar manner to example 5 from 2-(p-tolyloxy)acetic acid and 1-methyl-N-(thiophen-2-ylmethyl)-1H-imidazol-2-amine. $^1$H NMR (400 MHz, CD$_3$OD) δ 2.24 (s, 3H), 3.22 (s, 3H), 4.38 (s, 2H), 5.04 (br s, 2H), 6.67 (br d, J=8.5 Hz, 2H), 6.88 (br d, J=3.5 Hz, 1H), 6.91-6.96 (m, 2H), 7.04 (br d, J=8.4 Hz, 2H), 7.08 (br s, 1H), 7.36 (brd, J=5.1 Hz, 1H); M+H (342.1).

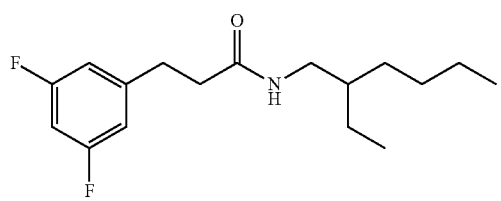 [SMILES: CCCCC(CC)CNC(=O)CCc1cc(F)cc(F)c1]

3-(3,5-difluorophenyl)-N-(2-ethylhexyl)propana-mide; Example 125

Prepared in a similar manner to example 5 from 3-(3,5-difluorophenyl)propanoic acid and 2-ethylhexan-1-amine. $^1$H NMR (400 MHz, DMSO-d6) δ 0.78 (t, J=7.4 Hz, 3H), 0.84 (t, J=6.9 Hz, 3H), 1.06-1.32 (m, 10H), 2.40 (t, J=7.4 Hz, 2H), 2.83 (t, J=7.4 Hz, 2H), 2.94 (m, 2H), 6.88-6.97 (m, 2H), 7.01 (tt, J=9.5, 2.4 Hz, 1H), 7.69 (t, J=5.6 Hz, 1H); M+H (298.2).

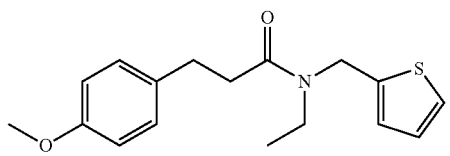

N-ethyl-3-(4-methoxyphenyl)-N-(thiophen-2-ylm-ethyl)propanamide; Example 126

Prepared in a similar manner to example 5 from 3-(4-methoxyphenyl)propanoic acid and N-(thiophen-2-ylm-ethyl)ethanamine. $^1$H NMR showed a mixture of rotamers in a ~2:1 ratio: $^1$H NMR (400 MHz, DMSO-d6) δ 1.01 (m, 3H), 2.64 (m, 2H), 2.75-2.89 (m, 2H), 3.24-3.33 (m, 2H), 3.71 (m, 3H), 4.65 (m, 2H), 6.70-6.84 (m, 3H), 6.91-7.04 (m, 2H), 7.12-7.22 (m, 1H), 7.42 (m, 1H); M+H (304.1).

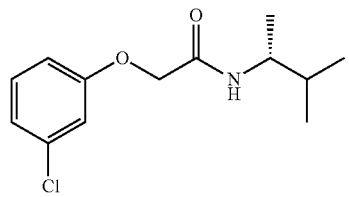 [SMILES: CC(C)[C@@H](C)NC(=O)COc1cccc(Cl)c1]

(R)-2-(3-chlorophenoxy)-N-(3-methylbutan-2-yl)acetamide; Example 129

Prepared in a similar manner to example 5 from 2-(3-chlorophenoxy)acetic acid and (R)-3-methylbutan-2-amine. $^1$H NMR (400 MHz, DMSO-d6) δ 0.77-0.85 (m, 6H), 1.01 (d, J=6.8 Hz, 3H), 1.54-1.73 (m, J=6.7 Hz, 1H), 3.58-3.73 (m, 1H), 4.52 (s, 2H), 6.92 (m, 1H), 7.01 (m, 2H), 7.27-7.36 (m, 1H), 7.81 (br d, J=8.7 Hz, 1H); M+H (256.1).

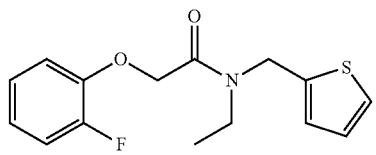 [SMILES: CCN(Cc1cccs1)C(=O)COc1ccccc1F]

N-ethyl-2-(2-fluorophenoxy)-N-(thiophen-2-ylm-ethyl)acetamide; Example 134

Prepared in a similar manner to example 5 from 2-(2-fluorophenoxy)acetic acid and N-(thiophen-2-ylmethyl)ethanamine. $^1$H NMR (400 MHz, DMSO-d6) δ 0.97-1.18 (m, 3H), 3.27-3.35 (m, 2H), 4.71 (m, 2H), 4.96 (m, 2H), 6.89-7.14 (m, 5H), 7.21 (m, 1H), 7.39-7.54 (m, 1H); M+H (294.1).

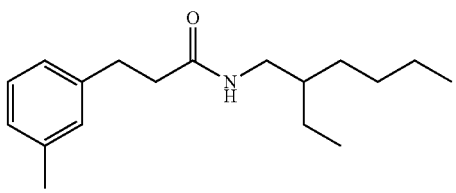 [SMILES: CCCCC(CC)CNC(=O)CCc1cccc(C)c1]

N-(2-ethylhexyl)-3-m-tolylpropanamide; Example 136

Prepared in a similar manner to example 5 from 3-m-tolylpropanoic acid and 2-ethylhexan-1-amine. $^1$H NMR (400 MHz, DMSO-d6) δ 0.79 (t, J=7.4 Hz, 3H), 0.85 (t, J=6.9 Hz, 3H), 1.09-1.36 (m, 9H), 2.35 (m, 2H), 2.75 (br t, J=7.6 Hz, 2H), 2.95 (m, 2H), 6.94-7.03 (m, 3H), 7.13 (t, J=7.5 Hz, 1H), 7.67 (t, J=5.7 Hz, 1H); M+H (276.2).

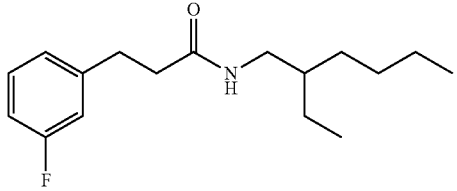 [SMILES: CCCCC(CC)CNC(=O)CCc1cccc(F)c1]

N-(2-ethylhexyl)-3-(3-fluorophenyl)propanamide; Example 140

Prepared in a similar manner to example 5 from 3-(3-fluorophenyl)propanoic acid and 2-ethylhexan-1-amine. ¹H NMR (400 MHz, DMSO-d6) δ 0.78 (t, J=7.4 Hz, 3H), 0.85 (t, J=6.8 Hz, 3H), 1.05-1.36 (m, 10H), 2.39 (t, J=7.5 Hz, 2H), 2.82 (t, J=7.5 Hz, 2H), 2.95 (t, J=6.1 Hz, 2H), 6.94-7.10 (m, 3H), 7.23-7.33 (m, 1H), 7.69 (t, J=5.6 Hz, 1H); M+H (280.2).

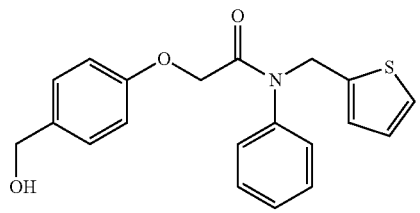 [SMILES: O=C(COc1ccc(CO)cc1)N(Cc1cccs1)c1ccccc1]

2-(4-(hydroxymethyl)phenoxy)-N-phenyl-N-(thiophen-2-ylmethyl)acetamide; Example 141

Prepared in a similar manner to example 5 from 2-(4-(hydroxymethyl)phenoxy)acetic acid and N-(thiophen-2-ylmethyl)aniline. ¹H NMR (400 MHz, DMSO-d6) δ 4.29-4.52 (m, 4H), 5.00 (br s, 2H), 6.70 (br d, J=8.2 Hz, 2H), 6.78-6.87 (m, 1H), 6.88-6.95 (m, 1H), 7.14-7.24 (dd, J=13.9, 8.7 Hz, 2H), 7.24-7.32 (m, 2H), 7.34-7.48 (m, 4H); M+H (354.1).

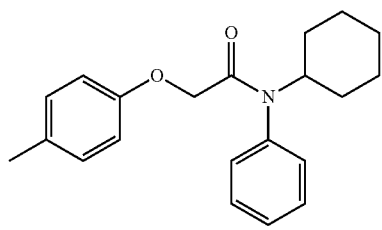 [SMILES: Cc1ccc(OCC(=O)N(c2ccccc2)C2CCCCC2)cc1]

N-cyclohexyl-N-phenyl-2-(p-tolyloxy)acetamide; Example 146

Prepared in a similar manner to example 5 from 2-(p-tolyloxy)acetic acid and N-cyclohexylaniline. ¹H NMR (400 MHz, DMSO-d6) δ 1.03-0.78 (m, 3H), 1.28 (m, 2H), 1.50 (d, J=12.5 Hz, 1H), 1.72 (dd, J=35.6, 12.4 Hz, 4H), 2.18 (s, 3H), 4.12 (s, 2H), 4.36 (t, J=12.0 Hz, 1H), 6.58 (d, J=8.6 Hz, 2H), 7.00 (d, J=8.3 Hz, 2H), 7.32 (d, J=6.4 Hz, 2H), 7.52-7.40 (m, 3H); M+H (324.2).

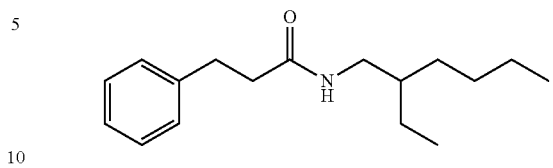

N-(2-ethylhexyl)-3-phenylpropanamide; Example 147

Prepared in a similar manner to example 5 from 3-phenylpropanoic acid and 2-ethylhexan-1-amine. ¹H NMR (400 MHz, DMSO-d6) δ 0.77 (t, J=7.4 Hz, 3H), 0.84 (t, J=6.9 Hz, 3H), 1.35-1.05 (m, 9H), 2.35 (m, 2H), 2.78 (t, J=7.7 Hz, 2H), 3.01-2.87 (m, 2H), 7.30-7.10 (m, 5H), 7.66 (t, J=5.7 Hz, 1H); M+H (261.2).

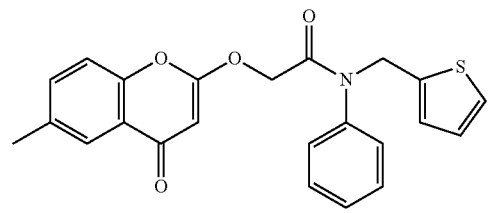 [SMILES: Cc1ccc2oc(OCC(=O)N(Cc3cccs3)c3ccccc3)cc(=O)c2c1]

2-(6-methyl-4-oxo-4H-chromen-2-yloxy)-N-phenyl-N-(thiophen-2-ylmethyl)acetamide; Example 149

Prepared in a similar manner to example 5 from 2-(6-methyl-4-oxo-4H-chromen-2-yloxy)acetic acid and N-(thiophen-2-ylmethyl)aniline. ¹H NMR (400 MHz, DMSO-d6) δ 2.33 (s, 3H), 5.21 (s, 2H), 6.46 (s, 1H), 6.91 (m, 2H), 7.09 (br d, J=8.0 Hz, 1H), 7.22 (m, 3H), 7.33-7.26 (m, 2H), 7.44 (dd, J=3.9, 2.5 Hz, 1H), 7.52 (br d, J=8.5 Hz, 1H), 7.68 (s, 1H); M+H (406.1).

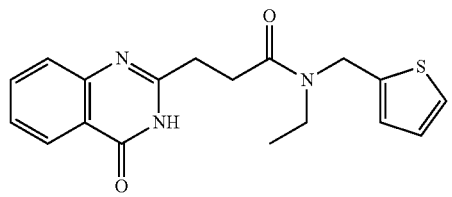 [SMILES: CCN(Cc1cccs1)C(=O)CCc1nc2ccccc2c(=O)[nH]1]

N-ethyl-3-(4-oxo-3,4-dihydroquinazolin-2-yl)-N-(thiophen-2-ylmethyl)propanamide; Example 150

Prepared in a similar manner to example 5 from 3-(4-oxo-3,4-dihydroquinazolin-2-yl)propanoic acid and N-(thiophen-2-ylmethyl)ethanamine. Room temperature ¹H NMR showed a mixture of rotamers in a ~2:1 ratio ¹H NMR (400 MHz, DMSO-d6) δ 1.05 (m, 3H), 3.00-2.79 (m, 4H), 3.29-3.43 (m, 2H), 4.69 (d, J=75.4 Hz, 2H), 7.13-6.80 (m, 2H), 7.56-7.25 (m, 3H), 7.80-7.70 (m, 1H), 8.05 (d, J=7.9 Hz, 1H), 12.19 (s, 1H); M+H (342.1).

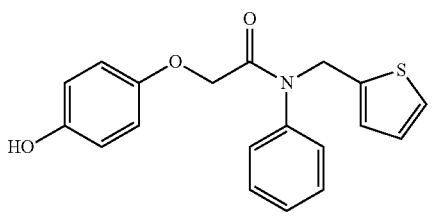 [SMILES: O=C(COc1ccc(O)cc1)N(Cc1cccs1)c1ccccc1]

2-(4-hydroxyphenoxy)-N-phenyl-N-(thiophen-2-ylmethyl)acetamide; Example 152

Prepared in a similar manner to example 5 from 2-(4-hydroxyphenoxy)acetic acid and N-(thiophen-2-ylmethyl)aniline. $^1$H NMR (400 MHz, DMSO-d6) δ 4.29 (s, 2H), 4.98 (s, 2H), 6.64-6.49 (m, 4H), 6.82 (br s, 1H), 6.88 (dd, J=5.1, 3.4 Hz, 1H), 7.25-7.19 (m, 2H), 7.39 (m, 4H), 8.91 (s, 1H); M+H (340.1).

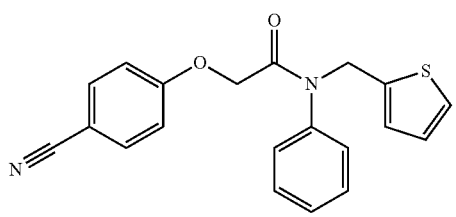 [SMILES: N#Cc1ccc(OCC(=O)N(Cc2cccs2)c2ccccc2)cc1]

2-(4-cyanophenoxy)-N-phenyl-N-(thiophen-2-ylmethyl)acetamide; Example 153

Prepared in a similar manner to example 5 from 2-(4-cyanophenoxy)acetic acid and N-(thiophen-2-ylmethyl)aniline. $^1$H NMR (400 MHz, DMSO-d6) δ 4.57 (s, 2H), 4.98 (s, 2H), 6.82 (s, 1H), 6.97-6.87 (m, 3H), 7.28 (d, J=7.0 Hz, 2H), 7.47-7.34 (m, 4H), 7.71 (d, J=8.9 Hz, 2H); M+H (349.1).

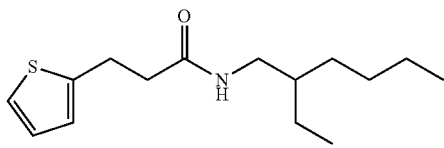 [SMILES: CCCCC(CC)CNC(=O)CCc1cccs1]

N-(2-ethylhexyl)-3-(thiophen-2-yl)propanamide; Example 155

Prepared in a similar manner to example 5 from 3-(thiophen-2-yl)propanoic acid and 2-ethylhexan-1-amine. $^1$H NMR (400 MHz, DMSO-d6) δ 0.78 (t, J=7.4 Hz, 3H), 0.84 (t, J=6.9 Hz, 3H), 1.35-1.09 (m, 10H), 2.40 (t, J=7.4 Hz, 2H), 3.02-2.90 (m, 4H), 6.81 (m, 1H), 6.89 (dd, J=5.1, 3.4 Hz, 1H), 7.27 (dt, J=5.1, 0.9 Hz, 1H), 7.73 (br t, J=5.5 Hz, 1H); M+H (268.2).

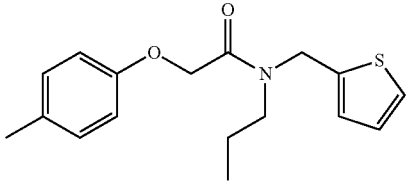 [SMILES: CCCN(Cc1cccs1)C(=O)COc1ccc(C)cc1]

N-propyl-N-(thiophen-2-ylmethyl)-2-(p-tolyloxy)acetamide; Example 156

Prepared in a similar manner to example 5 from 2-(p-tolyloxy)acetic acid and N-(thiophen-2-ylmethyl)propan-1-amine. $^1$H NMR (400 MHz, DMSO-d6) δ 0.89-0.75 (m, 3H), 1.53-1.31 (m, 2H), 2.17 (s, 3H), 3.66-3.52 (m, 2H), 4.30 (br s, 2H), 6.58 (d, J=8.1 Hz, 2H), 7.00 (d, J=8.2 Hz, 2H), 7.51-7.35 (m, 5H); M+H (304.1).

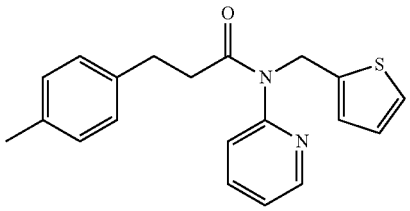

N-(pyridin-2-yl)-N-(thiophen-2-ylmethyl)-3-p-tolyl-propanamide; Example 158

Prepared in a similar manner to example 5 from 3-p-tolylpropanoic acid and N-(thiophen-2-ylmethyl)pyridin-2-amine. $^1$H NMR (400 MHz, DMSO-d6) δ 2.20 (s, 3H), 2.50 (m, 2H), 2.75 (t, J=7.7 Hz, 2H), 5.13 (br s, 2H), 6.83-6.76 (m, 1H), 6.85 (dd, J=5.1, 3.4 Hz, 1H), 6.98 (m 4H), 7.31-7.20 (m, 2H), 7.35 (dd, J=5.1, 1.3 Hz, 1H), 7.85-7.75 (m, 1H), 8.46 (ddd, J=4.8, 2.0, 0.8 Hz, 1H); M+H (337.1).

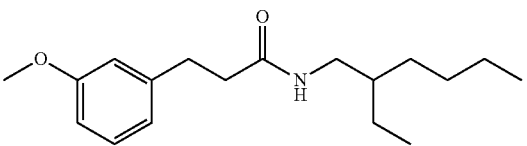 [SMILES: CCCCC(CC)CNC(=O)CCc1cccc(OC)c1]

N-(2-ethylhexyl)-3-(3-methoxyphenyl)propanamide; Example 160

Prepared in a similar manner to example 5 from 3-(3-methoxyphenyl)propanoic acid and 2-ethylhexan-1-amine. $^1$H NMR (400 MHz, DMSO-d6) δ 0.77 (t, J=7.4 Hz, 3H), 0.83 (t, J=6.9 Hz, 3H), 1.34-1.07 (m, 10H), 2.35 (t, J=7.7 Hz, 2H), 2.75 (t, J=7.6 Hz, 2H), 2.98-2.88 (m, 2H), 3.70 (s, 3H), 6.79-6.68 (m, 3H), 7.19-7.11 (m, 1H), 7.66 (t, J=5.7 Hz, 1H); M+H (292.2).

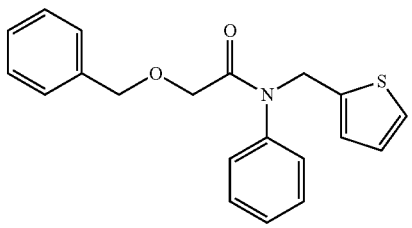 [SMILES: O=C(COCc1ccccc1)N(Cc1cccs1)c1ccccc1]

2-(benzyloxy)-N-phenyl-N-(thiophen-2-ylmethyl) acetamide; Example 161

Prepared in a similar manner to example 5 from 2-(benzyloxy)acetic acid and N-(thiophen-2-ylmethyl)aniline. ¹H NMR (400 MHz, DMSO-d6) δ 3.84 (br s, 2H), 4.41 (br s, 2H), 4.97 (br s, 2H), 6.80 (dd, J=3.4, 1.1 Hz, 1H), 6.88 (dd, J=5.1, 3.4 Hz, 1H), 7.17-7.10 (m, 2H), 7.38-7.19 (m, 8H), 7.40 (dd, J=5.1, 1.3 Hz, 1H); M+H (338.1).

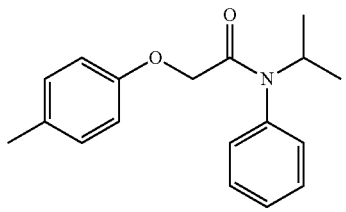 [SMILES: Cc1ccc(OCC(=O)N(c2ccccc2)C(C)C)cc1]

N-isopropyl-N-phenyl-2-(p-tolyloxy)acetamide; Example 164

Prepared in a similar manner to example 5 from 2-(p-tolyloxy)acetic acid and N-isopropylaniline. ¹H NMR (400 MHz, DMSO-d6) δ 0.97 (t, J=6.3 Hz, 6H), 2.17 (s, 3H), 4.13 (s, 2H), 4.76 (m, 1H), 6.58 (d, J=8.5 Hz, 2H), 7.00 (d, J=8.4 Hz, 2H), 7.33 (d, J=6.6 Hz, 2H), 7.57-7.39 (m, 3H); M+H (284.2).

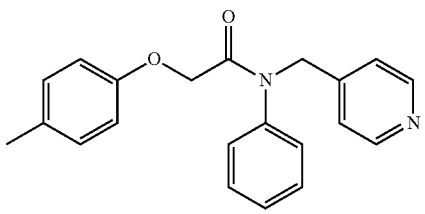 [SMILES: Cc1ccc(OCC(=O)N(Cc2ccncc2)c2ccccc2)cc1]

N-phenyl-N-(pyridin-4-ylmethyl)-2-(p-tolyloxy) acetamide; Example 167

Prepared in a similar manner to example 5 from 2-(p-tolyloxy)acetic acid and N-(pyridin-4-ylmethyl)aniline. ¹H NMR (400 MHz, DMSO-d6) δ 2.19 (s, 3H), 4.49 (br s, 2H), 4.88 (br s, 2H), 6.63 (d, J=8.4 Hz, 2H), 7.02 (dd, J=8.7, 0.6 Hz, 2H), 7.23 (d, J=6.0 Hz, 2H), 7.46-7.29 (m, 5H), 8.46 (dd, J=4.4, 1.6 Hz, 2H); M+H (333.2).

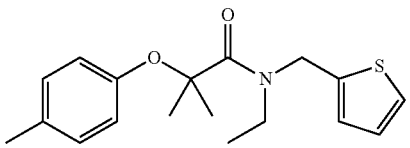 [SMILES: CCN(Cc1cccs1)C(=O)C(C)(C)Oc1ccc(C)cc1]

N-ethyl-2-methyl-N-(thiophen-2-ylmethyl)-2-(p-tolyloxy)propanamide; Example 170

Prepared in a similar manner to example 5 from 2-methyl-2-(p-tolyloxy)propanoic acid and N-(thiophen-2-ylmethyl) ethanamine. ¹H NMR (400 MHz, DMSO-d6) δ 0.89 (m, 3H), 1.62-1.42 (m, 6H), 2.20 (m, 3H), 3.20 (minor) (q, J=6.9 Hz, 2H), 3.63 (major) (q, J=6.9 Hz, 2H), 4.63 (major) (s, 2H), 5.04 (minor) (s, 2H), 6.62 (major) (d, J=8.5 Hz, 2H), 6.74 (minor) (d, J=8.5 Hz, 2H), 7.11-6.87 (m, 4H), 7.40 (dd, J=5.1, 1.2 Hz, 1H); M+H (318.1).

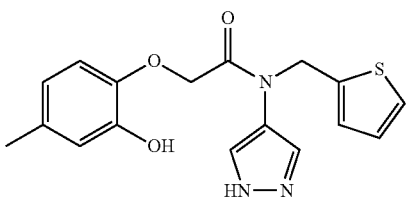 [SMILES: Cc1ccc(OCC(=O)N(Cc2cccs2)c2cn[nH]c2)c(O)c1]

2-(2-hydroxy-4-methylphenoxy)-N-(1H-pyrazol-4-yl)-N-(thiophen-2-ylmethyl)acetamide; Example 182

Prepared in a similar manner to example 5 from 2-(2-hydroxy-4-methylphenoxy)acetic acid and N-(thiophen-2-ylmethyl)-1H-pyrazol-4-amine. ¹H NMR (400 MHz, DMSO-d6): δ 2.15 (s, 3H), 4.47 (s, 2H), 4.88 (br s, 2H), 6.47 (ddd, J=8.1, 2.1, 0.6 Hz, 1H), 6.60 (d, J=2.0 Hz, 1H), 6.66 (d, J=8.1 Hz, 1H), 6.88 (br dd, J=3.4, 1.1 Hz, 1H), 6.94 (dd, J=5.1, 3.4 Hz, 1H), 7.44 (m, 2H), 7.78 (br s, 1H), 9.10 (br s, 1H), 13.00 (br s, 1H); M+H (344.1).

2-(2-hydroxy-4-methylphenoxy)acetic acid; Example 182a

To a 0° C. stirring solution of ethyl 2-(2-hydroxy-4-methylphenoxy)acetate (1.20 g, 5.82 mmol) in methanol (10.0 mL) and water (6.0 mL), was added a 10.0 M solution of NaOH (3.0 mL; 30.0 mmol). The ice bath was then removed and the reaction was allowed to warm to room temperature with stirring until reaction completion. The mixture was poured in to a stirring mixture of water (20.0 mL) and 6.0 M HCl (6.0 mL), and the product was collected by filtration and dried under vacuum affording, 692 mg of 2-(2-hydroxy-4-methylphenoxy)acetic acid as a white solid in 70% yield.

Ethyl 2-(2-hydroxy-4-methylphenoxy)acetate; Example 182b

To a 0° C. stirring solution of ethyl 2-(2-methoxy-4-methylphenoxy)acetate (2.73 g, 12.17 mmol) in DCM (25.0 mL) was added dropwise a 1.0 M solution of BBr₃ in DCM (18.27 mmol, 18.3 mL). The reaction was stirred for 1 hour then cooled to −78° C. and quenched with water. After warming to room temperature, the solution was extracted three times with EtOAc and the combined organic layers were washed with brine then dried Na$_2$SO$_4$. The obtained organic layer was concentrated by rotovap and then absorbed on Florisil with the aid of some EtOAc and all the volatiles were evaporated on the rotovap. The obtained powder was loaded on chromatographic column and purified with hexane/ethyl acetate gradient (Biotage system). After solvent evaporation from the desired fractions, 1.623 g of ethyl 2-(2-hydroxy-4-methylphenoxy)acetate were recovered in 71% yield.

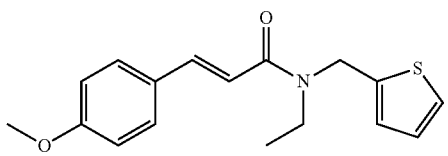 [SMILES: CCN(Cc1cccs1)C(=O)/C=C/c1ccc(OC)cc1]

(E)-N-ethyl-3-(4-methoxyphenyl)-N-(thiophen-2-ylmethyl)acrylamide; Example 188

Prepared in a similar manner to example 5 from (E)-3-(4-methoxyphenyl)acrylic acid and N-(thiophen-2-ylmethyl)ethanamine. Room temperature $^1$H NMR showed a mixture of rotamers in a ~2:1 ratio: $^1$H NMR (400 MHz, DMSO-d6) δ 1.03-1.11 (m, 3H), 3.34-3.60 (m, 2H), 3.77 (s, 3H), 4.70 (major) (s, 2H), 4.93 (minor) (s, 2H), 6.85-7.23 (m, 5H), 7.33-7.57 (m, 2H), 7.60-7.68 (m, 2H); M+H (302.1).

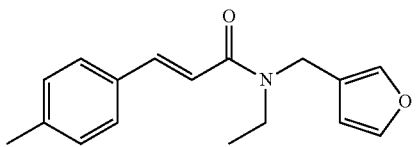 [SMILES: CCN(Cc1ccoc1)C(=O)/C=C/c1ccc(C)cc1]

(E)-N-ethyl-N-(furan-3-ylmethyl)-3-p-tolylacrylamide; Example 189

Prepared in a similar manner to example 5 from (E)-3-p-tolylacrylic acid and N-(furan-3-ylmethyl)ethanamine. Room temperature $^1$H NMR showed a mixture of rotamers in a~1.5:1 ratio: $^1$H NMR (400 MHz, DMSO-d6) δ 1.02-1.12 (m, 3H), 2.30 (s, 3H), 3.37 (minor) (br q, J=7.0 Hz, 2H), 3.47 (major) (br q, J=6.8 Hz, 2H), 4.38 (major) (s, 2H), 4.55 (minor) (s, 2H), 6.39 (br s, 1H), 6.97-7.27 (m, 3H), 7.37-7.75 (m, 5H); M+H (270.1).

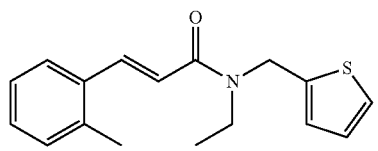 [SMILES: CCN(Cc1cccs1)C(=O)/C=C/c1ccccc1C]

(E)-N-ethyl-N-(thiophen-2-ylmethyl)-3-o-tolylacrylamide; Example 191

Prepared in a similar manner to example 5 from (E)-3-o-tolylacrylic acid and N-(thiophen-2-ylmethyl)ethanamine. Room temperature 1H NMR showed a mixture of rotamers in a~1.5:1 ratio: $^1$H NMR (400 MHz, DMSO-d6) δ 1.01-1.21 (m, 3H), 2.36-2.40 (m, 3H), 3.42 (minor) (br q, J=6.9 Hz, 2H), 3.54 (major) (br q, J=6.9 Hz, 2H), 4.73 (major) (br s, 2H), 4.96 (minor) (br s, 2H), 6.89-7.16 (m, 3H), 7.22-7.29 (m, 3H), 7.40-7.46 (m, 1H), 7.65-7.89 (m, 2H); M+H (286.1).

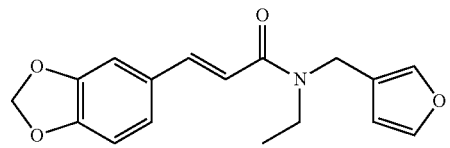 [SMILES: CCN(Cc1ccoc1)C(=O)/C=C/c1ccc2c(c1)OCO2]

(E)-3-(benzo[d][1,3]dioxol-5-yl)-N-ethyl-N-(furan-3-ylmethyl)acrylamide; Example 193

Prepared in a similar manner to example 5 from (E)-3-(benzo[d][1,3]dioxol-5-yl)acrylic acid and N-(furan-3-ylmethyl)ethanamine. Room temperature $^1$H NMR showed a mixture of rotamers in a ~ 1.5:1 ratio: $^1$H NMR (400 MHz, DMSO-d6) δ 1.02-1.13 (m, 3H), 3.37 (minor) (br q, J=6.9 Hz, 1H), 3.48 (major) (br q, J=6.9 Hz, 1H), 4.38 (major) (br s, 1H), 4.56 (minor) (br s, 1H), 6.06 (s, 2H), 6.40 (br s, 1H), 6.91-7.17 (m, 3H), 7.37-7.53 (m, 2H), 7.58-7.66 (m, 2H); M+H (300.1).

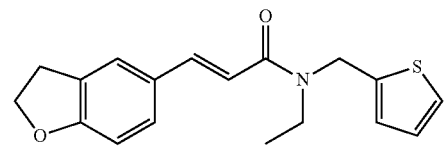 [SMILES: CCN(Cc1cccs1)C(=O)/C=C/c1ccc2c(c1)CCO2]

(E)-3-(2,3-dihydrobenzofuran-5-yl)-N-ethyl-N-(thiophen-2-ylmethyl)acrylamide; Example 194

Prepared in a similar manner to example 5 from (E)-3-(2,3-dihydrobenzofuran-5-yl)acrylic acid and N-(thiophen-2-ylmethyl)ethanamine. Room temperature 1H NMR showed a mixture of rotamers in a ~2:1 ratio: $^1$H NMR (400 MHz, DMSO-d6) δ 1.03-1.14 (m, 3H), 3.20 (br t, J=9.2 Hz, 2H), 3.39 (minor) (br q, J=6.9 Hz, 2H), 3.51 (major) (br q, J=6.9 Hz, 2H), 4.57 (t, J=8.7 Hz, 2H), 4.71 (major) (br s, 2H), 4.94 (minor) (br s, 2H), 6.78 (d, J=8.2 Hz, 1H), 6.88-7.02 (m, 2H), 7.06 (br s, 1H), 7.34-7.56 (m, 3H), 7.61-7.72 (m, 1H); M+H (314.1).

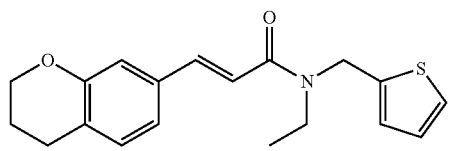 [SMILES: CCN(Cc1cccs1)C(=O)/C=C/c1ccc2c(c1)OCCC2]

(E)-3-(2,3-dihydrobenzo[b][1,4]dioxin-6-yl)-N-ethyl-N-(thiophen-2-ylmethyl)acrylamide; Example 198

Prepared in a similar manner to example 5 from (E)-3-(2,3-dihydrobenzo[b][1,4]dioxin-6-yl)acrylic acid and N-(thiophen-2-ylmethyl)ethanamine. Room temperature ¹H NMR showed a mixture of rotamers in a ~2:1 ratio: ¹H NMR (400 MHz, DMSO-d6) δ 1.00 (minor) (br t, J=7.0 Hz, 1H), 1.12 (major) (br t, J=7.1 Hz, 2H), 3.30 (m, 2H), 4.18 (m, 4H), 4.63 (major) (br s, 1H), 4.73 (br s, 2H), 4.74 (minor) (br s, 2H), 6.31-6.50 (m, 2H), 6.71-6.77 (m, 1H), 6.89-7.15 (m, 2H), 7.42 (major) (dd, J=5.1, 1.2 Hz, 1H), 7.50 (minor) (d, J=4.1 Hz, 1H); M+H (330.1).

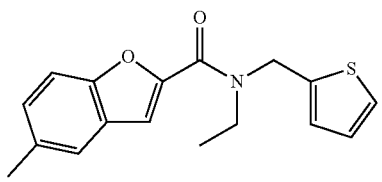 [SMILES: CCN(Cc1cccs1)C(=O)c1cc2cc(C)ccc2o1]

N-ethyl-5-methyl-N-(thiophen-2-ylmethyl)benzofuran-2-carboxamide; Example 202

Prepared in a similar manner to example 5 from 5-methylbenzofuran-2-carboxylic acid and N-(thiophen-2-ylmethyl)ethanamine. ¹H NMR (400 MHz, DMSO-d6) δ 1.22 (br s, 3H), 2.41 (s, 3H), 3.53 (br s, 2H), 4.83 (br s, 2H), 6.99 (dd, J=5.1, 3.4 Hz, 1H), 7.13 (br s, 1H), 7.23-7.30 (m, 1H), 7.38 (br s, 1H), 7.47 (br d, J=4.5 Hz, 1H), 7.50-7.56 (m, 2H); M+H (300.1).

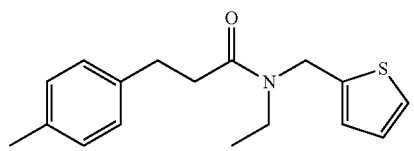 [SMILES: CCN(Cc1cccs1)C(=O)CCc1ccc(C)cc1]

N-ethyl-N-(thiophen-2-ylmethyl)-3-p-tolylpropanamide; Example 206

Prepared in a similar manner to example 5 from 3-p-tolylpropanoic acid and N-(thiophen-2-ylmethyl)ethanamine. Room temperature 1H NMR showed a mixture of rotamers in a ~2:1 ratio: ¹H NMR (400 MHz, DMSO-d6) δ 0.96-1.05 (m, 3H), 2.25 (s, 3H), 2.56-2.66 (m, 2H), 2.71-2.88 (m, 2H), 3.23-3.32 (m, 2H), 4.61 (major) (br s, 2H), 4.67 (minor) (br s, 2H), 6.90-7.02 (m, 2H), 7.03-7.16 (m, 4H), 7.39 (major) (dd, J=5.1, 1.2 Hz, 1H), 7.44 (minor) (dd, J=4.8, 1.5 Hz, 1H); M+H (288.1).

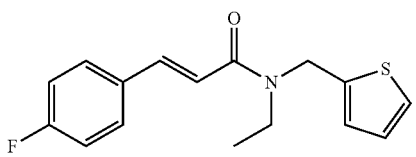 [SMILES: CCN(Cc1cccs1)C(=O)/C=C/c1ccc(F)cc1]

(E)-N-ethyl-3-(4-fluorophenyl)-N-(thiophen-2-ylmethyl)acrylamide; Example 207

Prepared in a similar manner to example 5 from (E)-3-(4-fluorophenyl)acrylic acid and N-(thiophen-2-ylmethyl)ethanamine. Room temperature ¹H NMR showed a mixture of rotamers in a ~2:1 ratio: ¹H NMR (400 MHz, DMSO-d6) δ 1.04-1.14 (m, 3H), 3.41 (minor) (br q, J=7.1 Hz, 2H), 3.53 (major) (br q, J=7.1 Hz, 2H), 4.73 (major) (br s, 2H), 4.97 (minor) (br s, 2H), 6.90-7.02 (m, 1H), 7.03-7.31 (m, 4H), 7.40-7.45 (m, 1H), 7.51-7.60 (m, 1H), 7.71-7.86 (m, 2H); M+H (290.1).

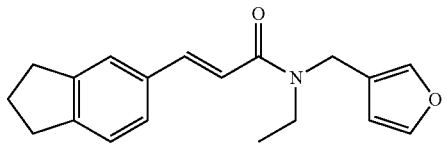 [SMILES: CCN(Cc1ccoc1)C(=O)/C=C/c1ccc2c(c1)CCC2]

(E)-3-(2,3-dihydro-1H-inden-5-yl)-N-ethyl-N-(furan-3-ylmethyl)acrylamide; Example 208

Prepared in a similar manner to example 5 from (E)-3-(2,3-dihydro-1H-inden-5-yl)acrylic acid and N-(furan-3-ylmethyl)ethanamine. Room temperature ¹H NMR showed a mixture of rotamers in a ~2:1 ratio: ¹H NMR (400 MHz, DMSO-d6) δ 1.03-1.14 (m, 3H), 2.02 (p, J=7.5 Hz, 2H), 2.86 (m, 4H), 3.38 (minor) (br q, J=7.0 Hz, 2H), 3.49 (major) (br q, J=7.0 Hz, 2H), 4.39 (major) (br s, 2H), 4.57 (minor) (br s, 2H), 6.40 (dd, J=1.7, 0.7 Hz, 1H), 7.05 (major) (d, J=15.3 Hz, 1H), 7.15 (minor) (d, J=15.5 Hz, 1H), 7.25 (br d, J=7.7 Hz, 1H), 7.35-7.69 (m, 5H); M+H (296.2).

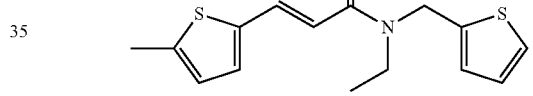

(E)-N-ethyl-3-(5-methylthiophen-2-yl)-N-(thiophen-2-ylmethyl)acrylamide; Example 209

Prepared in a similar manner to example 5 from (E)-3-(5-methylthiophen-2-yl)acrylic acid and N-(thiophen-2-ylmethyl)ethanamine. Room temperature ¹H NMR showed a mixture of rotamers in a~1.5:1 ratio: ¹H NMR (400 MHz, DMSO-d6) δ 1.03-1.12 (m, 3H), 2.46 (br s, 3H), 3.35-3.52 (m, 2H), 4.71 (major) (br s, 2H), 4.87 (minor) (br s, 2H), 6.62 (major) (d, J=15.1 Hz, 1H), 6.75 (minor) (d, J=14.9 Hz, 1H), 6.82 (br d, J=2.1 Hz, 1H), 6.90-7.12 (m, 2H), 7.23-7.29 (m, 1H), 7.39-7.46 (m, 1H), 7.56-7.67 (m, 1H); M+H (292.1).

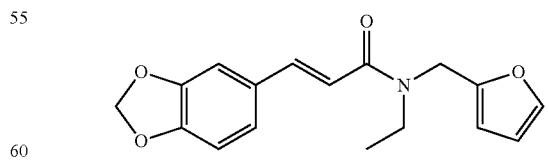

(E)-3-(benzo[d][1,3]dioxol-5-yl)-N-ethyl-N-(furan-2-ylmethyl)acrylamide; Example 210

Prepared in a similar manner to example 5 from (E)-3-(benzo[d][1,3]dioxol-5-yl)acrylic acid and N-(furan-2-ylmethyl)ethanamine. Room temperature ¹H NMR showed a mixture of rotamers in a ~1:1 ratio: ¹H NMR (400 MHz, DMSO-d6) δ 1.10-0.94 (m, 3H), 3.38 (br q, J=6.5 Hz, 1H), 3.52 (br q, J=6.8 Hz, 1H), 4.59 (br s, 1H), 4.75 (br s, 1H), 6.06 (s, 2H), 6.30-6.42 (m, 2H), 6.93 (d, J=8.0 Hz, 1H), 7.00 (br d, J=15.3 Hz, 0.5H), 7.11-7.20 (m, 1.5H), 7.40-7.48 (m, 2H), 7.60 (br d, J=13.6 Hz, 1H); M+H (300.1).

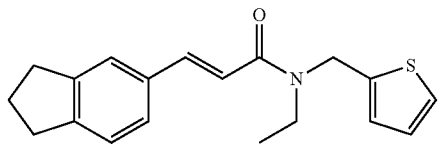 [SMILES: CCN(Cc1cccs1)C(=O)/C=C/c1ccc2c(c1)CCC2]

(E)-3-(2,3-dihydro-1H-inden-5-yl)-N-ethyl-N-(thiophen-2-ylmethyl)acrylamide; Example 211

Prepared in a similar manner to example 5 from (E)-3-(2,3-dihydro-1H-inden-5-yl)acrylic acid and N-(thiophen-2-ylmethyl)ethanamine. Room temperature ¹H NMR showed a mixture of rotamers in a ~2:1 ratio: ¹H NMR (400 MHz, DMSO-d6) δ 1.03-1.14 (m, 3H), 2.02 (p, J=7.4 Hz, 2H), 2.87 (m, 4H), 3.40 (minor) (br q, J=7.0 Hz, 2H), 3.52 (major) (br q, J=7.0 Hz, 2H), 4.72 (major) (br s, 2H), 4.95 (minor) (br s, 2H), 6.93-7.01 (m, 1H), 7.08 (br s, 1H), 7.21-7.28 (m, 1H), 7.35-7.69 (m, 4H); M+H (312.1).

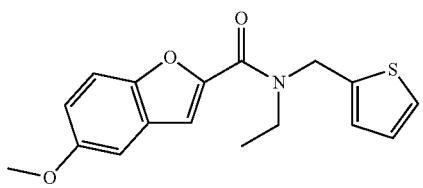 [SMILES: CCN(Cc1cccs1)C(=O)c1cc2cc(OC)ccc2o1]

N-ethyl-5-methoxy-N-(thiophen-2-ylmethyl)benzofuran-2-carboxamide; Example 213

Prepared in a similar manner to example 5 from 5-methoxybenzofuran-2-carboxylic acid and N-(thiophen-2-ylmethyl)ethanamine. ¹H NMR (400 MHz, DMSO-d6) 1.22 (br s, 3H), 3.53 (br s, 2H), 3.79 (s, 3H), 4.83 (br s, 2H), 6.99 (dd, J=5.1, 3.4 Hz, 1H), 7.04 (dd, J=9.0, 2.7 Hz, 1H), 7.14 (br s, 1H), 7.24 (d, J=2.4 Hz, 1H), 7.38 (br s, 1H), 7.47 (br d, J=4.8 Hz, 1H), 7.56 (br d, J=9.0 Hz, 1H); M+H (316.1).

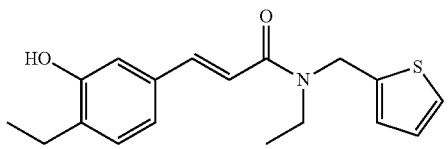 [SMILES: CCc1ccc(/C=C/C(=O)N(CC)Cc2cccs2)cc1O]

(E)-N-ethyl-3-(3-hydroxy-4-methoxyphenyl)-N-(thiophen-2-ylmethyl)acrylamide; Example 214

Prepared in a similar manner to example 5 from (E)-3-(3-hydroxy-4-methoxyphenyl)acrylic acid and N-(thiophen-2-ylmethyl)ethanamine. Room temperature ¹H NMR showed a mixture of rotamers in a ~2:1 ratio: ¹H NMR (400 MHz, DMSO-d6) δ 1.03-1.14 (m, 3H), 3.40 (minor) (br q, J=7.0 Hz, 2H), 3.50 (major) (br q, J=7.0 Hz, 2H), 3.80 (s, 3H), 4.71 (major) (br s, 2H), 4.92 (minor) (br s, 2H), 6.76-7.25 (m, 6H), 7.32-7.54 (m, 2H), 9.06 (s, 1H); M+H (318.1).

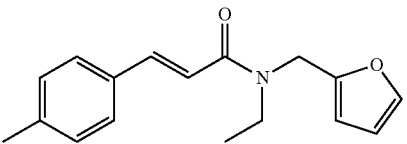 [SMILES: CCN(Cc1ccco1)C(=O)/C=C/c1ccc(C)cc1]

(E)-N-ethyl-N-(furan-2-ylmethyl)-3-p-tolylacrylamide; Example 215

Prepared in a similar manner to example 5 from (E)-3-p-tolylacrylic acid and N-(furan-2-ylmethyl)ethanamine. Room temperature ¹H NMR showed a mixture of rotamers in a ~1:1 ratio: ¹H NMR (400 MHz, DMSO-d6) δ 0.99-1.09 (m, 3H), 2.32 (s, 3H), 3.39 (q, J=6.9 Hz, 1H), 3.52 (q, J=7.0 Hz, 1H), 4.60 (br s, 1H), 4.75 (br s, 1H), 6.43-6.29 (m, 1H), 7.13-7.03 (m, 0.5H), 7.20-7.25 (m, 2.5H), 7.43-7.56 (m, 1H), 7.57-7.62 (m, 3H); M+H (270.1).

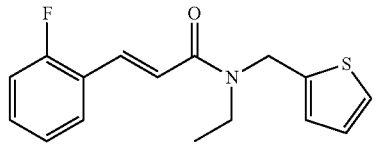

(E)-N-ethyl-3-(2-fluorophenyl)-N-(thiophen-2-ylmethyl)acrylamide; Example 216

Prepared in a similar manner to example 5 from (E)-3-(2-fluorophenyl)acrylic acid and N-(thiophen-2-ylmethyl)ethanamine. Room temperature ¹H NMR showed a mixture of rotamers in a ~2:1 ratio: ¹H NMR (400 MHz, DMSO-d6) δ 1.05-1.15 (m, 3H), 3.42 (minor) (br q, J=7.2 Hz, 2H), 3.53 (major) (br q, J=7.0 Hz, 2H), 4.74 (major) (br s, 2H), 4.96 (minor) (br s, 2H), 6.93-7.03 (m, 1H), 7.06-7.10 (m, 1H), 7.15-7.37 (m, 3H), 7.39-7.51 (m, 2H), 7.62-7.71 (m, 1H), 7.84-7.96 (m, 1H); M+H (290.1).

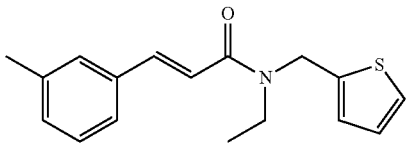 [SMILES: CCN(Cc1cccs1)C(=O)/C=C/c1cccc(C)c1]

(E)-N-ethyl-N-(thiophen-2-ylmethyl)-3-m-tolylacrylamide; Example 219

Prepared in a similar manner to example 5 from (E)-3-m-tolylacrylic acid and N-(thiophen-2-ylmethyl)ethanamine. Room temperature ¹H NMR showed a mixture of rotamers in a ~2:1 ratio: ¹H NMR (400 MHz, DMSO-d6) δ 1.04-1.15 (m, 3H), 2.33 (br s, 3H), 3.41 (minor) (br q, J=7.1 Hz, 2H), 3.53 (major) (br q, J=7.0 Hz, 2H), 4.73 (major) (br s, 2H), 4.96 (minor) (br s, 2H), 6.92-7.02 (m, 1H), 7.05-7.33 (m, 4H), 7.38-7.58 (m, 4H); M+H (286.1).

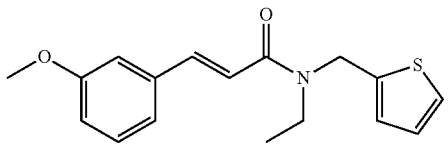 [SMILES: CCN(Cc1cccs1)C(=O)/C=C/c1cccc(OC)c1]

(E)-N-ethyl-3-(3-methoxyphenyl)-N-(thiophen-2-ylmethyl)acrylamide; Example 221

Prepared in a similar manner to example 5 from (E)-3-(3-methoxyphenyl)acrylic acid and N-(thiophen-2-ylmethyl)ethanamine. Room temperature $^1$H NMR showed a mixture of rotamers in a ~2:1 ratio: $^1$H NMR (400 MHz, DMSO-d6) δ 1.04-1.14 (m, 3H), 3.41 (minor) (br q, J=6.8 Hz, 2H), 3.54 (major) (br q, J=7.0 Hz, 2H), 3.77-3.80 (m, 3H), 4.73 (major) (br s, 2H), 4.97 (minor) (br s, 2H), 6.90-7.03 (m, 2H), 7.06-7.19 (m, 2H), 7.22-7.36 (m, 3H), 7.40-7.45 (m, 1H), 7.47-7.57 (m, 1H); M+H (302.1).

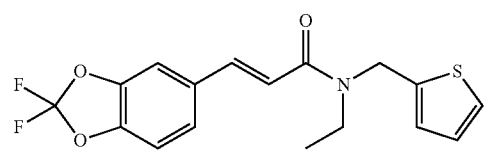 [SMILES: CCN(Cc1cccs1)C(=O)/C=C/c1ccc2c(c1)OC(F)(F)O2]

(E)-3-(2,2-difluorobenzo[d][1,3]dioxol-5-yl)-N-ethyl-N-(thiophen-2-ylmethyl)acrylamide; Example 222

Prepared in a similar manner to example 5 from (E)-3-(2,2-difluorobenzo[d][1,3]dioxol-5-yl)acrylic acid and N-(thiophen-2-ylmethyl)ethanamine. Room temperature $^1$H NMR showed a mixture of rotamers in a ~2:1 ratio: $^1$H NMR (400 MHz, DMSO-d6) δ 1.06 (minor) (br t, J=7.0 Hz, 3H), 1.11 (major) (br t, J=7.0 Hz, 3H), 3.40 (minor) (br q, J=6.8 Hz, 2H), 3.53 (major) (br q, J=7.0 Hz, 2H), 4.73 (major) (br s, 2H), 4.97 (minor) (br s, 2H), 6.92-7.03 (m, 1H), 7.08 (br s, 1H), 7.16 (major) (d, J=15.4 Hz, 1H), 7.33 (minor) (d, J=15.3 Hz, 1H), 7.37-7.63 (m, 4H), 7.95 (br d, J=17.3 Hz, 1H); M+H (352.1).

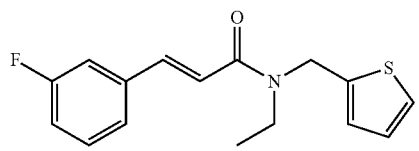 [SMILES: CCN(Cc1cccs1)C(=O)/C=C/c1cccc(F)c1]

(E)-N-ethyl-3-(3-fluorophenyl)-N-(thiophen-2-ylmethyl)acrylamide; Example 224

Prepared in a similar manner to example 5 from (E)-3-(3-fluorophenyl)acrylic acid and N-(thiophen-2-ylmethyl)ethanamine. Room temperature $^1$H NMR showed a mixture of rotamers in a 2:1 ratio: $^1$H NMR (400 MHz, DMSO-d6) δ 1.06 (minor) (br t, J=7.1 Hz, 3H), 1.12 (major) (br t, J=7.1 Hz, 3H), 3.41 (minor) (br q, J=6.8 Hz, 2H), 3.54 (major) (br q, J=7.0 Hz, 2H), 4.73 (major) (br s, 2H), 4.98 (minor) (br s, 2H), 6.94-7.03 (m, 1H), 7.08 (d, J=3.4 Hz, 1H), 7.16-7.26 (m, 1.6H), 7.34-7.49 (m, 2.4H), 7.49-7.61 (m, 2H), 7.62-7.72 (m, 1H); M+H (290.1).

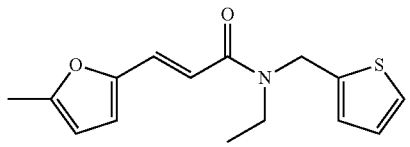

(E)-N-ethyl-3-(5-methylfuran-2-yl)-N-(thiophen-2-ylmethyl)acrylamide; Example 225

Prepared in a similar manner to example 5 from (E)-3-(5-methylfuran-2-yl)acrylic acid and N-(thiophen-2-ylmethyl)ethanamine. Room temperature $^1$H NMR showed a mixture of rotamers in a ~2:1 ratio: $^1$H NMR (400 MHz, DMSO-d6) δ 0.98-1.23 (m, 3H), 2.30 (minor) (br s, 3H), 2.33 (major) (br s, 3H), 3.36-3.51 (m, 2H), 4.71 (major) (br s, 2H), 4.86 (minor) (br s, 2H), 6.23 (br s, 1H), 6.62-6.80 (m, 2H), 6.94-7.08 (m, 2H), 7.28-7.45 (m, 2H); M+H (276.1).

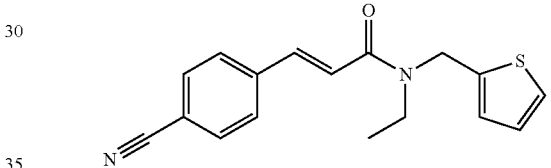

(E)-3-(4-cyanophenyl)-N-ethyl-N-(thiophen-2-ylmethyl)acrylamide; Example 226

Prepared in a similar manner to example 5 from (E)-3-(4-cyanophenyl)acrylic acid and N-(thiophen-2-ylmethyl)ethanamine. Room temperature 1H NMR showed a mixture of rotamers in a ~2:1 ratio: $^1$H NMR (400 MHz, DMSO-d6) δ 1.09 (m, 3H), 3.41 (minor) (br q, J=7.0 Hz, 2H), 3.55 (major) (br q, J=7.0 Hz, 2H), 4.74 (major) (br s, 2H), 4.99 (minor) (br s, 2H), 6.94-7.01 (m, 1H), 7.06-7.10 (m, 1H), 7.24-7.52 (m, 2H), 7.56-7.65 (m, 1H), 7.85-7.97 (m, 4H); M+H (297.1).

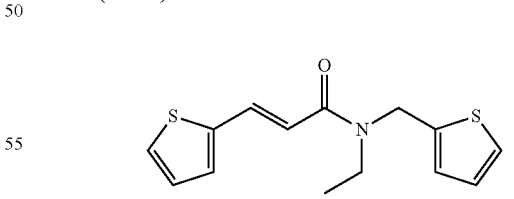

(E)-N-ethyl-3-(thiophen-2-yl)-N-(thiophen-2-ylmethyl)acrylamide; Example 227

Prepared in a similar manner to example 5 from (E)-3-(thiophen-2-yl)acrylic acid and N-(thiophen-2-ylmethyl)ethanamine. Room temperature $^1$H NMR showed a mixture of rotamers in a ~2:1 ratio: $^1$H NMR (400 MHz, DMSO-d6) δ 1.01-1.17 (m, 3H), 3.37-3.53 (m, 2H), 4.72 (major) (br s, 2H), 4.90 (minor) (br s, 2H), 6.79 (major) (d, J=15.2 Hz, 0.6H), 6.88-7.02 (m, 1.4H), 7.06-7.14 (m, 2H), 7.39-7.53 (m, 2H), 7.60-7.77 (m, 2H); M+H (278.1).

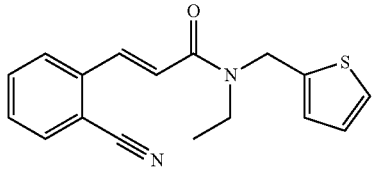 [SMILES: CCN(Cc1cccs1)C(=O)/C=C/c1ccccc1C#N]

(E)-3-(2-cyanophenyl)-N-ethyl-N-(thiophen-2-ylmethyl)acrylamide; Example 228

Prepared in a similar manner to example 5 from (E)-3-(2-cyanophenyl)acrylic acid and N-(thiophen-2-ylmethyl)ethanamine. Room temperature $^1$H NMR showed a mixture of rotamers in a ~2:1 ratio: $^1$H NMR (400 MHz, DMSO-d6) δ 1.05-1.16 (m, 3H), 3.43 (minor) (br q, J=7.0 Hz, 2H), 3.56 (major) (br q, J=7.0 Hz, 2H), 4.75 (major) (br s, 2H), 5.00 (minor) (br s, 2H), 6.90-7.04 (m, 1H), 7.05-7.15 (m, 1H), 7.34-7.62 (m, 3H), 7.72-7.84 (m, 2H), 7.91 (br d, J=7.8 Hz, 1H), 8.11-8.19 (m, 1H); M+H (297.1).

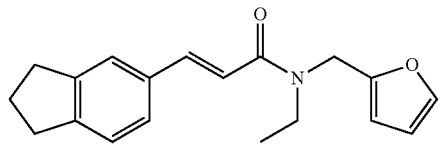

(E)-3-(2,3-dihydro-1H-inden-5-yl)-N-ethyl-N-(furan-2-ylmethyl)acrylamide; Example 231

Prepared in a similar manner to example 5 from (E)-3-(2,3-dihydro-1H-inden-5-yl)acrylic acid and N-(furan-2-ylmethyl)ethanamine. Room temperature $^1$H NMR showed a mixture of rotamers in a ~1:1 ratio: $^1$H NMR (400 MHz, DMSO-d6) δ 0.98-1.12 (m, 3H), 2.02 (p, J=7.4 Hz, 2H), 2.87 (m, 4H), 3.38 (br q, J=6.8 Hz, 1H), 3.53 (br q, J=6.8 Hz, 1H), 4.60 (br s, 1H), 4.75 (br s, 1H), 6.30-6.42 (m, 2H), 7.06 (d, J=15.3 Hz, 0.5H), 7.20-7.29 (m, 1.5H), 7.42 (br s, 1H), 7.46-7.55 (m, 1H), 7.57-7.67 (m, 2H); M+H (296.2).

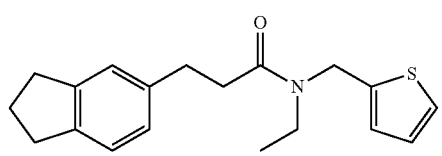 [SMILES: CCN(Cc1cccs1)C(=O)CCc1ccc2c(c1)CCC2]

3-(2,3-dihydro-1H-inden-5-yl)-N-ethyl-N-(thiophen-2-ylmethyl)propanamide; Example 234

Prepared in a similar manner to example 5 from 3-(2,3-dihydro-1H-inden-5-yl)propanoic acid and N-(thiophen-2-ylmethyl)ethanamine. Room temperature $^1$H NMR showed a mixture of rotamers in a ~2:1 ratio: $^1$H NMR (400 MHz, DMSO-d6) δ 0.95-1.08 (m, 3H), 1.93-2.02 (m, 2H), 2.55-2.66 (m, 2H), 2.73-2.83 (m, 6H), 3.22-3.32 (m, 2H), 4.61

(major) (br s, 2H), 4.67 (minor) (br s, 2H), 6.90-7.14 (m, 5H), 7.39 (major) (dd, J=5.1, 1.3 Hz, 1H), 7.45 (minor) (dd, J=4.9, 1.5 Hz, 1H); M+H (314.2).

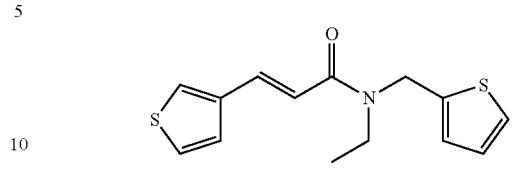

(E)-N-ethyl-N-(thiophen-2-ylmethyl)-3-(thiophen-3-yl)acrylamide; Example 245

Prepared in a similar manner to example 5 from (E)-3-(thiophen-3-yl)acrylic acid and N-(thiophen-2-ylmethyl)ethanamine. Room temperature $^1$H NMR showed a mixture of rotamers in a ~2:1 ratio: $^1$H NMR (400 MHz, DMSO-d6) δ 1.01-1.11 (m, 3H), 3.38 (minor) (br q, J=6.7 Hz, 2H), 3.49 (major) (br q, J=6.7 Hz, 2H), 4.70 (major) (br s, 2H), 4.92 (minor) (br s, 2H), 6.91-7.13 (m, 3H), 7.37-7.43 (m, 1H), 7.49-7.61 (m, 3H), 7.84-7.89 (m, 1H); M+H (278.1).

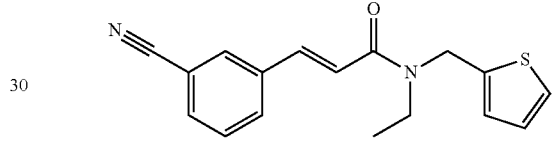

(E)-3-(3-cyanophenyl)-N-ethyl-N-(thiophen-2-ylmethyl)acrylamide; Example 246

Prepared in a similar manner to example 5 from (E)-3-(3-cyanophenyl)acrylic acid and N-(thiophen-2-ylmethyl)ethanamine. Room temperature $^1$H NMR showed a mixture of rotamers in a ~2:1 ratio: $^1$H NMR (400 MHz, DMSO-d6) δ 1.06 (minor) (br t, J=7.1 Hz, 3H), 1.13 (major) (br t, J=7.0 Hz, 3H), 3.40 (minor) (br q, J=6.9 Hz, 2H), 3.56 (major) (br q, J=7.0 Hz, 2H), 4.74 (major) (br s, 2H), 5.00 (minor) (br s, 2H), 6.94-7.01 (m, 1H), 7.06-7.11 (m, 1H), 7.31 (major) (d, J=15.5 Hz, 1H), 7.40-7.48 (m, 1H), 7.53 (minor) (d, J=19.1 Hz, 1H), 7.57-7.67 (m, 2H), 7.83 (br d, J=7.7 Hz, 1H), 8.03 (br t, J=9.0 Hz, 1H), 8.33 (br d, J=12.7 Hz, 1H); M+H (297.1).

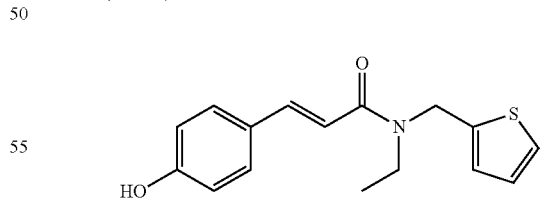

(E)-N-ethyl-3-(4-hydroxyphenyl)-N-(thiophen-2-ylmethyl)acrylamide; Example 247

Prepared in a similar manner to example 5 from (E)-3-(4-hydroxyphenyl)acrylic acid and N-(thiophen-2-ylmethyl)ethanamine. Room temperature $^1$H NMR showed a mixture of rotamers in a ~2:1 ratio: $^1$H NMR (400 MHz, DMSO-d6) δ 1.00-1.18 (m, 3H), 3.40 (minor) (br q, J=7.3 Hz, 2H), 3.50

(major) (br q, J=7.3 Hz, 2H), 4.71 (major) (br s, 2H), 4.92 (minor) (br s, 2H), 6.78 (br d, J=8.4 Hz, 2H), 6.83-7.04 (m, 2H), 7.06 (br d, J=3.0 Hz, 1H), 7.39-7.57 (m, 4H), 9.85 (s, 1H); M+H (288.1).

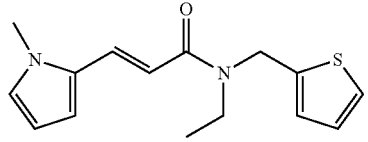 [SMILES: CCN(Cc1cccs1)C(=O)/C=C/c1cccn1C]

(E)-N-ethyl-3-(1-methyl-1H-pyrrol-2-yl)-N-(thiophen-2-ylmethyl)acrylamide; Example 248

Prepared in a similar manner to example 5 from (E)-3-(1-methyl-1H-pyrrol-2-yl)acrylic acid and N-(thiophen-2-ylmethyl)ethanamine. Room temperature ¹H NMR showed a mixture of rotamers in a ~2:1 ratio: ¹H NMR (400 MHz, DMSO-d6) δ 1.10 (br s, 3H), 3.46 (br s, 2H), 3.69 (s, 3H), 4.71 (major) (br s, 1H), 4.89 (minor) (br s, 1H), 6.07 (br s, 1H), 6.71 (br d, J=17.0 Hz, 2H), 6.91-7.07 (m, 3H), 7.40-7.55 (m, 2H); M+H (275.1).

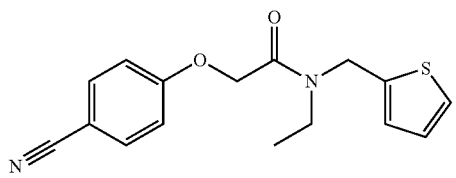 [SMILES: CCN(Cc1cccs1)C(=O)COc1ccc(C#N)cc1]

(E)-N-ethyl-3-(1-methyl-1H-pyrrol-2-yl)-N-(thiophen-2-ylmethyl)acrylamide; Example 250

Prepared in a similar manner to example 5 from 2-(4-cyanophenoxy)acetic acid and N-(thiophen-2-ylmethyl)ethanamine. Room temperature ¹H NMR showed a mixture of rotamers in a ~2:1 ratio: ¹H NMR (400 MHz, DMSO-d6) δ 1.01 (minor) (br t, J=7.1 Hz, 1H), 1.15 (major) (br t, J=7.1 Hz, 2H), 3.30-3.36 (m, 2H), 4.64 (major) (br s, 2H), 4.76 (minor) (br s, 2H), 5.01 (minor) (br s, 2H), 5.03 (major) (br s, 2H), 6.89-7.16 (m, 4H), 7.42 (major) (dd, J=5.1, 1.2 Hz, 1H), 7.51 (minor) (dd, J=5.1, 1.1 Hz, 1H), 7.73-7.83 (m, 2H); M+H (301.1).

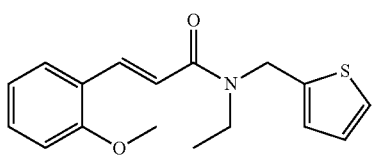 [SMILES: CCN(Cc1cccs1)C(=O)/C=C/c1ccccc1OC]

(E)-N-ethyl-3-(2-methoxyphenyl)-N-(thiophen-2-ylmethyl)acrylamide; Example 251

Prepared in a similar manner to example 5 from (E)-3-(2-methoxyphenyl)acrylic acid and N-(thiophen-2-ylmethyl)ethanamine. Room temperature 1H NMR showed a mixture of rotamers in a ~2:1 ratio: ¹H NMR (400 MHz, DMSO-d6) δ 1.03-1.15 (m, 3H), 3.42 (minor) (br q, J=6.9 Hz, 2H), 3.51 (major) (br q, J=6.7 Hz, 2H), 3.84 (minor) (br s, 3H), 3.86 (major) (br s, 3H), 4.72 (major) (br s, 2H), 4.92 (minor) (br s, 2H), 6.90-7.02 (m, 2H), 7.03-7.26 (m, 3H), 7.32-7.48 (m, 2H), 7.67-7.94 (m, 2H); M+H (302.1).

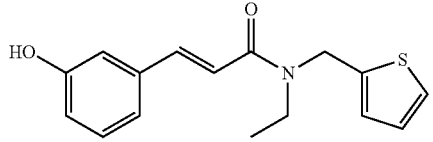 [SMILES: CCN(Cc1cccs1)C(=O)/C=C/c1cccc(O)c1]

(E)-N-ethyl-3-(3-hydroxyphenyl)-N-(thiophen-2-ylmethyl)acrylamide; Example 252

Prepared in a similar manner to example 5 from (E)-3-(3-hydroxyphenyl)acrylic acid and N-(thiophen-2-ylmethyl)ethanamine. Room temperature 1H NMR showed a mixture of rotamers in a 2:1 ratio: ¹H NMR (400 MHz, DMSO-d6) δ 1.04-1.14 (m, 3H), 3.41 (minor) (br q, J=7.0 Hz, 2H), 3.52 (major) (br q, J=7.2 Hz, 2H), 4.72 (major) (br s, 2H), 4.94 (minor) (br s, 2H), 6.79 (br d, J=7.9 Hz, 1H), 6.93-7.25 (m, 6H), 7.37-7.54 (m, 2H), 9.55 (br s, 1H); M+H (288.1).; Example 253

Prepared in a similar manner to example 5 from and N-(thiophen-2-ylmethyl)ethanamine. Room temperature ¹H NMR showed a mixture of rotamers in a ~2:1 ratio: ¹H NMR (400 MHz, DMSO-d6); M+H (2.1). ¹H NMR (400 MHz, dmso) δ 1.01 (dt, J=18.8, 7.1 Hz, 3H), 2.71 (dt, J=17.8, 7.5 Hz, 2H), 2.93 (q, J=7.8 Hz, 2H), 3.31-3.24 (m, 2H), 4.60 (s, 1H), 4.69 (s, 1H), 7.02-6.91 (m, 2H), 7.51-7.37 (m, 3H), 7.72 (d, J=8.3 Hz, 2H).

Scheme 3

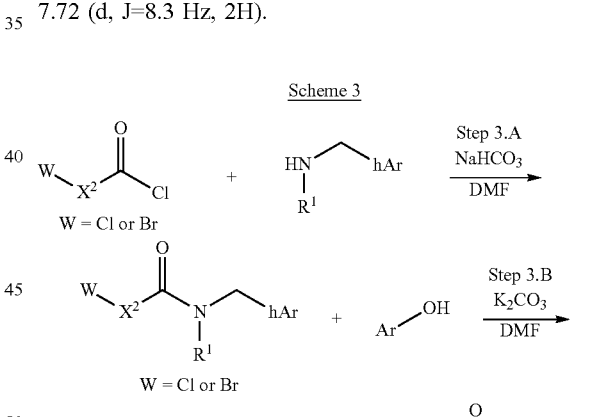

If not commercially available or differently described, all the secondary amines were prepared by reductive amination in a similar manner to example 6a or 21b utilizing one of the standard reducing agents and general conditions known to those skilled in the art such as: NaBH₄, LiAlH₄, Na(OAc)₃BH (STAB), Na(CN)BH₃, 2-picoline borane complex, 5-ethyl-2-methylpyridine borane (PEMB) or their equivalent, and DCM (dichloromethane), DCE (dichloroethane), Et₂O (diethyl ether), THF (tetrahydrofuran), dioxane, MeOH, EtOH, MeCN, AcOH alone or in binary or tertiary combinations thereof. All the employed phenols or alcohols were commercially available. One skilled in the art can readily derive the synthesis of the present compounds from the following descriptions according to the methods and principles discussed above.

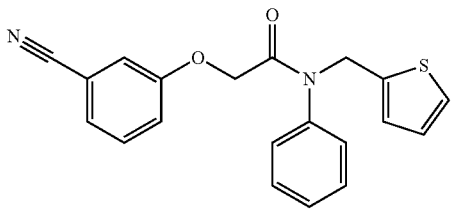 [SMILES: N#Cc1cccc(OCC(=O)N(Cc2cccs2)c2ccccc2)c1]

2-(3-cyanophenoxy)-N-phenyl-N-(thiophen-2-ylmethyl)acetamide; Example 44

To a microwave vial was added 3-hydroxybenzonitrile (60 mg, 0.50 mmol) in DMF (1.0 mL), followed by $K_2CO_3$ (140 mg, 1.0 mmol) and 2-bromo-N-phenyl-N-(thiophen-2-ylmethyl)acetamide (150 mg, 0.5 mmol) in DMF (4.0 mL). The microwave vial was capped and reacted under microwave irradiation (Emrys Optimizer reactor) at 120° C. for 10 minutes. The compound was purified on HPLC; clean fractions were combined and concentrated, affording 101 mg (0.29 mmol, 58%). $^1$H NMR (400 MHz, DMSO-d6) δ 4.57 (s, 2H), 5.00 (s, 2H), 6.84 (br s, 1H), 6.91 (dd, J=5.1, 3.4 Hz, 1H), 7.15 (br d, J=7.9 Hz, 1H), 7.23-7.33 (m, 3H), 7.34-7.52 (m, 6H); M+H (349.1).

2-bromo-N-phenyl-N-(thiophen-2-ylmethyl)acetamide; Example 44a

To a 0° C. stirring suspension of the N-(thiophen-2-ylmethyl)aniline (3.51 g, 18.53 mmol) and sodium bicarbonate (1.71 g, 20.38 mmol) in dimethylformamide (15.0 mL), it was added bromoacetyl chloride (1.54 mL, 18.53 mmol). The ice bath was removed and the flask was attached to a bubbler to allow gas evolution and expansion. The reaction was stirred overnight at room temp. Most of the volatiles were evaporated in vacuo, then the residue was taken up in dichloromethane and was washed with water first and then brine. The resulting organic layer was dried over $MgSO_{4(s)}$ and concentrated. The obtained crude was absorbed under vacuum on Florisil with the aid of DCM (dry load). The obtained dispersion was purified by column chromatography (Biotage system, hex:EtOAc 1-20% gradient over 30 CV, 40 g Silicycle silica column). The collected fractions were evaporated to afford 4.51 g of 2-bromo-N-phenyl-N-(thiophen-2-ylmethyl)acetamide (14.55 mmol; 78%), which was judged more than 97% pure by $^1$H-NMR analysis.

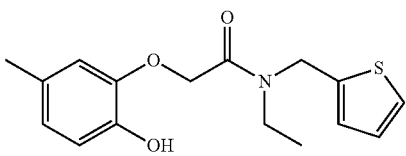 [SMILES: CCN(Cc1cccs1)C(=O)COc1cc(C)ccc1O]

N-ethyl-2-(2-hydroxy-5-methylphenoxy)-N-(thiophen-2-ylmethyl)acetamide; Example 27

Prepared in a similar manner to example 44 from 2-bromo-N-ethyl-N-(thiophen-2-ylmethyl)acetamide and 4-methylbenzene-1,2-diol. Yield 10%. $^1$H NMR showed a mixture of rotamers in a ~2:1 ratio: $^1$H NMR (400 MHz, DMSO-d6) δ 9.06 (major) (s, 1H), 9.04 (minor), (s, 1H), 7.51 (minor) (dd, J=5.1, 1.2 Hz, 1H), 7.43 (major) (dd, J=5.1, 1.2 Hz, 1H), 7.11-7.01 (minor) (m, 1H), 7.06-7.05 (major) (m, 1H), 7.03-7.01 (minor) (m, 1H), 6.96-6.94 (major) (m, 1H), 6.69-6.61 (m, 3H), 4.83 (minor) (s, 2H), 4.82 (major) (s, 2H), 4.76 (minor) (s, 2H), 4.66 (major) (s, 2H), 3.36-3.30 (m, 2H), 2.16 (major) (s, 3H), 2.14 (minor) (s, 3H), 1.12 (major) (t, J=7.1 Hz, 3H) 1.02 (minor) (t, J=7.1 Hz, 3H); M+H (306.1).

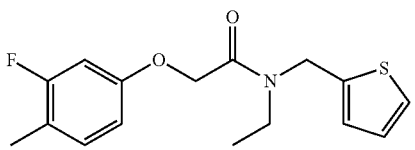 [SMILES: CCN(Cc1cccs1)C(=O)COc1ccc(C)c(F)c1]

N-ethyl-2-(3-fluoro-4-methylphenoxy)-N-(thiophen-2-ylmethyl)acetamide; Example 32

Prepared in a similar manner to example 44 from 2-bromo-N-ethyl-N-(thiophen-2-ylmethyl)acetamide and 3-fluoro-4-methylphenol. Yield 31%. $^1$H NMR showed a mixture of rotamers in a ~2:1 ratio: $^1$H NMR (400 MHz, DMSO-d6) δ 1.00 (minor) (t, J=7.1 Hz, 3H), 1.13 (major) (t, J=7.1 Hz, 3H), 2.14 (br s, 3H), 3.22-3.40 (m, 2H), 4.64 (major) (s, 2H), 4.75 (minor) (s, 2H), 4.84 (m, 2H), 6.61-6.80 (m, 2H), 6.87-7.20 (m, 3H), 7.42 (major) (dd, J=5.1, 1.2 Hz, 1H), 7.51 (minor) (d, J=4.0 Hz, 1H); M+H (308.1).

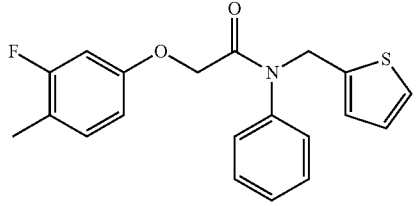 [SMILES: Cc1ccc(OCC(=O)N(Cc2cccs2)c2ccccc2)cc1F]

2-(3-fluoro-4-methylphenoxy)-N-phenyl-N-(thiophen-2-ylmethyl)acetamide; Example 55

Prepared in a similar manner to example 44 from 2-bromo-N-phenyl-N-(thiophen-2-ylmethyl)acetamide and 3-fluoro-4-methylphenol. $^1$H NMR (400 MHz, DMSO-d6) δ 2.11 (d, J=1.6 Hz, 3H), 4.42 (br s, 2H), 4.98 (br s, 2H), 6.52 (dd, J=26.4, 10.2 Hz, 2H), 6.81 (br s, 1H), 6.89 (dd, J=5.1, 3.4 Hz, 1H), 7.10 (t, J=8.8 Hz, 1H), 7.28-7.21 (m, 2H), 7.46-7.33 (m, 4H); M+H (356.1).

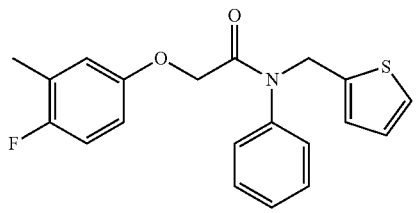 [SMILES: Cc1cc(OCC(=O)N(Cc2cccs2)c2ccccc2)ccc1F]

2-(4-fluoro-3-methylphenoxy)-N-phenyl-N-(thiophen-2-ylmethyl)acetamide; Example 64

Prepared in a similar manner to example 44 from 2-bromo-N-phenyl-N-(thiophen-2-ylmethyl)acetamide and 4-fluoro-3-methylphenol. ¹H NMR (400 MHz, DMSO-d6) δ 2.14 (d, J=1.8 Hz, 3H), 4.38 (br s, 2H), 4.98 (br s, 2H), 6.54 (br d, J=8.5 Hz, 1H), 6.64 (br s, 1H), 6.82 (br s, 1H), 6.89 (dd, J=5.1, 3.4 Hz, 1H), 6.97 (t, J=9.1 Hz, 1H), 7.28-7.21 (m, 2H), 7.48-7.32 (m, 4H); M+H (356.1).

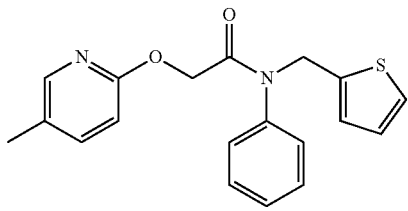 [SMILES: Cc1ccc(OCC(=O)N(Cc2cccs2)c2ccccc2)nc1]

2-(5-methylpyridin-2-yloxy)-N-phenyl-N-(thiophen-2-ylmethyl)acetamide; Example 75

Prepared in a similar manner to example 44 from 2-bromo-N-phenyl-N-(thiophen-2-ylmethyl)acetamide and 5-methylpyridin-2-ol. ¹H NMR (400 MHz, DMSO-d6) δ 2.17 (s, 3H), 4.57 (br s, 2H), 4.96 (br s, 2H), 6.71 (d, J=8.4 Hz, 1H), 6.81 (br s, 1H), 6.89 (dd, J=5.1, 3.4 Hz, 1H), 7.31-7.24 (m, 2H), 7.46-7.32 (m, 4H), 7.50 (dd, J=8.4, 2.0 Hz, 1H), 7.87 (br s, 1H); M+H (339.1).

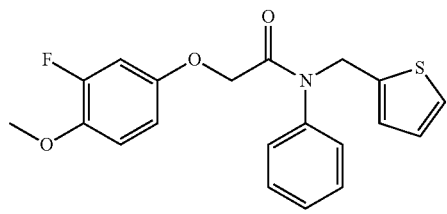 [SMILES: COc1ccc(OCC(=O)N(Cc2cccs2)c2ccccc2)cc1F]

2-(3-fluoro-4-methoxyphenoxy)-N-phenyl-N-(thiophen-2-ylmethyl)acetamide; Example 76

Prepared in a similar manner to example 44 from 2-bromo-N-phenyl-N-(thiophen-2-ylmethyl)acetamide and 3-fluoro-4-methoxyphenol. ¹H NMR (400 MHz, DMSO-d6) δ 3.74 (s, 3H), 4.39 (br s, 2H), 4.98 (br s, 2H), 6.50 (br d, J=8.6 Hz, 1H), 6.69 (br d, J=13.2 Hz, 1H), 6.81 (br s, 1H), 6.89 (dd, J=5.1, 3.4 Hz, 1H), 7.01 (t, J=9.5 Hz, 1H), 7.26 (m, 2H), 7.46-7.32 (m, 4H); M+H (372.1).

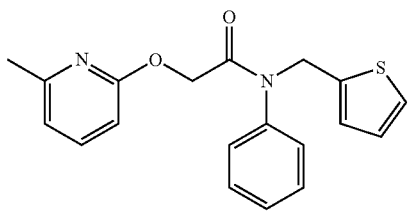 [SMILES: Cc1cccc(OCC(=O)N(Cc2cccs2)c2ccccc2)n1]

2-(6-methylpyridin-2-yloxy)-N-phenyl-N-(thiophen-2-ylmethyl)acetamide; Example 83

Prepared in a similar manner to example 44 from 2-bromo-N-phenyl-N-(thiophen-2-ylmethyl)acetamide and 6-methylpyridin-2-ol. ¹H NMR (400 MHz, DMSO-d6) δ 2.29 (s, 3H), 4.55 (br s, 2H), 4.96 (br s, 2H), 6.60 (d, J=8.2 Hz, 1H), 6.79 (m, 2H), 6.89 (dd, J=5.1, 3.4 Hz, 1H), 7.31 (d, J=7.2 Hz, 2H), 7.47-7.34 (m, 4H), 7.55 (dd, J=8.2, 7.3 Hz, 1H); M+H (339.1).

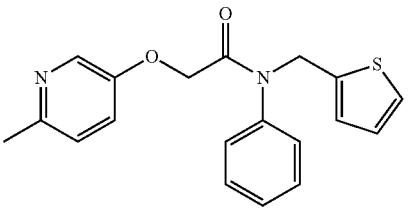 [SMILES: Cc1ccc(OCC(=O)N(Cc2cccs2)c2ccccc2)cn1]

2-(6-methylpyridin-3-yloxy)-N-phenyl-N-(thiophen-2-ylmethyl)acetamide; Example 90

Prepared in a similar manner to example 44 from 2-bromo-N-phenyl-N-(thiophen-2-ylmethyl)acetamide and 6-methylpyridin-3-ol. ¹H NMR (400 MHz, DMSO-d6) δ 2.25 (s, 3H), 4.59 (br s, 2H), 4.95 (br s, 2H), 6.63 (br s, 1H), 6.79 (m, 2H), 6.88 (dd, J=5.1, 3.4 Hz, 1H), 7.31-7.24 (m, 2H), 7.47-7.33 (m, 4H), 7.91 (d, J=5.2 Hz, 1H); M+H (339.1).

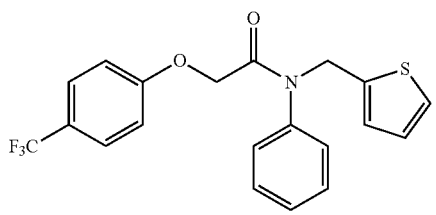 [SMILES: O=C(COc1ccc(C(F)(F)F)cc1)N(Cc1cccs1)c1ccccc1]

N-phenyl-N-(thiophen-2-ylmethyl)-2-(4-(trifluoromethyl)phenoxy)acetamide; Example 130

Prepared in a similar manner to example 44 from 2-bromo-N-phenyl-N-(thiophen-2-ylmethyl)acetamide and 4-(trifluoromethyl)phenol. ¹H NMR (400 MHz, DMSO-d6) δ 4.55 (s, 2H), 4.98 (br s, 2H), 6.82 (br s, 1H), 6.89 (dd, J=5.1, 3.4 Hz, 1H), 6.94 (br d, J=8.2 Hz, 2H), 7.28 (br d, J=7.0 Hz, 2H), 7.46-7.35 (m, 4H), 7.60 (br d, J=8.6 Hz, 2H); M+H (392.1).

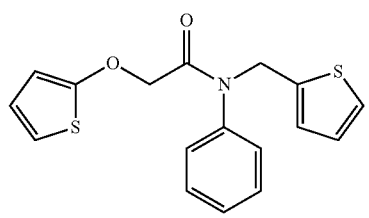 [SMILES: O=C(COc1cccs1)N(Cc1cccs1)c1ccccc1]

N-phenyl-N-(thiophen-2-ylmethyl)-2-(thiophen-2-yloxy)acetamide; Example 145

Prepared in a similar manner to example 44 from 2-bromo-N-phenyl-N-(thiophen-2-ylmethyl)acetamide and thiophen-2-ol. ¹H NMR (400 MHz, DMSO-d6) δ 4.43 (br s, 2H), 4.99 (br s, 2H), 6.13 (br s, 1H), 6.65 (dd, J=5.7, 3.8 Hz, 1H), 6.71 (dd, J=5.8, 1.5 Hz, 1H), 6.81 (br s, 1H), 6.89 (dd, J=5.1, 3.4 Hz, 1H), 7.25-7.20 (m, 2H), 7.44-7.33 (m, 4H); M+H (330.1).

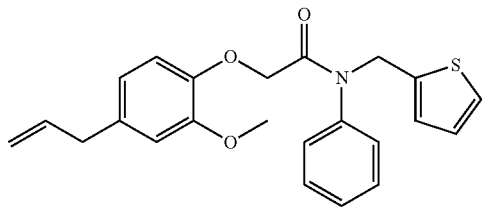 [SMILES: C=CCc1ccc(OCC(=O)N(Cc2cccs2)c2ccccc2)c(OC)c1]

2-(4-allyl-2-methoxyphenoxy)-N-phenyl-N-(thiophen-2-ylmethyl)acetamide; Example 154

Prepared in a similar manner to example 44 from 2-bromo-N-phenyl-N-(thiophen-2-ylmethyl)acetamide and 4-allyl-2-methoxyphenol. $^1$H NMR (400 MHz, DMSO-d6) δ 3.25 (m, 2H), 3.68 (s, 3H), 4.43-4.26 (m, 2H), 5.08-4.96 (m, 4H), 5.90 (m, 1H), 6.59 (br s, 2H), 6.74 (br s, 1H), 6.81 (br s, 1H), 6.89 (dd, J=5.1, 3.4 Hz, 1H), 7.26-7.20 (m, 2H), 7.40 (m, 4H); M+H (394.1).

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings.

What is claimed is:
1. A composition comprising a compound having structural Formula (II):

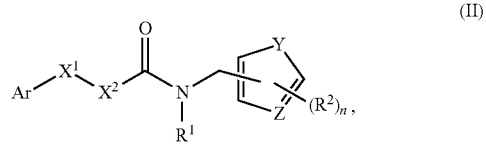

or a salt or solvate thereof;
wherein Ar is optionally substituted aryl, optionally substituted carbocyclyl, or optionally substituted pyrrolyl, furanyl, thienyl, pyrazolyl, triazolyl, oxazolyl, thiazolyl, isoxazolyl, isothiazolyl, pyridyl, pyrimidyl, or triazinyl;
$X^1$-$X^2$ is O—$CR^{2a}R^{2b}$, or $CR^5$=$CR^6$;
$R^{2a}$, $R^{2b}$, $R^5$, and $R^6$ are independently hydrogen or lower alkyl;
Y is oxygen or sulfur;
Z is nitrogen or CR;
n is 0, 1, or 2;
R is hydrogen or lower alkyl;

$R^1$ is an optionally substituted group selected from the group consisting of pyrrolyl, furanyl, thienyl, and pyrazolyl; and
each $R^2$ is independently optionally substituted $C_1$-$C_6$ alkyl, optionally substituted $C_2$-$C_6$ alkenyl, $C_1$-$C_6$ alkoxy, hydroxyl, halo, nitro, or cyano,
wherein each optional substituent is selected from the group consisting of $C_1$-$C_6$ alkyl, alkenyl, $C_1$-$C_6$ alkoxy, hydroxyl, halo, nitro, or cyano; or two substituents, together with the atoms to which they are attached, form an optionally substituted carbocyclyl or heterocyclyl containing one or more heteroatom(s) selected from nitrogen, oxygen, and sulfur; and
a carrier.
2. The composition of claim 1, wherein Y is sulfur.
3. The composition of claim 1, Z is nitrogen or CR.
4. The composition of claim 1, wherein n is 0.
5. The composition of claim 1, wherein $R^1$ is an optionally substituted group selected from the group consisting of furanyl, thienyl, and pyrazolyl.
6. A composition comprising a compound, wherein the compound selected from the group consisting of:

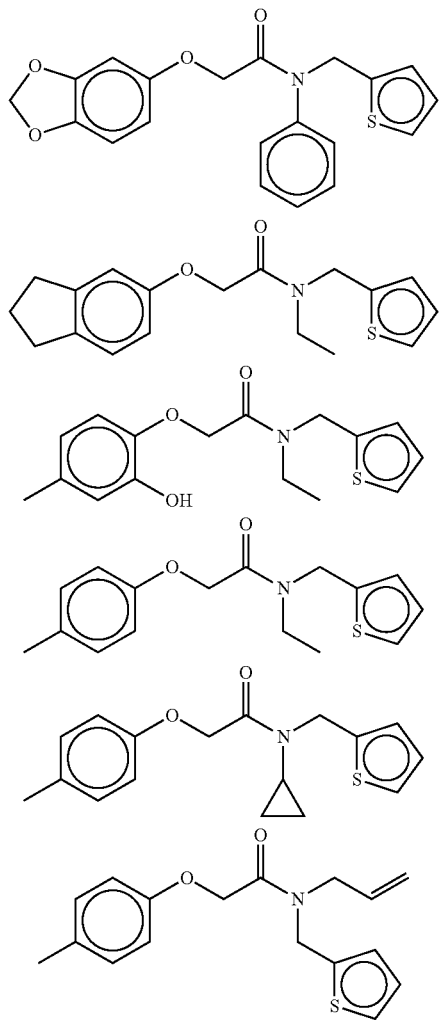

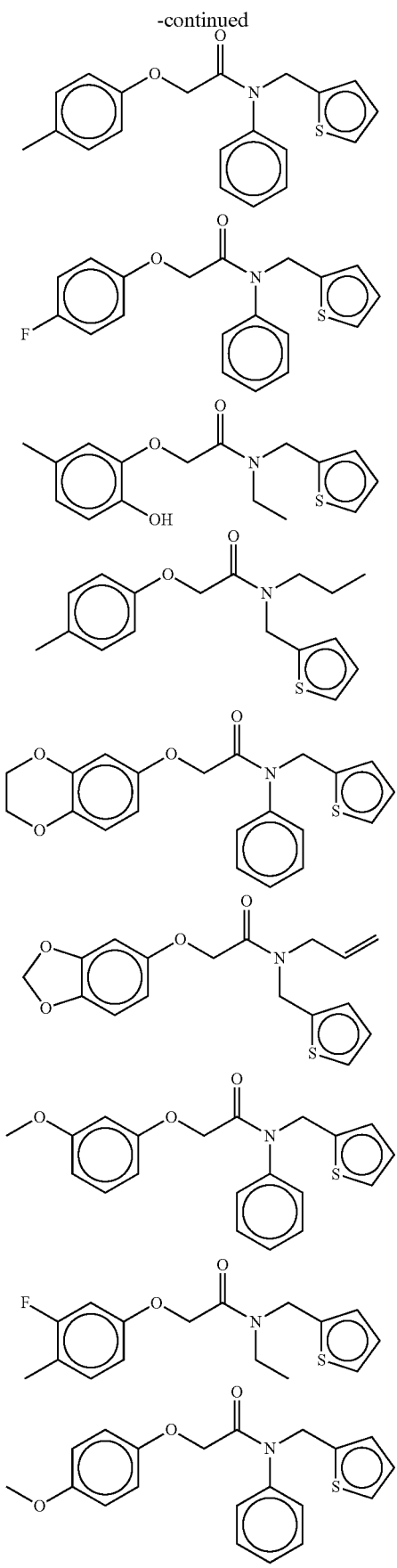
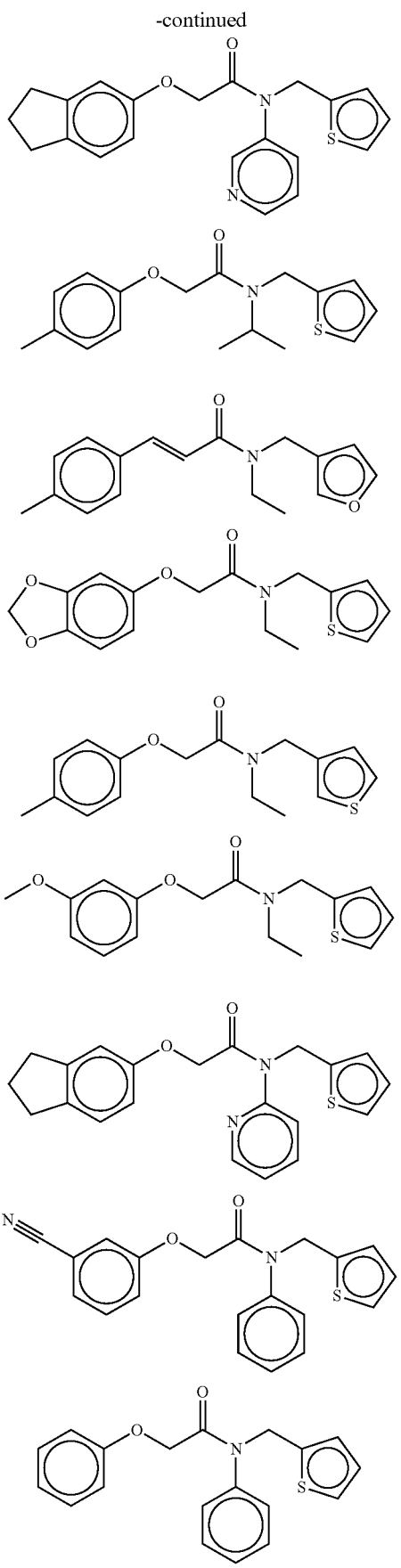

151
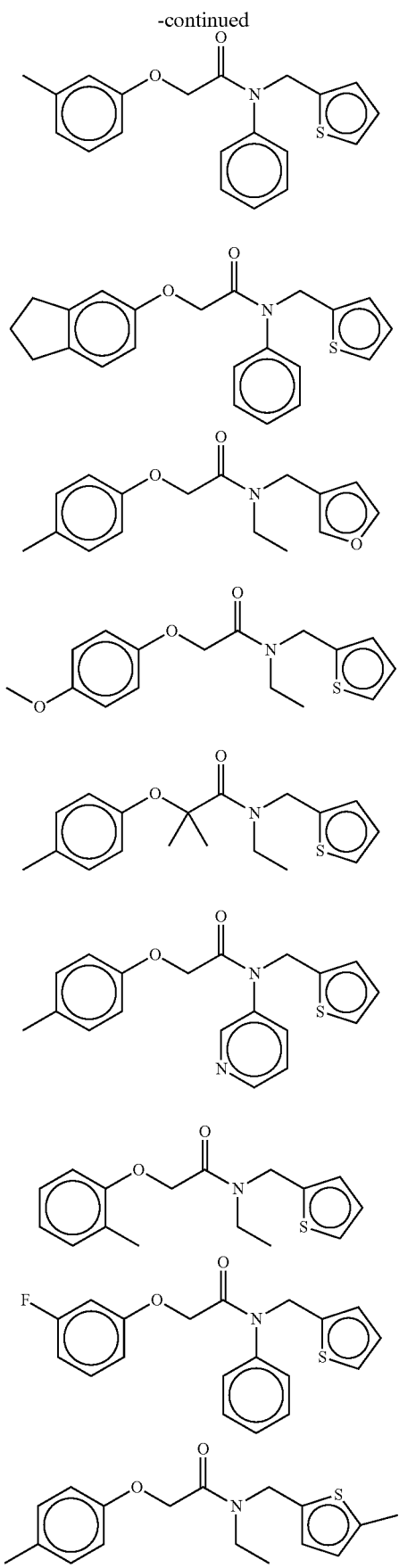
152
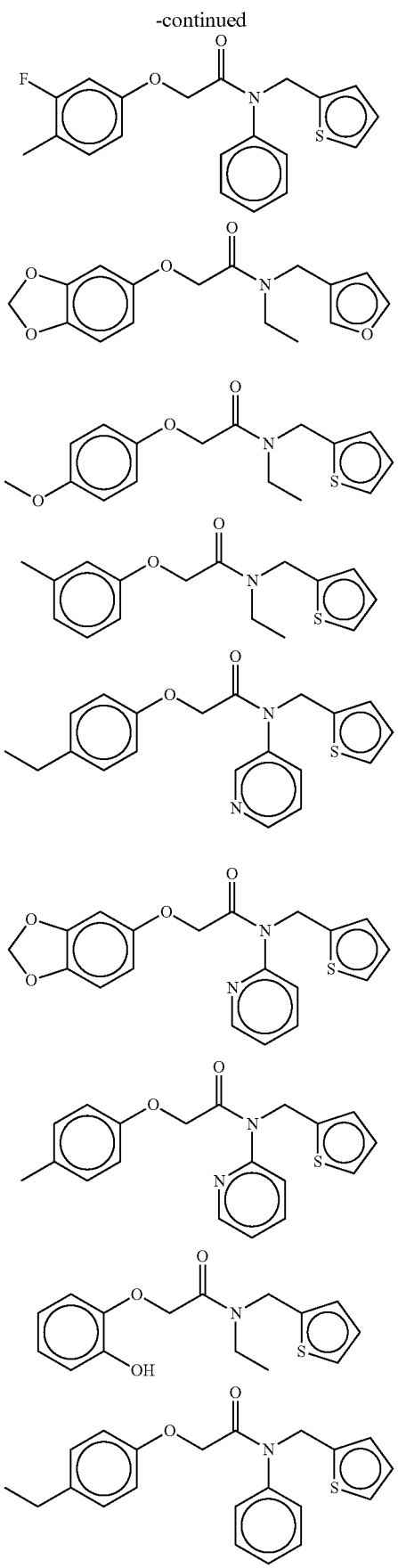

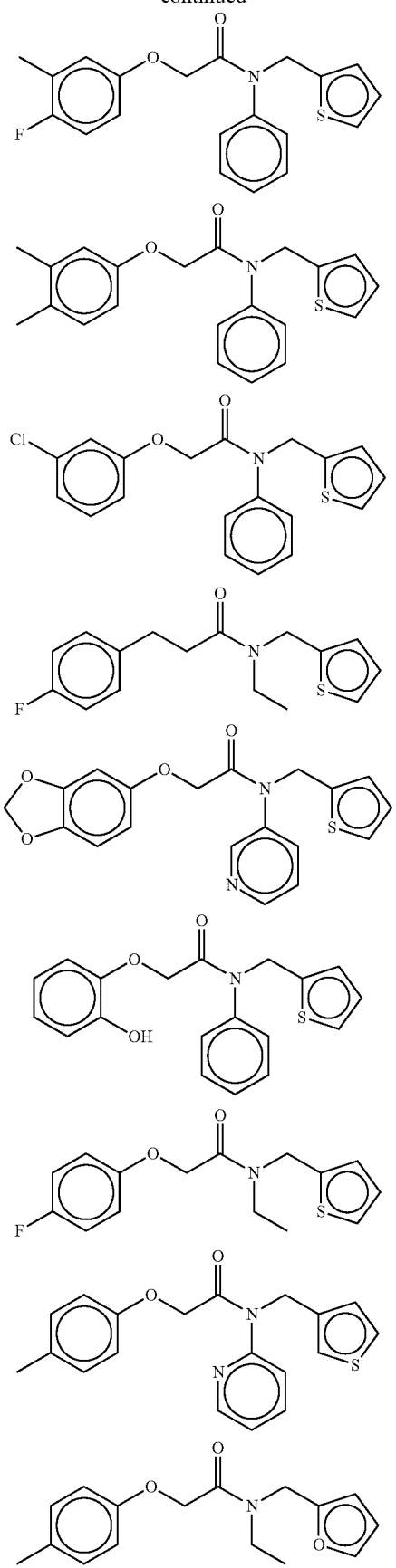
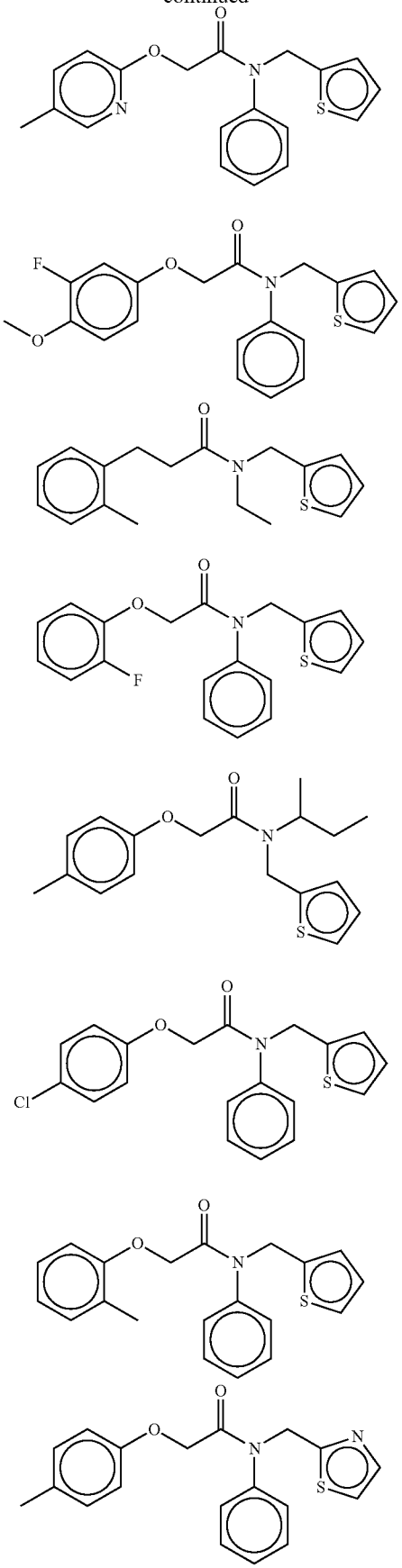

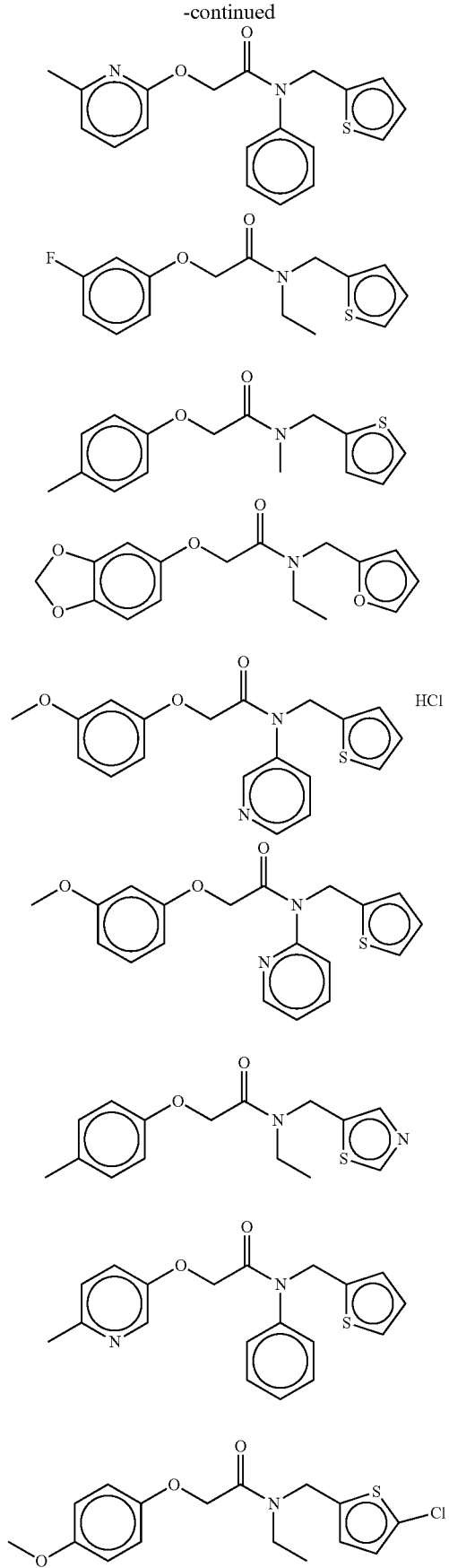
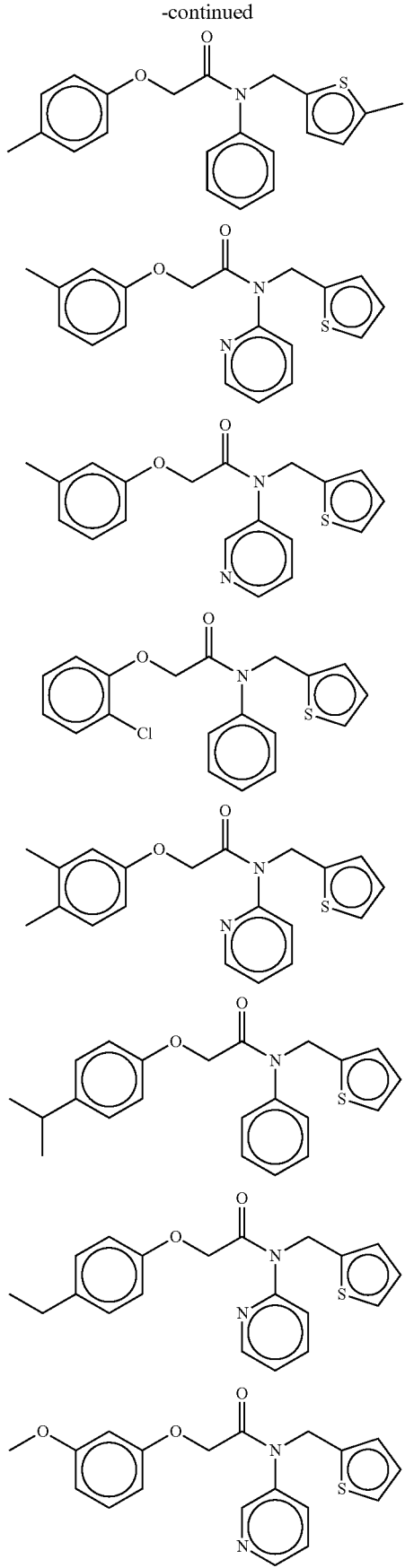

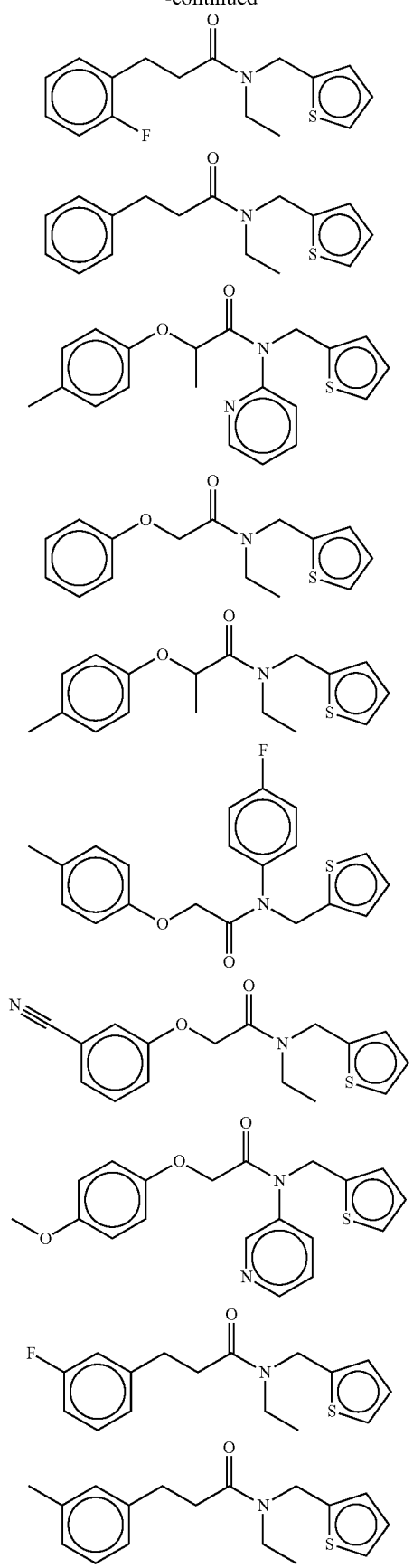
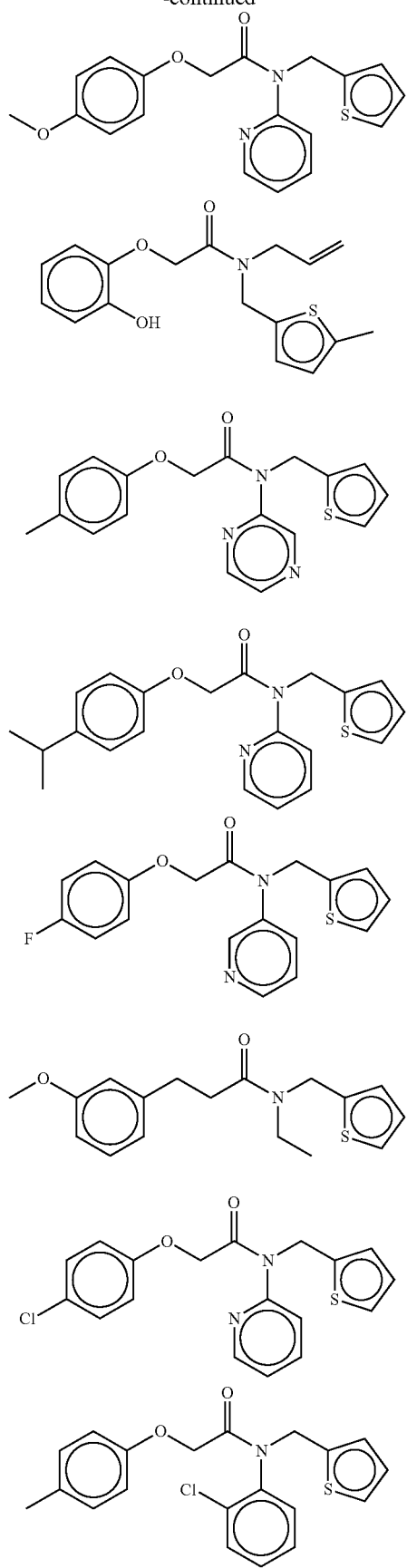

159
-continued
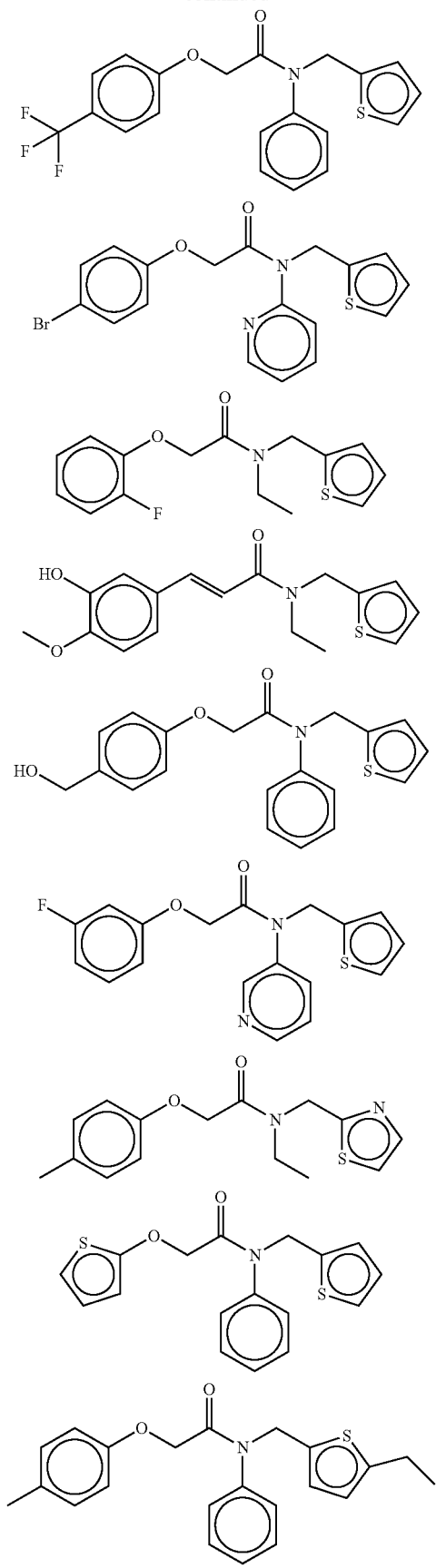
160
-continued
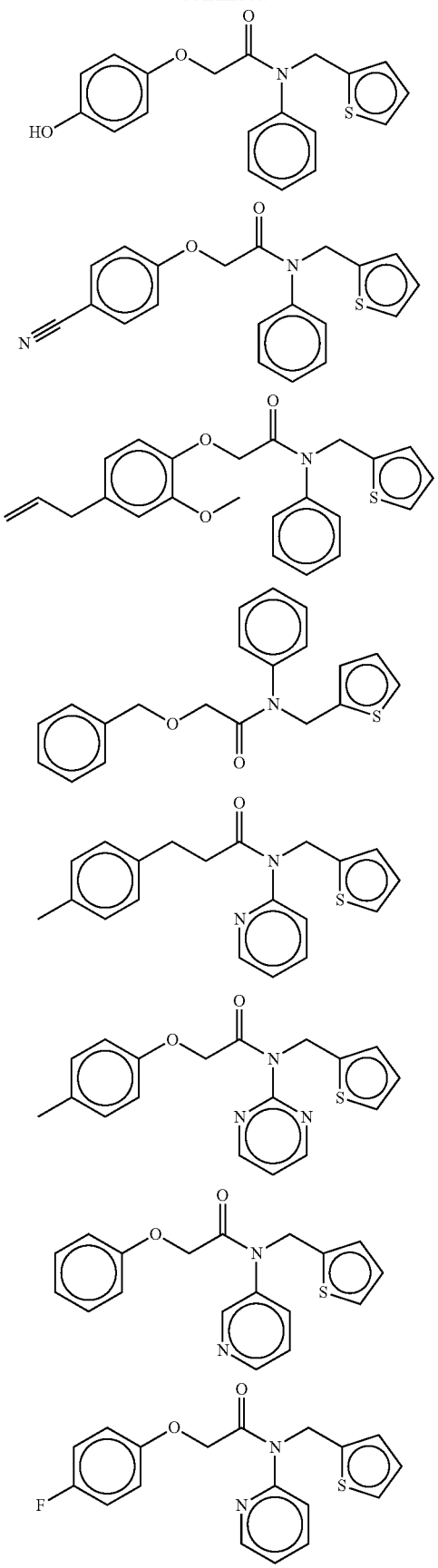

-continued
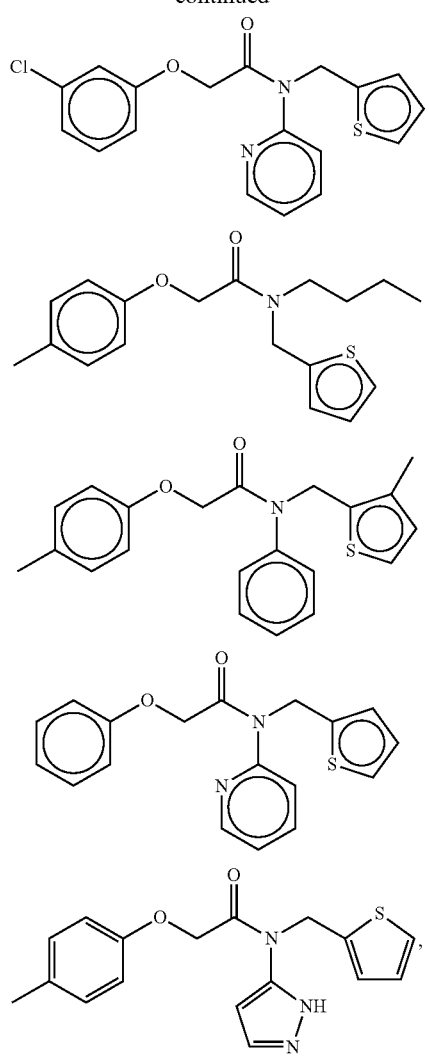
or a salt or solvate thereof, and
a carrier.
7. A composition comprising a compound, wherein the compound selected from the group consisting of:
-continued
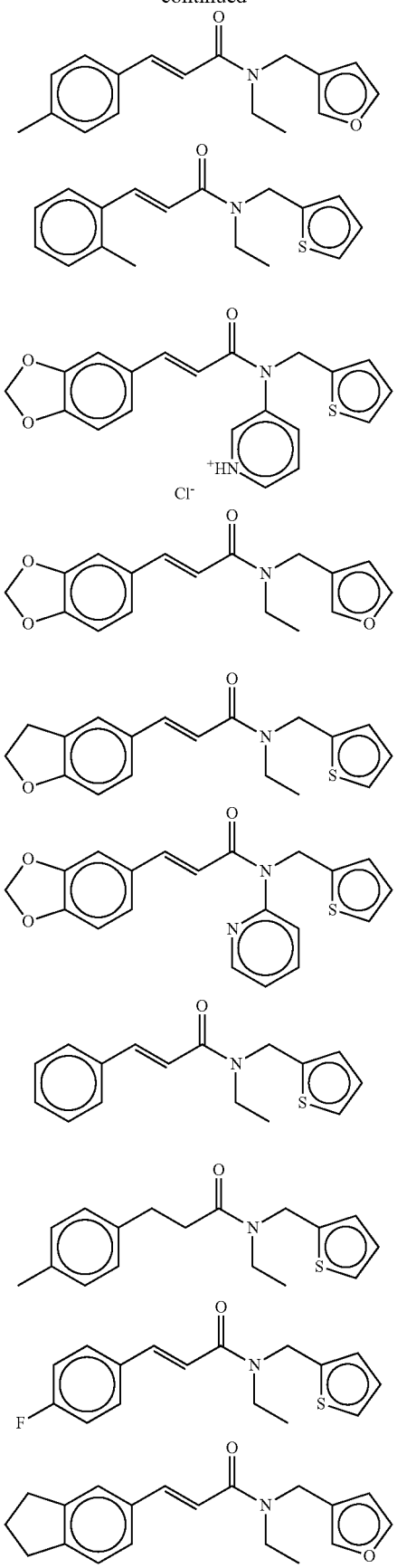

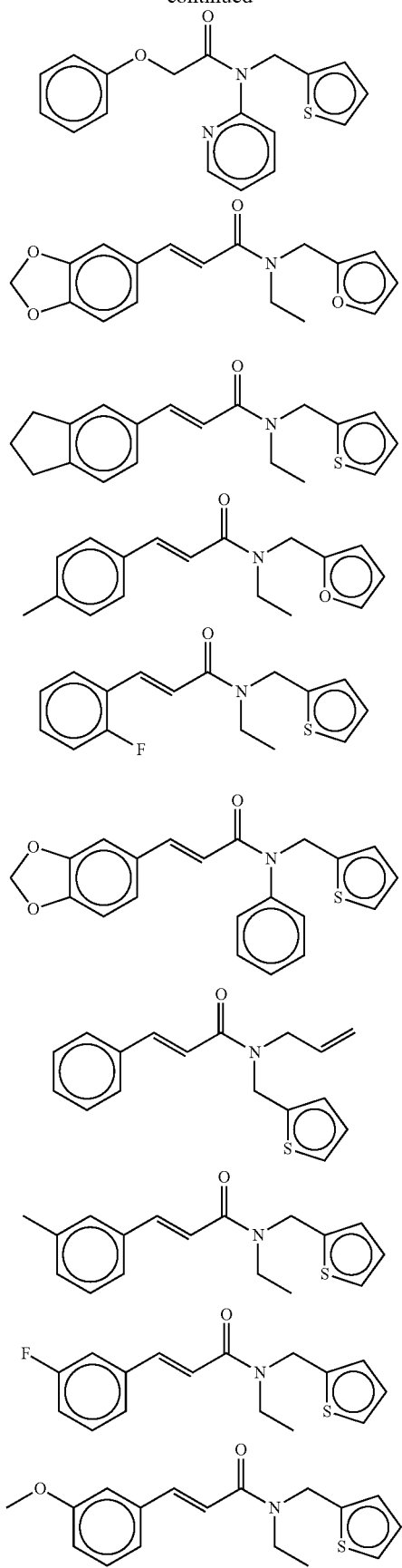
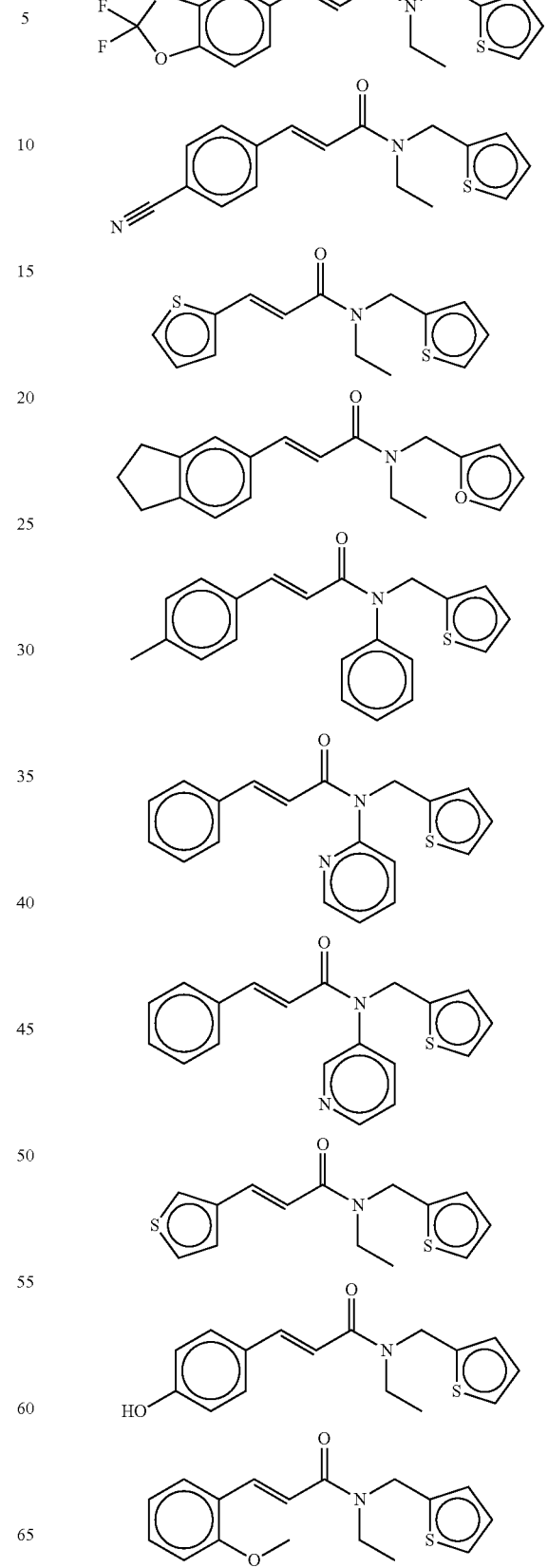

-continued
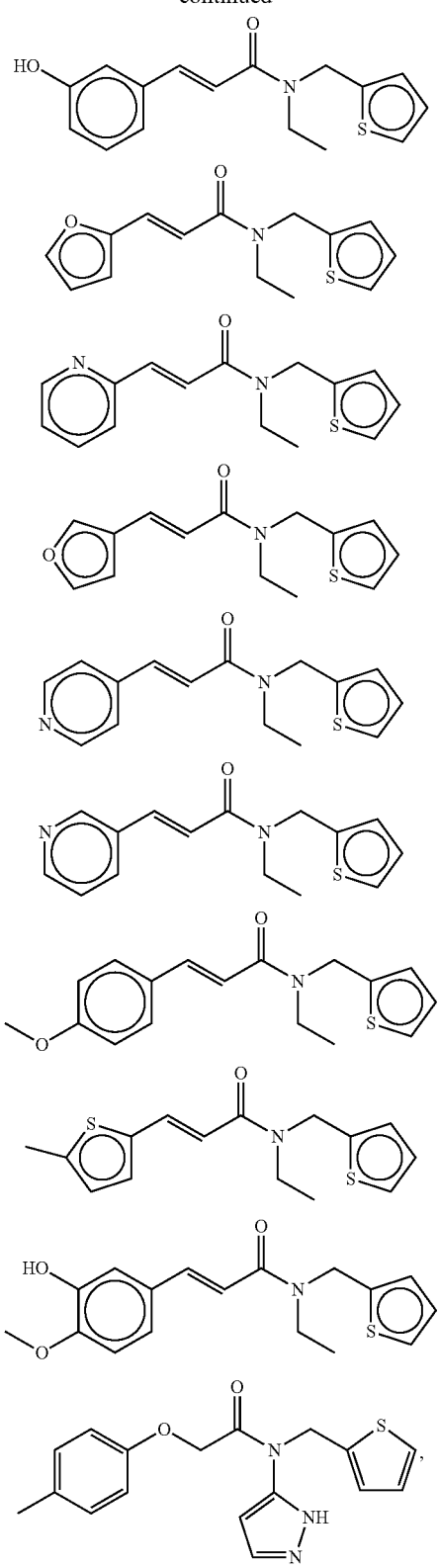
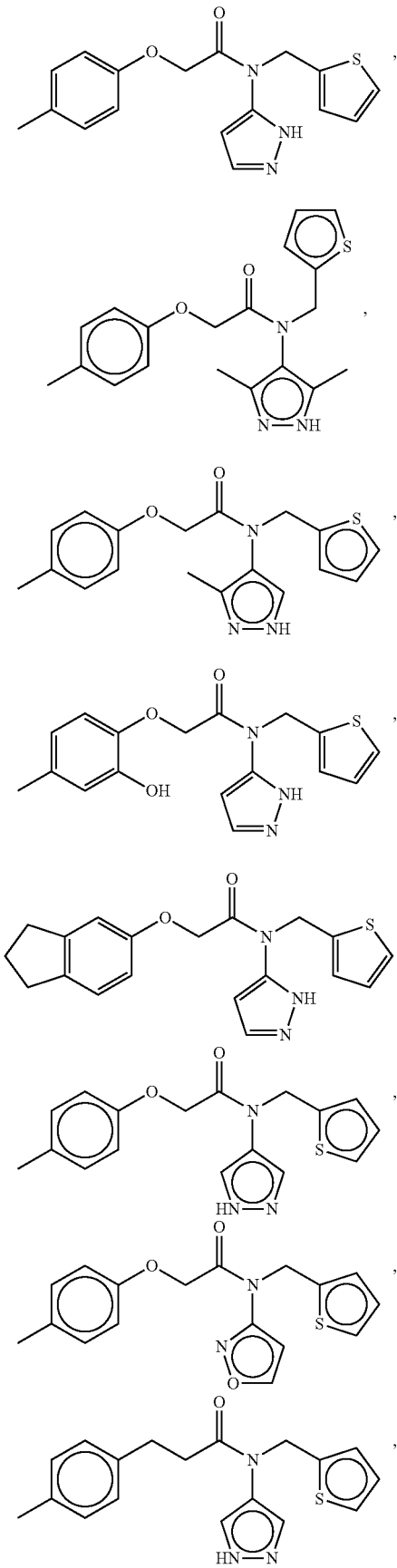
or a salt or solvate thereof, and
a carrier.
8. The composition of claim 1, wherein the compound selected from the group consisting of:

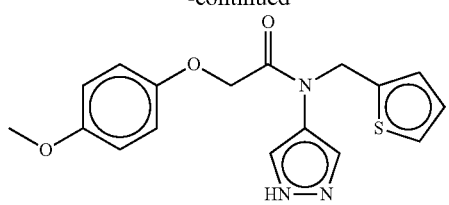,
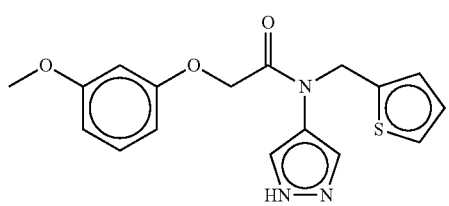,
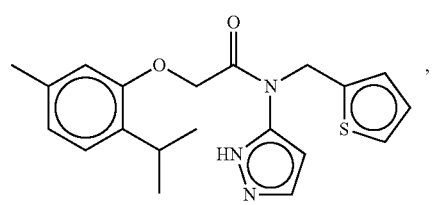,
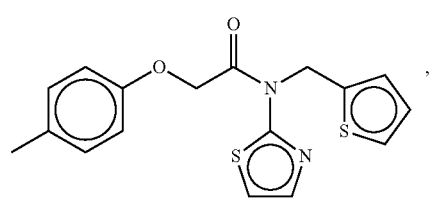,
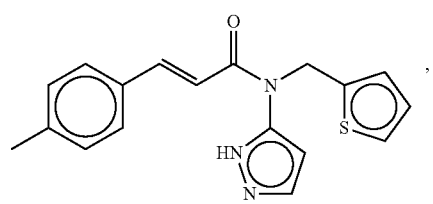,
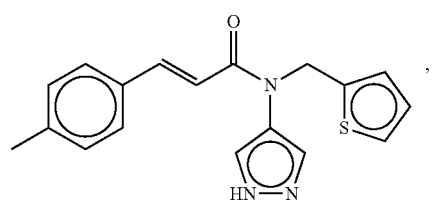,
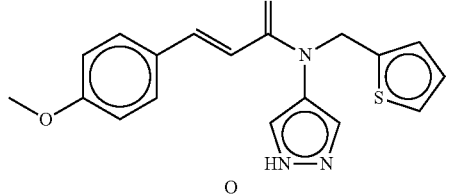,
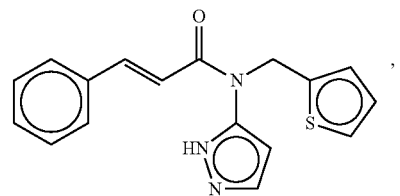,
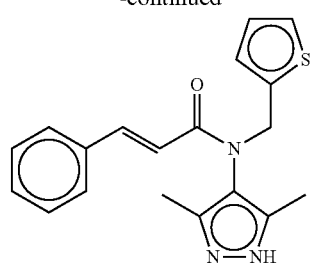,
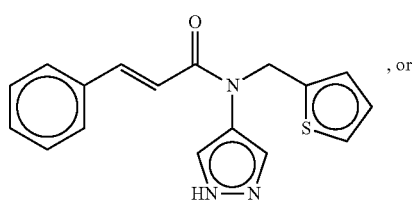, or
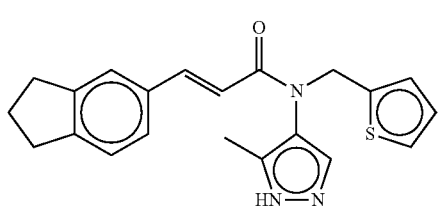,
or a salt or solvate thereof.
9. The composition of claim 1, wherein the compound selected from the group consisting of:
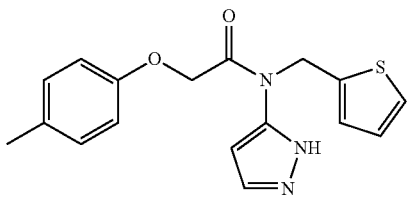,
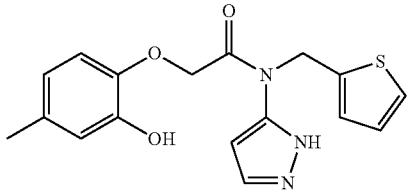,
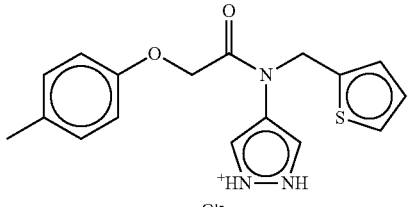,
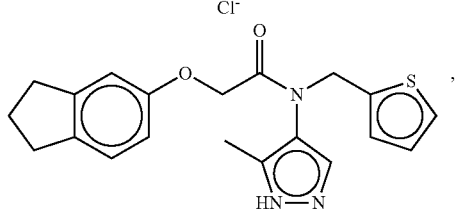,

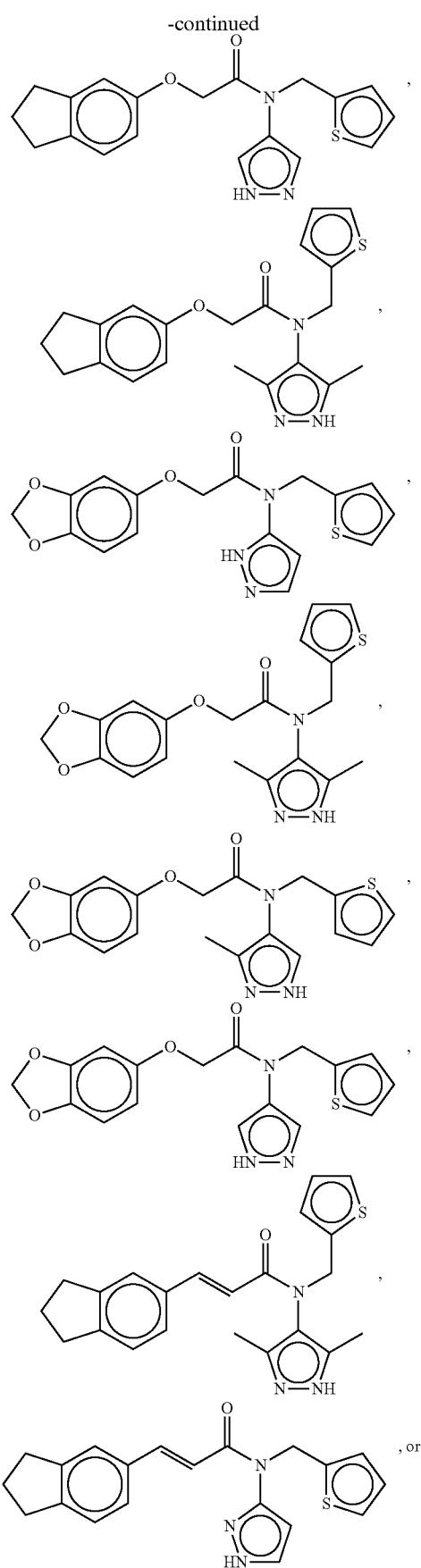

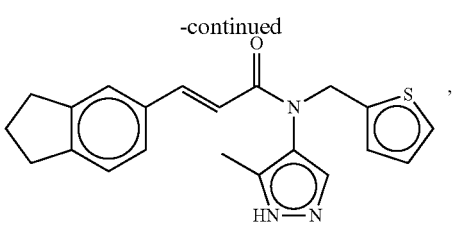

or a salt or solvate thereof.

10. The composition of claim 1, wherein the compound selected from the group consisting of:

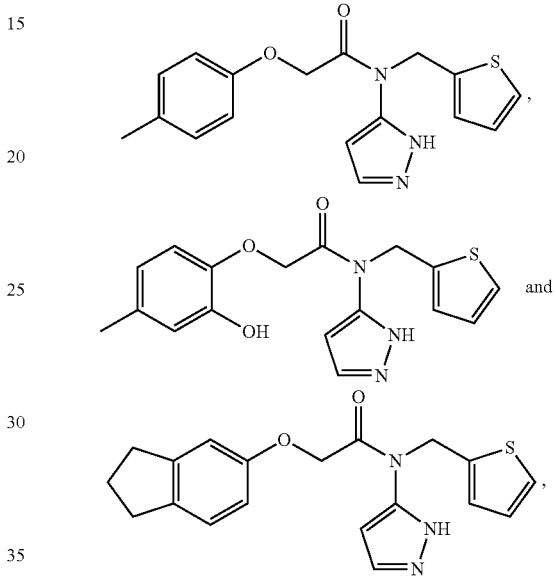

or a salt or solvate thereof.

11. The composition of claim 10, wherein the composition is an ingestible composition or personal care composition.

12. The composition of claim 11, wherein the ingestible composition is a food or beverage.

13. The composition of claim 1, wherein the composition is in form of a solid, semi-solid, plaster, solution, suspension, lotion, cream, foam, gel, paste, emulsion, or a combination thereof.

14. The composition of claim 1, wherein the compound in the composition is in a concentration ranging from about 0.0001 ppm to 100,000 ppm.

15. The composition of claim 1, wherein the compound in the composition is in a concentration ranging from about 1 ppm to 500 ppm.

16. The composition of claim 1, which is a component of a textile product or a packaging material.

17. The composition of claim 1, wherein the compound is:

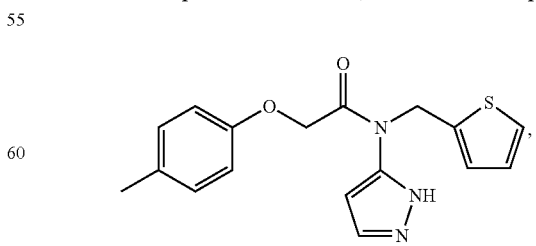

or a salt or solvate thereof.

* * * * *